United States Patent
Thess

(10) Patent No.: US 10,047,375 B2
(45) Date of Patent: *Aug. 14, 2018

(54) ARTIFICIAL NUCLEIC ACID MOLECULES

(71) Applicant: CureVac AG, Tübingen (DE)

(72) Inventor: Andreas Thess, Kusterdingen (DE)

(73) Assignee: CureVac AG, Tübingen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/195,934

(22) Filed: Jun. 28, 2016

(65) Prior Publication Data

US 2017/0029847 A1    Feb. 2, 2017

Related U.S. Application Data

(63) Continuation of application No. PCT/EP2014/003480, filed on Dec. 30, 2014.

(51) Int. Cl.

| C12P 21/02 | (2006.01) |
| C12N 15/67 | (2006.01) |
| C12N 15/85 | (2006.01) |
| C07H 21/02 | (2006.01) |
| C07H 21/04 | (2006.01) |
| C12N 15/09 | (2006.01) |
| C12N 15/63 | (2006.01) |
| C12N 15/68 | (2006.01) |
| A61K 48/00 | (2006.01) |

(52) U.S. Cl.
CPC ............ *C12N 15/85* (2013.01); *C12N 15/67* (2013.01)

(58) Field of Classification Search
None
See application file for complete search history.

(56) References Cited

U.S. PATENT DOCUMENTS

| 5,908,779 | A | 6/1999 | Carmichael et al. |
| 8,217,016 | B2 | 7/2012 | Hoerr et al. |
| 8,383,340 | B2 | 2/2013 | Ketterer et al. |
| 8,703,906 | B2 | 4/2014 | Baumhof et al. |
| 8,968,746 | B2 | 3/2015 | Baumhof et al. |
| 9,155,788 | B2 | 10/2015 | Hoerr et al. |
| 9,447,431 | B2 | 9/2016 | Thess et al. |
| 2005/0009028 | A1 | 1/2005 | Heintz et al. |
| 2005/0032730 | A1 | 2/2005 | Von Der Mülbe et al. |
| 2005/0048549 | A1 | 3/2005 | Cao et al. |
| 2005/0059624 | A1 | 3/2005 | Hoerr et al. |
| 2005/0250723 | A1 | 11/2005 | Hoerr et al. |
| 2006/0188490 | A1 | 8/2006 | Hoerr et al. |
| 2007/0111203 | A1 | 5/2007 | Cao et al. |
| 2007/0172949 | A9 | 7/2007 | Liu et al. |
| 2008/0025944 | A1 | 1/2008 | Hoerr et al. |
| 2008/0267873 | A1 | 10/2008 | Hoerr et al. |
| 2009/0324584 | A1 | 12/2009 | Hoerr et al. |
| 2010/0048883 | A1 | 2/2010 | Ketterer et al. |
| 2010/0120152 | A1 | 5/2010 | Wooddell et al. |
| 2010/0129392 | A1 | 5/2010 | Shi et al. |
| 2010/0189729 | A1 | 7/2010 | Hoerr et al. |
| 2010/0203076 | A1 | 8/2010 | Fotin-Mleczek et al. |
| 2010/0239608 | A1 | 9/2010 | Von Der Mülbe et al. |
| 2010/0291156 | A1 | 11/2010 | Barner et al. |
| 2010/0303851 | A1 | 12/2010 | Hoerr et al. |
| 2010/0305196 | A1 | 12/2010 | Probst et al. |
| 2011/0053829 | A1 | 3/2011 | Baumhof et al. |
| 2011/0077287 | A1 | 3/2011 | Von Der Mülbe et al. |
| 2011/0250225 | A1 | 10/2011 | Fotin-Mleczek et al. |
| 2011/0269950 | A1 | 11/2011 | Von Der Mülbe et al. |
| 2011/0311472 | A1 | 12/2011 | Hoerr et al. |
| 2012/0009221 | A1 | 1/2012 | Hoerr et al. |
| 2012/0021043 | A1 | 1/2012 | Kramps et al. |
| 2012/0213818 | A1 | 8/2012 | Hoerr et al. |
| 2012/0258046 | A1 | 10/2012 | Mutzke |
| 2013/0121988 | A1 | 5/2013 | Hoerr et al. |
| 2013/0129754 | A1 | 5/2013 | Thess et al. |
| 2013/0195867 | A1 | 8/2013 | Hoerr et al. |
| 2013/0202645 | A1 | 8/2013 | Barner et al. |
| 2013/0251742 | A1 | 9/2013 | Probst et al. |
| 2013/0259879 | A1 | 10/2013 | Baumhof et al. |
| 2013/0273001 | A1 | 10/2013 | Hoerr et al. |

(Continued)

FOREIGN PATENT DOCUMENTS

| WO | WO 1995/015394 | 6/1995 |
| WO | WO 1998/042856 | 10/1998 |

(Continued)

OTHER PUBLICATIONS

Schlake et al., "Developing mRNA-vaccine technologies" 9(11) 1319-1330 (Oct. 12, 2012).*
Mignone et al., "Untranslated regions of mRNAs" 3(3) Genome Biology 1-10 (2002).*
Attwood, "The babel of bioinformatics," *Science*, 290(5491):471-473, 2000.
Avni et al., "The 5' terminal oligopyrimidine tract confers translational control on TOP mRNAs in a cell type-and sequence context-dependent manner," *Nucleic Acids Research*, 25(5):995-1001, 1997.
Avni et al., "Vertebrate mRNAs woth 5'-terminal pyrimidine tract are candidates for translational repression in quiescent cells: characterization of the translational cis-regulatory element," *Mol. Cell. Biol.*, 14(6):3822-3833, 1994.

(Continued)

*Primary Examiner* — Nancy J Leith
(74) *Attorney, Agent, or Firm* — Parker Highlander PLLC

(57) ABSTRACT

The invention relates to an artificial nucleic acid molecule comprising at least one open reading frame and at least one 3'-untranslated region element (3'-UTR) element comprising a nucleic acid sequence which is derived from the 3'-UTR of a ribosomal protein gene. The invention further relates to the use of such an artificial nucleic acid molecule in gene therapy and/or genetic vaccination. Furthermore, the invention relates to the use of a 3'-UTR element comprising a nucleic acid sequence which is derived from the 3'-UTR of a ribosomal protein gene for enhancing, stabilizing and/or prolonging protein expression from a nucleic acid sequence comprising such 3'-UTR element.

18 Claims, 9 Drawing Sheets

(56) References Cited

U.S. PATENT DOCUMENTS

| | | |
|---|---|---|
| 2013/0280283 A1 | 10/2013 | Lorenz et al. |
| 2013/0295043 A1 | 11/2013 | Kallen et al. |
| 2013/0336998 A1 | 12/2013 | Kallen et al. |
| 2014/0037660 A1 | 2/2014 | Fotin-Mleczek et al. |
| 2014/0147454 A1 | 5/2014 | Chakraborty et al. |
| 2014/0294877 A1 | 10/2014 | Baumhof et al. |
| 2015/0050302 A1 | 2/2015 | Thess |
| 2015/0057340 A1 | 2/2015 | Thess et al. |
| 2015/0093413 A1 | 4/2015 | Thess |
| 2015/0104476 A1 | 4/2015 | Von Der Mülbe et al. |
| 2015/0118183 A1 | 4/2015 | Baumhof |
| 2015/0118264 A1 | 4/2015 | Baumhof et al. |
| 2015/0141498 A1 | 5/2015 | Mutzke |
| 2015/0165006 A1 | 6/2015 | Thess et al. |
| 2015/0184195 A1 | 7/2015 | Thess et al. |
| 2015/0218554 A1 | 8/2015 | Thess |
| 2015/0258214 A1 | 9/2015 | Baumhof et al. |
| 2015/0306249 A1 | 10/2015 | Baumhof et al. |
| 2015/0320847 A1 | 11/2015 | Thess et al. |

FOREIGN PATENT DOCUMENTS

| | | |
|---|---|---|
| WO | WO 2001/007590 | 2/2001 |
| WO | WO 2001/012824 | 2/2001 |
| WO | WO 2002/098443 | 12/2002 |
| WO | WO 2006/008154 | 1/2006 |
| WO | WO 2006/022712 | 3/2006 |
| WO | WO 2006/024518 | 3/2006 |
| WO | WO 2006/123097 | 11/2006 |
| WO | WO 2007/024708 | 3/2007 |
| WO | WO 2007/068265 | 6/2007 |
| WO | WO 2009/030481 | 3/2009 |
| WO | WO 2009/095226 | 8/2009 |
| WO | WO 2009/155961 | 12/2009 |
| WO | WO 2010/023260 | 3/2010 |
| WO | WO 2010/132867 | 11/2010 |
| WO | WO 2011/069529 | 6/2011 |
| WO | WO 2012/013326 | 2/2012 |
| WO | WO 2012/019630 | 2/2012 |
| WO | WO 2012/019780 | 2/2012 |
| WO | WO 2012/116714 | 9/2012 |
| WO | WO 2013/120626 | 8/2013 |
| WO | WO 2013/120627 | 8/2013 |
| WO | WO 2013/120628 | 8/2013 |
| WO | WO 2013/120629 | 8/2013 |
| WO | WO 2013/143698 | 10/2013 |
| WO | WO 2013/143699 | 10/2013 |
| WO | WO 2013/143700 | 10/2013 |
| WO | WO 2015/024665 | 2/2015 |
| WO | WO 2015/024668 | 2/2015 |
| WO | WO 2015/062738 | 5/2015 |
| WO | WO 2015/101414 | 7/2015 |
| WO | WO 2015/101415 | 7/2015 |
| WO | WO 2015/101416 | 7/2015 |
| WO | WO 2015/135558 | 9/2015 |
| WO | WO 2015/149944 | 10/2015 |

OTHER PUBLICATIONS

Battle and Doudna, "The stem-loop binding protein forms a highly stable and specific complex with the 3' stem-loop of histone mRNAs," RNA, 7:123-132, 2001.

Blumenthal et al., "Definition of an allergen (immunobiology)," Allergens and Allergen Immunotherapy, Ed. R. Lockey, S. Bukantz and J. Bousquet, pp. 37-50, 2004.

Caldarola et al., "Translational regulation of terminal oligopyrimidine mRNAs induced by serum and amino acids involves distinct signaling events." The Journal of Biological Chemistry, 279(14):13522-135531, 2004.

Cameron et al., "Recent advances in transgenic technology," Molecular Biotechnology, 7:253-265, 1997.

Chakrabarti et al., "The mammalian target of rapamycin complex 1 regulates leptin biosynthesis in adipocytes at the level of translation: the role of the 5'-untranslated region in the expression of leptin messenger ribonucleic acid," Molecular Endocrinology, 22(10):2260-2267, 2008.

Cheung et al., "Specific interaction of HeLa cell proteins with cosackievirus B3 B'UTR: La autoantigen binds the 3' and 5' UTR independently of the poly(A) tail," Cell Microbiol., 9(7):1705-1715, 2007.

Collart et al., "A human histone H2B.1 variant gene, located on chromosome 1, utilizes alternative 3' end processing," Journal of Cellular Biochemistry, 50:374-385, 1992.

Damgaard and Lykke-Andersen, "Translational coregulation of 5'TOP mRNAs by TIA-1 and TIAR," Genes Dev., 25:2057-2068, 2011.

Database EMBL Accession No. EN_STD:AB063609, "Homosapiens RPL36AL mRNA for ribosomal protein L36a-like, complete cds," 2002.

Database Geneseq Accession No. ATN08647, "Human transcriptional regulatory element SEQ ID No. 6587," 2008.

Database Nucleotide, "Human ribosomal protein L9 mRNA, complete cds," XP002729678, Database accession No. U09953.1, 1996.

Davuluri et al., "CART classification of human 5' UTR sequences," Genome Research, 10(11):1807-1816, 2000.

Deml et al., "Multiple effects of codon usage optimization on expression and immunogenicity of DNA candidate vaccines encoding the human immunodeficiency virus type 1 Gag protein," Journal of Virology, 75(22):10991-11001, 2001.

Dollé et al., "Nerve growth factor overexpression and autocrine loop in breast cancer cells," Oncogene, 22(36):5592-5601, 2003.

Dominski et al., "Stem-loop binding protein facilitates 3'-end formation by stabilizing U7 snRNP binding to histone pre-mRNA," Mol Cell Biol., 19(5):3561-3570, 1999.

Eckner et al., "Mature mRNA 3' end formation stimulates RNA export from the nucleus," The EMBO Journal, 10(11):3513-3522, 1991.

Gallie et al., "The histone 3'-terminal stem-loop is necessary for translation in Chinese hamster ovary cells," Nucleic Acids Res., 24(10):1954-1962, 1996.

Gerwitz et al., "Nucleic acid therapeutics: state of the art and future prospects," Blood, 92(3):712-736, 1998.

Ginn et al., "Gene therapy clinical trails worldwide to 2012—an update," Journal of Gene Medicine, 15:65-77, 2013.

Gorgoni et al., "The stem-loop binding protein stimulates histone step in the initiation pathway," RNA, 11:1030-1042, 2005.

Haines et al , "CL22—a novel cationic peptide for efficient transfection of mammalian cells," Gene Ther., 8:99-110, 2001.

Henke et al, "Coxsackievirus B3 vaccines: use as an expression vector for prevention of myocarditis," Expert Rev. Vaccines, 7(10):1557-1567, 2008.

Holtkamp et al., "Modification of antigen-encoding RNA increases stability, translational efficacy, and T-cell stimulatory capacity of dendritic cells," Blood, 108(13):4009-17, 2006.

Iadevaia et al., "All translation elongation factors and the e, f, and h subunits of translation initiation factor 3 are encoded by 5'-terminal oligopyrimidine (TOP) mRNAs," RNA, 14:1730-1736, 2008.

International Search Report and Written Opinion issued in the corresponding PCT Application No. PCT/EP2014/003480, dated Aug. 10, 2015.

Kato et al., "Histone H2B as an antigen recognized by lung cancer-specific human monoclonal antibody HB4C5," Human Antibodies and Hybridomas, 2(2):94-101, 1991.

Kenmochi et at, "A map of 75 human ribosomal protein genes," Gene Res., 8(5):509-523, 1998.

Kim et al., "Coxsackievirus B3 used as a gene therapy vector to express functional FGF2," Gene Ther., 19(12):1159-1165, 2012.

Kim et al., "Systematic analysis of attenuated Coxsackievirus expressing a foreign gene as a viral vaccine vector," Vaccine, 28(5):1234-1240, 2010.

Knapinska et al., "Molecular pathological regulation mRNA stability: physiological and pathological significance," Current Genomics, 6(6):1-16, 2005.

Kramarova et al., "A sequence predicted to form a stem-loop is proposed to be required for formation of an RNA-protein complex

(56) References Cited

OTHER PUBLICATIONS involving the 3'UTR of β-subunit $F_0F_1$-ATPase mRNA," *Biochim. Biophys. Acta.*, 1777(7-8):747-757, 2008.
Kudla et al., "High Guanine and Cytosine Content Increases mRNA Levels in Mammalian Cells," *PLoS Biol.*, 4:0933-0942, 2006.
Ledda et al., "Effect of 3' UTR length on the translational regulation of 5'-terminal oligopyrimidine mRNAs," *Gene*, 344:213-220, 2005.
Levy et al., "Oligopyrimidine tract at the 5' end of mammalian ribosomal protein mRNAs is required for their translational control," *Proc. Natl. Acad. Sci. USA*, 88:3319-3323, 1991.
Levy et al., "Sequence and functional characterization of the terminal exon of the human insulin receptor gene," *Biochim Biophys Acta.*, 1263(3):253-257, 1995.
Ling et al., "The histone 3'-terminal stem-loop-binding protein enhances translation through a functional and physical interaction with eukaryotic initiation factor 4G (eIF4G) and eIF3," *Mol Cell Biol.*, 22:7853-7867, 2002.
Lopez and Samuelsson, "Early evolution of histone mRNA 3' end processing," *Bioinformatics*, 14(1):1-10, 2008.
Lorenzi et al., "Intranasal vaccination with messenger RNA as a new approach in gene therapy: Use against tuberulosis," *BMC Biotechnol.*, 10:77, 2010.
Mazuruk et al., "Structural organization and chromosomal localization of the human ribosomal protein L9 gene," *Biochim. Biophys. Acta*, 1305(3):151-162, 1996.
Meier et al., "Fibroblast growth factor-2 but not Mel-CAM and/or β3 integrin promotes progression of melanocytes to melanoma," *Exp. Dermatol.*, 12(3):296-306, 2003.
Meyuhas, "Synthesis of the translational apparatus is regulated at the translational level," *Eur. J. Biochem.*, 267:6321-6330, 2000.
Montoliu, "Gene transfer strategies in animal transgenesis," *Cloning and Stem Cells*, 4(1):39-46, 2002.
Moor et al., "Mechanisms of translational control by the 3' UTR in development and differentiation," *Sem. Cell Develop. Biol.*, 16(1):49-58, 2005.
Narita et al., "NELF interacts with CDC and participates in 3' end processing of replication-dependent histone mRNAs," *Molecular Cell*, 26(3):349-365, 2007.
Ngo et al., "Computational complexity, protein structure prediction, and the levinthal paradox," *The Protein Folding Problem and Tertiary Structure Prediction*, Ed. K. Merz and S. Le Grand, pp. 491-495, 1994.
Niemann, "Transgenic farm animals get off the ground," *Transgenic Research*, 7:73-75, 1998.
Office Action issued in U.S. Appl. No. 13/321,474, dated Apr. 6, 2015.
Office Action issued in U.S. Appl. No. 13/321,474, dated May 20, 2014.
Office Action issued in U.S. Appl. No. 14/378,538, dated Jun. 21, 2016.
Office Action issued in U.S. Appl. No. 14/378,538, dated Nov. 12, 2015.
Office Action issued in U.S. Appl. No. 14/378,538, dated Oct. 11, 2016.
Office Action issued in U.S. Appl. No. 14/378,572, dated Aug. 12, 2016.
Office Action issued in U.S. Appl. No. 14/378,572, dated Mar. 3, 2016.
Office Action issued in U.S. Appl. No. 14/378,572, dated Mar. 14, 2017.
Office Action issued in U.S. Appl. No. 14/378,591, dated Aug. 22, 2016.
Office Action issued in U.S. Appl. No. 14/378,591, dated Jan. 27, 2017.
Office Action issued in U.S. Appl. No. 14/378,606, dated May 27, 2015.
Office Action issued in U.S. Appl. No. 14/378,606, dated Nov. 3, 2015.
Office Action issued in U.S. Appl. No. 14/388,226, dated Jun. 21, 2016.
Office Action issued in U.S. Appl. No. 14/388,226, dated Nov. 6, 2015.
Office Action issued in U.S. Appl. No. 14/945,349, dated Feb. 6, 2017.
Oliveira et al., "Inhibition of translational initiation in *Saccharomyces cerevisiae* by secondary structure: the roles of the stability and position of stem-loops in the mRNA leader," *Mol. Microbiol.*, 9(3):521-532, 1993.
Orom et al., "MicroRNA-10a binds the 5'UTR of ribosomal protein mRNAs and enhances their translation," *Molecular Cell*, 30:460-471, 2008.
Palmowski et al., "Intravenous injection of a lentiviral vector encoding NY-ESO-1 induces an effective CTL response," *J. Immunol.*, 172(3):1582-1587, 2004.
Pandey et al., "Introns in histone genes alter the distribution of 3' ends," *Nucleic Acids Res.*, 18(11):3161-3170, 1990.
PCT International Search Report and Written Opinion issued in International Application No. PCT/EP2013/000938, dated Nov. 13, 2013.
PCT International Search Report and Written Opinion issued in International Application No. PCT/EP2013/000461, dated Apr. 16, 2013.
PCT International Search Report and Written Opinion issued in International Application No. PCT/EP2013/000458, dated Apr. 24, 2013.
PCT International Search Report and Written Opinion issued in International Application No. PCT/EP2013/000459, dated Apr. 23, 2013.
PCT International Search Report and Written Opinion issued in International Application No. PCT/EP2013/000460, dated Apr. 22, 2013.
PCT International Search Report and Written Opinion issued in International Application No. PCT/EP2011/004077, dated Nov. 10, 2011.
PCT International Search Report and Written Opinion issued in International Application No. PCT/EP2013/000937, dated Aug. 30, 2013.
Prelle et al., "Establishment of pluripotent cell lines from vertebrate species—present status and future prospects," *Cells Tissues Organs*, 165:220-236, 1999.
Ristevski, "Making better transgenic models," *Molecular Biotechnology*, 29:153-163, 2005.
Roesler et al., "Immunize and disappear—safety-optimized mRNA vaccination with a panel of 29 allergens," *Journal of Allergy and Clinical Immunology*, 124(5):1070-1077, 2009.
Russell et al., "The stability of human beta-globin mRNA is dependent on stuctural determinants positioned within its 3' untranslated region," *Blood*, 87:5314-5323, 1996.
Sanchez et al., "Increased levels of polyadenylated histone H2B mRNA accumulate during *Entamoeba invadens* cyst formation," *Molecular and Biochemical Parasitology*, 67(1):137-146, 1994.
Sanchez et al., "The oligo(A) tail on histone mRNA plays an active role in translational silencing of histone mRNA during Xenopus oogenesis," *Mol Cell Biol.*, 24(6):2513-2525, 2004.
Sharma et al., "Functional role of the 5' terminal cloverleaf in Coxsackievirus RNA replication," *Virology*, 393(2):238-249, 2009.
Shen et al., "Structures required for poly(A) tail-independent translation overlap with, but ar distinct from, cap-independent translation and RNA replication signals at the 3' end of *Tobacco necrosis virus* RNA," *Virology*, 358:448-458, 2007.
Sigmund, "Viewpoint: are studies in genetically altered mice out of control?" *Arteriosclerosis, Thrombosis, and Vascular Biology*, 20:1425-1429, 2000.
Skolnick et al., "From genes to protein structure and function: novel applications of computational approaches in the genomic em," *Trends in Biotech.*, 18:34-39, 2000.
Smith, "Gene transfer in higher animals: Theoretical considerations and key concepts," *Journal of Biotechnology*, 99:1-22, 2002.
Stauber et al., "A signal regulating mouse histone H4 mRNA levels in a mammalian cell cycle mutant and sequences controlling RNA 3' processing are both contained within the same 80-bp fragment," *EMBO J.*, 5(12):3297-3303, 1986.

(56) References Cited

OTHER PUBLICATIONS

Svoboda et al., "Hairpin RNA; a secondary structure of primary importance," *Cell Mol Life Sci.*, 63(7-8):901-908, 2006.

Thess et al., "Sequence-engineered mRNA without chemical in large nucleoside modifications enables an effective protein therapy in large animals," *Molecular Therapy*, pp. 1-9 and Supplementary Material, 2015.

van Ooij et al., "Polyadenylation of genomic RNA and initiation of antigenomic RNA in a positive-strand RNA virus are controlled by the same *cis*-element," *Nucleic Acids Res.*, 34(10):2953-2965, 2006.

Wagner et al., "A genome-wide RNA interference screen reveals that variant histones are necessary for replication-dependent histone pre-mRNA processing", *Molecular Cell*, 28(4):692-699, 2007.

Weiss et al., "Prophylactic mRNA vaccination against allergy," *Current Opinion in Allergy and Clinical Immunology*, 10(6):567-574, 2010.

Wilkie et al., "Regulation of mRNA translation by 5'- and 3'-UTR-binding factors," *Trends Biochem. Sci.*, 28(4):182-188, 2003.

Williams et al., "A simple, highly efficient method for heterologous expression in mammalian primary neurons using cationic lipid-mediated mRNA transfection," *Frontiers in Neuroscience*, 4:1-20, 2010.

Wooddell et al., "Sustained liver-specific transgene expression from the albumin promoter in mice following hydrodynamic plasmid DNA delivery," *The Journal of Gene Medicine*, 10:551-563, 2008.

Yamashita et al., "Comprehensive detection of human terminal oligo-pyrimidine (TOP) genes and analysis of their characteristics," *Nucleic Acids Res*, 36(11):3707-3715 and Supplementary Data (six pages), 2008.

Zhong et al., "A double-stranded RNA binding protein required for activation of repressed messages in mammalian germ cells," *Nat Genet.*, 22(2):171-174, 1999.

Zhu et al., "Binding of the La autoantigen to the 5' untranslated region of a chimeric human translation elongation factor 1A reporter mRNA inhibits translation in vitro," *Biochimica et Biophysica Acta*, 1521:19-29, 2001.

\* cited by examiner rpl32 – PpLuc(GC) – A64 – C30 – histoneSL:

GGGGCGCTGCCTACGGAGGTGGCAGCCATCTCCTTCTCGGCATCAAGCTTGAGGA*TGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTAGATCTAAAAAAAAAAAAAAAAAAAA
AAAAAAAAAAAAAAAAAAAAAAAAAAAAAAAAAAAAAAAAAAAATGCATCCCCCCCCCCC
CCCCCCCCCCCCCCCCCCCAAAGGCTCTTTTCAGAGCCACCAGAATT

Fig. 1 rpl32 – PpLuc(GC) – ag – A64 – C30 – histoneSL:

GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTTATAAGACTGACTAG<u>CCCGATGGGCC
TCCCAACGGGCCCTCCTCCCCTCCTTGCACC</u>GAGATTAATAGATCTAAAAAAAAAAAAAA
AAAAAAAAAAAAAAAAAAAAAAAAAAAAAAAAAAAAAAAAAAAAAAAAAATGCATCCCCC
CCCCCCCCCCCCCCCCCCCCCCCCAAAGGCTCTTTTCAGAGCCACCAGAATT

Fig. 2 rpl32 – PpLuc(GC) – rps9 – A64 – C30 – histoneSL ):

GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTGTCCACCTGTCCCTCCTGGGCTGCTG
GATTGTCTCGTTTTCCTGCCAAATAAACAGGATCAGCGCTTTACAGATCTAAAAAAAAAA
AAAAAAAAAAAAAAAAAAAAAAAAAAAAAAAAAAAAAAAAAAAAAAAAAAAAAATGCATC
CCCCCCCCCCCCCCCCCCCCCCCCCCCCCCAAAGGCTCTTTTCAGAGCCACCAGAATT

Fig. 3 rpl32 – PpLuc(GC) – albumin7 – A64 – C30 – histoneSL

GGGGCGCTGCCTACGGAGGTGGCAGCCATCTCCTTCTCGGCATCAAGCTTGAGGATGGAG
GACGCCAAGAACATCAAGAAGGGCCCGGCGCCCTTCTACCCGCTGGAGGACGGGACCGCC
GGCGAGCAGCTCCACAAGGCCATGAAGCGGTACGCCCTGGTGCCGGGCACGATCGCCTTC
ACCGACGCCCACATCGAGGTCGACATCACCTACGCGGAGTACTTCGAGATGAGCGTGCGC
CTGGCCGAGGCCATGAAGCGGTACGGCCTGAACACCAACCACCGGATCGTGGTGTGCTCG
GAGAACAGCCTGCAGTTCTTCATGCCGGTGCTGGGCGCCCTCTTCATCGGCGTGGCCGTC
GCCCCGGCGAACGACATCTACAACGAGCGGGAGCTGCTGAACAGCATGGGGATCAGCCAG
CCGACCGTGGTGTTCGTGAGCAAGAAGGGCCTGCAGAAGATCCTGAACGTGCAGAAGAAG
CTGCCCATCATCCAGAAGATCATCATCATGGACAGCAAGACCGACTACCAGGGCTTCCAG
TCGATGTACACGTTCGTGACCAGCCACCTCCGCCGGGCTTCAACGAGTACGACTTCGTC
CCGGAGAGCTTCGACCGGGACAAGACCATCGCCCTGATCATGAACAGCAGCGGCAGCACC
GGCCTGCCGAAGGGGGTGGCCCTGCCGCACCGGACCGCCTGCGTGCGCTTCTCGCACGCC
CGGGACCCCATCTTCGGCAACCAGATCATCCCGGACACCGCCATCCTGAGCGTGGTGCCG
TTCCACCACGGCTTCGGCATGTTCACGACCCTGGGCTACCTCATCTGCGGCTTCCGGGTG
GTCCTGATGTACCGGTTCGAGGAGGAGCTGTTCCTGCGGAGCCTGCAGGACTACAAGATC
CAGAGCGCGCTGCTCGTGCCGACCCTGTTCAGCTTCTTCGCCAAGAGCACCCTGATCGAC
AAGTACGACCTGTCGAACCTGCACGAGATCGCCAGCGGGGCGCCCCGCTGAGCAAGGAG
GTGGGCGAGGCCGTGGCCAAGCGGTTCCACCTCCCGGGCATCCGCCAGGGCTACGGCCTG
ACCGAGACCACGAGCGCGATCCTGATCACCCCCGAGGGGGACGACAAGCCGGGCGCCGTG
GGCAAGGTGGTCCCGTTCTTCGAGGCCAAGGTGGTGGACCTGGACACCGGCAAGACCCTG
GGCGTGAACCAGCGGGGCGAGCTGTGCGTGCGGGGCCGATGATCATGAGCGGCTACGTG
AACAACCCGGAGGCCACCAACGCCCTCATCGACAAGGACGGCTGGCTGCACAGCGGCGAC
ATCGCCTACTGGGACGAGGACGAGCACTTCTTCATCGTCGACCGGCTGAAGTCGCTGATC
AAGTACAAGGGCTACCAGGTGGCGCCGGCCGAGCTGGAGAGCATCCTGCTCCAGCACCCC
AACATCTTCGACGCCGGCGTGGCCGGGCTGCCGGACGACGACGCCGGCGAGCTGCCGGCC
GCGGTGGTGGTGCTGGAGCACGGCAAGACCATGACGGAGAAGGAGATCGTCGACTACGTG
GCCAGCCAGGTGACCACCGCCAAGAAGCTGCGGGGCGGCGTGGTGTTCGTGGACGAGGTC
CCGAAGGGCCTGACCGGGAAGCTCGACGCCCGGAAGATCCGCGAGATCCTGATCAAGGCC
AAGAAGGGCGGCAAGATCGCCGTGTAAGACTAGTG<u>CATCACATTTAAAAGCATCTCAGCC</u>
<u>TACCATGAGAATAAGAGAAAGAAAATGAAGATCAATAGCTTATTCATCTCTTTTTCTTTT</u>
<u>TCGTTGGTGTAAAGCCAACACCCTGTCTAAAAAACATAAATTTCTTTAATCATTTTGCCT</u>
<u>CTTTTCTCTGTGCTTCAATTAATAAAAAATGGAAAGAACCTAGATCTAAAAAAAAAAAA</u>
AAAAAAAAAAAAAAAAAAAAAAAAAAAAAAAAAAAAAAAAAAAAAAAAAAAATGCATCCCC
CCCCCCCCCCCCCCCCCCCCCCCCCAAAGGCTCTTTTCAGAGCCACCAGAATT

Fig. 5

ARTIFICIAL NUCLEIC ACID MOLECULES

This application is a continuation of International Application No. PCT/EP2014/003480, filed Dec. 30, 2014, which claims the benefit of International Application No. PCT/EP2013/003946, filed Dec. 30, 2013, the entirety of each of which is incorporated herein by reference.

The present invention was made with support from the Government under Agreement No. HR0011-11-3-0001 awarded by DARPA. The Government has certain rights in the invention.

The invention relates to artificial nucleic acid molecules comprising an open reading frame, a 3'-untranslated region element (3'-UTR element) and optionally a poly(A) sequence and/or a polyadenylation-signal. The invention relates further to a vector comprising a 3'-UTR element, to a cell comprising the artificial nucleic acid molecule or the vector, to a pharmaceutical composition comprising the artificial nucleic acid molecule or the vector and to a kit comprising the artificial nucleic acid molecule, the vector and/or the pharmaceutical composition, preferably for use in the field of gene therapy and/or genetic vaccination.

Gene therapy and genetic vaccination belong to the most promising and quickly developing methods of modern medicine. They may provide highly specific and individual options for therapy of a large variety of diseases. Particularly, inherited genetic diseases but also autoimmune diseases, cancerous or tumour-related diseases as well as inflammatory diseases may be the subject of such treatment approaches. Also, it is envisaged to prevent early onset of such diseases by these approaches.

The main conceptual rational behind gene therapy is appropriate modulation of impaired gene expression associated with pathological conditions of specific diseases. Pathologically altered gene expression may result in lack or overproduction of essential gene products, for example, signalling factors such as hormones, housekeeping factors, metabolic enzymes, structural proteins or the like. Altered gene expression may not only be due to mis-regulation of transcription and/or translation, but also due to mutations within the ORF coding for a particular protein. Pathological mutations may be caused by e.g. chromosomal aberration, or by more specific mutations, such as point or frame-shift-mutations, all of them resulting in limited functionality and, potentially, total loss of function of the gene product. However, misregulation of transcription or translation may also occur, if mutations affect genes encoding proteins which are involved in the transcriptional or translational machinery of the cell. Such mutations may lead to pathological up- or down-regulation of genes which are—as such—functional. Genes encoding gene products which exert such regulating functions, may be, e.g., transcription factors, signal receptors, messenger proteins or the like. However, loss of function of such genes encoding regulatory proteins may, under certain circumstances, be reversed by artificial introduction of other factors acting further downstream of the impaired gene product. Such gene defects may also be compensated by gene therapy via substitution of the affected gene itself.

Genetic vaccination allows evoking a desired immune response to selected antigens, such as characteristic components of bacterial surfaces, viral particles, tumour antigens or the like. Generally, vaccination is one of the pivotal achievements of modern medicine. However, effective vaccines are currently available only for a limited number of diseases. Accordingly, infections that are not preventable by vaccination still affect millions of people every year.

Commonly, vaccines may be subdivided into "first", "second" and "third" generation vaccines. "First generation" vaccines are, typically, whole-organism vaccines. They are based on either live and attenuated or killed pathogens, e.g. viruses, bacteria or the like. The major drawback of live and attenuated vaccines is the risk for a reversion to life-threatening variants. Thus, although attenuated, such pathogens may still intrinsically bear unpredictable risks. Killed pathogens may not be as effective as desired for generating a specific immune response. In order to minimize these risks, "second generation" vaccines were developed. These are, typically, subunit vaccines, consisting of defined antigens or recombinant protein components which are derived from pathogens.

Genetic vaccines, i.e. vaccines for genetic vaccination, are usually understood as "third generation" vaccines. They are typically composed of genetically engineered nucleic acid molecules which allow expression of peptide or protein (antigen) fragments characteristic for a pathogen or a tumor antigen in vivo. Genetic vaccines are expressed upon administration to a patient after uptake by target cells. Expression of the administered nucleic acids results in production of the encoded proteins. In the event these proteins are recognized as foreign by the patient's immune system, an immune response is triggered.

As can be seen from the above, both methods, gene therapy and genetic vaccination, are essentially based on the administration of nucleic acid molecules to a patient and subsequent transcription and/or translation of the encoded genetic information. Alternatively, genetic vaccination or gene therapy may also comprise methods which include isolation of specific body cells from a patient to be treated, subsequent ex vivo transfection of such cells, and re-administration of the treated cells to the patient.

DNA as well as RNA may be used as nucleic acid molecules for administration in the context of gene therapy or genetic vaccination. DNA is known to be relatively stable and easy to handle. However, the use of DNA bears the risk of undesired insertion of the administered DNA-fragments into the patient's genome potentially resulting mutagenic events such as in loss of function of the impaired genes. As a further risk, the undesired generation of anti-DNA antibodies has emerged. Another drawback is the limited expression level of the encoded peptide or protein that is achievable upon DNA administration because the DNA must enter the nucleus in order to be transcribed before the resulting mRNA can be translated. Among other reasons, the expression level of the administered DNA will be dependent on the presence of specific transcription factors which regulate DNA transcription. In the absence of such factors, DNA transcription will not yield satisfying amounts of RNA. As a result, the level of translated peptide or protein obtained is limited.

By using RNA instead of DNA for gene therapy or genetic vaccination, the risk of undesired genomic integration and generation of anti-DNA antibodies is minimized or avoided. However, RNA is considered to be a rather unstable molecular species which may readily be degraded by ubiquitous RNAses.

In vivo, RNA degradation contributes to the regulation of the RNA half-life time. That effect was considered and proven to fine tune the regulation of eukaryotic gene expression (Friedel et al., 2009. Conserved principles of mammalian transcriptional regulation revealed by RNA half-life, Nucleic Acid Research 37(17): 1-12). Accordingly, each naturally occurring mRNA has its individual half-life depending on the gene from which the mRNA is derived and in which cell type it is expressed. It contributes to the regulation of the expression level of this gene. Unstable RNAs are important to realize transient gene expression at distinct points in time. However, long-lived RNAs may be associated with accumulation of distinct proteins or continuous expression of genes. In vivo, the half-life of mRNAs may also be dependent on environmental factors, such as hormonal treatment, as has been shown, e.g., for insulin-like growth factor I, actin, and albumin mRNA (Johnson et al., Newly synthesized RNA: Simultaneous measurement in intact cells of transcription rates and RNA stability of insulin-like growth factor I, actin, and albumin in growth hormone-stimulated hepatocytes, Proc. Natl. Acad. Sci., Vol. 88, pp. 5287-5291, 1991).

For gene therapy and genetic vaccination, usually stable RNA is desired. This is, on the one hand, due to the fact that it is usually desired that the product encoded by the RNA sequence accumulates in vivo. On the other hand, the RNA has to maintain its structural and functional integrity when prepared for a suitable dosage form, in the course of its storage, and when administered. Thus, efforts were made to provide stable RNA molecules for gene therapy or genetic vaccination in order to prevent them from being subject to early degradation or decay.

It has been reported that the G/C-content of nucleic acid molecules may influence their stability. Thus, nucleic acids comprising an increased amount of guanine (G) and/or cytosine (C) residues may be functionally more stable than nucleic acids containing a large amount of adenine (A) and thymine (T) or uracil (U) nucleotides. In this context, WO02/098443 provides a pharmaceutical composition containing an mRNA that is stabilised by sequence modifications in the coding region. Such a sequence modification takes advantage of the degeneracy of the genetic code. Accordingly, codons which contain a less favourable combination of nucleotides (less favourable in terms of RNA stability) may be substituted by alternative codons without altering the encoded amino acid sequence. This method of RNA stabilization is limited by the provisions of the specific nucleotide sequence of each single RNA molecule which is not allowed to leave the space of the desired amino acid sequence. Also, that approach is restricted to coding regions of the RNA.

As an alternative option for mRNA stabilisation, it has been found that naturally occurring eukaryotic mRNA molecules contain characteristic stabilising elements. For example, they may comprise so-called untranslated regions (UTR) at their 5'-end (5'-UTR) and/or at their 3'-end (3'-UTR) as well as other structural features, such as a 5'-cap structure or a 3'-poly(A) tail. Both, 5'-UTR and 3'-UTR are typically transcribed from the genomic DNA and are, thus, an element of the premature mRNA. Characteristic structural features of mature mRNA, such as the 5'-cap and the 3'-poly(A) tail (also called poly(A) tail or poly(A) sequence) are usually added to the transcribed (premature) mRNA during mRNA processing.

A 3'-poly(A) tail is typically a monotonous sequence stretch of adenosine nucleotides added to the 3'-end of the transcribed mRNA. It may comprise up to about 400 adenosine nucleotides. It was found that the length of such a 3'-poly(A) tail is a potentially critical element for the stability of the individual mRNA.

Also, it was shown that the 3'-UTR of α-globin mRNA may be an important factor for the well-known stability of α-globin mRNA (Rodgers et al., Regulated α-globin mRNA decay is a cytoplasmic event proceeding through 3'-to-5' exosome-dependent decapping, RNA, 8, pp. 1526-1537, 2002). The 3'-UTR of α-globin mRNA is apparently involved in the formation of a specific ribonucleoprotein-complex, the α-complex, whose presence correlates with mRNA stability in vitro (Wang et al., An mRNA stability complex functions with poly(A)-binding protein to stabilize mRNA in vitro, Molecular and Cellular biology, Vol 19, No. 7, July 1999, p. 4552-4560).

An interesting regulatory function has further been demonstrated for the UTRs in ribosomal protein mRNAs: while the 5'-UTR of ribosomal protein mRNAs controls the growth-associated translation of the mRNA, the stringency of that regulation is conferred by the respective 3'-UTR in ribosomal protein mRNAs (Ledda et al., Effect of the 3'-UTR length on the translational regulation of 5'-terminal oligopyrimidine mRNAs, Gene, Vol. 344, 2005, p. 213-220). This mechanism contributes to the specific expression pattern of ribosomal proteins, which are typically transcribed in a constant manner so that some ribosomal protein mRNAs such as ribosomal protein S9 or ribosomal protein L32 are referred to as housekeeping genes (Janovick-Guretzky et al., Housekeeping Gene Expression in Bovine Liver is Affected by Physiological State, Feed Intake, and Dietary Treatment, J. Dairy Sci., Vol. 90, 2007, p. 2246-2252). The growth-associated expression pattern of ribosomal proteins is thus mainly due to regulation on the level of translation.

Irrespective of factors influencing mRNA stability, effective translation of the administered nucleic acid molecules by the target cells or tissue is crucial for any approach using nucleic acid molecules for gene therapy or genetic vaccination. As can be seen from the examples cited above, along with the regulation of stability, also translation of the majority of mRNAs is regulated by structural features like UTRs, 5'-cap and 3'-poly(A) tail. In this context, it has been reported that the length of the poly(A) tail may play an important role for translational efficiency as well. Stabilizing 3'-elements, however, may also have an attenuating effect on translation.

It is the object of the invention to provide nucleic acid molecules, which may be suitable for application in gene therapy and/or genetic vaccination. Particularly, it is the object of the invention to provide an mRNA species, which is stabilized against preterm degradation or decay without exhibiting significant functional loss in translational efficiency. It is also an object of the invention to provide an artificial nucleic acid molecule, preferably an mRNA, which is characterized by enhanced expression of the respective protein encoded by said nucleic acid molecule. One particular object of the invention is the provision of an mRNA, wherein the efficiency of translation of the respective encoded protein is enhanced. Another object of the present invention is to provide nucleic acid molecules coding for such a superior mRNA species, which may be amenable for use in gene therapy and/or genetic vaccination. It is a further object of the present invention to provide a pharmaceutical composition for use in gene therapy and/or genetic vaccination. In summary, it is the object of the present invention to provide improved nucleic acid species which overcome the above discussed disadvantages of the prior art by a cost-effective and straight-forward approach.

The object underlying the present invention is solved by the claimed subject matter.

For the sake of clarity and readability the following definitions are provided. Any technical feature mentioned for these definitions may be read on each and every embodiment of the invention. Additional definitions and explanations may be specifically provided in the context of these embodiments.

Adaptive immune response: The adaptive immune response is typically understood to be an antigen-specific response of the immune system. Antigen specificity allows for the generation of responses that are tailored to specific pathogens or pathogen-infected cells. The ability to mount these tailored responses is usually maintained in the body by "memory cells". Should a pathogen infect the body more than once, these specific memory cells are used to quickly eliminate it. In this context, the first step of an adaptive immune response is the activation of naïve antigen-specific T cells or different immune cells able to induce an antigen-specific immune response by antigen-presenting cells. This occurs in the lymphoid tissues and organs through which naïve T cells are constantly passing. The three cell types that may serve as antigen-presenting cells are dendritic cells, macrophages, and B cells. Each of these cells has a distinct function in eliciting immune responses. Dendritic cells may take up antigens by phagocytosis and macropinocytosis and may become stimulated by contact with e.g. a foreign antigen to migrate to the local lymphoid tissue, where they differentiate into mature dendritic cells. Macrophages ingest particulate antigens such as bacteria and are induced by infectious agents or other appropriate stimuli to express MHC molecules. The unique ability of B cells to bind and internalize soluble protein antigens via their receptors may also be important to induce T cells. MHC-molecules are, typically, responsible for presentation of an antigen to T-cells. Therein, presenting the antigen on MHC molecules leads to activation of T cells, which induces their proliferation and differentiation into armed effector T cells. The most important function of effector T cells is the killing of infected cells by CD8+ cytotoxic T cells and the activation of macrophages by Th1 cells, which together make up cell-mediated immunity, and the activation of B cells by both Th2 and Th1 cells to produce different classes of antibody, thus driving the humoral immune response. T cells recognize an antigen by their T cell receptors which do not recognize and bind the antigen directly, but instead recognize short peptide fragments e.g. of pathogen-derived protein antigens, e.g. so-called epitopes, which are bound to MHC molecules on the surfaces of other cells.

Adaptive immune system: The adaptive immune system is essentially dedicated to eliminate or prevent pathogenic growth. It typically regulates the adaptive immune response by providing the vertebrate immune system with the ability to recognize and remember specific pathogens (to generate immunity), and to mount stronger attacks each time the pathogen is encountered. The system is highly adaptable because of somatic hypermutation (a process of accelerated somatic mutations), and V(D)J recombination (an irreversible genetic recombination of antigen receptor gene segments). This mechanism allows a small number of genes to generate a vast number of different antigen receptors, which are then uniquely expressed on each individual lymphocyte. Because the gene rearrangement leads to an irreversible change in the DNA of each cell, all of the progeny (offspring) of such a cell will then inherit genes encoding the same receptor specificity, including the Memory B cells and Memory T cells that are the keys to long-lived specific immunity.

Adjuvant/adjuvant component: An adjuvant or an adjuvant component in the broadest sense is typically a pharmacological and/or immunological agent that may modify, e.g. enhance, the effect of other agents, such as a drug or vaccine. It is to be interpreted in a broad sense and refers to a broad spectrum of substances. Typically, these substances are able to increase the immunogenicity of antigens. For example, adjuvants may be recognized by the innate immune systems and, e.g., may elicit an innate immune response. "Adjuvants" typically do not elicit an adaptive immune response. Insofar, "adjuvants" do not qualify as antigens. Their mode of action is distinct from the effects triggered by antigens resulting in an adaptive immune response.

Antigen: In the context of the present invention "antigen" refers typically to a substance which may be recognized by the immune system, preferably by the adaptive immune system, and is capable of triggering an antigen-specific immune response, e.g. by formation of antibodies and/or antigen-specific T cells as part of an adaptive immune response. Typically, an antigen may be or may comprise a peptide or protein, which may be presented by the MHC to T-cells. In the sense of the present invention an antigen may be the product of translation of a provided nucleic acid molecule, preferably an mRNA as defined herein. In this context, also fragments, variants and derivatives of peptides and proteins comprising at least one epitope are understood as antigens. In the context of the present invention, tumour antigens and pathogenic antigens as defined herein are particularly preferred.

Artificial nucleic acid molecule: An artificial nucleic acid molecule may typically be understood to be a nucleic acid molecule, e.g. a DNA or an RNA, that does not occur naturally. In other words, an artificial nucleic acid molecule may be understood as a non-natural nucleic acid molecule. Such nucleic acid molecule may be non-natural due to its individual sequence (which does not occur naturally) and/or due to other modifications, e.g. structural modifications of nucleotides, which do not occur naturally. An artificial nucleic acid molecule may be a DNA molecule, an RNA molecule or a hybrid-molecule comprising DNA and RNA portions. Typically, artificial nucleic acid molecules may be designed and/or generated by genetic engineering methods to correspond to a desired artificial sequence of nucleotides (heterologous sequence). In this context an artificial sequence is usually a sequence that may not occur naturally, i.e. it differs from the wild type sequence by at least one nucleotide. The term "wild type" may be understood as a sequence occurring in nature. Further, the term "artificial nucleic acid molecule" is not restricted to mean "one single molecule" but is, typically, understood to comprise an ensemble of identical molecules. Accordingly, it may relate to a plurality of identical molecules contained in an aliquot.

Bicistronic RNA, multicistronic RNA: A bicistronic or multicistronic RNA is typically an RNA, preferably an mRNA, that typically may have two (bicistronic) or more (multicistronic) open reading frames (ORF). An open reading frame in this context is a sequence of codons that is translatable into a peptide or protein.

Carrier/polymeric carrier: A carrier in the context of the invention may typically be a compound that facilitates transport and/or complexation of another compound (cargo). A polymeric carrier is typically a carrier that is formed of a polymer. A carrier may be associated to its cargo by covalent or non-covalent interaction. A carrier may transport nucleic acids, e.g. RNA or DNA, to the target cells. The carrier may—for some embodiments—be a cationic component.

Cationic component: The term "cationic component" typically refers to a charged molecule, which is positively charged (cation) at a pH value typically from 1 to 9, preferably at a pH value of or below 9 (e.g. from 5 to 9), of or below 8 (e.g. from 5 to 8), of or below 7 (e.g. from 5 to 7), most preferably at a physiological pH, e.g. from 7.3 to 7.4. Accordingly, a cationic component may be any positively charged compound or polymer, preferably a cationic peptide or protein, which is positively charged under physiological conditions, particularly under physiological conditions in vivo. A "cationic peptide or protein" may contain at least one positively charged amino acid, or more than one positively charged amino acid, e.g. selected from Arg, His, Lys or Orn. Accordingly, "polycationic" components are also within the scope exhibiting more than one positive charge under the conditions given.

5'-cap: A 5'-cap is an entity, typically a modified nucleotide entity, which generally "caps" the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an RNA. Further examples of 5'cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety.

Cellular immunity/cellular immune response: Cellular immunity relates typically to the activation of macrophages, natural killer cells (NK), antigen-specific cytotoxic T-lymphocytes, and the release of various cytokines in response to an antigen. In more general terms, cellular immunity is not based on antibodies, but on the activation of cells of the immune system. Typically, a cellular immune response may be characterized e.g. by activating antigen-specific cytotoxic T-lymphocytes that are able to induce apoptosis in cells, e.g. specific immune cells like dendritic cells or other cells, displaying epitopes of foreign antigens on their surface. Such cells may be virus-infected or infected with intracellular bacteria, or cancer cells displaying tumor antigens. Further characteristics may be activation of macrophages and natural killer cells, enabling them to destroy pathogens and stimulation of cells to secrete a variety of cytokines that influence the function of other cells involved in adaptive immune responses and innate immune responses.

DNA: DNA is the usual abbreviation for deoxy-ribo-nucleic acid. It is a nucleic acid molecule, i.e. a polymer consisting of nucleotides. These nucleotides are usually deoxy-adenosine-monophosphate, deoxy-thymidine-monophosphate, deoxy-guanosine-monophosphate and deoxy-cytidine-monophosphate monomers which are—by themselves—composed of a sugar moiety (deoxyribose), a base moiety and a phosphate moiety, and polymerise by a characteristic backbone structure. The backbone structure is, typically, formed by phosphodiester bonds between the sugar moiety of the nucleotide, i.e. deoxyribose, of a first and a phosphate moiety of a second, adjacent monomer. The specific order of the monomers, i.e. the order of the bases linked to the sugar/phosphate-backbone, is called the DNA sequence. DNA may be single stranded or double stranded. In the double stranded form, the nucleotides of the first strand typically hybridize with the nucleotides of the second strand, e.g. by A/T-base-pairing and G/C-base-pairing.

Epitope: (also called "antigen determinant") can be distinguished in T cell epitopes and B cell epitopes. T cell epitopes or parts of the proteins in the context of the present invention may comprise fragments preferably having a length of about 6 to about 20 or even more amino acids, e.g. fragments as processed and presented by MHC class I molecules, preferably having a length of about 8 to about 10 amino acids, e.g. 8, 9, or 10, (or even 11, or 12 amino acids), or fragments as processed and presented by MHC class II molecules, preferably having a length of about 13 or more amino acids, e.g. 13, 14, 15, 16, 17, 18, 19, 20 or even more amino acids, wherein these fragments may be selected from any part of the amino acid sequence. These fragments are typically recognized by T cells in form of a complex consisting of the peptide fragment and an MHC molecule, i.e. the fragments are typically not recognized in their native form. B cell epitopes are typically fragments located on the outer surface of (native) protein or peptide antigens as defined herein, preferably having 5 to 15 amino acids, more preferably having 5 to 12 amino acids, even more preferably having 6 to 9 amino acids, which may be recognized by antibodies, i.e. in their native form.

Such epitopes of proteins or peptides may furthermore be selected from any of the herein mentioned variants of such proteins or peptides. In this context antigenic determinants can be conformational or discontinuous epitopes which are composed of segments of the proteins or peptides as defined herein that are discontinuous in the amino acid sequence of the proteins or peptides as defined herein but are brought together in the three-dimensional structure or continuous or linear epitopes which are composed of a single polypeptide chain.

Fragment of a sequence: A fragment of a sequence may typically be a shorter portion of a full-length sequence of e.g. a nucleic acid molecule or an amino acid sequence. Accordingly, a fragment, typically, consists of a sequence that is identical to the corresponding stretch within the full-length sequence. A preferred fragment of a sequence in the context of the present invention, consists of a continuous stretch of entities, such as nucleotides or amino acids corresponding to a continuous stretch of entities in the molecule the fragment is derived from, which represents at least 5%, 10%, 20%, preferably at least 30%, more preferably at least 40%, more preferably at least 50%, even more preferably at least 60%, even more preferably at least 70%, and most preferably at least 80% of the total (i.e. full-length) molecule from which the fragment is derived.

G/C modified: A G/C-modified nucleic acid may typically be a nucleic acid, preferably an artificial nucleic acid molecule as defined herein, based on a modified wild-type sequence comprising a preferably increased number of guanosine and/or cytosine nucleotides as compared to the wild-type sequence. Such an increased number may be generated by substitution of codons containing adenosine or thymidine nucleotides by codons containing guanosine or cytosine nucleotides. If the enriched G/C content occurs in a coding region of DNA or RNA, it makes use of the degeneracy of the genetic code. Accordingly, the codon substitutions preferably do not alter the encoded amino acid residues, but exclusively increase the G/C content of the nucleic acid molecule.

Gene therapy: Gene therapy may typically be understood to mean a treatment of a patient's body or isolated elements of a patient's body, for example isolated tissues/cells, by nucleic acids encoding a peptide or protein. It typically may comprise at least one of the steps of a) administration of a nucleic acid, preferably an artificial nucleic acid molecule as defined herein, directly to the patient—by whatever administration route—or in vitro to isolated cells/tissues of the patient, which results in transfection of the patient's cells either in vivo/ex vivo or in vitro; b) transcription and/or translation of the introduced nucleic acid molecule; and optionally c) re-administration of isolated, transfected cells to the patient, if the nucleic acid has not been administered directly to the patient.

Genetic vaccination: Genetic vaccination may typically be understood to be vaccination by administration of a nucleic acid molecule encoding an antigen or an immunogen or fragments thereof. The nucleic acid molecule may be administered to a subject's body or to isolated cells of a subject. Upon transfection of certain cells of the body or upon transfection of the isolated cells, the antigen or immunogen may be expressed by those cells and subsequently presented to the immune system, eliciting an adaptive, i.e. antigen-specific immune response. Accordingly, genetic vaccination typically comprises at least one of the steps of a) administration of a nucleic acid, preferably an artificial nucleic acid molecule as defined herein, to a subject, preferably a patient, or to isolated cells of a subject, preferably a patient, which usually results in transfection of the subject's cells either in vivo or in vitro; b) transcription and/or translation of the introduced nucleic acid molecule; and optionally c) re-administration of isolated, transfected cells to the subject, preferably the patient, if the nucleic acid has not been administered directly to the patient.

Heterologous sequence: Two sequences are typically understood to be 'heterologous' if they are not derivable from the same gene. I.e., although heterologous sequences may be derivable from the same organism, they naturally (in nature) do not occur in the same nucleic acid molecule, such as in the same mRNA.

Humoral immunity/humoral immune response: Humoral immunity refers typically to antibody production and optionally to accessory processes accompanying antibody production. A humoral immune response may be typically characterized, e.g., by Th2 activation and cytokine production, germinal center formation and isotype switching, affinity maturation and memory cell generation. Humoral immunity also typically may refer to the effector functions of antibodies, which include pathogen and toxin neutralization, classical complement activation, and opsonin promotion of phagocytosis and pathogen elimination.

Immunogen: In the context of the present invention, an immunogen may be typically understood to be a compound that is able to stimulate an immune response. Preferably, an immunogen is a peptide, polypeptide, or protein. In a particularly preferred embodiment, an immunogen in the sense of the present invention is the product of translation of a provided nucleic acid molecule, preferably an artificial nucleic acid molecule as defined herein. Typically, an immunogen elicits at least an adaptive immune response.

Immunostimulatory composition: In the context of the invention, an immunostimulatory composition may be typically understood to be a composition containing at least one component which is able to induce an immune response or from which a component, which is able to induce an immune response, is derivable. Such immune response may be preferably an innate immune response or a combination of an adaptive and an innate immune response. Preferably, an immunostimulatory composition in the context of the invention contains at least one artificial nucleic acid molecule, more preferably an RNA, for example an mRNA molecule. The immunostimulatory component, such as the mRNA may be complexed with a suitable carrier. Thus, the immunostimulatory composition may comprise an mRNA/carrier-complex. Furthermore, the immunostimulatory composition may comprise an adjuvant and/or a suitable vehicle for the immunostimulatory component, such as the mRNA.

Immune response: An immune response may typically be a specific reaction of the adaptive immune system to a particular antigen (so called specific or adaptive immune response) or an unspecific reaction of the innate immune system (so called unspecific or innate immune response), or a combination thereof.

Immune system: The immune system may protect organisms from infection. If a pathogen succeeds in passing a physical barrier of an organism and enters this organism, the innate immune system provides an immediate, but non-specific response. If pathogens evade this innate response, vertebrates possess a second layer of protection, the adaptive immune system. Here, the immune system adapts its response during an infection to improve its recognition of the pathogen. This improved response is then retained after the pathogen has been eliminated, in the form of an immunological memory, and allows the adaptive immune system to mount faster and stronger attacks each time this pathogen is encountered. According to this, the immune system comprises the innate and the adaptive immune system. Each of these two parts typically contains so called humoral and cellular components.

Immunostimulatory RNA: An immunostimulatory RNA (isRNA) in the context of the invention may typically be an RNA that is able to induce an innate immune response. It usually does not have an open reading frame and thus does not provide a peptide-antigen or immunogen but elicits an immune response e.g. by binding to a specific kind of Toll-like-receptor (TLR) or other suitable receptors. However, of course also mRNAs having an open reading frame and coding for a peptide/protein may induce an innate immune response and, thus, may be immunostimulatory RNAs.

Innate immune system: The innate immune system, also known as non-specific (or unspecific) immune system, typically comprises the cells and mechanisms that defend the host from infection by other organisms in a non-specific manner. This means that the cells of the innate system may recognize and respond to pathogens in a generic way, but unlike the adaptive immune system, it does not confer long-lasting or protective immunity to the host. The innate immune system may be, e.g., activated by ligands of Toll-like receptors (TLRs) or other auxiliary substances such as lipopolysaccharides, TNF-alpha, CD40 ligand, or cytokines, monokines, lymphokines, interleukins or chemokines, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, IFN-alpha, IFN-beta, IFN-gamma, GM-CSF, G-CSF, M-CSF, LT-beta, TNF-alpha, growth factors, and hGH, a ligand of human Toll-like receptor TLR1, TLR2, TLR3, TLR4, TLR5, TLR6, TLR7, TLR8, TLR9, TLR10, a ligand of murine Toll-like receptor TLR1, TLR2, TLR3, TLR4, TLR5, TLR6, TLR7, TLR8, TLR9, TLR10, TLR11, TLR12 or TLR13, a ligand of a NOD-like receptor, a ligand of a RIG-I like receptor, an immunostimulatory nucleic acid, an immunostimulatory RNA (isRNA), a CpG-DNA, an antibacterial agent, or an anti-viral agent. The pharmaceutical composition according to the present invention may comprise one or more such substances. Typically, a response of the innate immune system includes recruiting immune cells to sites of infection, through the production of chemical factors, including specialized chemical mediators, called cytokines; activation of the complement cascade; identification and removal of foreign substances present in organs, tissues, the blood and lymph, by specialized white blood cells; activation of the adaptive immune system; and/or acting as a physical and chemical barrier to infectious agents.

Cloning site: A cloning site is typically understood to be a segment of a nucleic acid molecule, which is suitable for insertion of a nucleic acid sequence, e.g., a nucleic acid sequence comprising an open reading frame. Insertion may be performed by any molecular biological method known to the one skilled in the art, e.g. by restriction and ligation. A cloning site typically comprises one or more restriction enzyme recognition sites (restriction sites). These one or more restrictions sites may be recognized by restriction enzymes which cleave the DNA at these sites. A cloning site which comprises more than one restriction site may also be termed a multiple cloning site (MCS) or a polylinker.

Nucleic acid molecule: A nucleic acid molecule is a molecule comprising, preferably consisting of nucleic acid components. The term nucleic acid molecule preferably refers to DNA or RNA molecules. It is preferably used synonymous with the term "polynucleotide". Preferably, a nucleic acid molecule is a polymer comprising or consisting of nucleotide monomers, which are covalently linked to each other by phosphodiester-bonds of a sugar/phosphate-backbone. The term "nucleic acid molecule" also encompasses modified nucleic acid molecules, such as base-modified, sugar-modified or backbone-modified etc. DNA or RNA molecules.

Open reading frame: An open reading frame (ORF) in the context of the invention may typically be a sequence of several nucleotide triplets, which may be translated into a peptide or protein. An open reading frame preferably contains a start codon, i.e. a combination of three subsequent nucleotides coding usually for the amino acid methionine (ATG), at its 5'-end and a subsequent region, which usually exhibits a length which is a multiple of 3 nucleotides. An ORF is preferably terminated by a stop-codon (e.g., TAA, TAG, TGA). Typically, this is the only stop-codon of the open reading frame. Thus, an open reading frame in the context of the present invention is preferably a nucleotide sequence, consisting of a number of nucleotides that may be divided by three, which starts with a start codon (e.g. ATG) and which preferably terminates with a stop codon (e.g., TAA, TGA, or TAG). The open reading frame may be isolated or it may be incorporated in a longer nucleic acid sequence, for example in a vector or an mRNA. An open reading frame may also be termed "protein coding region".

Peptide: A peptide or polypeptide is typically a polymer of amino acid monomers, linked by peptide bonds. It typically contains less than 50 monomer units. Nevertheless, the term peptide is not a disclaimer for molecules having more than 50 monomer units. Long peptides are also called polypeptides, typically having between 50 and 600 monomeric units.

Pharmaceutically effective amount: A pharmaceutically effective amount in the context of the invention is typically understood to be an amount that is sufficient to induce a pharmaceutical effect, such as an immune response, altering a pathological level of an expressed peptide or protein, or substituting a lacking gene product, e.g., in case of a pathological situation.

Protein A protein typically comprises one or more peptides or polypeptides. A protein is typically folded into 3-dimensional form, which may be required for to protein to exert its biological function.

Poly(A) sequence: A poly(A) sequence, also called poly (A) tail or 3'-poly(A) tail, is typically understood to be a sequence of adenosine nucleotides, e.g., of up to about 400 adenosine nucleotides, e.g. from about 20 to about 400, preferably from about 50 to about 400, more preferably from about 50 to about 300, even more preferably from about 50 to about 250, most preferably from about 60 to about 250 adenosine nucleotides. A poly(A) sequence is typically located at the 3' end of an mRNA. In the context of the present invention, a poly(A) sequence may be located within an mRNA or any other nucleic acid molecule, such as, e.g., in a vector, for example, in a vector serving as template for the generation of an RNA, preferably an mRNA, e.g., by transcription of the vector.

Polyadenylation: Polyadenylation is typically understood to be the addition of a poly(A) sequence to a nucleic acid molecule, such as an RNA molecule, e.g. to a premature mRNA. Polyadenylation may be induced by a so-called polyadenylation signal. This signal is preferably located within a stretch of nucleotides at the 3'-end of a nucleic acid molecule, such as an RNA molecule, to be polyadenylated. A polyadenylation signal typically comprises a hexamer consisting of adenine and uracil/thymine nucleotides, preferably the hexamer sequence AAUAAA. Other sequences, preferably hexamer sequences, are also conceivable. Polyadenylation typically occurs during processing of a pre-mRNA (also called premature-mRNA). Typically, RNA maturation (from pre-mRNA to mature mRNA) comprises the step of polyadenylation.

Restriction site: A restriction site, also termed restriction enzyme recognition site, is a nucleotide sequence recognized by a restriction enzyme. A restriction site is typically a short, preferably palindromic nucleotide sequence, e.g. a sequence comprising 4 to 8 nucleotides. A restriction site is preferably specifically recognized by a restriction enzyme. The restriction enzyme typically cleaves a nucleotide sequence comprising a restriction site at this site. In a double-stranded nucleotide sequence, such as a double-stranded DNA sequence, the restriction enzyme typically cuts both strands of the nucleotide sequence.

RNA, mRNA: RNA is the usual abbreviation for ribonucleic-acid. It is a nucleic acid molecule, i.e. a polymer consisting of nucleotides. These nucleotides are usually adenosine-monophosphate, uridine-monophosphate, guanosine-monophosphate and cytidine-monophosphate monomers which are connected to each other along a so-called backbone. The backbone is formed by phosphodiester bonds between the sugar, i.e. ribose, of a first and a phosphate moiety of a second, adjacent monomer. The specific succession of the monomers is called the RNA-sequence. Usually RNA may be obtainable by transcription of a DNA-sequence, e.g., inside a cell. In eukaryotic cells, transcription is typically performed inside the nucleus or the mitochondria. In vivo, transcription of DNA usually results in the so-called premature RNA which has to be processed into so-called messenger-RNA, usually abbreviated as mRNA. Processing of the premature RNA, e.g. in eukaryotic organisms, comprises a variety of different posttranscriptional-modifications such as splicing, 5'-capping, polyadenylation, export from the nucleus or the mitochondria and the like. The sum of these processes is also called maturation of RNA. The mature messenger RNA usually provides the nucleotide sequence that may be translated into an amino-acid sequence of a particular peptide or protein. Typically, a mature mRNA comprises a 5'-cap, a 5'-UTR, an open reading frame, a 3'-UTR and a poly(A) sequence. Aside from messenger RNA, several non-coding types of RNA exist which may be involved in regulation of transcription and/or translation.

Sequence of a nucleic acid molecule: The sequence of a nucleic acid molecule is typically understood to be the particular and individual order, i.e. the succession of its nucleotides. The sequence of a protein or peptide is typically understood to be the order, i.e. the succession of its amino acids.

Sequence identity: Two or more sequences are identical if they exhibit the same length and order of nucleotides or amino acids. The percentage of identity typically describes the extent to which two sequences are identical, i.e. it typically describes the percentage of nucleotides that correspond in their sequence position with identical nucleotides of a reference-sequence. For determination of the degree of identity, the sequences to be compared are considered to exhibit the same length, i.e. the length of the longest sequence of the sequences to be compared. This means that a first sequence consisting of 8 nucleotides is 80% identical to a second sequence consisting of 10 nucleotides comprising the first sequence. In other words, in the context of the present invention, identity of sequences preferably relates to the percentage of nucleotides of a sequence which have the same position in two or more sequences having the same length. Gaps are usually regarded as non-identical positions, irrespective of their actual position in an alignment.

Stabilized nucleic acid molecule: A stabilized nucleic acid molecule is a nucleic acid molecule, preferably a DNA or RNA molecule that is modified such, that it is more stable to disintegration or degradation, e.g., by environmental factors or enzymatic digest, such as by an exo- or endonuclease degradation, than the nucleic acid molecule without the modification. Preferably, a stabilized nucleic acid molecule in the context of the present invention is stabilized in a cell, such as a prokaryotic or eukaryotic cell, preferably in a mammalian cell, such as a human cell. The stabilization effect may also be exerted outside of cells, e.g. in a buffer solution etc., for example, in a manufacturing process for a pharmaceutical composition comprising the stabilized nucleic acid molecule.

Transfection: The term "transfection" refers to the introduction of nucleic acid molecules, such as DNA or RNA (e.g. mRNA) molecules, into cells, preferably into eukaryotic cells. In the context of the present invention, the term "transfection" encompasses any method known to the skilled person for introducing nucleic acid molecules into cells, preferably into eukaryotic cells, such as into mammalian cells. Such methods encompass, for example, electroporation, lipofection, e.g. based on cationic lipids and/or liposomes, calcium phosphate precipitation, nanoparticle based transfection, virus based transfection, or transfection based on cationic polymers, such as DEAE-dextran or polyethylenimine etc. Preferably, the introduction is non-viral.

Vaccine: A vaccine is typically understood to be a prophylactic or therapeutic material providing at least one antigen, preferably an immunogen. The antigen or immunogen may be derived from any material that is suitable for vaccination. For example, the antigen or immunogen may be derived from a pathogen, such as from bacteria or virus particles etc., or from a tumor or cancerous tissue. The antigen or immunogen stimulates the body's adaptive immune system to provide an adaptive immune response.

Vector: The term "vector" refers to a nucleic acid molecule, preferably to an artificial nucleic acid molecule. A vector in the context of the present invention is suitable for incorporating or harboring a desired nucleic acid sequence, such as a nucleic acid sequence comprising an open reading frame. Such vectors may be storage vectors, expression vectors, cloning vectors, transfer vectors etc. A storage vector is a vector, which allows the convenient storage of a nucleic acid molecule, for example, of an mRNA molecule. Thus, the vector may comprise a sequence corresponding, e.g., to a desired mRNA sequence or a part thereof, such as a sequence corresponding to the open reading frame and the 3'-UTR of an mRNA. An expression vector may be used for production of expression products such as RNA, e.g. mRNA, or peptides, polypeptides or proteins. For example, an expression vector may comprise sequences needed for transcription of a sequence stretch of the vector, such as a promoter sequence, e.g. an RNA polymerase promoter sequence. A cloning vector is typically a vector that contains a cloning site, which may be used to incorporate nucleic acid sequences into the vector. A cloning vector may be, e.g., a plasmid vector or a bacteriophage vector. A transfer vector may be a vector, which is suitable for transferring nucleic acid molecules into cells or organisms, for example, viral vectors. A vector in the context of the present invention may be, e.g., an RNA vector or a DNA vector. Preferably, a vector is a DNA molecule. Preferably, a vector in the sense of the present application comprises a cloning site, a selection marker, such as an antibiotic resistance factor, and a sequence suitable for multiplication of the vector, such as an origin of replication. Preferably, a vector in the context of the present application is a plasmid vector.

Vehicle: A vehicle is typically understood to be a material that is suitable for storing, transporting, and/or administering a compound, such as a pharmaceutically active compound. For example, it may be a physiologically acceptable liquid, which is suitable for storing, transporting, and/or administering a pharmaceutically active compound.

3'-untranslated region (3'-UTR): Generally, the term "3'-UTR" refers to a part of the artificial nucleic acid molecule, which is located 3' (i.e. "downstream") of an open reading frame and which is not translated into protein. Typically, a 3'-UTR is the part of an mRNA which is located between the protein coding region (open reading frame (ORF) or coding sequence (CDS)) and the poly(A) sequence of the mRNA. In the context of the invention, the term 3'-UTR may also comprise elements, which are not encoded in the template, from which an RNA is transcribed, but which are added after transcription during maturation, e.g. a poly(A) sequence. A 3'-UTR of the mRNA is not translated into an amino acid sequence. The 3'-UTR sequence is generally encoded by the gene, which is transcribed into the respective mRNA during the gene expression process. The genomic sequence is first transcribed into pre-mature mRNA, which comprises optional introns. The pre-mature mRNA is then further processed into mature mRNA in a maturation process. This maturation process comprises the steps of 5'capping, splicing the pre-mature mRNA to excise optional introns and modifications of the 3'-end, such as polyadenylation of the 3'-end of the pre-mature mRNA and optional endo-/or exonuclease cleavages etc. In the context of the present invention, a 3'-UTR corresponds to the sequence of a mature mRNA, which is located between the stop codon of the protein coding region, preferably immediately 3' to the stop codon of the protein coding region, and the poly(A) sequence of the mRNA. The term "corresponds to" means that the 3'-UTR sequence may be an RNA sequence, such as in the mRNA sequence used for defining the 3'-UTR sequence, or a DNA sequence, which corresponds to such RNA sequence. In the context of the present invention, the term "a 3'-UTR of a gene", such as "a 3'-UTR of a ribosomal protein gene", is the sequence, which corresponds to the 3'-UTR of the mature mRNA derived from this gene, i.e. the mRNA obtained by transcription of the gene and maturation of the pre-mature mRNA. The term "3'-UTR of a gene" encompasses the DNA sequence and the RNA sequence (both sense and antisense strand and both mature and immature) of the 3'-UTR.

5'-untranslated region (5'-UTR): A 5'-UTR is typically understood to be a particular section of messenger RNA (mRNA). It is located 5' of the open reading frame of the mRNA. Typically, the 5'-UTR starts with the transcriptional start site and ends one nucleotide before the start codon of the open reading frame. The 5'-UTR may comprise elements for controlling gene expression, also called regulatory elements. Such regulatory elements may be, for example, ribosomal binding sites. The 5'-UTR may be post-transcriptionally modified, for example by addition of a 5'-CAP. In the context of the present invention, a 5'-UTR corresponds to the sequence of a mature mRNA, which is located between the 5'-CAP and the start codon. Preferably, the 5'-UTR corresponds to the sequence, which extends from a nucleotide located 3' to the 5'-CAP, preferably from the nucleotide located immediately 3' to the 5'-CAP, to a nucleotide located 5' to the start codon of the protein coding region, preferably to the nucleotide located immediately 5' to the start codon of the protein coding region. The nucleotide located immediately 3' to the 5'-CAP of a mature mRNA typically corresponds to the transcriptional start site. The term "corresponds to" means that the 5'-UTR sequence may be an RNA sequence, such as in the mRNA sequence used for defining the 5'-UTR sequence, or a DNA sequence, which corresponds to such RNA sequence. In the context of the present invention, the term "a 5'-UTR of a gene" is the sequence, which corresponds to the 5'-UTR of the mature mRNA derived from this gene, i.e. the mRNA obtained by transcription of the gene and maturation of the pre-mature mRNA. The term "5'-UTR of a gene" encompasses the DNA sequence and the RNA sequence of the 5'-UTR. By the inventive embodiments such a 5''-UTR may be provided 5'-terminal to the ORF. Its length is typically less than 500, 400, 300, 250 or less than 200 nucleotides. In other embodiments its length may be in the range of at least 10, 20, 30 or 40, preferably up to 100 or 150, nucleotides.

5'Terminal Oligopyrimidine Tract (TOP): The 5'terminal oligopyrimidine tract (TOP) is typically a stretch of pyrimidine nucleotides located in the 5' terminal region of a nucleic acid molecule, such as the 5' terminal region of certain mRNA molecules or the 5' terminal region of a functional entity, e.g. the transcribed region, of certain genes. The sequence starts with a cytidine, which usually corresponds to the transcriptional start site, and is followed by a stretch of usually about 3 to 30 pyrimidine nucleotides. For example, the TOP may comprise 3, 4, 5, 6, 7, 8, 9, 10, 11, 12, 13, 14, 15, 16, 17, 18, 19, 20, 21, 22, 23, 24, 25, 26, 27, 28, 29, 30 or even more nucleotides. The pyrimidine stretch and thus the 5' TOP ends one nucleotide 5' to the first purine nucleotide located downstream of the TOP. Messenger RNA that contains a 5'terminal oligopyrimidine tract is often referred to as TOP mRNA. Accordingly, genes that provide such messenger RNAs are referred to as TOP genes. TOP sequences have, for example, been found in genes and mRNAs encoding peptide elongation factors and ribosomal proteins.

TOP motif: In the context of the present invention, a TOP motif is a nucleic acid sequence which corresponds to a 5'TOP as defined above. Thus, a TOP motif in the context of the present invention is preferably a stretch of pyrimidine nucleotides having a length of 3-30 nucleotides. Preferably, the TOP-motif consists of at least 3 pyrimidine nucleotides, preferably at least 4 pyrimidine nucleotides, preferably at least 5 pyrimidine nucleotides, more preferably at least 6 nucleotides, more preferably at least 7 nucleotides, most preferably at least 8 pyrimidine nucleotides, wherein the stretch of pyrimidine nucleotides preferably starts at its 5'end with a cytosine nucleotide. In TOP genes and TOP mRNAs, the TOP-motif preferably starts at its 5'end with the transcriptional start site and ends one nucleotide 5' to the first purin residue in said gene or mRNA. A TOP motif in the sense of the present invention is preferably located at the 5' end of a sequence, which represents a 5'UTR, or at the 5'end of a sequence, which codes for a 5'UTR. Thus, preferably, a stretch of 3 or more pyrimidine nucleotides is called "TOP motif" in the sense of the present invention if this stretch is located at the 5' end of a respective sequence, such as the artificial nucleic acid molecule, the 5'UTR element of the artificial nucleic acid molecule, or the nucleic acid sequence which is derived from the 5'UTR of a TOP gene as described herein. In other words, a stretch of 3 or more pyrimidine nucleotides, which is not located at the 5'-end of a 5'UTR or a 5'UTR element but anywhere within a 5'UTR or a 5'UTR element, is preferably not referred to as "TOP motif".

TOP gene: TOP genes are typically characterised by the presence of a 5' terminal oligopyrimidine tract. Furthermore, most TOP genes are characterized by a growth-associated translational regulation. However, also TOP genes with a tissue specific translational regulation are known. As defined above, the 5'UTR of a TOP gene corresponds to the sequence of a 5'UTR of a mature mRNA derived from a TOP gene, which preferably extends from the nucleotide located 3' to the 5'-CAP to the nucleotide located 5' to the start codon. A 5'UTR of a TOP gene typically does not comprise any start codons, preferably no upstream AUGs (uAUGs) or upstream open reading frames (uORFs). Therein, upstream AUGs and upstream open reading frames are typically understood to be AUGs and open reading frames that occur 5' of the start codon (AUG) of the open reading frame that should be translated. The 5'UTRs of TOP genes are generally rather short. The lengths of 5'UTRs of TOP genes may vary between 20 nucleotides up to 500 nucleotides, and are typically less than about 200 nucleotides, preferably less than about 150 nucleotides, more preferably less than about 100 nucleotides. Exemplary 5'UTRs of TOP genes in the sense of the present invention are the nucleic acid sequences extending from the nucleotide at position 5 to the nucleotide located immediately 5' to the start codon (e.g. the ATG) in the sequences according to SEQ ID Nos. 1-1363 of the patent application WO2013/143700, whose disclosure is incorporated herewith by reference. In this context, a particularly preferred fragment of a 5'UTR of a TOP gene is a 5'UTR of a TOP gene lacking the 5'TOP motif. The terms "5'UTR of a TOP gene" or "5'-TOP UTR" preferably refer to the 5'UTR of a naturally occurring TOP gene.

In a first aspect, the present invention relates to an artificial nucleic acid molecule comprising
 a. at least one open reading frame (ORF); and
 b. at least one 3'-untranslated region element (3'-UTR element) comprising or consisting of a nucleic acid sequence which is derived from the 3'-UTR of a ribosomal protein gene.

The term "3'-UTR element" refers to a nucleic acid sequence, which comprises or consists of a nucleic acid sequence that is derived from a 3'-UTR or from a variant of a 3'-UTR. A "3'-UTR element" preferably refers to a nucleic acid sequence which represents a 3'-UTR of an artificial nucleic acid sequence, such as an artificial mRNA, or which codes for a 3'-UTR of an artificial nucleic acid molecule. Accordingly, in the sense of the present invention, preferably, a 3'-UTR element may be the 3'-UTR of an mRNA, preferably of an artificial mRNA, or it may be the transcription template for a 3'-UTR of an mRNA. Thus, a 3'-UTR element preferably is a nucleic acid sequence, which corresponds to the 3'-UTR of an mRNA, preferably to the 3'-UTR of an artificial mRNA, such as an mRNA obtained by transcription of a genetically engineered vector construct. Preferably, a 3'-UTR element in the sense of the present invention functions as a 3'-UTR or codes for a nucleotide sequence that fulfils the function of a 3'-UTR.

The term "ribosomal protein gene" typically refers to a gene encoding a ribosomal protein. As used herein, the term refers to any ribosomal protein gene, irrespective of the species, from which it is derived. Specifically, the term refers to an eukaryotic ribosomal protein gene. Furthermore, in the context of the invention, the term "ribosomal protein gene" may also refer to a gene, which is similar to a ribosomal protein gene, either structurally or functionally. In particular, the term also comprises "ribosomal protein-like" genes, pseudogenes and genes sharing sequence or structural features, particularly in their 3'-UTR region, with a ribosomal protein gene. Preferably, the term refers to a vertebrate ribosomal protein gene, more preferably to a mammalian ribosomal protein gene, even more preferably to a primate ribosomal protein gene, in particular to a human ribosomal protein gene. Further, the term "ribosomal protein gene" also encompasses a rodent ribosomal protein gene, in particular a murine ribosomal protein gene. Examples of ribosomal protein genes in the meaning of the invention include, but are not limited to, ribosomal protein L9 (RPL9), ribosomal protein L3 (RPL3), ribosomal protein L4 (RPL4), ribosomal protein L5 (RPL5), ribosomal protein L6 (RPL6), ribosomal protein L7 (RPL7), ribosomal protein L7a (RPL7A), ribosomal protein L11 (RPL11), ribosomal protein L12 (RPL12), ribosomal protein L13 (RPL13), ribosomal protein L23 (RPL23), ribosomal protein L18 (RPL18), ribosomal protein L18a (RPL18A), ribosomal protein L19 (RPL19), ribosomal protein L21 (RPL21), ribosomal protein L22 (RPL22), ribosomal protein L23a (RPL23A), ribosomal protein L17 (RPL17), ribosomal protein L24 (RPL24), ribosomal protein L26 (RPL26), ribosomal protein L27 (RPL27), ribosomal protein L30 (RPL30), ribosomal protein L27a (RPL27A), ribosomal protein L28 (RPL28), ribosomal protein L29 (RPL29), ribosomal protein L31 (RPL31), ribosomal protein L32 (RPL32), ribosomal protein L35a (RPL35A), ribosomal protein L37 (RPL37), ribosomal protein L37a (RPL37A), ribosomal protein L38 (RPL38), ribosomal protein L39 (RPL39), ribosomal protein, large, P0 (RPLP0), ribosomal protein, large, P1 (RPLP1), ribosomal protein, large, P2 (RPLP2), ribosomal protein S3 (RPS3), ribosomal protein S3A (RPS3A), ribosomal protein S4, X-linked (RPS4X), ribosomal protein S4, Y-linked 1 (RPS4Y1), ribosomal protein S5 (RPS5), ribosomal protein S6 (RPS6), ribosomal protein S7 (RPS7), ribosomal protein S8 (RPS8), ribosomal protein S9 (RPS9), ribosomal protein S10 (RPS10), ribosomal protein S11 (RPS11), ribosomal protein S12 (RPS12), ribosomal protein S13 (RPS13), ribosomal protein S15 (RPS15), ribosomal protein S15a (RPS15A), ribosomal protein S16 (RPS16), ribosomal protein S19 (RPS19), ribosomal protein S20 (RPS20), ribosomal protein S21 (RPS21), ribosomal protein S23 (RPS23), ribosomal protein S25 (RPS25), ribosomal protein S26 (RPS26), ribosomal protein S27 (RPS27), ribosomal protein S27a (RPS27a), ribosomal protein S28 (RPS28), ribosomal protein S29 (RPS29), ribosomal protein L15 (RPL15), ribosomal protein S2 (RPS2), ribosomal protein L14 (RPL14), ribosomal protein S14 (RPS14), ribosomal protein L10 (RPL10), ribosomal protein L10a (RPL10A), ribosomal protein L35 (RPL35), ribosomal protein L13a (RPL13A), ribosomal protein L36 (RPL36), ribosomal protein L36a (RPL36A), ribosomal protein L41 (RPL41), ribosomal protein S18 (RPS18), ribosomal protein S24 (RPS24), ribosomal protein L8 (RPL8), ribosomal protein L34 (RPL34), ribosomal protein S17 (RPS17), ribosomal protein SA (RPSA), ubiquitin A-52 residue ribosomal protein fusion product 1 (UBA52), Finkel-Biskis-Reilly murine sarcoma virus (FBR-MuSV) ubiquitously expressed (FAU), ribosomal protein L22-like 1 (RPL22L1), ribosomal protein S17 (RPS17), ribosomal protein L39-like (RPL39L), ribosomal protein L10-like (RPL10L), ribosomal protein L36a-like (RPL36AL), ribosomal protein L3-like (RPL3L), ribosomal protein S27-like (RPS27L), ribosomal protein L26-like 1 (RPL26L1), ribosomal protein L7-like 1 (RPL7L1), ribosomal protein L13a pseudogene (RPL13AP), ribosomal protein L37a pseudogene 8 (RPL37AP8), ribosomal protein S10 pseudogene 5 (RPS10P5), ribosomal protein S26 pseudogene 11 (RPS26P11), ribosomal protein L39 pseudogene 5 (RPL39P5), ribosomal protein, large, P0 pseudogene 6 (RPLP0P6) and ribosomal protein L36 pseudogene 14 (RPL36P14). Preferably, the term "ribosomal protein gene" refers to one of the aforementioned genes, which is derived from a mammalian, preferably from *Homo sapiens* or *Mus musculus*.

Preferably, the at least one open reading frame and the at least one 3'-UTR element are heterologous. The term "heterologous" in this context means that two sequence elements comprised by the artificial nucleic acid molecule, such as the open reading frame and the 3'-UTR element, are not occurring naturally (in nature) in this combination. Preferably, the 3'-UTR element is derived from a different gene than the open reading frame. For example, the ORF may be derived from a different gene than the 3'-UTR element, e.g. encoding a different protein or the same protein but of a different species etc. Preferably, the open reading frame does not code for a ribosomal protein. In a preferred embodiment, the ORF does not encode a human ribosomal protein or a plant (in particular *Arabidopsis*) ribosomal protein, in particular human ribosomal protein S6 (RPS6), human ribosomal protein L36a-like (RPL36AL) or *Arabidopsis* ribosomal protein S16 (RPS16). In a further preferred embodiment, the open reading frame (ORF) does not encode ribosomal protein S6 (RPS6), ribosomal protein L36a-like (RPL36AL) or ribosomal protein S16 (RPS16).

In specific embodiments it is preferred that the open reading frame does not code for a reporter protein, e.g., selected from the group consisting of globin proteins (particularly beta-globin), luciferase protein, GFP proteins or variants thereof, for example, variants exhibiting at least 70% sequence identity to a globin protein, a luciferase protein, or a GFP protein. In a particularly preferred embodiment, the open reading frame (ORF) does not encode a reporter gene or is not derived from a reporter gene, wherein the reporter gene is preferably not selected from group consisting of globin proteins (particularly beta-globin), luciferase protein, beta-glucuronidase (GUS) and GFP proteins or variants thereof, preferably not selected from EGFP, or variants of any of the above genes, typically exhibiting at least 70% sequence identity to any of these reporter genes, preferably to a globin protein, a luciferase protein, or a GFP protein.

Even more preferably, the 3'-UTR element is heterologous to any other element comprised in the artificial nucleic acid as defined herein. For example, if the artificial nucleic acid according to the invention comprises a 3'-UTR element from a given gene, it does preferably not comprise any other nucleic acid sequence, in particular no functional nucleic acid sequence (e.g. coding or regulatory sequence element) from the same gene, including its regulatory sequences at the 5' and 3' terminus of the gene's ORF. In a particularly preferred embodiment, the artificial nucleic acid molecule comprises an ORF, a 3'-UTR and a 5'-UTR, all of which are heterologous to each other, e.g. they are recombinant as each of them is derived from different genes (and their 5' and 3' UTR's). In another preferred embodiment, the 3'-UTR is not derived from a 3'-UTR of a viral gene or is of non-viral origin.

Preferably, the at least one 3'-UTR element is functionally linked to the ORF. This means preferably that the 3'-UTR element is associated with the ORF such that it may exert a function, such as an enhancing or stabilizing function on the expression of the encoded peptide or protein or a stabilizing function on the artificial nucleic acid molecule. Preferably, the ORF and the 3'-UTR element are associated in 5'→3' direction. Thus, preferably, the artificial nucleic acid molecule comprises the structure 5'-ORF-(optional)-linker-3'-UTR element-3', wherein the linker may be present or absent. For example, the linker may be one or more nucleotides, such as a stretch of 1-50 or 1-20 nucleotides, e.g., comprising or consisting of one or more restriction enzyme recognition sites (restriction sites).

Preferably, the at least one 3'-UTR element comprises a nucleic acid sequence which is derived from the 3'-UTR of a eukaryotic ribosomal protein gene, preferably from the 3'-UTR of a vertebrate ribosomal protein gene, more preferably from the 3'-UTR of a mammalian ribosomal protein gene, even more preferably from the 3'-UTR of a primate ribosomal protein gene, in particular of a human ribosomal protein gene, or from the 3'-UTR of a rodent ribosomal protein gene, in particular of a murine ribosomal protein gene.

In a preferred embodiment, the at least one 3'-UTR element comprises or corresponds to a nucleic acid sequence, which is derived from the 3'-UTR sequence of a transcript selected from the group consisting of NM_000661.4, NM_001024921.2, NM_000967.3, NM_001033853.1, NM_000968.3, NM_000969.3, NM_001024662.1, NM_000970.3, NM_000971.3, NM_000972.2, NM_000975.3, NM_001199802.1, NM_000976.3, NM_000977.3, NM_033251.2, NM_001243130.1, NM_001243131, NM_000978.3, NM_000979.3, NM_001270490.1, NM_000980.3, NM_000981.3, NM_000982.3, NM_000983.3, NM_000984.5, NM_000985.4, NM_001035006.2, NM_001199340.1, NM_001199341.1, NM_001199342.1, NM_001199343.1, NM_001199344.1, NM_001199345.1, NM_000986.3, NM_000987.3, NM_000988.3, NM_000989.3, NM_000990.4, NM_001136134.1, NM_000991.4, NM_001136135.1, NM_001136136.1, NM_001136137.1, NM_000992.2, NM_000993.4, NM_001098577.2, NM_001099693.1, NM_000994.3, NM_001007073.1, NM_001007074.1, NM_000996.2, NM_000997.4, NM_000998.4, NM_000999.3, NM_001035258.1, NM_001000.3, NM_001002.3, NM_053275.3, NM_001003.2, NM_213725.1, NM_001004.3, NM_001005.4, NM_001256802.1, NM_001260506.1, NM_001260507.1, NM_001006.4, NM_001267699.1, NM_001007.4, NM_001008.3, NM_001009.3, NM_001010.2, NM_001011.3, NM_001012.1, NM_001013.3, NM_001203245.2, NM_001014.4, NM_001204091.1, NM_001015.4, NM_001016.3, NM_001017.2, NM_001018.3, NM_001030009.1, NM_001019.4, NM_001020.4, NM_001022.3, NM_001146227.1, NM_001023.3, NM_001024.3, NM_001025.4, NM_001028.2, NM_001029.3, NM_001030.4, NM_002954, NM_001135592.2, NM_001177413.1, NM_001031.4, NM_001032.4, NM_001030001.2, NM_002948.3, NM_001253379.1, NM_001253380.1, NM_001253382.1, NM_001253383.1, NM_001253384.1, NM_002952.3, NM_001034996.2, NM_001025071.1, NM_001025070.1, NM_005617.3, NM_006013.3, NM_001256577.1, NM_001256580.1, NM_007104.4, NM_007209.3, NM_012423.3, NM_001270491.1, NM_033643.2, NM_015414.3, NM_021029.5, NM_001199972.1, NM_021104.1, NM_022551.2, NM_033022.3, NM_001142284.1, NM_001026.4, NM_001142285.1, NM_001142283.1, NM_001142282.1, NM_000973.3, NM_033301.1, NM_000995.3, NM_033625.2, NM_001021.3, NM_002295.4, NM_001012321.1, NM_001033930.1, NM_003333.3, NM_001997.4, NM_001099645.1, NM_001021.3, NM_052969.1, NM_080746.2, NM_001001.4, NM_005061.2, NM_015920.3, NM_016093.2, NM_198486.2, NG_011172.1, NG_011253.1, NG_000952.4, NR_002309.1, NG_010827.2, NG_009952.2, NG_009517.1, NM_052835.3, NM_011287.2, NM_001162933.1, NM_009076.3, NM_009438.5, NM_025974.2, NM_025586.3, NM_001002239.3, NM_009077.2, NM_029751.4, NM_009078.2, NM_019647.6, NM_009079.3, NM_022891.3, NM_024218.4, NM_011975.3, NM_009081.2, NM_009082.2, NM_009083.4, NM_053257.3, ENSMUST00000081840 (NM_172086.2), NM_026724.2, NM_025592.3, NM_025589.4, NM_026069.3, NM_009084, NM_026055.1, NM_026594.2, NM_001163945.1, NM_024212.4, NM_016980.2, NM_011290.5, NM_011291.5, ENSMUST00000102898 (NM_013721.3), NM_025433.3, NM_012053.2, NM_011292.2, NM_007475.5, NM_018853.3, NM_026020.6, NM_025963.3, NM_013725.4, NM_011295.6, NM_020600.4, NM_009091.2, NM_170669.2, NM_013647.2, NM_009092.3, NM_008503.5, NM_026147.5/ENSMUST00000138502, NM_207635.1, NM_024266.3, NM_013765.2, NM_024277.2, NM_026467.3, NM_012052.2, NM_016959.4, ENSMUST00000071745, NM_009095.2, NM_009096.3, NM_011300.3, NM_011029.4, NM_018860.4, NM_001277113.1, NM_001277114.1, NM_001271590.1, NM_007990, NM_025919, NM_016738, NM_026517, NM_207523, NM_009080, NM_011289, NM_013762, NM_021338, NM_018730, NM_019865, NM_023372.2, NM_026533.3, NM_009092, NM_011296, NM_023133, ENSMUST00000059080 (NM_025587.2), NM_024175, NM_027015, NM_016844, NM_009093.2, NM_009094, NM_009098, NM_029767, and NM_019883.

The phrase "nucleic acid sequence which is derived from the 3'-UTR of a ribosomal protein gene" preferably refers to a nucleic acid sequence, which is based on the 3'-UTR sequence of a ribosomal protein gene or on a fragment or part thereof. This phrase includes sequences corresponding to the entire 3'-UTR sequence, i.e. the full length 3'-UTR sequence of a ribosomal protein gene, and sequences corresponding to a fragment of the 3'-UTR sequence of a ribosomal protein gene. Preferably, a fragment of a 3'-UTR of a ribosomal protein gene consists of a continuous stretch of nucleotides corresponding to a continuous stretch of nucleotides in the full-length 3'-UTR of a ribosomal protein gene, which represents at least 5%, 10%, 20%, preferably at least 30%, more preferably at least 40%, more preferably at least 50%, even more preferably at least 60%, even more preferably at least 70%, even more preferably at least 80%, and most preferably at least 90% of the full-length 3'-UTR of a ribosomal protein gene. Such a fragment, in the sense of the present invention, is preferably a functional fragment as described herein. Preferably, the fragment retains a regulatory function for the translation of the ORF linked to the 3'-UTR or fragment thereof. The term "3'-UTR of a ribosomal protein gene" preferably refers to the 3'-UTR of a naturally occurring ribosomal protein gene.

The terms "variant of the 3'-UTR of a ribosomal protein gene" and "variant thereof" in the context of a 3'-UTR of a ribosomal protein gene refers to a variant of the 3'-UTR of a naturally occurring ribosomal protein gene, preferably to a variant of the 3'-UTR of a vertebrate ribosomal protein gene, more preferably to a variant of the 3'-UTR of a mammalian ribosomal protein gene, even more preferably to a variant of the 3'-UTR of a primate ribosomal protein gene, in particular a human ribosomal protein gene as described above. Such variant may be a modified 3'-UTR of a ribosomal protein gene. For example, a variant 3'-UTR may exhibit one or more nucleotide deletions, insertions, additions and/or substitutions compared to the naturally occurring 3'-UTR from which the variant is derived. Preferably, a variant of a 3'-UTR of a ribosomal protein gene is at least 40%, preferably at least 50%, more preferably at least 60%, more preferably at least 70%, even more preferably at least 80%, even more preferably at least 90%, most preferably at least 95% identical to the naturally occurring 3'-UTR the variant is derived from. Preferably, the variant is a functional variant as described herein.

The phrase "a nucleic acid sequence which is derived from a variant of the 3'-UTR of a ribosomal protein gene" preferably refers to a nucleic acid sequence which is based on a variant of the 3'-UTR sequence of a ribosomal protein gene or on a fragment or part thereof as described above. This phrase includes sequences corresponding to the entire sequence of the variant of the 3'-UTR of a ribosomal protein gene, i.e. the full length variant 3'-UTR sequence of a ribosomal protein gene, and sequences corresponding to a fragment of the variant 3'-UTR sequence of a ribosomal protein gene. Preferably, a fragment of a variant of the 3'-UTR of a ribosomal protein gene consists of a continuous stretch of nucleotides corresponding to a continuous stretch of nucleotides in the full-length variant of the 3'-UTR of a ribosomal protein gene, which represents at least 20%, preferably at least 30%, more preferably at least 40%, more preferably at least 50%, even more preferably at least 60%, even more preferably at least 70%, even more preferably at least 80%, and most preferably at least 90% of the full-length variant of the 3'-UTR of a ribosomal protein gene. Such a fragment of a variant, in the sense of the present invention, is preferably a functional fragment of a variant as described herein.

The terms "functional variant", "functional fragment", and "functional fragment of a variant" (also termed "functional variant fragment") in the context of the present invention, mean that the fragment of the 3'-UTR, the variant of the 3'-UTR, or the fragment of a variant of the 3'-UTR of a ribosomal protein gene fulfils at least one, preferably more than one function of the naturally occurring 3'-UTR of a ribosomal protein gene of which the variant, the fragment, or the fragment of a variant is derived. Such function may be, for example, stabilizing mRNA and/or enhancing, stabilizing and/or prolonging protein production from an mRNA and/or increasing protein expression or total protein production from an mRNA, preferably in a mammalian cell, such as in a human cell. Preferably, the function of the 3'-UTR concerns the translation of the protein encoded by the ORF. More preferably, the function comprises enhancing translation efficiency of the ORF linked to the 3'-UTR or fragment or variant thereof. It is particularly preferred that the variant, the fragment, and the variant fragment in the context of the present invention fulfil the function of stabilizing an mRNA, preferably in a mammalian cell, such as a human cell, compared to an mRNA comprising a reference 3'-UTR or lacking a 3'-UTR, and/or the function of enhancing, stabilizing and/or prolonging protein production from an mRNA, preferably in a mammalian cell, such as in a human cell, compared to an mRNA comprising a reference 3'-UTR or lacking a 3'-UTR, and/or the function of increasing protein production from an mRNA, preferably in a mammalian cell, such as in a human cell, compared to an mRNA comprising a reference 3'-UTR or lacking a 3'-UTR. A reference 3'-UTR may be, for example, a 3'-UTR naturally occurring in combination with the ORF. Furthermore, a functional variant, a functional fragment, or a functional variant fragment of a 3'-UTR of a ribosomal protein gene preferably does not have a substantially diminishing effect on the efficiency of translation of the mRNA which comprises such variant, fragment, or variant fragment of a 3'-UTR compared to the wild type 3'-UTR from which the variant, the fragment, or the variant fragment is derived. A particularly preferred function of a "functional fragment", a "functional variant" or a "functional fragment of a variant" of the 3'-UTR of a ribosomal protein gene in the context of the present invention is the enhancement, stabilization and/or prolongation of protein production by expression of an mRNA carrying the functional fragment, functional variant or functional fragment of a variant as described above.

Preferably, the efficiency of the one or more functions exerted by the functional variant, the functional fragment, or the functional variant fragment, such as mRNA and/or protein production stabilizing efficiency and/or the protein production increasing efficiency, is increased by at least 5%, more preferably by at least 10%, more preferably by at least 20%, more preferably by at least 30%, more preferably by at least 40%, more preferably by at least 50%, more preferably by at least 60%, even more preferably by at least 70%, even more preferably by at least 80%, most preferably by at least 90% with respect to the mRNA and/or protein production stabilizing efficiency and/or the protein production increasing efficiency exhibited by the naturally occurring 3'-UTR of a ribosomal protein gene from which the variant, the fragment or the variant fragment is derived.

In the context of the present invention, a fragment of the 3'-UTR of a ribosomal protein gene or of a variant of the 3'-UTR of a ribosomal protein gene preferably exhibits a length of at least about 3 nucleotides, preferably of at least about 5 nucleotides, more preferably of at least about 10, 15, 20, 25 or 30 nucleotides, even more preferably of at least about 50 nucleotides, most preferably of at least about 70 nucleotides. Preferably, such fragment of the 3'-UTR of a ribosomal protein gene or of a variant of the 3'-UTR of a ribosomal protein gene is a functional fragment as described above. In a preferred embodiment, the 3'-UTR of a ribosomal protein gene or a fragment or variant thereof exhibits a length of between 3 and about 500 nucleotides, preferably of between 5 and about 150 nucleotides, more preferably of between 10 and 100 nucleotides, even more preferably of between 15 and 90, most preferably of between 20 and 70.

Preferably, the at least one 3'-UTR element of the artificial nucleic acid molecule according to the present invention comprises or consists of a "functional fragment", a "functional variant" or a "functional fragment of a variant" of the 3'-UTR of a ribosomal protein gene.

In a preferred embodiment, the at least one 3'-UTR element of the artificial nucleic acid molecule according to the present invention increases the stability of the artificial nucleic acid molecule, e.g. increases the stability of an mRNA according to the present invention, compared to a respective nucleic acid (reference nucleic acid) lacking a 3'-UTR or comprising a reference 3'-UTR, such as a 3'-UTR naturally occurring in combination with the ORF. Preferably, the at least one 3'-UTR element of the artificial nucleic acid molecule according to the present invention increases the stability of protein production from the artificial nucleic acid molecule according to the present invention, e.g. from an mRNA according to the present invention, compared to a respective nucleic acid lacking a 3'-UTR or comprising a reference 3'-UTR, such as a 3'-UTR naturally occurring in combination with the ORF. Preferably, the at least one 3'-UTR element of the artificial nucleic acid molecule according to the present invention prolongs protein production from the artificial nucleic acid molecule according to the present invention, e.g. from an mRNA according to the present invention, compared to a respective nucleic acid lacking a 3'-UTR or comprising a reference 3'-UTR, such as a 3'-UTR naturally occurring in combination with the ORF. Preferably, the at least one 3'-UTR element of the artificial nucleic acid molecule according to the present invention increases the protein expression and/or total protein production from the artificial nucleic acid molecule according to the present invention, e.g. from an mRNA according to the present invention, compared to a respective nucleic acid lacking a 3'-UTR or comprising a reference 3'-UTR, such as a 3'-UTR naturally occurring in combination with the ORF. Preferably, the at least one 3'-UTR element of the artificial nucleic acid molecule according to the present invention does not negatively influence translational efficiency of an nucleic acid compared to the translational efficiency of a respective nucleic acid lacking a 3'-UTR or comprising a reference 3'-UTR, such as a 3'-UTR naturally occurring in combination with the ORF. Even more preferably, the translation efficiency is enhanced by the 3'-UTR in comparison to the translation efficiency of the protein encoded by the respective ORF in its natural context.

The term "respective nucleic acid molecule" or "reference nucleic acid molecule" in this context means that—apart from the different 3'-UTRs—the reference nucleic acid molecule is comparable, preferably identical, to the inventive artificial nucleic acid molecule comprising the 3'-UTR element.

The term "stabilizing and/or prolonging protein production" from an artificial nucleic acid molecule such as an artificial mRNA preferably means that the protein production from the artificial nucleic acid molecule such as the artificial mRNA is stabilized and/or prolonged compared to the protein production from a reference nucleic acid molecule such as a reference mRNA, e.g. comprising a reference 3'-UTR or lacking a 3'-UTR, preferably in a mammalian expression system, such as in HeLa or HDF cells. Thus, protein produced from the artificial nucleic acid molecule such as the artificial mRNA is observable for a longer period of time than what may be seen for a protein produced from a reference nucleic acid molecule. In other words, the amount of protein produced from the artificial nucleic acid molecule such as the artificial mRNA measured over time undercuts a threshold value at a later time point than the amount of protein produced from a reference nucleic acid molecule such as a reference mRNA measured over time. Such a threshold value may be, for example, the amount of protein measured in the initial phase of expression, such as 1, 2, 3, 4, 5 or 6 hours post initiation of expression, such as post transfection of the nucleic acid molecule.

For example, the protein production from the artificial nucleic acid molecule such as the artificial mRNA—in an amount which is at least the amount observed in the initial phase of expression, such as 1, 2, 3, 4, 5, or 6 hours post initiation of expression, such as post transfection of the nucleic acid molecule—is prolonged by at least about 5 hours, preferably by at least about 10 hours, more preferably by at least about 24 hours compared to the protein production from a reference nucleic acid molecule, such as a reference mRNA, in a mammalian expression system, such as in mammalian cells, e.g. in HeLa or HDF cells. Thus, the artificial nucleic acid molecule according to the present invention preferably allows for prolonged protein production in an amount which is at least the amount observed in the initial phase of expression, such as 1, 2, 3, 4, 5, or 6 hours post initiation of expression, such as post transfection, by at least about 5 hours, preferably by at least about 10 hours, more preferably by at least about 24 hours compared to a reference nucleic acid molecule lacking a 3'-UTR or comprising a reference 3'-UTR.

In preferred embodiments, the period of protein production from the artificial nucleic acid molecule according to the present invention is extended at least 1.5 fold, preferably at least 2 fold, more preferably at least 2.5 fold compared to the protein production from a reference nucleic acid molecule lacking a 3'-UTR or comprising a reference 3'-UTR.

This effect of prolonging protein production may be determined by (i) measuring protein amounts, e.g. obtained by expression of an encoded reporter protein such as luciferase, preferably in a mammalian expression system such as in HeLa or HDF cells, over time, (ii) determining the time point at which the protein amount undercuts the amount of protein observed, e.g., at 1, 2, 3, 4, 5, or 6 hours post initiation of expression, e.g. 1, 2, 3, 4, 5, or 6 hours post transfection of the artificial nucleic acid molecule, and (iii) comparing the time point at which the protein amount undercuts the protein amount observed at 1, 2, 3, 4, 5, or 6 hours post initiation of expression to said time point determined for a nucleic acid molecule lacking a 3'-UTR or comprising a reference 3'-UTR.

Preferably, this stabilizing and/or prolonging effect on protein production is achieved, while the total amount of protein produced from the artificial nucleic acid molecule according to the present invention, e.g. within a time span of 48 or 72 hours, is at least the amount of protein produced from a reference nucleic acid molecule lacking a 3'-UTR or comprising a reference 3'-UTR, such as a 3'-UTR naturally occurring with the ORF of the artificial nucleic acid molecule. Thus, the present invention provides an artificial nucleic acid molecule which allows for prolonged and/or stabilized protein production in a mammalian expression system, such as in mammalian cells, e.g. in HeLa or HDF cells, as specified above, wherein the total amount of protein produced from said artificial nucleic acid molecule, e.g. within a time span of 48 or 72 hours, is at least the total amount of protein produced, e.g. within said time span, from a reference nucleic acid molecule lacking a 3'-UTR or comprising a reference 3'-UTR, such as a 3'-UTR naturally occurring with the ORF of the artificial nucleic acid molecule.

Thus, "stabilized protein expression" preferably means that there is more uniform protein production from the artificial nucleic acid molecule according to the present invention over a predetermined period of time, such as over 24 hours, more preferably over 48 hours, even more preferably over 72 hours, when compared to a reference nucleic acid molecule, for example, an mRNA comprising a reference 3'-UTR or lacking a 3'-UTR. Accordingly, the level of protein production, e.g. in a mammalian system, from the artificial nucleic acid molecule comprising a 3'-UTR element according to the present invention, e.g. from an mRNA according to the present invention, preferably does not drop to the extent observed for a reference nucleic acid molecule, such as a reference mRNA as described above. For example, the amount of a protein (encoded by the ORF) observed 6 hours after initiation of expression, e.g. 6 hours post transfection of the artificial nucleic acid molecule according to the present invention into a cell, such as a mammalian cell, may be comparable to the amount of protein observed 48 hours after initiation of expression, e.g. 48 hours post transfection. Thus, the ratio of the amount of protein encoded by the ORF, such as of a reporter protein, e.g., luciferase, observed at 48 hours post initiation of expression, e.g. 48 hours post transfection, to the amount of protein observed 6 hours after initiation of expression, e.g. 6 hours post transfection, is preferably at least about 0.4, more preferably at least about 0.5, more preferably at least about 0.6, even more preferably at least about 0.7. Preferably, the ratio is between about 0.4 and about 4, preferably between about 0.65 and about 3, more preferably between about 0.7 and 2 for a nucleic acid molecule according to the present invention. For a respective reference nucleic acid molecule, e.g. an mRNA comprising a reference 3'-UTR or lacking a 3'-UTR, said ratio may be, e.g. between about 0.05 and about 0.3.

Thus, the present invention provides an artificial nucleic acid molecule comprising an ORF and a 3'-UTR element as described above, wherein the ratio of the (reporter) protein amount, e.g. the amount of luciferase, observed 48 hours after initiation of expression to the (reporter) protein amount observed 6 hours after initiation of expression, preferably in a mammalian expression system, such as in mammalian cells, e.g. in HeLa cells, is preferably above about 0.4, more preferably above about 0.5, more preferably above about 0.6, even more preferably above about 0.7, e.g. between about 0.4 and about 4, preferably between about 0.65 and about 3, more preferably between about 0.7 and 2, wherein preferably the total amount of protein produced from said artificial nucleic acid molecule, e.g. within a time span of 48 hours, is at least the total amount of protein produced, e.g. within said time span, from a reference nucleic acid molecule lacking a 3'-UTR or comprising a reference 3'-UTR, such as a 3'-UTR naturally occurring with the ORF of the artificial nucleic acid molecule. In a preferred embodiment, the present invention provides an artificial nucleic acid molecule comprising an ORF and a 3'-UTR element as described above, wherein the ratio of the (reporter) protein amount, e.g. the amount of luciferase, observed 72 hours after initiation of expression to the (reporter) protein amount observed 6 hours after initiation of expression, preferably in a mammalian expression system, such as in mammalian cells, e.g. in HeLa cells, is preferably above about 0.4, more preferably above about 0.5, more preferably above about 0.6, even more preferably above about 0.7, e.g. between about 0.4 and 1.5, preferably between about 0.65 and about 1.15, more preferably between about 0.7 and 1.0, wherein preferably the total amount of protein produced from said artificial nucleic acid molecule, e.g. within a time span of 72 hours, is at least the total amount of protein produced, e.g. within said time span, from a reference nucleic acid molecule lacking a 3'-UTR or comprising a reference 3'-UTR, such as a 3'-UTR naturally occurring with the ORF of the artificial nucleic acid molecule.

"Increased protein expression" or "enhanced protein expression" in the context of the present invention preferably means an increased/enhanced protein expression at one time point after initiation of expression or an increased/enhanced total amount of expressed protein compared to the expression induced by a reference nucleic acid molecule. Thus, the protein level observed at a certain time point after initiation of expression, e.g. after transfection, of the artificial nucleic acid molecule according to the present invention, e.g. after transfection of an mRNA according to the present invention, for example, 6, 12, 24, 48 or 72 hours post transfection, is preferably higher than the protein level observed at the same time point after initiation of expression, e.g. after transfection, of a reference nucleic acid molecule, such as a reference mRNA comprising a reference 3'-UTR or lacking a 3'-UTR. In a preferred embodiment, the maximum amount of protein (as determined e.g. by protein activity or mass) expressed from the artificial nucleic acid molecule is increased with respect to the protein amount expressed from a reference nucleic acid comprising a reference 3'-UTR or lacking a 3'-UTR. Peak expression levels are preferably reached within 48 hours, more preferably within 24 hours and even more preferably within 12 hours after, for instance, transfection.

In one embodiment, "increased total protein production" or "enhanced total protein production" from an artificial nucleic acid molecule according to the invention refers to an increased/enhanced protein production over the time span, in which protein is produced from an artificial nucleic acid molecule, preferably in a mammalian expression system, such as in mammalian cells, e.g. in HeLa or HDF cells in comparison to a reference nucleic acid molecule lacking a 3'-UTR or comprising a reference 3'-UTR. According to a preferred embodiment, the cumulative amount of protein expressed over time is increased when using the artificial nucleic acid molecule according to the invention.

According to the invention, an artificial nucleic acid molecule is provided, which is characterized by increased expression of the encoded protein in comparison to a respective nucleic acid molecule lacking the at least one 3'-UTR element or comprising a reference 3'-UTR ("reference nucleic acid") comprising a nucleic acid sequence which is derived from the 3'-UTR of a ribosomal protein gene or from a variant of the 3'-UTR of a ribosomal protein gene In order to assess the in vivo protein production by the inventive artificial nucleic acid molecule, the expression of the encoded protein is determined following injection/transfection of the inventive artificial nucleic acid molecule into target cells/tissue and compared to the protein expression induced by the reference nucleic acid. Quantitative methods for determining protein expression are known in the art (e.g. Western-Blot, FACS, ELISA, mass spectometry). Particularly useful in this context is the determination of the expression of reporter proteins like luciferase, Green fluorescent protein (GFP), or secreted alkaline phosphatase (SEAP). Thus, an artificial nucleic acid according to the invention or a reference nucleic acid is introduced into the target tissue or cell, e.g. via transfection or injection. Several hours or several days (e.g. 6, 12, 24, 48 or 72 hours) post initiation of expression or post introduction of the nucleic acid molecule, a target cell sample is collected and measured via FACS and/or lysed. Afterwards the lysates can be used to detect the expressed protein (and thus determine the efficiency of protein expression) using several methods, e.g. Western-Blot, FACS, ELISA, mass spectrometry or by fluorescence or luminescence measurement.

Therefore, if the protein expression from an artificial nucleic acid molecule according to the invention is compared to the protein expression from a reference nucleic acid molecule at a specific time point (e.g. 6, 12, 24, 48 or 72 hours post initiation of expression or post introduction of the nucleic acid molecule), both nucleic acid molecules are introduced separately into target tissue/cells, a sample from the tissue/cells is collected after a specific time point, protein lysates are prepared according to the particular protocol adjusted to the particular detection method (e.g. Western Blot, ELISA, etc. as known in the art) and the protein is detected by the chosen detection method. As an alternative to the measurement of expressed protein amounts in cell lysates—or, in addition to the measurement of protein amounts in cell lysates prior to lysis of the collected cells or using an aliquot in parallel—protein amounts may also be determined by using FACS analysis.

If the total amount of protein for a specific time period is to be measured, tissue or cells can be collected after several time points after introduction of the artificial nucleic acid molecule (e.g. 6, 12, 24, 48 and 72 hours post initiation of expression or post introduction of the nucleic acid molecule; usually from different test animals), and the protein amount per time point can be determined as explained above. In order to calculate the cumulative protein amount, a mathematical method of determining the total amount of protein can be used, e.g. the area under the curve (AUC) can be determined according to the following formula:

$$AUC = \int_a^b f(x)d(x)$$

In order to calculate the area under the curve for total amount of protein, the integral of the equation of the expression curve from each end point (a and b) is calculated.

Thus, "total protein production" preferably refers to the area under the curve (AUC) representing protein production over time.

Said increase in stability of the artificial nucleic acid molecule, said increase in stability of protein production, said prolongation of protein production and/or said increase/enhancement in protein expression and/or total protein production is preferably determined by comparison with a respective reference nucleic acid molecule lacking a 3'-UTR, e.g. an mRNA lacking a 3'-UTR, or a reference nucleic acid molecule comprising a reference 3'-UTR, such as a 3'-UTR naturally occurring with the ORF as describe above.

The mRNA and/or protein production stabilizing effect and efficiency and/or the protein production increasing effect and efficiency of the variants, fragments and/or variant fragments of the 3'-UTR of a ribosomal protein gene as well as the mRNA and/or protein production stabilizing effect and efficiency and/or the protein production increasing effect and efficiency of the at least one 3'-UTR element of the artificial nucleic acid molecule according to the present invention may be determined by any method suitable for this purpose known to skilled person. For example, artificial mRNA molecules may be generated comprising a coding sequence/open reading frame (ORF) for a reporter protein, such as luciferase, and no 3'-UTR, a 3'-UTR derived from a naturally occurring ribosomal protein gene, a 3'-UTR derived from a reference gene (i.e., a reference 3'-UTR, such as a 3'-UTR naturally occurring with the ORF), as 3'-UTR a variant of a 3'-UTR of a ribosomal protein gene, as 3'-UTR a fragment of a naturally occurring ribosomal protein gene, or as 3'-UTR a fragment of a variant of a 3'-UTR of a ribosomal protein gene. Such mRNAs may be generated, for example, by in vitro transcription of respective vectors such as plasmid vectors, e.g. comprising a T7 promoter and a sequence encoding the respective mRNA sequences. The generated mRNA molecules may be transfected into cells by any transfection method suitable for transfecting mRNA, for example they may be electroporated into mammalian cells, such as HELA cells, and samples may be analyzed certain time points after transfection, for example, 6 hours, 24 hours, 48 hours, and 72 hours post transfection. Said samples may be analyzed for mRNA quantities and/or protein quantities by methods well known to the skilled person. For example, the quantities of reporter mRNA present in the cells at the sample time points may be determined by quantitative PCR methods. The quantities of reporter protein encoded by the respective mRNAs may be determined, e.g., by Western Blot, ELISA assays, FACS analysis or reporter assays, such as luciferase assays, depending on the reporter protein used. The effect of stabilizing protein expression and/or prolonging protein expression may be, for example, analyzed by determining the ratio of the protein level observed 48 hours post transfection and the protein level observed 6 hours post transfection. Preferably, the value of that ratio is greater than 1, i.e. the protein expression at the later time point is greater than the protein expression at the earlier time point. If the value for that ratio is lower than 1, the protein is more stable the closer said value is to 1. Such measurements may, of course, also be performed up at 72 or more hours and the ratio of the protein level observed 72 hours post transfection and the protein level observed 6 hours post transfection may be determined to determine stability of protein expression.

In a preferred embodiment, the 3'-UTR element of the artificial nucleic acid molecule according to the present invention is derived from the 3'-UTR region of a gene encoding a ribosomal protein, preferably from the 3'-UTR region of ribosomal protein L9 (RPL9), ribosomal protein L3 (RPL3), ribosomal protein L4 (RPL4), ribosomal protein L5 (RPL5), ribosomal protein L6 (RPL6), ribosomal protein L7 (RPL7), ribosomal protein L7a (RPL7A), ribosomal protein L11 (RPL11), ribosomal protein L12 (RPL12), ribosomal protein L13 (RPL13), ribosomal protein L23 (RPL23), ribosomal protein L18 (RPL18), ribosomal protein L18a (RPL18A), ribosomal protein L19 (RPL19), ribosomal protein L21 (RPL21), ribosomal protein L22 (RPL22), ribosomal protein L23a (RPL23A), ribosomal protein L17 (RPL17), ribosomal protein L24 (RPL24), ribosomal protein L26 (RPL26), ribosomal protein L27 (RPL27), ribosomal protein L30 (RPL30), ribosomal protein L27a (RPL27A), ribosomal protein L28 (RPL28), ribosomal protein L29 (RPL29), ribosomal protein L31 (RPL31), ribosomal protein L32 (RPL32), ribosomal protein L35a (RPL35A), ribosomal protein L37 (RPL37), ribosomal protein L37a (RPL37A), ribosomal protein L38 (RPL38), ribosomal protein L39 (RPL39), ribosomal protein, large, P0 (RPLP0), ribosomal protein, large, P1 (RPLP1), ribosomal protein, large, P2 (RPLP2), ribosomal protein S3 (RPS3), ribosomal protein S3A (RPS3A), ribosomal protein S4, X-linked (RPS4X), ribosomal protein S4, Y-linked 1 (RPS4Y1), ribosomal protein S5 (RPS5), ribosomal protein S6 (RPS6), ribosomal protein S7 (RPS7), ribosomal protein S8 (RPS8), ribosomal protein S9 (RPS9), ribosomal protein S10 (RPS10), ribosomal protein S11 (RPS11), ribosomal protein S12 (RPS12), ribosomal protein S13 (RPS13), ribosomal protein S15 (RPS15), ribosomal protein S15a (RPS15A), ribosomal protein S16 (RPS16), ribosomal protein S19 (RPS19), ribosomal protein S20 (RPS20), ribosomal protein S21 (RPS21), ribosomal protein S23 (RPS23), ribosomal protein S25 (RPS25), ribosomal protein S26 (RPS26), ribosomal protein S27 (RPS27), ribosomal protein S27a (RPS27a), ribosomal protein S28 (RPS28), ribosomal protein S29 (RPS29), ribosomal protein L15 (RPL15), ribosomal protein S2 (RPS2), ribosomal protein L14 (RPL14), ribosomal protein S14 (RPS14), ribosomal protein L10 (RPL10), ribosomal protein L10a (RPL10A), ribosomal protein L35 (RPL35), ribosomal protein L13a (RPL13A), ribosomal protein L36 (RPL36), ribosomal protein L36a (RPL36A), ribosomal protein L41 (RPL41), ribosomal protein S18 (RPS18), ribosomal protein S24 (RPS24), ribosomal protein L8 (RPL8), ribosomal protein L34 (RPL34), ribosomal protein S17 (RPS17), ribosomal protein SA (RPSA) or ribosomal protein S17 (RPS17). In an alternative embodiment, the 3'-UTR element may be derived from a gene encoding a ribosomal protein or from a gene selected from ubiquitin A-52 residue ribosomal protein fusion product 1 (UBA52), Finkel-Biskis-Reilly murine sarcoma virus (FBR-MuSV) ubiquitously expressed (FAU), ribosomal protein L22-like 1 (RPL22L1), ribosomal protein L39-like (RPL39L), ribosomal protein L10-like (RPL10L), ribosomal protein L36a-like (RPL36AL), ribosomal protein L3-like (RPL3L), ribosomal protein S27-like (RPS27L), ribosomal protein L26-like 1 (RPL26L1), ribosomal protein L7-like 1 (RPL7L1), ribosomal protein L13a pseudogene (RPL13AP), ribosomal protein L37a pseudogene 8 (RPL37AP8), ribosomal protein S10 pseudogene 5 (RPS10P5), ribosomal protein S26 pseudogene 11 (RPS26P11), ribosomal protein L39 pseudogene 5 (RPL39P5), ribosomal protein, large, P0 pseudogene 6 (RPLP0P6) and ribosomal protein L36 pseudogene 14 (RPL36P14). Furthermore, the 3'-UTR element of the artificial nucleic acid molecule according to the present invention is preferably derived from the 3'-UTR region of a gene selected from the group consisting of ribosomal protein S4-like (RPS41), putative 60S ribosomal protein L13a, putative 60S ribosomal protein L37a-like protein, putative 40S ribosomal protein S10-like, putative 40S ribosomal protein S26-like 1, putative 60S ribosomal protein L39-like 5, or 60S acidic ribosomal protein P0-like.

In a particularly preferred embodiment, the 3'-UTR element of the artificial nucleic acid molecule according to the present invention is derived from the 3'-UTR region of a gene encoding a ribosomal protein, preferably from the 3'-UTR region of ribosomal protein L3 (RPL3), ribosomal protein L11 (RPL11), ribosomal protein L13 (RPL13), ribosomal protein L23 (RPL23), ribosomal protein L23a (RPL23A), ribosomal protein L26 (RPL26), ribosomal protein L27 (RPL27), ribosomal protein L35a (RPL35A), ribosomal protein L38 (RPL38), ribosomal protein S4, X-linked (RPS4X), ribosomal protein S8 (RPS8), ribosomal protein S9 (RPS9), ribosomal protein S13 (RPS13), ribosomal protein S19 (RPS19), to ribosomal protein S21 (RPS21), ribosomal protein S23 (RPS23), ribosomal protein S27 (RPS27), ribosomal protein S28 (RPS28), ribosomal protein S29 (RPS29), ribosomal protein L36 (RPL36), ribosomal protein L36a (RPL36A), ribosomal protein S18 (RPS18) or ribosomal protein S17 (RPS17). In another preferred embodiment, the 3'-UTR element may be derived from a gene encoding a ribosomal protein or from a gene selected from ubiquitin A-52 residue ribosomal protein fusion product 1 (UBA52), Finkel-Biskis-Reilly murine sarcoma virus (FBR-MuSV) ubiquitously expressed (FAU) and ribosomal protein L22-like 1 (RPL22L1).

Preferably, the at least one 3'-UTR element of the artificial nucleic acid molecule according to the present invention comprises or consists of a nucleic acid sequence which has an identity of at least about 1, 2, 3, 4, 5, 10, 15, 20, 30 or 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the nucleic acid sequence of a 3'-UTR of a ribosomal protein gene, such as to the nucleic acid sequences according to SEQ ID NOs:10 to 115 or the corresponding RNA sequence:

```
Homo sapiens ribosomal protein L9 (RPL9)
                                                                (SEQ ID NO: 10)
gatctaagagttacctggctacagaaagaagatgccagatgacacttaagacctacttgtgatatttaaatgatgcaataaaagacctattgatt tggaccttcttctt Homo sapiens ribosomal protein L3 (RPL3)
                                                                (SEQ ID NO: 11)
tgccaggaacagattttgcagttggtggggtctcaataaaagttattttccactgac Homo sapiens ribosomal protein L4 (RPL4)
                                                                (SEQ ID NO: 12)
actcttaaatttgattattccataaaggtcaaatcattttggacagcttcttttgaataaagacctgattatacaggcagtgagaaacatg Homo sapiens ribosomal protein L5 (RPL5)
                                                                (SEQ ID NO: 13)
acccagcaattttctatgattttttcagatatagataataaacttatgaacagcaact Homo sapiens ribosomal protein L6 (RPL6)
                                                                (SEQ ID NO: 14)
atgtcttaagaacctaattaaatagctgactac Homo sapiens ribosomal protein L7 (RPL7)
                                                                (SEQ ID NO: 15)
ggtgtctaccatgattattttctaagctggttggttaataaacagtacctgctctcaaattgaaat
```

*Homo sapiens* ribosomal protein L7a (RPL7A)                                                (SEQ ID NO: 16)

atgtacactgttgagttttctgtacataaaaataattgaaataatacaaattttccttc

*Homo sapiens* ribosomal protein L11 (RPL11)                                                (SEQ ID NO: 17)

attcccgtttctatccaaaagagcaataaaaagttttcagtgaaatgtgc

*Homo sapiens* ribosomal protein L12 (RPL12)                                                (SEQ ID NO: 18)

gcacaaaggaaaacatttcaataaaggatcatttgacaactggtgg

*Homo sapiens* ribosomal protein L13 (RPL13)                                                (SEQ ID NO: 19)

agccctcctggggacttggaatcagtcggcagtcatgctgggtctccacgtggtgtgtttcgtgggaacaactgggcctgggatgggcttc actgctgtgacttcctcctgccaggggatttggggctttcttgaaagacagtccaagccctggataatgctttactttctgtgttgaagcactgtt ggttgtttggttagtgactgatgtaaaacggttttcttgtggggaggttacagaggctgacttcagagtggacttgtgtttttttcttttttaaagaggc aaggttgggctggtgctcacagctgtaatcccagcactttgaggttggctgggagttcaagaccagcctggccaacatgtcagaactactaa aaataaagaaatcagccatgcttggtgctgcacacttgtagttgcagctcctgggaggcagaggtgagggatcacttaacccaggaggcag aggctgcactgagccaggatcacgccactgcactctagcctgggcaacagtgagactgtctcaaaaaaaaaaaagagacagggtcttcg gcacccaggctggagtacagtgccacaatcatggctcactgcagtcttgaactcatggcctcaagcagtcctccctcagcctcccaagtaga gggtttataggcacgagaccctgcacccaacctagagttgcctttttttaagcaaagcagtttctagttaatgtagcatcttggactttggggcg tcattcttaagcttgttgtgcccggtaaccatggtcctcttgctctgattaaccccttccttcaatgggcttcttcacccagacaccaaggtatgaga tggccctgccaagtgtcggcctctcctgttaaacaaaaacattctaaagccattgttcttgcttcatggacaagaggcagccagagagagtgc cagggtgccctggtctgagctggcatccccatgtcttctgtgtccgagggcagcatggtttctcgtgcagtgctcagacacagcctgccctagtcctaccagctcacagcagccactgctctccttggcagctatggccatgacaaccccagagaagcagcttcagggaccgagtcagattct gtttgtctacatgcctctgccgggtgccggtattgaggcacccagggagctgttactggcgtggaaataggtgatgctgctacctctgctgct gcactcacagccacacttgatacacgatgacaccttgcttgtttggaaacatctaaacatctagtagatgacttgcaggctgttggctaccagtt tcctgtctgaggtgtatatgttaacttcgtgatcagtttgtatgtttgggactcttgtcctatgtaaagttaaggtgggccgggtgcagtggctcac gcctgtaatcctaacactggaggccgaggcgggtggatcacctgatggtgaaacctcatctctactgaaaatacaaaaattagctgagtgg tgacacacgcctgtaatcccagctacttggtaggcttgaacccaggaggcagagattgcagtgagccgagctgcaccactgtgctccagcc tgggtgacagcgagactcagtctcaaaaaaagttgtacaaggtggatggttggaagcttgagcctaggctcgaatccctctcacgtgagag ggcctgaagatttctggtggattccaacctggctgaagactggccgtgggggtgcaggggtctccagcgctctgccctccagcctgcttc ctccctgcccacaccgcactagggaagggcctttcctgctgcctgcggggccgcacctggagtaggtaatgccatgtggtgacgtgaat ggagcagaggtctgtgcccatcacaccgccttgctgtttttactgtgggacaaaagcactctgatctgcgtgttccgggggccctcctacca gccgacttgacgggaagtcagggttcaggtatcatctgtgcacctggggcggggtagtctgcactgaacctgccagagtccctcctcatttt cactgaaagtcacagtctccagggctgtgttgctaaccttacgttctctccgtttgcttaatctattaagagccctaacaggagaggatgggctt tctctgttgtctggggccctgctgttggccggtgctcttagcaagaggtcattttttctaggttgcgctgggacattgtgagtttggtgagggtcat ggatgtgggctgggctgggctgggctgggccgggctgcctgctgcctgctgctcccctacctgaaatgcagctagtgcggctctgcccttc ctggggctgaggaaggcttctgcaggatagctgggggctgggcaggtgggtgaggcagcctccctgctgacactcagtccttgtagctg gagcaagatctcctgatccaggtacgggcctgtctgctccaagaaagactctgccaccagatgcaaaggggccctttgttttaacttagtccc tggggaccgcctgattcagcacctgtcggcccaggataccccgctggtgggacaagtgcctgagtgtgggccgtgcccgagtgtggcc atccctgagtggggccgtcctgactaggaagtggcttttcagttgtgatgtgtgggcctgacctaggggcgctgtggaacccgggctgga accagccctctgtgccaggccgcagacaggttccgccggccctgaggggcagctgccatggcgtgggtcactgggagctgagaggaag ggcccccaccgcacctcaggcaaagcggctctgggaacaccttgatttcgtccatgtgagccgtcccagggagggcagccaagctgtga agctgagaaactgacctgtgtgccacgagcttgtggtctgctgcccggtggaggaagtgcaggtgcgcccaggctcctcattccgttttgc aggattccttcggggtgtgagcatttcctattcagcctgtcgcccccggggagcacgggctggctctgtggtgccgtgccttttgtagaag cgttggttttacggcaggttcatctctggggcagcctcccacagtgggtgggctttgccagcagtgcccacgggggtcatggggccagg -continued cgcgctccggcgcctgcagaactgatcggggatagtctcaggaggcgctagtcacgtgccccggtgatcggggatagtctcagaaggcg ctagtctcctgccccggtgatcggggatagtctcaggaggcacgagtcgcctgcctcggtgatgcaccgtttctcacaccggctgctctggc ccgagctaaaggggaagacgtgtgcggataggagctgcacacaattttcctccatgtattgtttattttgcttttctttttggctagacattaggaa tttcagttttcccaagttgtattttcttttctattttaaaattatcatgcagggctgggtgaggtcgctcacgcctatagtctcaaaactttgggag gctgagggggaggatggcatgagcccaggagtttaaggctgcagtgagccgagatcgctccactgtcctccagcctgcatgacagagc gagaccctatctcaggaaaaaaaaaacaaaactattatgcagtagtttcgaccctggaagacgagtgtgcatctttgagttgtaacacgtgt acctcgcccatccaggcgtagtttcatttggaatctggttatcctgtagttgctttgttaaaaatatatgtaattgcaaatcattt

*Homo sapiens* ribosomal protein L23 (RPL23)

(SEQ ID NO: 20)

ttctccagtatatttgtaaaaaataaaaaaaaaaactaaacccattaaaaagtatttgtttgc

*Homo sapiens* ribosomal protein L18 (RPL18)

(SEQ ID NO: 21)

ccctggatcctactctcttattaaaaagattttttgctgacagtgc

*Homo sapiens* ribosomal protein L18a (RPL18A)

(SEQ ID NO: 22)

gtgcagggccctcgtccgggtgtgccccaaataaactcaggaacgccccggtgctcgccgc

*Homo sapiens* ribosomal protein L19 (RPL19)

(SEQ ID NO: 23)

aacctcccactttgtctgtacatactggcctctgtgattacatagatcagccattaaaataaaacaagccttaatctgc

*Homo sapiens* ribosomal protein L21 (RPL21)

(SEQ ID NO: 24)

taggtgttaaaaaaaaaaataaaggacctctgggctac

*Homo sapiens* ribosomal protein L22 (RPL22)

(SEQ ID NO: 25)

atttcatttatctggaaaattttgtatgagttcttgaataaaacttgggaaccaaaatggtggtttatccttgtatctctgcagtgtggattgaacaga aaattggaaatcatagtcaaagggcttcccttggttcgccactcatttatttgtaacttgacttcttttttttttctgcttaaaaatttcaattctcgtggta ataccagagtagaaggagagggtgactttaccgaactgacagccattggggaggcagatgcgggtgtggaggtgtgggctgaaggtagt gactgtttgattttaaaaagtgtgactgtcagttgtatctgttgcttttctcaatgattcagggatacaaatgggcttctctcattcattaaaagaaaa cgcgacatctttctaagattctctgtgggaaaatgactgtcaataaaatgcgggtttctgggccattcgtcttacttttcatttttttgattacaaatttct cttgacgcacacaattatgtctgctaatcctcttcttcctagagagagaaactgtgctccttcagtgttgctgccataaagggggtttggggaatc gattgtaaaagtcccaggttctaaattaactaaatgtgtacagaaatgaacgtgtaagtaatgtttctacaggtctttgcaacaaactgtcactttc gtctccagcagagggagctgtaggaatagtgcttccagatgtggtctcccgtgtggggcccagcaatgggggcccctgatgccaagagct ctggaggttcttgaaagaggggacacgaaggaggagtgactgggaagcctcccatgccaaggaggtgggaggtgccctgaaatagct gcctcatgccacttaggccatgactggatttaatgtcagtggtgtgccacagtgcagaggctagacaactgaaaggggctaccaaggctgg gaaaaaaatgcaattgttgctgtgagtgactttgaaagactctggtgccttgtggtgcccttctgaaattcaaacagtaatgcaaagtgtctgc attagaatttacggtgtctaaaattcatgttttttaaaagagcttgcctacagatggtttccacacttgaaattgtgccctgcgagttgcatagctgg aagttcaatgctcagtcctaccttggctcccattaaacatttggtgctctgtggattgagttgaacgtgttgaggctttgcaatttcacttgtgttaa aggctctggcattttccatttctatgcaaatttctttgaagcagaattgcttgcatatttcttctctgccgtcacagaaagcagagtttctttcaaact tcactgaggcatcagttgctctttggcaatgtcccttaaccatgattattaactaagtttgtggcttgagtttacaaattctacttgttgcattgatgtt cccatgtagtaagtcatttttagtttggttgtgaaaaaccctgggctgaagttggcatttcagttaaaagaaaaaagaaactagtcccagattt gaaaacttgtaataaaattgaaactcactggttttctatgtctttttgaactatgtaatcgagttttgatcatattttctattaaagtggctaacacctg gctactcttactgt

*Homo sapiens* ribosomal protein L23a (RPL23A)

(SEQ ID NO: 26)

actgagtccagctgcctaattctgaatatatatatatatatctttcaccatatacatgcctgtctgtcaatttctggttgggctgggaggccaca cacacacactgacatgacagggcttgggcaagactcctgttctacttatccttttgaaatacctcaccctgccactccaccatgtatgatcattc cagagatctttgtgactagagttagtgtcctaggaaaaccagaactcagaacttgcctccatggttgagtaacaagctgtacaagaaccccttt -continued tatccctggaagaggctgtgtatgaaaccaatgcccagggtttgaagggtgttagcatccatttcaggggagtgtggattggctggctctctg gtagcattttgtcctcacacacccatctactatgtccaaccggtctgtctgcttccctaccccttgcccaataaaggacaaggacttcagagg Homo sapiens ribosomal protein L17 (RPL17)

(SEQ ID NO: 27)

attcagcattaaaataaatgtaattaaaaggaaaag

Homo sapiens ribosomal protein L24 (RPL24)

(SEQ ID NO: 28)

actggcagattagattttttaaataaagattggattataaactctag

Homo sapiens ribosomal protein L26 (RPL26)

(SEQ ID NO: 29)

agtaatcttatatacaagctttgattaaaacttgaaacaaagagcctg

Homo sapiens ribosomal protein L27 (RPL27)

(SEQ ID NO: 30)

atgctttgttttgatcattaaaaattataaag

Homo sapiens ribosomal protein L30 (RPL30)

(SEQ ID NO: 31)

acctttcacctacaaaatttcacctgcaaaccttaaacctgcaaaattttccttaataaaatttgcttgttttaaaaacattgtatct Homo sapiens ribosomal protein L27a (RPL27A)

(SEQ ID NO: 32)

agccacatggagggagtttcattaaatgctaactacttttttccttgtggtgtgagtgtaggttcttcagtggcacctctacatcctgtgtgcattgg gagcccaggttctagtacttagggtatgaagacatggggtcctctcctgacttccctcaaatatatggtaaacgtaagaccaacacagacgtt ggccagttaaacatttctgtttataaagtcagaataatacctgttgatcactgaaaggcctgcatgtattgtactctgaattttacagtgaatgaga gaatgtaccctaattgttcaacagggctcaaaaggaaagattccattttgatgggtcacattctaaagaggggcagtgtgataggaatgagat ggtcctttaggacttaagttctcagcccaaggttttttccacgtggccccctcatctttttttttttttttaaacggagtctctcttgccaggctggagtg cagtggcacgatctcggctcactgcagcctccgcctcccaggttaagcgattctcctgcctcagcttcctgactaactgggattacaggcgc ccaccaccatgcccagctaattttttgtattttcagtagagatgggggtttcaccatgttggccatgctggtctctaactcctaacctcaagtgatctg cccacatcggcctccaaaagttctgggattatagtgtgagccactgcgcccggccatggctccttaatcttgatccaaattattgttacatccag aatgtgatgaatcaaaatctcgagatgggggtccagcaatctgaaatttcagtatgccagggcttttctgtatgtcaaagtgggtttgaaatagt taattttttcttctagtctgaaatgtatcgggaaaatttggaaatcctgaaggctggaaattgaaataagttttttctaggatttgtgtctcttgctattgg aaaactgatggtgaccaattcatgtttacaaataagatcctcatagatctcggtaaattataatttgctacagttttatggttcttcctgtgattttga gctttttttgacccaaaataatacagtctaaaactatagacaaataagatgcacttagactcctgggttttagttagtggaggtttccttagtgca ctgtggggtcataataagccgagaaccatggctgtctatgggacacatctgtcaggacaaccttagaggatgttggggatcaaatagaagg cacagagaagcactgaattggcttacataagaataggctagaattacaagtagtgaaacctcgattcagctggacaattttttaaacaaatgtatc atttggcttgtatcttctgttgtgctggagaagttagaaataaggggctctccagaccagcctgaccaacctggagaaaccttgtctctactaaat acacaaaattagccaggcgtggtggcacatgcctgtaatcccagctactttggaggctgagccaggagaatctccaggaggcggaggttg ctgtgagccgagatcgtgccattgcactccagcttgggcaacaagagtgaaactctgtccacccccccaaaaaaagtaagggctctccatt agggcccatagaggacttgtaatatgtgaacctgaatccaaggatcccacaataagtggtcagtagttcatgatgaattaaaagactcaatatttt ggtcttcacccaatacctgtgtgacttttagtcctaatttcctcatctttaaaatttcagtgaaagtgcctacctgaggattgtgtagattaaaatgg aaaccgtgcacttaatttttgttttgttttgagacggagtctcgctctgtcgcccaggctggagtgcagtggtgcgatctcagatcactgcaag ctccgcctcctaggttcagaccattctcctgcctcagcttcccaagtagctgggactacaggcgcccgccactgcgcccggctaattttttgc attttttagtagagacagggtttcaccgtgttagccaggatggtctcgatctcctgatctgcccgcctcagcctcccaaagtgctgggattacag gcatgagccaccgcgcccggcccaggcacttaattttttgtgtttgacttagtaacttaagtgcaaactattacgggagcagatggagtcaattg gccttcatgtgattgtcagtgggaaattggtccaagcagagggaatactggttcaggaaactggtttgggaaggttaggcaaacgggaagt gctatggtggagagaaagattactctggccgggctgtaaaggacggctacaatgggaggctgaaggcagaaccaagaaaatgggagtg agtatggaaaaggtacgattcagacggcataatgacgggacttggagactgaattgtagtgggccgaccacaaaatgataaggcatgga aggaagtagagtttggggggaaggatccctagtcccttaatggctaccttcttccccaggagttgttaggccatccgatcccctggcctggg aaagaaacactgatttcgttgctggcttgttcactcaccagaagctacagctactaacagttctaaaaactgtttcatgtgatgaggaacagac -continued gaaaatagttttgagccctaagtccgccgattccagtgctttcttgaacccgcatttactaaaatattttcatgactgccaagctttgaatagcctg ctgtgttcatggaggctcatactggcgatctctagtggctggctaaagcttgaattgcaaaagatctaatttctggtctaatgtatatatgccttaa atatagttgcgttcaaacgtgggagctgcaggtgcaacttgatttttatgacaaatggctgccacataatttgcacaagcagtgctcgtcaaggg cagctaaatcaggcgagctttcaatcaaaataaatgtactactaaaccctacttagcggctaactagcccaagagcagacagcccacggac ggactgcaagtcggaagcgcgggcggaagctgtgcagcgcccacctggtggctccatcggccgcgttcatcagtcagcacgacccgac ctcagtggcgtcctcacaacacagaccggaccttgggtcttaccccggcacctgagaaccacttccggtgagtagcttctacttccggagac gatgactccccgcgtcccagaccggaagaagcccggcggagaccggcctcgctcggccacttccggcaagggcggagccggccagt ggtgcgcgagcgcagataactcccctggagaggcgggatgttcaactccaccccctggtccttgggcggccgtgggtccccttcgaagcg gaggaatggccaacctcgccgcacttcgagccccttlagggtgcgtttaagaacagtgggcgtggcctttacgtaaatcttcgagatgggaa cctccagaatttgtctcaattgtctaaaaggtaatgagcgtcagcgacattcaagggcacttlgggctaaaaagaaagtgcttgtacacggat ggaaatattctagaagaacataaaaggaatttcctcttaggaggttagggaaatgagcacgaagtatgttttggtgcagttttttgttcaaccca atgcgtattttcatattgagaggcaatataaatggagcgaaagtatcttgagaaaaaaaaaaaaactaccagaacttgccgttgctgaaaagta atattttctctttcgagagttttcatggccttttaaattacacccccacctccacaggcaaataaatttgttttggaatgcataccacatcatctggct ctagaaacgtattttgtgtagctcccctagcaagaatataggttaaagcgtaaatttaattcctggctctattttacatcccaatttttattttcctctc attcccactttacgttgtttcaaataacctagtttgtgtatccctgtaagtcattttggtataaagtaggttataagtgtacatgcgaaaagatgttttt aacaaaaatgtaactg Homo sapiens ribosomal protein L28 (RPL28)

(SEQ ID NO: 33)

gccttgctctgctccccgccccaggcagccatccgcagggccagcgccatcctgcgcagccagaagcctgtgatggtgaagaggaa gcggacccgccccaccaagagctcctgagccccctgccccagagcaataaagtcagctggctttctcacctgcctcgactgggcctccc tttttgaaacgctctggggagctctggccctgtgtgttgtcattcaggccatgtcatcaaaactctgcatgtcaccttgtccatctggaggtgatg tcaatggctggccatgcaggaggggtggggtagctgccttgtccctggtgagggcaagggtcactgtcttcacagaaaaagtttgctgactt gtgattgagacctactgtcccattgtgaggtggcctgaagaatcccagctggggcagtggcttccattcagaagaagaaaggcctttttctagc ccagaagggtgcaggctgagggctgggccctgggccctggtgctgtagcacggtttggggacttggggtgttcccaagacctgggggac gacagacatcacggaggaagatgagatgacttttgcatccagggagtgggtgcagccacatttggaggggatgggctttacttgatgcaa cctcatctctgagatgggcaacttggtgggtggtggcttataactgtaagggagatggcagcccagggtacagccagcaggcattgagca gccttagcattgtccccctactcccgtcctccaggtgtcccatccctccctgtctctttgagctggctcttgtcacttaggtctcatctcagtgg ccgctcctgggccaccctgtcacccaagctttcctgattgcccagccctcttgtttcctttggcctgtttgctcccagtgtttattacagcttgtga ggccaggagtttgagaccatcctaggcaacataatgagacaccgtctctaaaataaaattagctgggtgtggtggtgcaccgcctgtggtcc cagctcctcagaggttgagtagaggctgaggtgagcggagcacttgagccaagagtatgaggctgcagtgagcccatgagccccaccac tacactccagcctggaagacaccatgacacacagtgaggcctggatggggaaagagtcctgctgttgatcctcacatgtttcctgggcacct aactctgtcagccactgccagggaccaaggatccagcatccatggcacccctggttcctgccatcctggggtacccgattcaaagaaggac tctgctccctgtctgagaccaccccggctctgactgagagtaaggggactgtcagggcctcgacttgccattggttggggtcgtacgggg ctgggagccctgcgttttgaggcagaccactgcccttccgacctcagtcctgtctgctccagtcttcccagctcgaaggagagcagatctg accacttgccagcccctgtctgctgtgaattaccatttcctttgtccttcccttagttgggtctattagctcagattgagaggtgttgccttaaaact gagttgggtgacttggtacctgctcaggaccccccgcactgtcccaatcccactcaggcccacctccagctggcctcactccgctggtgact tcgtacctgctcaggagcccccactgtcccagtcccactcaggcccatctctggctggcctcactgcgctgggactccgccttcataaggag agctcactgctcacgttagtagatggccccttctcgtgaggcctctcccctggcacctgcttcagttgtcctccacagcactgatttgcagccc acaagctggcaggtttatctgtctcatgtttgtcttgtgctggtgggcaaggggtttgtctagcacaccagcatataatgagatgcttgatgaat ggtgcatattgaatgtataaagccaccggtcctgagagtttgctcactggagactttctggagatggagtctcgctctgttgcccaggctggc gagtgcaatggcgcgatcttggctcactgcagcctccacctcctgggttcaagcgattctcctgcctcagcctcccgagtagctgggattaca

```
ggtgggtgtcaccacacccagctcagtattgtattttagcagagatgggtttcaccattttgcccaggctggtttggaactcctgacttcaaat tacccacctgcctcagcctcccaaagtgctggcattacaggcgctcgaggctttctgatgtggctgctgctgctcagaaggccttgtccttaa ccacctccttgcctgccctggaggcttgtgcctctaggccccaccccctgtggagtcctgctggcttctccatccctatctgaatcctcctgc tgtgtggcctccctggtctcatccgtaacacagcccagcttagtgggcctctgttcctgcgggtggccagcctgtctgtgtggctgggctgg ggaggccacgtctggtatctgaatgctatcggtggttgggtggaggaaccaggagagggctggagggagggagatggtctcagccc cacagagtttggagtcctcagtgtgctgagcaaacgtggagacaccatttccctcctctagacctcatcttggagagagagatgttggatggg gccatctattccagctttattcacacaaatcatgtctgttggcctggaaattggaaaaccagttaaaccaaaaacatgatattaagaaaacagg caggctcaccatagtaaaaatgctgaaagccaaagacaaaattgggagaacaaaagaaaagcgtcttgtcacatacagaaggtccctgata aagttagtagctgccctcatcagaaaccaggcccaggcagtggggacacatccagagtgctgaaagaaccctccccaggtcatcctatcc ccaagagtgatgcccggcagcattcccagctcagggctaatggttcacggaagccaggaatcaaactgcctgggttccagtcccagctctg ccagttatgcccagctgtggggacttgggcagctcgtttagtagcaccgtgcctcagtttcccatatgtaaaaggccattttgagtgcctttcac agccctgcataaggcaggtgtctcagtgttcactgctgtctctccagctcttagtccagtagctgcatggtgagtgagcgtagggcgcaccct ggaaggctgccaagcccaaagttgtgcagagcgctggggactccagactcccacagcagcagagactcgggactgaggcatcctctgt tcacaggacatgctggcatctactgggtcagggctctgctgctcggtggctgtgcaaccttgggcaagttcctcaacctctctgtgtcttcgta ccctcatctgtaacatgcgtgtcgatagaccctactactcagggttgatgagaagattaaatgtgcaaacctgcttgactgtgcccacaaatc ctgattgtaggaataaattaatgacttttttataaatattttgatcagatggactcatgatcacagatgtcttcacatgcctatgactaatttgtacaca aactaatgctcgtgtttcccaagcacctggaagacatgccagatccatgtgcagtaatgcctggtggctccaggtctgccccgccgtcctgtg gggctgtgagctttccagcctcctgcccgtgtttgtgaatatcattctgtcctcagctgcatttccagcccaggctgtttggcgctgcccagga atggtatcaattcccctgtttctcttgtagccagttactagaataaaatcatctacttt
```

Homo sapiens ribosomal protein L28 (RPL28)
(SEQ ID NO: 34)

```
ttttttactgtcaggcaggaagagcggtaactgccatcgcggcgggcatccctggcgccagggtgttggtctgggtaccggcttccctctcg gccgacttgtcagctctgtgagccgcgcgcgtctgagcccgtgtcctcacctgtaaagtggagaaatgaaaaaggacctgaacttcctcggt ggttgttgagagttaaggcacggggttgatgttttcagatgaaattctcaaagcaagtcagggtgggatggatggtttcatcccacaggtgg gaagattgagg
```

Homo sapiens ribosomal protein L28 (RPL28)
(SEQ ID NO: 35)

```
gttttttctcaggtccttgattggaactgcctcagagccaagggtccttttactcagtggcagcaacaaacgcagtctgttggctagtgatcctcc tgtctcagggacacgtagtccaggagcagccaattgcttggcacttggggaccccgttctggggagtcctgaaagctttcacctcttggatt gccgaatacatgggtggcccttcctagactaagggactggcctgagtgaggctgggcctctcagccaagctgatgttgaaccactgctgtg gggatgggcctgggttcctgggaagctgttcatacccattgccaggagcgtgggctctggctggacctggatcagatcctaactgaagcg gcagctttctggcatgagaaggagtgttttcatggtggacagaattgggctatgagtgt
```

Homo sapiens ribosomal protein L29 (RPL29)
(SEQ ID NO: 36)

```
atatctctgccaacatgaggacagaaggactggtgcgacccccaccccgccctgggctaccatctgcatgggctgggtcctcctgt gctatttgtacaaataaacctgaggcagg
```

Homo sapiens ribosomal protein L31 (RPL31)
(SEQ ID NO: 37)

```
agggagccctcctggaagtggatgaggccttgggtctcggctcttcattgcttcctgagctgcagcagatgcctttacaaccaagctcaccg aggacgtctgtctcccatattaccctggcagagggccaggcctgttctacacggccgggggtttcaacaaggtactgatgtcttctgcccttgc ctcttcgacaggcaagtaataagacttaagtgaagagaattcttaggcacacaaattcacatttgatgtaatctcattatacttcctgatctgtga ttgaaactttcatttcgtaactagtatgtctgtcccaccttttaaaaagttttcattatgaaagtaagtatttgttagaattaagtctatttaaatgaaa aaaacttagatatgagtctgcatggcctcaggaaaatgatgttttaaaatagagattttaggttgtctgcactctagcttttttgtcgttttcttaagg ctttttttaactgcatcaaaaattcagatacgaaacatacactaaaaaataatacatcatatcttaatttccactgaacttgatttaaattcagagttac acagtatgaatatcacaatcagatatgttcaaaaaggtctgaacaattgattttctgaaaccatgaaggactac
```

-continued

Homo sapiens ribosomal protein L31 (RPL31)
(SEQ ID NO: 38)
agccatttaaattcattagaaaaatgtccttacctcttaaaatgtgaattcatctgttaagctagggggtgacacacgtcattgtacccttttttaaattg ttggtgtgggaagatgctaaagaatgcaaaactgatccatatctgggatgtaaaaaggttgtggaaaatagaatgcccagacccgtctacaa aaggtttttagagttgaaatatgaaatgtgatgtgggtatggaaattgactgttacttccttttacagatctacagacagtcaatgtggatgagaac taatcgctgatcgtcagatcaaataaagttataaaattgccttc Homo sapiens ribosomal protein L32 (RPL32)
(SEQ ID NO: 39)
gcagctcatgtgcacgttttctgttttaaataaatgtaaaaactgccatctggcatcttccttccttgatttttaagtcttcagcttcttggccaacttagt ttgccacagagattgttcttttgcttaagccccttt ggaatctcccatttggaggggatttgtaaaggacactcagtccttgaacaggggaatgt ggcctcaagtgcacagactagccttagtcatctccagttgaggctgggtatgaggggtacagacttggccctcacaccaggtaggttctgag acacttgaagaagcttgtggctcccaagccacaagtagtcattcttagccttgcttttgtaaagttaggtgacaagttattccatgtgatgcttgtg agaattgagaaaatatgcatggaaatatccagatgaatttcttacacagattcttacgggatgcctaaattgcatcctgtaacttctgtccaaaaa gaacaggatgatgtacaaattgctcttccaggtaatccaccacggttaactggaaaagcactttcagtctcctataaccctcccaccagctgct gcttcaggtataatgttacagcagtttgccaaggcgggggacctaactggtgacaattgagcctcttgactggtactcagaatttagtgacacgt ggtcctgatttttttttggagacggggtcttgctctcacccaggctgggagtgcagtggcacactgactacagccttgacctcccaggctcag gtgatcttcccacctcagccttccaagtagctgggactacagatgcacacctccaaacctgggtagttttgaagttttttttgtagaggtggtcta gccatgttgcctaggctcccgaactcctgagctcaagcaatcctgcttcagcctcccaaagtactgggattacaggcatcttctgtagtatata ggtcatgagggatatgggatgtggtacttatgagacagaaatgcttacaggatgttttctgtaaccatcctggtcaacttagcagaaatgctgc gctgggtataataaagcttttctacttctagtctagacaggaatcttacagattgtctcctgttcaaaacctagtcataaatatttataatgcaaact ggtccttc Homo sapiens ribosomal protein L35a (RPL35A)
(SEQ ID NO: 40)
actaacgaaaaatcaataaataaatgtggatttgtgctcttgtattttaagtggattaaaaaacttactacctt Homo sapiens ribosomal protein L37 (RPL37)
(SEQ ID NO: 41)
gaatgtcaacgattagtcatgcaataaatgttctggttttaaaaaatacatatctggttttggtaaggtatttttaatcaattaggcttgtagtatcagt gaaatactgtaggtttagggactgggctagcttcatatcagatttacttgttaagtgactgttttggaatgtttacttttggactgggtttgtaacac ggttaaaggcaatgagaaacaagcagaattccaggagtccttgaagcagagggcactggaagacaatatagcagattaaaatagcacagc tcatgtggcataggtgggtattttagatgtttgagtaaatttgaaagagtatgatgtttaaattaccttagcaacatgttcatctgctatgctgtcat gactagggggatgattattagtcacatagagcttgggagtaccactggaaacgtatgggtaggagtttaggtggcttctgttttcaaaagatg atcttatcctagtatctgtaatgctcacttggcacacctgacttgtgggctgtgtgtaaggtggctagctaagtgaaaaaagcctgctaggtgtg agtcaacttaagaatatgtaaataggtttgagaaaaagtagggcttgggtgcaagtaaagattgagcaggaaataaaggaaaatcaagtata atccctgagatttgtagactaaaggcaatgatgtgggactacttggtcgaattttttttagccctcaacttggtaattgggtgtttctgtgttaaagc actgaaacttgctgtcgtgccttcctagttttcgtgtttattgacagggttgggggttttttttgtttttttaaaatgaagggacaaagtcaactgga ctgctgagtgagagggcaggggcagttgaagggaacatgaattgctggaacagctacataaaatagtgatgtagccaagtcatgctatttaa attataattctccactgtgtttagaataacatctgaggttcttaacctggccttggaagggtatcacttttacttgtaacctggaatggctttataatg tgctagctaattgctactctcatcttgtattttaactcctaatttacccttcaggtctcagcttcagaacattcacttataaagaaaccctgctgatta aatctctcttgggcttcctccc Homo sapiens ribosomal protein L37a (RPL37A)
(SEQ ID NO: 42)
acgctcctctactctttgagacatcactggcctataataaatgggttaatttatgtaac Homo sapiens ribosomal protein L38 (RPL38)
(SEQ ID NO: 43)
accagacacactgattggaactgtattatattaaaatactaaaaatcct Homo sapiens ribosomal protein L39 (RPL39)
(SEQ ID NO: 44)

-continued ggaattgcacatgagatggcacacatatttatgctgtctgaaggtcacgatcatgttaccatatcaagctgaaaatgtcaccactatctggagat
ttcgacgtgttttcctctctgaatctgttatgaacacgtggttggctggattcagtaataaatatgtaaggcctttctttt

*Homo sapiens* ribosomal protein, large, P0 (RPLP0)

(SEQ ID NO: 45)

tcaccaaaaagcaaccaacttagccagtttttatttgcaaaacaaggaaataaaggcttacttctttaaaaagt

*Homo sapiens* ribosomal protein, large, P1 (RPLP1)

(SEQ ID NO: 46)

acctcttttataacatgttcaataaaaagctgaacttt

*Homo sapiens* ribosomal protein, large, P2 (RPLP2)

(SEQ ID NO: 47)

attcctgctcccctgcaaataaagccttttacacatctc

*Homo sapiens* ribosomal protein S3 (RPS3)

(SEQ ID NO: 48)

cagggtctccttggcagctgtattctggagtctggatgttgctctctaaagacctttaataaaattttgtacaaagacacaaggtctgactagact
gttcagtattcagactgaggggcatgttggcctctggagcattacatatcttcttggttttaaccatacttgtggtatttgcaagggccagaacag
taagacccaagcagagccaaccagagaaataatatttgtgtgatagagaaggctgatagcaagcaaggcagcaccttgattcgttgtcctgt
agttcaggattgtaggtttagaagagggatatgtttgagttttcctatgcataaggcgatccacgttgcacatagaaagtgaatataaatggcc
attatattttgtgtcatgctgtgctctaagtgttctttacatatgtactcgttaatcaacctctctaaagtgtaaaggaaatttgcttgcaccactgaa
ggcacataaggctcagaagtaaatttgcctaagcagtataaagctatcattagaatccacattcctaagttgtgttctcttaggggatcatggaa
ccagtcattggtactacaggctattatgttctggagaactgtgaagaacatttaaattgtctctgatttttatctatcaatgttttgaagtattttctacc
agtgtctgtacttcacaagaaattcggcactattttttcaggcaaaactagtgagggacaggttggcttgaaaatcatgagactgttgttaaatc
agatgctggttgatcacagaggggacttccagggaaagctgttatcaggtggctgcttcctggtgatgcagcctggctgatgagataaccct
ggctccacagatggcttagcaggtgctgtgatgatttggttttcttctcaattagactgagctgcacatggtgtttatattgcttggcacatggtaa
gggcttaatatttgaggtaattatgtagggcgtacactgacaagtatctgacccccccttccttttttgactcataaattggtcatcttaaccatttaa
gtgtacacttctatagtgacagagttagccctctgtccaagggatttgcatctgtggattcaaccaactttgggtcaaaaataatcaaaaaggat
ggttgtgtgtgtattgaacatgtagacttattttcttattttcaaaatactatattttcttgtcacttattttcttgtacactgcagttgtaacagctatgta
gcatgtacattaggtattaaaagtaatccagtgaagattgaaagtct

*Homo sapiens* ribosomal protein S3 (RPS3)

(SEQ ID NO: 49)

cagcctcttccatgagtggggagcccgctgcttgtctccagctcctagcagtgagtcctgataatctcaaatttaaggacagtaactttgtctgg
gatgagtgtgggaaaggatgtgtttgggaacagacgcgagcctgcagaggtgtttgtaaccatctctttctaagtggtgggaagcagacattt
tattcttttaactgttaatatatatagtgtgtgtttttttatgcatgaaatattttatagttttttaaaaatgcccacactactattttgaaagtaaatgaggta
atgtatgtcagaacccaatacccaaagcgatcgtagtaagaggtggggcctttgggaaggcattaaattgcttagggaatgagggtgga
accctcatgaatgagattagagccttataggagaggttggagggagttgcctggcctccctctcccatgtgaagactcagcaagaaaacatt
atttaggaagcagagagccctcatcaaacaccagatctgctggccacctgatctggcactttccagccttcagaactgtgagaaataaatttct
gttgtctat

*Homo sapiens* ribosomal protein S3A (RPS3A)

(SEQ ID NO: 50)

agttcagacttcaaatagtggcaaataaaaagtgctatttgtgatggtttgcttctg

*Homo sapiens* ribosomal protein S3A (RPS3A)

(SEQ ID NO: 51)

agctcacgttgatgtcaagactaccgatggttacttgcttcgtctgttctgtgttggttttactaaaaaacgcaacaatcagatacggaagacctc
ttatgctcagcaccaacaggtccgccaaatccggaagaagatgatggaaatcatgacccgagaggtgcagacaaatgacttgaaagaagt
ggtcaataaattgtaagtgtttctttgcttcctcacacaacacaaccttgagtattggattattcctgagatgagagaacgcatatgagacaaggt
aaaggtctgttgaaatcctgtctgtgaatccttctagctatatctctttaagtgaaagagtgttaagtactcagtaaatatgattattattactattatt
atttgagtcagagtcttgctctgttgcccaggctcgagtgcagtattgtgatcctccttggctcactgtaaccactgcttcctgggttcaagcagt
tcttgagcctcagcctcctgagtatctgggaatacagggactgccaccatacccagctaatttttttaaattttttagtagagatgggtttcatc
atgttggccaggctggtcttgaactcctgacttcaggtgatctgccagtactctaaatgataacagttttttcgtgtttatttattttgaatgaagctg -continued tctcacagtagatggagttgaaggacaggaaatgttttccctacttggaaaatacactgaataagttgagtggggtgggatgtgcctggag tcccagctactcaggaggctgaggtggtaggattgtttgagcccaggagtttgaggccagcctgggcaatataggggagaccctgtcccaaa aaataaaaaatatacgtatatatatatacacacacaaagaaaaaatacactgaatagacaaaacctttcatgattaatgatgcacgggaataag tgatgaaaaagtttcggtcccagatgatggccagtgataacaacattttttctgatgttcccatgcaatatacagttagctaagagggtgtaatg gaaaaagcataaggcttggactcagaagactctactaactttgccactagctagctatgtaattcagatcatctatcctttacatgtgaaaggta aataatggcttatcttaacaggaggatttatgcaggttaaatgaggtaggtgttatgtgtaggtttattccaaggcttctctacttttaaaggaaat ggcttatatctgagaactaggacttttagaaaaaaatttactgttactggtttgcaggattccagacagcattggaaaagacatag

*Homo sapiens* ribosomal protein S4, X- linked (RPS4X)

(SEQ ID NO: 52)

aatgggtccctgggtgacatgtcagatctttgtacgtaattaaaaatattgtggcaggattaatagca

*Homo sapiens* ribosomal protein S4, Y- linked 1 (RPS4Y1)

(SEQ ID NO: 53)

attgcagtagcagcatatcttttttttctttgcacaaataaacagtgaattctcgtttctt

*Homo sapiens* ribosomal protein S5 (RPS5)

(SEQ ID NO: 54)

ttttcccagctgctgcccaataaacctgtctgccctttggggcagtcccagcc

*Homo sapiens* ribosomal protein S6 (RPS6)

(SEQ ID NO: 55)

gatttttgagtaacaaataaataagatcagactctg

*Homo sapiens* ribosomal protein S7 (RPS7)

(SEQ ID NO: 56)

acaaaaatgactaaataaaaagtatatattcacagt

*Homo sapiens* ribosomal protein S8 (RPS8)

(SEQ ID NO: 57)

atccttgttttgtcttcacccatgtaataaaggtgtttattgttttgttcccaca

*Homo sapiens* ribosomal protein S9 (RPS9)

(SEQ ID NO: 58)

gtccacctgtccctcctgggctgctggattgtctcgttttcctgccaaataaacaggatcagcgctttac

*Homo sapiens* ribosomal protein S10 (RPS10)

(SEQ ID NO: 59)

aattggagaggattcttttgcattgaataaacttacagccaaaaaacctt

*Homo sapiens* ribosomal protein S11 (RPS11)

(SEQ ID NO: 60)

ggctggacatcggcccgctccccacaatgaaataaagttattttctcattcccaggccagacttgggatcttccgcg

*Homo sapiens* ribosomal protein S12 (RPS12)

(SEQ ID NO: 61)

agaaataaatctttggctcac

*Homo sapiens* ribosomal protein S13 (RPS13)

(SEQ ID NO: 62)

atttgtctgtgtactcaagcaataaaatgattgtttaacta

*Homo sapiens* ribosomal protein S15 (RPS15)

(SEQ ID NO: 63)

tggctcagctaataaaggcgcacatgactcc

*Homo sapiens* ribosomal protein S15a (RPS15A)

(SEQ ID NO: 64)

ggatgtaatacatatatttacaaataaaatgcctcatggactctggtgcttcc

*Homo sapiens* ribosomal protein S16 (RPS16)

(SEQ ID NO: 65)

gcccatcgtgactcaaaactcacttgtataataaacagttttgagggattttaaagtttcaag

*Homo sapiens* ribosomal protein S19 (RPS19)

(SEQ ID NO: 66)

aacaaaccatgctgggttaataaattgcctcattcgt

*Homo sapiens* ribosomal protein S20 (RPS20)

(SEQ ID NO: 67)

ctgcattctcctccgccaaaaaagtgaccaagcagagtctttctctgtcacccaggctggagtgcaatggcgtgatctcagctcactgcaacc tctgcctcctgggttcaagtgattctcgtgtctcagcctcctgagtagctgagactacaggtgtgcaccagtgttcccagctgattttttgtatttat -continued gtagagatggggttatgccatttttggccaggctagtctcgaactcctgagctcaggtgatacacacacctcagcaaatctttttaaattatacatt ctgtgatatttccttgactttatatccagcacttgtattgattattttttcattttgataatgttgggttttttaaaaactcctttatgatggaaaatttc

*Homo sapiens* ribosomal protein S20 (RPS20)

(SEQ ID NO: 68)

gtcaactattttaataaattgatgaccagttgttaacttctgttggttttttattcagaatactggcagattttaggaatataaaggtgtactatgagact tccacttttcaggtggaatatatgggtatcttagagtggtctatcctgttttcgttgtcgtttgagtcatttgaaaactggattccgttaactacataat atgtgagacctgactggttttattggacactggcagtttataactttggcatactctagataaattctgattggtatgggg

*Homo sapiens* ribosomal protein S21 (RPS21)

(SEQ ID NO: 69)

ctggagagaatcacagatgtggaatatttgtcataaataaataatgaaaacct

*Homo sapiens* ribosomal protein S23 (RPS23)

(SEQ ID NO: 70)

atattaatggtgaaaacactgtagtaataaatttttcatatgccaaaaaatgtttgtatcttactgtccctgttctcaccacgaagatcatgttcatta ccaccaccaccccccttatttttttttatcctaaaccagcaaacgcaggacctgtaccaattttaggagacaataagacagggttgtttcaggat tctctagagttaataacatttgtaacctggcacagtttccctcatcctgtggaataagaaaatgggatagatctggaataaatgtgcagtattgta gtattactttaagaactttaagggaacttcaaaaactcactgaaattctagtgagatactttcttttttattcttggtattttccatatcgggtgcaaca cttcagttaccaaatttcattgcacatagattatcttaggtaccttggaaatgcacattcttgtatccatcttacaggggcccaagatgataaata gtaaactcaaaattgctccccactctgttttattattttaaaggtgtcaggatctgtgttgtaatgtgtctacattaatgtgtttaggagaatacaggca ttggatcatttagttgatggaagtatatgccaggcaagggagataaggtatacgacaagactgatgttttcagtatcttctcatgaggttgtcag agaccttcatgtcttcaaagactagtcagcaaatgaagtggtttagtgtagagacaagattggttgtgttttgataaatttaagctaggtattgagta catgtggattttgctgtccacaaatacttgtttcagagttttcatggatacagtggcatggttgaaatgaagctgtgagccttctgctttaaatctga tgtaagaaactcctgttaacaaatagtaagtatgggttaattagccccttgatcaaagcctagctttacattgtttaggatctttggaaaacaattg gtttggttgcccactttccgtaggatcaagagcagaacctttcacatggcacagaagaacccaggttgcgcttcatacctgcatattccagcct tagcctgccatttctctccttggcactttgtgctccagcaacactggtctcagttggtcatcctcaaacttgggttccatatccagcctcaggacc tctgttcctgttactatggttccttgcatgtcgcctgctcttactaaagagctcgtgtgttttccagcacacttcggtttatctcttgatgatgatgcta gtctctccctccgcaagggcggaaaggctgcctgttggtttgtaccagtgtttcctaacgtgtagctgcagtcagtatttggctaagctgttccc agggggctcaacagatgctttcggatgagccttaactgacccaatcctttgtgatgcgggagagattgctaggcctcgctcacctggccagaa ccagggaaagaggccgcggttgcagcgcgattccaggccctgggcgtcaggcgcggggtgggcagctctccccgggcggtggggcc cttgtgaccgcgaggcggggcgcaccaggaagggagtgggacagcgcgggcgcccagggatgtggcctggttacctgccttctctgat acgtcaagacaccttcaacaatggcttgcagctgtaccctgttggctgcacccaggacgcccttttcactgctaagcagtcctacctgaggcc caggggctgccagattgacccataaataatctccggcgcctcagatccagaagctgctgagcctgatcttagtgccttctccttttctctgtgtg gccccccagcccctttccccactgccttgtgtccaaggccctttccttcatgtatccatggaggagagacaaaaatacacatcaataaaataa gatagggaatccataaatagacattcagaagtatggccaacggatttatcttaaaaccaatggaggaagaagagtttcaataaatgttgtgga cttccatttgtcaaagaccaaaacaaaggaacccaaccttacatgtaatacaaacttaactcaaaatggatcatatatctaaatgtaaaatgga aagctataaaactgaaaacagactatctttacaacctaggcgtaggtatagttttagacattacaccaaaagcacatgccgtaaaagaaaaa atagataaattggtggatttcattaaaattaaaaaactttttctctctgaaaaatcctgttaagctgggcgctgtggttcatgcctgtaatcccagc actttgggaggctgagttgggaagaaattaatagcttgaggccaggagttcaagatcatcctgggcagcaaagtcatacactcttgagggaa gagagagaccttctcatattgttttatattgttttatactcagtacctgttttaagaaaaaaacaaggaagtgaaatcaaagacaggcagcccgg caccaggcctgaaaccagccctgggcctgcctggcctaaacctagtagttaaaaatcaacttacgacttagaacctgatgttatccgtagatt ccaagcattgtataaaaaaattgtgaaactcccgttgtgttctgtaccagtgcatgaaacccctgtcacatatccctagattgctcaatcaatc acgacccttcatgtgaaatctttagtgttgtgagcccttaaaagggacagaaattgtgcacttgaggagctcagatttttaaggctgtagcttgc cgatgctcccagctgaataaagcccttccttct

*Homo sapiens* ribosomal protein S25 (RPS25)

(SEQ ID NO: 71)

ataggtccaaccagctgtacatttggaaaaataaaactttattaaatc

*Homo sapiens* ribosomal protein S26 (RPS26)

(SEQ ID NO: 72)

ggagctgagttcttaaagactgaagacaggctattctctggagaaaaataaaatggaaattgtactt

*Homo sapiens* ribosomal protein S27 (RPS27)

(SEQ ID NO: 73)

aagcactctgagtcaagatgagtgggaaaccatctcaataaacacattttggataaatcctg

*Homo sapiens* ribosomal protein S27a (RPS27a)

(SEQ ID NO: 74)

ctgtatgagttaataaaagacatgaactaacatttattgttgggttttattgcagtaaaaagaatggttttaagcaccaaattgatggtcacacca tttccttttagtagtgctactgctatcgctgtgtgaatgttgcctctggggattatgtgacccagtggtctgtatacctgccaggtgccaaccact tgtaaaggtcttgatattttcaattcttagactacctatactttggcagaagttatatttaatgtaagttgtctaaatataa

*Homo sapiens* ribosomal protein S28 (RPS28)

(SEQ ID NO: 75)

gcttggctgctcgctgggtcttggatgtcgggttcgaccacttggccgatgggaatggtctgtcacagtctgctcctttttttttgtccgccacac gtaactgagatgctcctttaaataaagcgtttgtgtttcaagtt

*Homo sapiens* ribosomal protein S29 (RPS29)

(SEQ ID NO: 76)

atgctcttccttcagaggattatccggggcatctactcaatgaaaaaccatgataattctttgtatataaaataaacatttgaaaaaaccccttc

*Homo sapiens* ribosomal protein L15 (RPL15)

(SEQ ID NO: 77)

tataagtaaagtttgtaaaattcatacttaataaacaatttaggacagtcatgtctgcttacaggtgttatttgtctgttaaaactagtctgcagatgt ttcttgaatgctttgtcaaattaagaaagttaaagtgcaataatgtttgaagacaataagtggtggtgtatcttgtttctaataagataaacttttttgt ctttgctttatcttattagggagttgtatgtcagtgtataaaacatactgtgtggtataacaggcttaataaaattctttaaaaggagagaactgaaac tagccctgtagatttgtctggtgcatgtgatgaaacctgcagctttatcggagtgatggcaatgctctgctggtttattttcaagtggctgcgttttt tttagtttggcaggtgtagacttttttaagttgggctttagaaaatctgggttagcctgaagaaaattgcctcagcctccacagtaccatttttaaatt cacataaaaggtgaaagctcctggttcagtgccatggcttcatggcattcagtgattagtggtaatggtaaacactggtgtgttttgaagttgaa tgtgcgataaaattattagccttaagattggtaagctagcaatgaatgctagggtgggaagctggtgagccagtggccattagataaataccctt tcaagtgtgagcttagacgtcaacccaaaatacttaaccgtaatgctaattgtgatcattatgaatcccttcagtcacattagggggaaagtag ttggctataagtacgtcattcttagtccagtcagtcttaaaaacatcttgggttaccactctgtccactcccataggctacagaaaaagtcacaa gcgcatggttttccaaccatatgtgttttctgcagttatttctcttgttctggccaaacaaccctaaaaatccttaccattccacaaagttggaccatc acttgtgcacccactttgactatgagtataccaccacattgcatttctgtttgcaccatgtcttccaggagactagactactgttgtccagggtca atttgagtgtaaagaaaatgtagacaaggaattgcccaattttaaattctgactttgctgacttaatttaaatgctcgttctgaaccaattttctccta tcttctctaggggtttcaaaagactcagttaattgatttccaggaagtactcatagcaagttcataaaagttcttgagacctaaatttcttcacaaa aaaagaaaagatcttaagtcatacatttttaattgtgtagaggttgttcaactgaaggaataaatgtctattaaactaaaacaaatggaccttc

*Homo sapiens* ribosomal protein L15 (RPL15)

(SEQ ID NO: 78)

gcaattcttctgcctcggcctcccaaatagccaggactacaggcgcacactgccatgcccagctaagttttgtattttagtagagactgggttt cactatgttggccaggctggtctcgaactcctgacctcaagtgatccacctgccttggcctcccaaagtgctgggattacaggcgtgagcca ccaccccagcccaatttttatttttgtacagacaggatctcactatgttgcccaggttggtctcaaactactggcctcaagcaatcctgccttg gcctcccaaagtgctggaattataggaatgagccaccacaccgggcccaaatttactttagtaataacaacaattggctgggtgcggtggct cacgcctgcaatcccaacactttcggtaaccaaggtgggcttgagctcatgagttagagagcagcctgagcaacgtggtgagagcccatct cacaaaaaataacaaatcagctgggcatggtgttgcacgcctgtagtctccgaaatcacaccactgcactcccatcttgggtgatagagcca gaacttgtctcaaaaataacaattggtttcttacaatcccaaaaggtgcagttactagtattaatccttttttgccaatgaggaaacacaaagatg aagcaacttgctcaaagtcatacagtgacagtctgaattcaaatcctatacacttaaagtttatttgttttgttttggtttttttgagatggagtctca ctgtgtcgcaaggctggagtgcagtggcacgatctcagctcactgcaacccgggttcaagcgattctcctgcctcagcctcccgagtagctg ggactacaggcacgcaccaccacacccagctaatttttgtatttttagtagagacggttccaccatgttggccaggatggtctcgagctcctga cctcaggtgatcctcccgccttggcctcccaaagtgccgggattacaggtgtcagccactgcacgtggccaacttaaagttttttgatagataat -continued acattaacgttaaaaattcaaaagataagtataggctctacagtacaaacccttctgcctcctagttcctctccctggaggcaaggtgatcagtt taacaatatttttttattttgagacagggtctcactgttgcccaggctggagtgtagtggcgcgttcacaacttactgtagcctcaacctcctggct caagcaatcctcccacctcagcctgtcgagtagctggaaccacaggtgcacaccaccatgccaggctaattttgtatttttgtagagacag ggtttcaccatgttgttcaggctggtctcaaagtcctgggctcaagcaatcttcctgtctctgcttcccaaagtgctgggattacagatgtgggc cacggtgcctggcctacatatgtatttttttcctttcttcccccaagtggtaggatatgatacacattgttgattttttttgtttagttatgtatctcagagc ttattctttatcagctcatgaggaacttcattttttttttttttttgagatgtagttttgctcttatagcccaggttggagtacagtaacacaatcttggct cgcagcaacttctgcctcccaggttcaagcgattctcctgcctcagcctccgagtagctaggattacaggtgcctgccactacatccagctatt tttgtattttcagtagagacggggtttcaccatttttggccaagctggtctcgaactcctgacctcaggtgatccgcccatctcagcctcccaaag tagtgggattacaggcatgagcaaccgtgcccggctggaacttcattcttttggtataactgcatggtatcccatcatgtggatgtaccatgatt cattggatgtggaccctcctgatggacatttaaatttcttccaatctgttgctattacaaaagaaaaatgtgtgcatacatctttattcatctgtag aataaaattcttagaagt

*Homo sapiens* ribosomal protein S2 (RPS2)
(SEQ ID NO: 79)
ggttttatacaagaaaaataaagtgaattaagcgtg

*Homo sapiens* ribosomal protein L14 (RPL14)
(SEQ ID NO: 80)
gtggcaatcataaaaagtaataaaggttctttttgacctgttgacaaatgtatttaagcctttggatttaaagcctgttgaggctggagttaggag gcagattgatagtaggattataataaacattaaataatcagttc

*Homo sapiens* ribosomal protein S14 (RPS14)
(SEQ ID NO: 81)
acaagattcctcaaaatattttctgttaataaattgccttcatgtaaactgtttc

*Homo sapiens* ribosomal protein L10 (RPL10)
(SEQ ID NO: 82)
gggcttccaatgtgctgccccctcttaatactcaccaataaattctacttcctgtccacctatgtctttgtatctacattcttgacggggaaggaa cttcctctgggaacctttgggtcattgcccttcacttcagaaacaggttgacaactcagccctgctcatgaggcagcaaacccctgcaaggg ctgggactggtggccttatgtcagttgtctactctggagcttgacttggacctccccaggtcctaggcagtaggttgaaaaacactgaagtgct tttcatgaagcacagctgcagcaaagccttgcaatcccaggctgggtcagcctacagttgtgttgcttattacaacacatgcggaccaaga ggggcttgtgggctagaggctgaccagcagcgtttatttagcaagggtaggtgtgcatcacattgggcttgttctcacccatctggtttggcca ttcctccttggtgggaatcatccaggtactgctgaggtcacctgcgatttgccccatttcctatctctagcaacctcctgggccccatgccccca cccttctagaacctgcattcccagggccttcaccacctgaccaaaggtctaggctaaccttggtcatttgtaacaagacctcggaacagac acgtgtgtggcatggtttggcctggggatcttagatgtctgacctgaactattgtagaacagcgctggcttttgggggagcagcaaaaatgag aggagtgctaggtgggtggcctgagcatctgtatccagggacaggactccaaaggcttttggtcccagagctggggtatgttggccccagc ccccagcctgtggctcccaaaaggcctctggttttttgtaatctcagttacagccatttcttaggttttaattaccttatttttattttgccaaacata cctgggaataccttttattttttttttaccttggggtgatggttccaaaccataaatgtgattatagttaacacatgaccttctagcgtcccagcca gtgtttttcctgacctctgttcttggagaggaggatggaagggaggggtccggcacgctgctggcattttgctgtgtcctgcagccccttcc gggacacctgggttcacacagcttttagcttacataactggtgcagattttctgtgtggagatgttgccttgaccagccttggctggactttacc aggcatgcagaagcctgtaccaacacagactacagcacccaggaggtgcgagtgtggctgctcagcggttataacaggcctgactgcatt gttcaccggattataatgagccaaaatgtttcccggtgtttgctggtttcagggaaggagtttgatatagcagattaaccaccctccttgtagcta ttgggggcttaatggtttcctggtgattcttaccaatccacaataaacatggcccattggcatatctgc

*Homo sapiens* ribosomal protein L10a (RPL10A)
(SEQ ID NO: 83)
ggcacatttgaataaattctattaccagttc

*Homo sapiens* ribosomal protein L35 (RPL35)
(SEQ ID NO: 84)
ggggcgcattgtcaataaagcacagctggctgagactgc

*Homo sapiens* ribosomal protein L13a (RPL13A)
(SEQ ID NO: 85)
gcccaataaagactgttaattcctcatgcgttgcctgcccttcctccattgttgccctggaatgtacgggacccaggggcagcagcagtccag

```
gtgccacaggcagccctgggacataggaagctgggagcaaggaaagggtcttagtcactgcctcccgaagttgcttgaaagcactcgga gaattgtgcaggtgtcatttatctatgaccaataggaagagcaaccagttactatgagtgaaagggagccagaagactgattggagggccct atcttgtgagtggggcatctgttggacttTccacctggtcatatactctgcagctgttagaatgtgcaagcacttggggacagcatgagcttgct gttgtacacagggtatttctagaagcagaaatagactgggaagatgcacaaccaaggggttacaggcatcgcccatgctcctcacctgtattt tgtaatcagaaataaattgctttt
```

*Homo sapiens* ribosomal protein L36 (RPL36)

(SEQ ID NO: 86)

```
gccctccctgccctctccctgaaataaagaacagcttgacag
```

*Homo sapiens* ribosomal protein L36a (RPL36A)

(SEQ ID NO: 87)

```
gtgtcatctttTattatgaagacaataaaatcttgagtttatgttcacttcatttgtttgctgttcatcttttgggagggaataagctagagccatcaat acaattccgcttgtggggaaatttatgcctcttactggtactacttgttttgcattgaagctgactggttgagttcacatcatatgttgcaatttTcta atttggcacttcaatcactaggggccttatgaggcagtttgtcattatgcaatggttattggttatcatgtgagtagacacatttcaggctaatagg gagaagtcagtaacacattcatagtgaatatgagatgtctttgctaagagttaagtgtcagatctttgttataacagttaatttaataaagaattttg gcattgttcttc
```

*Homo sapiens* ribosomal protein L36a (RPL36A)

(SEQ ID NO: 88)

```
ttgccgtaaggatatgcacttgtctctagtccacacacttcatgatataggtatagcgttagtttagcgaagttttcactgcactgatatatctagta ggtgatggagctgggaatgcaactcatgtctgactagtccacaatactgcactatttcagtgtttacgattttttatccttTccttctgaagaggc aaaaaattgaggaatgtgccctgattcctaagaactgaagtgtgagtacactggtaaatcctttcatttgccttgttccttatctgtcaatatgtct gaatcctcgcttgttggttgcactaagaattgttctgttgtttctcatcacagaaatctgcagtcaactacctgttctcgtgaagtcttaaaactctta tagaatagccatttaggcctttctgctagcctcctgaattctgtattctcaggctgagcgagtttctgtttactctcaaaccttaggtgatttggcta actcttaaagtaattagcacgatgattggaacggagcattctctccaacacagcattTcttttggcactttgcttcttgtgcagtttagctccagaa agtattaaggaatgactttagtgctcatttggatgcagtaagtggtttgatctcagggtggcaaaaagaatgctttTtttataccttTtcacattcgg ataacttgtttagaagacagaggttctaactaggttttggcctattaagaactgcaaactagcagcagcagaactctggctaaaggggcaagc ttattaggaaattgagtatttaaaagttgagctaccatatgatccaacaatcccactgctgggtatataccCagaagaaaatcggtatatcaaag agatatctgcactcctatgtttgttgtagcactgtttataatagctaagatttagaagcaaccttagtgtccatcgggatgaatggataaagaaaa tgtacctatacgcggccaggcacggtggcttgtgcctagcactttggaaagccgaggcgggtggatcacctgaggtcaggagttcgagac cagcctggccaagatagtgaaaccccgtctctagtaaaaatacaaaaattagccgggcttgtggtgtgggcctgtaatctcagccacccgg gaggctgaggcaggagaatcgcttggaacctgggaggcagaggctgcagtgagccgagatcacgccactgtactccagcctgggcgac agagcaagactccatctcaaaaaaaaaaaaaaaaaagggaaaagaaaatgcacctatacacagtggtactattcagccataaaaaga atgagatccagtcatttacaacaacatgggtggaactggagatcgttatgttaagtgaaataggcacacaaagacaagcatcacatgttcttgt ttgtgggatctaaaaatcaaaacaagtggacttgtcatatagagagtagaaggatggttaccagaagctgagaacttctggtggcgggaggt ggggatggttaatgggtacaaaaagaaaaagaatgaattagaccaactatttgatagcacgacagcgtgactaaagtcaataacttagttac atattttaaaataacttagagtgtaattggattgtttgtacctcaaagaaaaatgcaataaaactttacagtggagaaacctaacaagcactacc tcagccaggtaatcaaggttaacatcaacagtcacgagtcatgttgatatatacccttgataaggtgtgatgaaaatgacacttaaacctaaaa atccataaccctatctaatgagaaaaataacaaatcccaagaggggcattTtacaaaatacttgaccagtagtgcggaaattgtcaaggtcatc aaaaaagtctgagaaattgccacagccaaaggagtctagagacatgatgactaaatgttaggtggtgtcctgcgtggggtcctagaacaga aaaaggacattag
```

*Homo sapiens* ribosomal protein L41 (RPL41)

(SEQ ID NO: 89)

```
accgctagcttgttgcaccgtggaggccacaggagcagaaacatggaatgccagacgctggggatgctggtacaagttgtgggactgcat gctactgtctagagcttgtctcaatggatctagaacttcatcgccctctgatcgccgatcacctctgagacccaccttgctcataaacaaaatgc ccatgttggtcctctgccctggacctgtgacattctggactatttctgtgtttatttgtggccgagtgtaacaaccatataataaatcacctcttccg
``` ctgttttagctgaagaattaaatc

*Homo sapiens* ribosomal protein S18 (RPS18)

(SEQ ID NO: 90)

gtctgtaggccttgtctgttaataaatagtttatatac

*Homo sapiens* ribosomal protein S24 (RPS24)

(SEQ ID NO: 91)

agtgtctagcagtgagctggagattggatcacagccgaaggagtaaaggtgctgcaatgatgttagctgtggccactgtggattttcgcaa gaacattaataaactaaaaacttcatgtgtctggttgtttg

*Homo sapiens* ribosomal protein S24 (RPS24)

(SEQ ID NO: 92)

tgtcactgccatggccgccttgctgcatttctgaggatgcttcatctctccaccttcttctccactcagcagccagcagggcactgtggaaatc ggagtcacatgagctggcacctctgttcagaaccctccagggctccacatctctctcacccaaatgccaaagacctccccacgcccccaca atccccacgacctggccactggcctccaccacctccagctccagcggctcctaccacatttaaggctttccttcctagttttaattttcctc gtcagcagttgattttattattttcttgtttattggtattttcccactagaaatgaagctgcgtgaagttagagattttttttttggtctgtgttcctaatta gctcattgctataccctggcgcccagaacaatgccttggacacagtacgcagtagactaaataaatacttgttgaatgactgactgacggaa tgacggctgtgtggggagtggattgggtcgtgaggcagaggctgcggtggaaactcaggcaggaggtgatggtggttcttggggctgcg gaatgccaagtttagaagctcttcctctgctgtggcacatgaaccggtcactcgagaaggcttttagatttactttgcctaatccctcttagtgc atgtggggaaactgaggtacacaaaaggaattccccaccaagttaggggcagaacctagccccttgtctcccagatggatatcttcttttttt tttgagacggagtcttgctctgttgcccaggctggagtgcagtggtaccatcttggctcactgcaacctctgcttcccaggttcaagcgattctc ctgcctcagcctcctgagtgtctgcgattacaggtgcacacaaccacgcctggctaattttttgtattttagtagagacggggtttcaccgtgttg gtcagggtgacctcaaactcctgacctcatgatccacccagctcagcctcccaacgtgctgggattacaggcatgagccaccgtgcctggc tggacatcttgttattaaagcttcttctctctttgtaggggaggggagatgcctctggtggagaagaccagtgtggcagtgactgtgtctgtta gtgaacctggtggctggttgagggtctgtcgtggtgactgaggacacatacaaagtgcttttctcagtggtcaccttggtgttggtgaataagg gtcagaagatggctcctgtcctagggcactgccagtcggtttggaagctgaaatgcctgcttagcagtttgaggaaacacagaccttggagg atcttctggttgcctcttcaagaattcattctattcccttctgctccccaaatttgcttttcttggggtgggtcttggttggcctaagccaagaaagt atggcatctactccttccatagcaatagctcaggaataggcagtgacccagacctgaaccaatcagtgcatggaattacccctggccaaagt ggttgattgaggctgggtgcaagcagagttgtgagaaggctcccatttggtggttggagagatcgcacttgctccagaggtcataatgtgca gatctgaggcttggaactgctgcagacattttgctaccacaagtgaagccaccctgacgacacagttgacaatttggagcagggcagagct gagagaacagcagggaaacagccagagtcttgctcaagcctccctgaagtatctataccctggactctagttatgggggctaataaatgtt atatactgtttaaggt

*Homo sapiens* ribosomal protein L8 (RPL8)

(SEQ ID NO: 93)

tgctgagggcctcaataaagtttgtgtttatgcc

*Homo sapiens* ribosomal protein L34 (RPL34)

(SEQ ID NO: 94)

aaaaatgaaactttttgagtaataaaaatgaaaagacgctgtccaatagaaaaagttggtgtgctggagctacctcacctcagcttgagaga gccagttgtgtgcatctctttccagttttgcatccagtgacgtctgcttggcatcttgagattgttatggtgagagtatttacacctcagcaaatgct gcaaaatcctgttttccccagagagctggaggttaaatactaccagcacatccctagatactactcaagttacagtatatgatcactaatatag tatgctcttggtaccaggagctctgatatatatctggtacatgtttgataatgacttgattgttattataagtacttattaatacttcgattctgtaaag agtttagggtttgattttataaaatccaaaatgagccttttattgaatccagttctctatgtgaccagttctctgtatgaatggaagggaaaagaatt aaaaatcttgcaaagggg

*Homo sapiens* ribosomal protein L34 (RPL34)

(SEQ ID NO: 95)

aaaaatgaaactttttgagtaataaaaatgaaaagacgctgtccaatagaaaaagttggtgtgctggagctacctcacctcagcttgagaga gccagttgtgtgcatctctttccagttttgcatccagtgacgtctgcttggcatcttgagattgttatggtgagagtatttacacctcagcaaatgct gcaaaatcctgttttccccagagagctggaggttaaatactaccagcacatccctagatactactcaagttacagtatatgatcactaatatag tatgctcttggtaccaggagctctgatatatatctggtacatgtttgataatgacttgattgttattataagtacttattaatacttcgattctgtaaag -continued agtttagggtttgattttataaaatccaaaatgagcctttattgaatccagttctctatgtgaccagttctctgtatgaatggaagggaaaagaatt aaaaatcttgcaaagggg

*Homo sapiens* ribosomal protein S17 (RPS17)

(SEQ ID NO: 96)

attttttctgtagtgctgtattattttcaataaatctgggacaacagc

*Homo sapiens* ribosomal protein SA (RPSA)

(SEQ ID NO: 97)

gctgttcttgcataggctcttaagcagcatggaaaaatggttgatggaaaataaacatcagtttctaaaagttgtcttcatttagtttgcttttttactc cagatcagaatacctgggattgcatatcaaagcataataataaatacatgtctcgacatgagttgtacttct

*Homo sapiens* ubiquitin A-52 residue ribosomal protein fusion product 1 (UBA52)

(SEQ ID NO: 98)

ggtggttctttccttgaagggcagcctcctgcccaggccccgtggccctggagcctcaataaagtgtccctttcattgactggagcagcaatt ggtgtcctcatggctgatctgtccagggaggtggctgaagagtgggcatctcccttagggactctactcagcactccattctgtgccacctgt ggggtcttctgtcctagattctgtcacatcggcattggtcctgccctatgcccctgactctggatttgtcatctgtaaaactggagtaaaaacct cagtcgtgtaattggtgggactgaggatcagttttgtcattgctgggatcctgtcaggcactttgaggtgtcccctcaggccttggccctgaagt gtctaggtgtgtggagatgggtagaaaattaggtacacccaatggtgtagaacgttgattctcaaattttttattttatacaaatggggtctcact atgttgtccaggctggtcttgaactcctgggctcaagccatccgcccatctcagcccctcaaagtgttgggattacaagcaagaactgccatg cctgacccagttctcagttttttgtttgtttgtttgtttgttttgagacggagtcttgctctgtcgcccaggctggagtgcagtggcgcagtctc ggcttactacaacctctgcctccggggttcacatccttctcctgcctcagcctcccgagtagctgggactacaggtgcccgccacaactcctg gctaattttttgtattttagtagagacggggtttcactgggttagccaggttggtctcgatctcctgaccttgtgatccattcgccttggcctccca gaatgctggtattacaggcgtgagccagcacgcctggcccagttactcagttttgaatctgaggccgtgacatcactcatggtctgcagtcag tgctctgcccctgagctgtaccctctcctatgataatcactcttaagaagggcaaccctttggtgttttcccttaaggtcacccaggctggaatg cagtggtgtggtcatggctccctgtaccctggaactcaggcttgggtgatcctctctcctttgcctccgaagtagccaggactacaggtgtgc acccaccaccacactcagataattgctttggtgttttaaagcttgtaatgatcagtaggctgaggtgggcaaatcataaggtcaagagttttta gatggggtgagcacagaccaattcctgtttattactgattaaaattttgagacagtctcactgtcacccaggttgggtgcagtggtaggat catagcttgctgcagccttgatctcccaggatcttgcctcagcctcccgagtagctgggactgcatgcttgtgccaccacactcggttaatattt tgtagagatggggtcttgctatgttgcccaggctggcttcaaactcctgaacttaaaagcctcctgtttagttttggttttttatcacttttttttttttttt ttgagatggagccttgctcccatcgtgcaggctggagtgcggtggcgcagtctcggctcactgcagcttctgcctctcgggttcaagcgattc tcctttctcagcctcttgagtagctggaattaccagtgtgcgccaccaccacgcctggctagttttctgtttttagtagagacagggttttgc tatgttggccaggctggtcttgaactactgacctcttgtgatctacctgtcttggccttccaaagtgctaggattacaagcgtaagccacagcgc ctggccttgctacatttttttttttttttttttttttacagacatggtctcgctatgttgcccagaatggttttgcactgggtccaagcagttctgccgca gcctcccaaagtgctgggattacaggggtgaggcaccttgctggccctgttttgattagggtgcagtgctggtgaagccggtgcacgagg ccagtgatgcatcctaatgaggggtggagttggcgggacttcctgggccagtttggggactttcacaaaagacccccatgactcagggtttt gagttcttaactgatcgaatgaaggattcaaaattaaccactccaagggggattgaaggaagaaccactcttaatggacaaaaagaaaga aaggggagggagtaacagggatatgagctctagccgcccaagctagcaatggcaacccttctgggtcccttccagcatgtggaagctttc ctttcgcttcattcaataaacagctgctgctc

*Homo sapiens* Finkel-Biskis-Reilly murine sarcoma virus (FBR-MuSV) ubiquitously expressed (FAU)

(SEQ ID NO: 99)

gtcttttgtaattctggctttctctaataaaaaagccacttagttcagtcatcgaaaa

*Homo sapiens* ribosomal protein L22-like 1 (RPL22L1)

(SEQ ID NO: 100)

gcaaaggctcccttacagggctttgcttattaataaaataaatgaagtatacatgagaaataccaagaaattggcttttagtttatcagtgaata aaaaatattatactcttgaacttttgtctcattttttgagtatgctgtttatatgattttgatttccctctgataactatcaacagtatttaaatagcttata gctggtataatttttcccacgattttccaaaatctttttatgtactcaggtaaaagtagcgttatataggaaatcttttttttagacactctcgttctgtca cccaggctggagtgcagtgactcagcttcctaaatagctggaattacaggtgtgagccaccatgcccggctaatttttttgtacttttagtagagt

```
agggtttggccatgttggccaggctggtttcaaactcctgacctcaagtgatctacccacctcggcttcccaaagtgctgattatagctgtgaa
ccaccatgcccggccaggaaatcttactgtagaacaattttttatatagctgtataaatgtatatgattgtcttgacagtctcaaatactgtttttaa
tagcttgtaaatgtaatctcaagtgcttagaacagttcttacatataagttgctctgtagtttgctcttatagttagcccaaagactctgggtgtgag
gcctgctgtaaaccaatgttaaactgcttattagaaagccctaaccacctgctttgtaggcaccagaaactcaaaaccaaatctcaactcagct
acagaatctactgtggtccttgtctgaaaaaattagttcactcggttggaatcttgtctcagagcatcctcatctctttctcaaaagcccctacccc
aacaccggcgtgttggttgtctattgaaacttacaagtggatggacccttctcccgaataaactggcctttgaaagctctaatcgaaatggttt
ggcaaaatccatactgcaggagattagggaggacaagaatgatgtgccttttgtactgctgagcctgatggtggtgccactacttcaggtac
ttagatgagtcttgatgctaatagaattgtgtcgccaaacatatctggacagttacaacctaatctatgcattaattggtttgggaattgcttgaaat
tattgtttaattcaatgttttaattcgttttcctaaaaatttaagtgcccccatcatcgtgcaatacctcagtgcagcaactccttgattcttggatgac
tgaacttcctaacttggctctgccccattgttcccatttttcatgttttttcacaaatagttaaccaggtacctactactgtgcaccgctgcagagcat
tgaggatgtatgtgatgagtaaaaacacccagcctgctctgctgtgttagtattatgacggaaactgatcaaatcacatgtgaacaaatttactg
ctacaaaagggagggcttaataaaaggaatttcatctgggaaggc
```

Homo sapiens ribosomal protein S17 (RPS17)
(SEQ ID NO: 101)
```
attttttctgtagtgctgtattattttcaataaatctgggacaacagc
```

Homo sapiens ribosomal protein L39-like (RPL39L)
(SEQ ID NO: 102)
```
ggaattgcacatgagatggcacacatatttatgctgtatcaagttcacgatcatcttacgatatcaagctgaaaatgtcaccactacctggaca
gttgcacatgttttactgggaatattttttctgttttctgtatgctctgtgctagtagggtggattcagtaataaatatgtgaaagcttttgtttcc
```

Homo sapiens ribosomal protein L10-like (RPL10L)
(SEQ ID NO: 103)
```
aggttttggcagtactgtctccttgggccatgctggtctgacttatgcttactaataaattctgtttactggc
```

Homo sapiens ribosomal protein L36a-like (RPL36AL)
(SEQ ID NO: 104)
```
actttgggatattttttcttcaattttgaagagaaaatggtgaagccatagaaaagttaccccgagggaaaataaatacagtgatattcttacgc
```

Homo sapiens ribosomal protein L3-like (RPL3L)
(SEQ ID NO: 105)
```
gctgtgtggggtggatgaaccctgaagcgcaccgcactgtctgccccaatgtctaacaaaggccggaggcgactcttcctgcgaggtctca
gagcgctgtgtaaccgcccaagggggttcaccttgcctgctgcctagacaaagccgattcattaagacaggggaattgcaatagagaaaga
gtaattcacacagagctggctgtgcgggagaccggagtttttatgttttattattactcaaatcgatctctttgagc
```

Homo sapiens ribosomal protein S27-like (RPS27L)
(SEQ ID NO: 106)
```
tgattcaaacagcttcctgaattttaattttgtgttgtctcacagaaagccttatcataaattccataattctaattaatttaccaagataatgtaattac
atttggttttgtaaggtatacagcagtaatctcctattttggtgtcagttttcaataaagttttgattatgggcaaatcccctcttttctttttttaaaat
atatttgagtatgccatacatttatatatatggtgtatatgaatttggtttaaacatttttaaaatttattctgattagtttgtgtattttttttttttttgagag
agagagtcctgctctgtcactcaagctggagtgcagtggtgcgatctcggctcactgcaacctccgcctcccaggtccaagcaattctcttgc
cttgtcctcccaagtagctgggattataggcacacaccaccatgcctggctaatttgtgtctcatttttcaagagtagaaaccctaaatattttattt
cattccttttccaaattgctatgaatgggattaaaggattacagatgtaaagtctattatttgtgaattctaaatgtagttctgctgttgtacctgtgg
aaacatcttaaagaagtacatatttgcacgtcctgcacgtgtaccccagaacttaaactataattaaaaagaatagtttcaaaaaaataca
```

Homo sapiens ribosomal protein L26-like 1 (RPL26L1)
(SEQ ID NO: 107)
```
atagaacctgttgtgcaaccacggtttaaccggagattttgaggctagggtgtgtttctttcgaacttttcggaatgtctggaacatttcatttcct
gttttgttacctgtgcctctgtaaatctacttttgcaattttaagtaataattttatgaataaaaatgggaaatgcttcctaattccacatagtatttgca
ttgttttataaataaattccacttactatc
```

Homo sapiens ribosomal protein L7-like 1 (RPL7L1)
(SEQ ID NO: 108)
```
acccaggtgaggcagggctgaaaactgcccttgggctgacttttgataggccatgccttgccactttacaagttcttttttgcatttactagtattta
agagtaaccttgagattgggaggaatagaggaggctggtacaaatagatggagacctgctgggatcagtgaatgcctgattaggacatgg
```

```
ggctatgcatagcctaagagttataggcttaaagatgtcgagtaactaaaaactgtattgctggccgggcgcggtggctcacgcctgtaatcc cagcactttgggaggccaaggcgggcagaccatgaggtcaggagattgagaccatcctggccaacatggtgaaaccctgtctctactaaa aatacaaaaatgagctgggtgtggtggcacgtgcctgtagtcccagctactcgagaggctaaggcaggaaaatcgcttgaacccaggagg cagagattgcagtgagccaagattgcaccagtgcactccagctgggcgacagagcgagactccatctcg
```

Homo sapiens ribosomal protein L13a pseudogene (RPL13AP)

(SEQ ID NO: 109)

```
gtggaaaagaacatgaaaaagaaaactgacaaatacacacaggtctcctcaagatccatggacttctggtctgagcctaataaagactgttt gtttattcctcaaaaacaaacaaacaaaaaaaaaccctctgtattataaattattctgtgtaatggtgtgttaccatacatt
```

Homo sapiens ribosomal protein L37a pseudogene 8 (RPL37AP8)

(SEQ ID NO: 110)

```
atgctcctctactctttgagacatctctggcctataacaaatggttaatttatgttaaaaaaaaaaaagagagagagagtgaaacaacaatct acacaatcagagaaaatatttgcaaatcttatatctgattagaaattagtatctggaacat
```

Homo sapiens ribosomal protein S10 pseudogene 5 (RPS10P5)

(SEQ ID NO: 111)

```
aattggagaggattatttcacattgaataaacttacagccaaaaaa
```

Homo sapiens ribosomal protein S26 pseudogene 11 (RPS26P11)

(SEQ ID NO: 112)

```
ggagctgagttcttaaagactgaagacaggctattctctggagaaaaataaaatggaaattgtactt
```

Homo sapiens ribosomal protein L39 pseudogene 5 (RPL39P5)

(SEQ ID NO: 113)

```
ggaattgaacatgagatggcacacatatttatgctgtctaaaggtcacaatcatgttaccatatcaagctgaaaatgtcaccactatctggaca gttggacatgttttttttgggaatatacttttttctctctgaatctgttaggaacttttctggttggctgggttccgtaataaatacatgagacctttcatttc aaaaaaaagaaaaataggcctccttcccaggggctccggatttcatcagccttctgtgcatgcccagccatacaaaccacgcagggatggc tccaagtg
```

Homo sapiens ribosomal protein, large, P0 pseudogene 6 (RPLP0P6)

(SEQ ID NO: 114)

```
tcaccaaaaagcaaccaacttagccagctttatttgcaaaacaaggaaataaaggcttacttctttaaaaaataaataaataaataaataa ataataaataaataaataaataaataaatagataaataaataaaaagttttctactcacactgaagtgacgaagtc
```

Homo sapiens ribosomal protein L36 pseudogene 14 (RPL36P14)

(SEQ ID NO: 115)

```
gccccctt ccctgccctctccctgaaataaagaatagcttgacagaaa
```

Further preferably, the at least one 3'-UTR element of the artificial nucleic acid molecule according to the present invention comprises or consists of a nucleic acid sequence which has an identity of at least about 1, 2, 3, 4, 5, 10, 15, 20, 30 or 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the nucleic acid sequence of a 3'-UTR of a ribosomal protein gene, such as to the nucleic acid sequences according to SEQ ID NOs:116 to 205 or the corresponding RNA sequence:

Mus musculus ribosomal protein L9 (RPL9)

(SEQ ID NO: 116)

```
GGAGGCCTCAGTTCCTGGCCCCAGAAACGAGATCCTGACCACATGAACAA

TTTGGGCTCTTTTGGGAGAATAAAAGACTTATATATTG
```

Mus musculus ribosomal protein L3 (RPL3)

(SEQ ID NO: 117)

```
TTCCAGGACCACTTTGTGCAGATGGTGGGGTCTCACCAATAAAATATTTC

TACTCACACTGGTTTTCCC
```

Mus musculus ribosomal protein L4 (RPL4)

(SEQ ID NO: 118)

```
ACTATTAAAAATTGTTAAATTCCAGAGAGCAAGTAGAGACCGCATATTTC

AATAAATCAAACATGTGGTGACAAACCCTTGTGTGACTCTTAAATTGTGG

ATGTTTCCAAGCCCCTTG
```

Mus musculus ribosomal protein L5 (RPL5)

(SEQ ID NO: 119)

```
AGCAGTTTTCTATGAAGATTTTTTCATAAAGACAATAAACATATTGATCA

AGCAGCTTTTTCTGTGTTAAGCTGTTATTAATGAGACTATAGGAAATAGT

GTGAAATTACAAAAGCAAAGAAGTAGATAGTTATTTAATTAATTAAATTA

ATTTTACCTTTTGTGTTGCACCATAACCTACCACTGGTGGGATTAAGGGC

AAGTATTACCATGCCTAGCTGAGAGTCTTTCTCCAGGAAAAACCAGCTTA

CATGGGTTCCTGCAAATCTCATGAGTGTTTCTTGGGTTTCTAGTCTTCCT

GGGAGGTGTCCTTATCTTTCAGATTTTCAGATCTGGTAATTAGCATGATC

ATCAGGACATTTATTACAAACAAATTGATTAGTGGGAAGAAAGTATCTCA

AGGTCAATCTTGGAAGTGAACAACTGGTGCTAATCCATGGCTTTAAAGAT

TTGAGAACAACGGTGAATTTGGTTTGAGGAGAAGGGGGTGTCTAGGACG

TTTCATTTTTATGGTACATGCCAGACATGAATGTACATAGGAAAATAACT
```

TGAAAGGGTCAAATATTAAACCTTGAATATCAGGTTCACTTGGGAAAGCA

TTAGGTGCTTATGCCTCTTAGTAAATAGCCCTTCATCCCAGAAGGAGCAA

GAATTGTCTTCCTGACTTAATCCAGTCTTAGCTGAGGTGCTGTGCATCTT

TATCATCTTTGCCTTGCCTCACAGTGTCAGGCTCTGTGGTACTGGGCTA

CACAGGTCAGGTAAACAGTTAACTGCTTACCTACATCCCCAGCAAAGATA

ATGTGACGATACTAAGATGAACCTATCAGAGCTTAAAGATAATGAGTTTC

AGTCACAGTGATAACTGCATGCTAACTTCAGCATGTAGAATATATGCCGA

AGCTAAAAGCCATTCCACAGTTGACTCCATCTGAAGTTAAAGTGTGTAAG

TACACAGTAAATCATGCTATATTAACTGAACTTTTTAATAAATGAGTCAT

TTGAATTT

Mus musculus ribosomal protein L6 (RPL6)
(SEQ ID NO: 120)
ATTGTTAACCTAATTAAACAGCTTCATAGGTTCTTTTGGTGTCCTTTTTG

TGTGTTGTGTGTGCACATGTTTGTTGGGTGGGTGTTTTGCTGGTGTCTTT

TCCTCTGTGTCTTCCTCTGGCCCTTTCTGGAAAGACCTGCTTAATCTGAA

GCATGTGAGCTAGGCTAGTCCACTGGGTCCTGCTCTCTGCCCATCCCCAG

CTGGCTTTGGATTAGAGGCACATACACTGCCATGGCTGCCTTTTACTGTG

GCTGTGGTTTTGCCCTTTTTTTTTAAGCAAATAGAAAATGCTGCTGACTA

TACTGG

Mus musculus ribosomal protein L7 (RPL7)
(SEQ ID NO: 121)
GGTGTCACCCATTGTATTTTTGTAATCTGGTCAGTTAATAAACAGTCACA

GCTTGGCAAATTG

Mus musculus ribosomal protein L7a (RPL7A)
(SEQ ID NO: 122)
ATGTACACTAAATTTTCTGTACCTAAATATAATTACAAAATTATCTTGA Mus musculus ribosomal protein L11 (RPL11)
(SEQ ID NO: 123)
ACTTGATCCAAAAAGCTAATAAAATTTTCTCAGAAATGC Mus musculus ribosomal protein L12 (RPL12)
(SEQ ID NO: 124)
GAAGCAACAAGAAAATATTCCAATAAAAGACTATCTGATAACCAGTG Mus musculus ribosomal protein L13 (RPL13)
(SEQ ID NO: 125)
TTCTGTGTTGGAGAGCTGCAATAAATTTTCCATAAAGCAAAA Mus musculus ribosomal protein L23 (RPL23)
(SEQ ID NO: 126)
TTCTCCAGTGTATTTGTAAAATATATTCATTAAAGTCTCTGCTCTGAGAG

CTGGTCTTCTTGACACCTTTTCCAATATCAGCTTTGCAGAAGGAAACTTA

AATTTCAGTTCAGGGCATGACCTTCATGACCTTGCAGAACTTCTTCACTT

TCCAGGTTAAGTAAAGGCGATCTTTAGGGGCTGTCCAGATGGATCAGCTA

TAAAGATTCAATTGTAGAAGGTTCACGTCTCAATGCCCACGTGGTAGCTG

TAACTTCAATTAAAAAACAAAACAGCCGGGCGTGGTGGTGCACGCCTTT

AATCCCAGCACTTGGGAGGCAGAGGCAGGCGGATTTCTGAGGCCAGCCTG

ATCTACAGAGTGAGTTCCAGGACAGCCAGGAATACACAGAGAAACCCTTG

TCTCCAAAAACCAAAAAAAACAAAACACGCATTCTTTTCAGGTCTTTGCT

GGGACCAGGTACACATAACACAGATAAATATTAGAGCAAACCATGCACAT

ATGGTAAATTATCTTTGGGTTTTGGGTCCCTAAAATAAAGTGGTGTGTTC

ATTGTG

Mus musculus ribosomal protein L18 (RPL18)
(SEQ ID NO: 127)
CCCTGGATCTTAACTGTTAATAAAAAAAAACATTGGATGATGATGGTA Mus musculus ribosomal protein L18a (RPL18A)
(SEQ ID NO: 128)
ACACAGAGACCCACTGAATAAAAACTTGAGACTGTCCTTGCTTGTTTGCT

TCTATGTCCCTGGAGAGGTCCCAGTTGGTCCCGTCCCTAACAACATGCTA

GCCCTGCTCACCTGCCTGTCAGCCTTGCTCAGTGGCATCTTTCCATAGGT

GTGTATCCCCTTAGATTAGCTTCAGCCCCACTACGATTTGTCTAGGACAT

AGCCTGAGCCCTGCCTGTGACACTGAGGGGTAGCAGTCTGTTTCTGGACT

CCAGGGTGCTGCTGTCTCAGGCCTAAGAATTCCAGACATGACTATAATCC

AAGCCTGGGGACCTGGTTGAGCTTTTTATCCTGCTGGCTCTAAGCTTCAG

CTAGGTGGAAATGAGGCCAGCCAAGCCCCACAGTGAGCTTGCAAGCTTTA

GATGGGGACAGGGTTACGCTTTGGTGAATGATGGAGGAAACATGGGGGTT

CCTTTTGTTGGGTGCAGCCAGCACGGCATCATCATGGTGCCCAATCTTGA

AAGGGCACAGGCCTGAAGCTTCCTGGGACTGTTCTGTCACAGGGAGGAAC

CTACTGCAGTTGCCTACAATTGCTACCTCTGAGGGACTTGCCTCTGGCCC

CTTGTAGACATTTCCATGTCTACACATGGCCCAGAGTACTTTCAGGGATA

GCAATGTGTGAATGGCACTTAGAAGATAACATGTGAAAGCCAT

Mus musculus ribosomal protein L19 (RPL19)
(SEQ ID NO: 129)
AGCTTCCCTCGTGTCTGTACATAGCGGCCTGGCTGTGGCCTCATGTGGAT

CAGTCTTTAAAATAAAACAAGCCTTTGTCTGTTGCCCTCTTGTTTAGC

Mus musculus ribosomal protein L21 (RPL21)
(SEQ ID NO: 130)
TGTACACAAAGAAATAAAATACCAGCACCAGGACTGTGAAGTGTTTCCT

TAGACTGTAGTGTGGGGTTTGCTCATTGGCTTTCTTGTTCAGATTTTACT

AATTGTTCTAAATGATACAGCTTAGTGTGCAGAAAATATCCTCTTGATTG

GAAAATAGCCAAATATTTACAAAACAGGTATACTAGTTTGAAGAGGCTCT

ATATGGGGGAGGGGGTGCTGGAAAACATTAGTGGGTGACCAGTAATGGT

GGTACAGCTCTAACTCCTAGCACCAGGAGTCCGAGGCAGGGGGATCTTCA

GGCTGCATGATGTGCATAGTAGCATGCTGGTATTAGGGAGTGGGTATCTG

TGGTTCCCACTTTGAAAATAACCAAAATTCTCCAAAGTGGGCAGACCTAA

GCCAGGAGAGGGCTGGCCACAGACATTTGGTACTGCTTGCTGAGAAAGCA

CTGATTGTTTTCCTAACCTAAAGATTATATATGCCCACCATACCATCTT

TGAAACAATGTGTACTGGCCTTTGGTTCACCTTTCTTGTCTTTGAAGTTG

TACTTGGTGGGTGCATTTAACCTTGCCACAGAGTGGGGAGGATAGAGTCT

AATGGACCTTAAGTGGTCTCTGGTGGCCATGTCGGCAGTGCTTAGGTTGT

AGCCCAGGGTTGGAGTCGGCAGTGACAAGCAAATAACTATATTCTTGCTT

GCTGTGGCAGCTATACAGAAATTTACGGTATAGGTAAGAGGGTTCTCTAG

AAGTACTACCTGTCTTAGTGAAAGAGATTGCTTGGTTAACATCCTGTTAT

GTAGTGGGCTACTTTTAAACTGTGTGAAGTCCCCATTAGCCACCTCCAT

AGGCAATGGAGCTAACATTCTTGCTACAGTGGCCGCAGCTCATTAACACC

TAATGATGTGTTTAACATGTGTCCACATGGTGTGAATGTGGGTACGCATG

TGCCCAGTATTCAGTTCACAGAATTGTCATCATCTTCCATCATGTCTTCA

GTGAGGGACTCTGCAGATGCCCACCCCAGTCCTTGGTTGTGGTGATTCTG

TTAGCATTAAATGCACTGGAGAGCTTC

*Mus musculus* ribosomal protein L22 (RPL22)
(SEQ ID NO: 131)
GACACATTGGTCTGCAATGTTTTGTATTAATTCATAAATAAAATTTAGGA

ACAAAACCGGTGGTTTATCCTTGCATCTCTGCAGTGTGGATTGGACAGGA

AGTTGGAAATGACAGGGACTTTAACTGGGCTGCTGCTCCTTTGTATATAG

ACACTTTTTTCCTGCTCAGAAACTTGAGTTCTCCAGTAGCAATGGCCAAA

CAGAAGAACCAGGCTAGGGGGCTGCATCTGACAGAGCAAGTAGACGAGAG

GCTGGGTGGTGGGCTCCGGCCAGCCCGAGTCTTAGAGCTGGTGGTTGGTT

ATATCTGGTGCCTGTCTCGAGGAGGGCTTGAGACACAGTGTGGTGCTCCT

CAGAAGCAGACAGGTGATTTCTTTGTGTGATTTTTCTTTTCCCCTGGGAC

AATGACAGTCAGTAAGACAGGTTTCAGGGACTTTTGTGTCCAGGTCTGAG

CACTAGTCGCTCACAGTTGTGTGTACTAACCTTCTTCCTTCCTATTGAAA

TGGCAGGGGTCTTTGAGTCTCACTGCTGCATGTTCTGCCTTCATAGGGAT

CTGTAAGTATGCTGGGCATCTGGGCTTTTAGGGGGCTCTCTATAGGGTGT

CTGAGATAGAGGTCAACAAGGGCTTATAGACAACTCAAACAAAGCCCATG

GCTTGAGCAAGTCTGCAACAAGCTGTTTGTCTAGCCTCCAGCAGAGGGCG

AGGGAGACAGCTTCCAGATGTTCCCAGTAGGTGGAGCCCCTCCAAGCCCA

GGGCTCAGGAGGCTTACAGGGTGGGAACTCCAATACTGGTGGAGGGAGGA

GGGCGTTTGATGGGAAGATAGGGAAGTTGCTGCTTCCTAAACTGTCACAA

CTGGGCTTGGATAGGAGTCATAGTCTGGGACCACAGCCCTGTGGTAGAAT

GCTAGCCTGGTGTGCTCCAGGTTTAATCTCCATCACTGCAGAAATGAGTC

CAAGCTGTGTGTACCTCCAGGGCACTGGGCATGGGGTTCCCTTGCCATTG

TGTGTGCCCGGAGAACTGGCAGGCGGGAAATGTCTTTATCAAGGGTTACC

TTGGAAGAGGTCCCAACACTGTAGGGTGCTCCTGTTGTCAAAACCTATGC

AGAGGCATCTGCTTGCTCTCTAATAACAGTATGCAATGCTAAAGGGCTCG

CTTACAGCCGGTGGCCACACTGGAGGCCTGCACATCAGGTGGCCACAAGT

TCTGCTGCTGCGCCTCCGAGGAAACACTTGGTCCTCCGATCGATTTTAAC

CTGTTGAGGCTTTGCAATCCCCTGTGGCAAAGGCTCCAGTGTTTTCTAT

TTCTATGCAAATTTCTTGAAGCAGAACTGTTACTGTCTTTCTCCTCTGCC

CTGGGAGGAGGCGCTAGCGTTTCCTTCCAACTTCAGGTGCAGCCCCCCTC

GTGGTTAGCGGTCTTAAGTTCGTGACTTGGGTTTGCAGATCTTTTTTGTT

ACATCGCCGGACCATGTGGTGGTCTTTAGCTGTAAACAACATTAACCCTG

GGTTGATTAGCATATGCTTCTAAAAGATGGTCCCAGATTCTGCGACTTGT

AATAAAATGGAAACTTGCTGGTTTTTATGCCTTTCTAACTCTTGTATTTG

AATGAATGTTGATCACTTTTTGTATTAAAGTGGCTGACACATGGCTACTG

TCACTGTG

*Mus musculus* ribosomal protein L22 (RPL22)
(SEQ ID NO: 132)
AATATCTCACCAAAAAATATTTGAAGAAGAACAACCTCCGAGACTGGCTG

CGTGTTGTCGCCAACAGCAAAGAGAGTTACGAGCTGCGTTACTTCCAGAT

TAACCAGGATGAAGAGGAGGAGGAAGACGAGGATTAGGACACATTGGTCT

GCAATGTTTTGTATTAATTCATAAATAAAATTTAGGAACAAAACCGGTGG

TTTATCCTTGCATCTCTGCAGTGTGGATTGGACAGGAAGTTGGAAATGAC

AGGGACTTTAACTGGGCTGCTGCTCCTTTGTATATAGACACTTTTTTCCT

GCTCAGAAACTTGAGTTCTCCAGTAGCAATGGCCAAACAGAAGAACCAGG

CTAGGGGGCTGCATCTGACAGAGCAAGTAGACGAGAGGCTGGGTGGTGGG

CTCCGGCCAGCCCGAGTCTTAGAGCTGGTGGTTGGTTATATCTGGTGCCT

GTCTCGAGGAGGGCTTGAGACACAGTGTGGTGCTCCTCAGAAGCAGACAG

GTGATTTCTTTGTGTGATTTTTCTTTTCCCCTGGGACAATGACAGTCAGT

AAGACAGGTTTCAGGGACTTTTGTGTCCAGGTCTGAGCACTAGTCGCTCA

CAGTTGTGTGTACTAACCTTCTTCCTTCCTATTGAAATGGCAGGGGTCTT

TGAGTCTCACTGCTGCATGTTCTGCCTTCATAGGGATCTGTAAGTATGCT

GGGCATCTGGGCTTTTAGGGGGCTCTCTATAGGGTGTCTGAGATAGAGGT

CAACAAGGGCTTATAGACAACTCAAACAAAGCCCATGGCTTGAGCAAGTC

TGCAACAAGCTGTTTGTCTAGCCTCCAGCAGAGGGCGAGGGAGACAGCTT

CCAGATGTTCCCAGTAGGTGGAGCCCCTCCAAGCCCAGGGCTCAGGAGGC

TTACAGGGTGGGAACTCCAATACTGGTGGAGGGAGGAGGGCGTTTGATGG

GAAGATAGGGAAGTTGCTGCTTCCTAAACTGTCACAACTGGGCTTGGATA

GGAGTCATAGTCTGGGACCACAGCCCTGTGGTAGAATGCTAGCCTGGTGT

GCTCCAGGTTTAATCTCCATCACTGCAGAAATGAGTCCAAGCTGTGTGTA

CCTCCAGGGCACTGGGCATGGGGTTCCCTTGCCATTGTGTGTGCCCGGAG

AACTGGCAGGCGGGAAATGTCTTTATCAAGGGTTACCTTGGAAGAGGTCC

CAACACTGTAGGGTGCTCCTGTTGTCAAAACCTATGCAGAGGCATCTGCT

TGCTCTCTAATAACAGTATGCAATGCTAAAGGGCTCGCTTACAGCCGGTG

GCCACACTGGAGGCCTGCACATCAGGTGGCCACAAGTTCTGCTGCTGCGC

CTCCGAGGAAACACTTGGTCCTCCGATCGATTTTAACCTGTTGAGGCTTT

GCAATCCCCTGTGGCAAAGGCTCCAGTGTTTTCTATTTCTATGCAAATT

TCTTGAAGCAGAACTGTTACTGTCTTTCTCCTCTGCCCTGGGAGGAGGCG

CTAGCGTTTCCTTCCAACTTCAGGTGCAGCCCCCCTCGTGGTTAGCGGTC

TTAAGTTCGTGACTTGGGTTTGCAGATCTTTTTTGTTACATCGCCGGACC

ATGTGGTGGTCTTTAGCTGTAAACAACATTAACCCTGGGTTGATTAGCAT

ATGCTTCTAAAAGATGGTCCCAGATTCTGCGACTTGTAATAAAATGGAAA

CTTGCTGGTTTTTATGCCTTTCTAACTCTTGTATTTGAATGAATGTTGAT

CACTTTTTGTATTAAAGTGGCTGACACATGGCTACTGTCACTGTG

*Mus musculus* ribosomal protein L23a (RPL23A)
(SEQ ID NO: 133)
ACTGAGTCCAGATGGCTAATTCTAAATATATACTTTTTTCACCATAAA

*Mus musculus* ribosomal protein L17 (RPL17)
(SEQ ID NO: 134)
ATTCAGCATAAAATAAAGGCAGATAAAGTTAAAGGTCTTCTGGTGGTCTT

TAATGAGCCCTGTTGGGAGTGAGGTGCTTTAACATGGAGAAGCATGTTAT

*Mus musculus* ribosomal protein L24 (RPL24)
(SEQ ID NO: 135)
TGTGGTAGAGCAGAGTTGGAAATAAAGCTCTATCTTTAACTCTAGG

*Mus musculus* ribosomal protein L26 (RPL26)
(SEQ ID NO: 136)
AGACATCTCGTGCACGGCTTTCATTAAAGACTGCTTAAGT

*Mus musculus* ribosomal protein L27 (RPL27)
(SEQ ID NO: 137)
GTATATTTTTGTTTTGGTCATTAAAAATTAAAAAAAAAAAAATACAAGTG

TCTGCCTATTGCATTTGTGTGGGAAGAGACTGG GGAAATAAAACAGGTG

TGCTGTTGTG

*Mus musculus* ribosomal protein L30 (RPL30)
(SEQ ID NO: 138)
ACAAGAAAGTTTTCCTTTAATAAAACTTTGCCAGAGCTCCTTTTG

*Mus musculus* ribosomal protein L27a (RPL27A)
(SEQ ID NO: 139)
AAGCCACACCGGAGGTTAATTAAATGCTAACATTTTCCATGTGGTCTTTG

CATCCTTCCTTGTCTGCATGTTGGAAATCTGCCTAACATTCTAGGAAGAG

GTGAGGTGTGGGCCCTTGAGAGTCAGTCTGTGGGAATAAGTGTAGCCCAA

CTATGCACAGTTGTAAATTCCTACATCCCCGTGTGTATTGGTCTTGATAT

TCAAAGAATTGATGAATGCCATTACTTTCAGTCCAAAGTGAAGAAACCTG

GTCTCAAAAAATCCCGAGGACCAGAAATGAGATGGGTTTTCCTGAAAATC

TAAAGTTCTTGAAAAACCTTGCCATCCAGATTGCTAGCAACTGCCTAGCT

TTGTAAGCTTACTGTGATGGACAGGTAGCTCAGGACGACTGGTCACTTAA

TACTGGACAGATTAGCATGGAAAACTTAAGGGGAGGAGGAGGTAGTAGGT

TCCATCCAGCTTCGCTTTGTTGGTGGCATCTAGGTGTTGTTCCAAGGGAG

CATGCCTACCTGCAACAGGACATCACTGGTTGGGAATACTGTAGAACCAG

AGCTGTGACCTTTGAACTACTAGAAAGATGAAATTTTATGTAAAGAGTAC

CTTGGAGTAAATAAATAAAGCCCAAGATCCTGATTGTCTA

*Mus musculus* ribosomal protein L28 (RPL28)
(SEQ ID NO: 140)
GCCCCACACGCCCGAAGCAATAAAGAGTCCACTGACTTCC

*Mus musculus* ribosomal protein L29 (RPL29)
(SEQ ID NO: 141)
AAAAGGCTCCTGCCAGTGTGAAGACAGACGGACTGCTGTGACACACCTCC

CCACACACTATTTGCAGATGACCAGTGTCCTATGCTGTTCTTACAAATAA

ACTCAGGCAAGATCTGTTAGCTTG

*Mus musculus* ribosomal protein L31 (RPL31)
(SEQ ID NO: 142)
CCTGCTCGTGTCAAATAAAGTTGCAGAACTGCCTTCAGGGTTTGGTTTTC

CTTTCTGTTGTCTGCCTCATGGGTGGAATTTTTGGGTCTACAGGGTGTTG

GAAATTAATCTGAGAATCTCTGTTCTGGGTACATGGGAAATTAGAAATAC

GTGAAACATTCTTTTCACAGAAGTCACTTTATTAGGATTGTGGATTTGGG

TTGGTTTTGAAACAGGGTTTCTTGTGGCACTGCTTGTTCTATAGAATAGG

GTGGCCTTGAACTCAGAAATCCACCTGCCTTTTCCTCCCTAGTATTGGCA

ATTAAATGCCCAGCTTGTTTGTAAGCTCTCATTTTCAGTTCCAGGTTTAT

GTGTGAGCCTAAGATTAGGTAAAGATTGAGGTTATAACTTAAACGTACTG

AATTAACTTATGTTGTGTGGGTCCCAGGAATTGGACCTGGGACATCAACT

CTGCCTTTCCAGCCATCTTTGCCAACCAGTAGCTCATCTCTGGGATGTGT

CTGCCCTCAAAATGACATTTTAAAAAAGTCAGTACAAAAGAACGATTTTT

ATTAAAAACCTTGAGGACAAACATT

*Mus musculus* ribosomal protein L32 (RPL32)
(SEQ ID NO: 143)
ATGGCTTGTGTGCATGTTTTATGTTTAAATAAAATCACAAAACCTGCCGT

CGTA

*Mus musculus* ribosomal protein L35a (RPL35A)
(SEQ ID NO: 144)
ACTAATGGAGAGTAAATAAATAAAAGTAGATTTGTGCTCTTGTATTTTTT

TTTCACATCTGTCCTAAA

*Mus musculus* ribosomal protein L37 (RPL37)
(SEQ ID NO: 145)
GGATTTCAATCAGTCATAAAATAAATGTTCTGCTTTCAAAAATTCTGTGG

TGATCTAAGGTACTTTAACATCGGTTCAGAGTTCGGTTATATGATTGCTC

TGGGATCCTACGCTTCTTCCTTCATAGTTCCTGTGGGTCCGAAGCTGGGA

GGGGCTGGGTGGACTCTCGGGAAAGTACTCTGAGCCTGTCTCGGTCCCC

ATCGTGTTTGCTTGGCCCTGGGCATGGAAGTGGGTGAGTGATGAGCTGAA

CGAGCAGGCTTGCTAGAGATGAGGACAGTTACTGGTGTGGTTATATCACT

ACCATGCCTACAGTGTCTTAAGACGCTTACAGTCTGTAAGGGACTTAAAT

GATTTGAGCTCTTACTTATCCTGTAGTTTCTGATTTTTAACATTTACTTG

AATAAAGCCAAGCAAGATAAGCCTTTATTCCCAGCACTTGGTGACAGGTG

GATCTATGAGTTGGGGATCAGAGCTACACATTAAAACTCTTAATTCATCT

TACT

*Mus musculus* ribosomal protein L37 (RPL37)
(SEQ ID NO: 146)
GGATTTCAATCAGTCATAAAATAAATGTTCTGCTTTCAAAAAAAAAAAAA

ATTAATCCTCTGTGATGGCCAGCAGTTAACATTCAACAGTTTCTCTCTAG

GCTCTTGATTCTCTGACTATTGTAGGGATTCGATCAGCACTCGCATACCA

GAAGTGTGAGATGGTCCGTCCTTTTTCAAGACAAGATTTCTCTGTGTAGC

CCTGGCTGTCCTGGAACCCACTCTGTAGACCAGGCTGGCCTTGAATTTAC

AGAGATCCCCTTGCCTCCGCTTGCTGAGTGCTAGGATTAAAGGCATGCGC

ACTATG

*Mus musculus* ribosomal protein L37a (RPL37A)
(SEQ ID NO: 147)
AAGCCCTGCTGTCTGAGACTTGCCTAGCCTGCAATAAACGGGTTATTTAC

GTAACTTTTTTTTTTGCCTTGTTTGTGGTTAATTAAAACATTTGGTGT

GTGTTCTATTTTTTATTTTCGAAAGATGCTTGTTTTGAGACATACTGTGT

GACCCTGGCTGGCCTTGAGTGCCTGGTTCTCCTTACAAGTGTAGATACAT

CTGGCTTAAGATTTTAGTCTTTCAGAAATAAAAATGTTGCTAAGAC

*Mus musculus* ribosomal protein L38 (RPL38)
(SEQ ID NO: 148)
ACCAGCCCTCTGCGTGTGACTATTAAAAACCCTGAAAAGTG

*Mus musculus* ribosomal protein L39 (RPL39)
(SEQ ID NO: 149)
GGATTCACACAATGGCAAGACTGAGGATTTATACTGAATTGTCATCAATC

AGTCCTACCAGATGGATTTCAACATTTAAACCTGGAGACTCTTCGTGTCT

TGAATTAGGATGTTTGTCCAGTAATAAAATATAGAACCTTTCAAAATGCT

TTTCTGGTTTATAAAGTACTGAATTGCCCTT

*Mus musculus* ribosomal protein, large, P0 (RPLP0)

(SEQ ID NO: 150)
TCCCGCCAAAGCAACCAAGTCAGCCTGCTTAATTTGAGAAAGATGGAAAT

AAAGGCTTACTTCTCTTAAAACTCCGGTCTGGATTTATTTAGTTTGTTCA

CTTAAGCAGGATGAAAAAGCAAAACCGCTACTGTTTACTTTGTGTTGGCA

TCTTTGTTTCTAAAATTAAAGCTCCTAGTGTTTTTGTGGGCTTTGTTTGT

TTTTTGAGACAGTCTCTTGACTTGGTGCCATAGCTAGTCTGGGACAAAGA

TTTTCCAGGTGTGAATTAAAGGTGTATGTCATCAA

*Mus musculus* ribosomal protein, large, P1 (RPLP1)

(SEQ ID NO: 151)
ACTGCTTTTGTTAAGTTGGCTAATAAAGAGCTGAACCTGT

*Mus musculus* ribosomal protein, large, P2 (RPLP2)

(SEQ ID NO: 152)
ATTCCTGCTCCCCTGCAAATAAAGTCTTTTTATGTATCTTGA

*Mus musculus* ribosomal protein S3 (RPS3)

(SEQ ID NO: 153)
CAGGGTCTTGGCAGCTGCATCTGGAGGCATTTAATAAAATAAAGACATTT

AATAAAATCTTGAACAAAGACAAGGCCTGACTGGATTGTGTCCAGTATTC

AACTGAGTTATGTTGTCTATGGAGCCATGCTTATTCTGTTGGTTTAAGCT

GGAGGGCATGAGCAGAGCTGACCAGAGAAGTCATGAAGTTGGTGACCCTG

TGTTGAACAATTGAGGGTTAGAAGAGCAGTTTGGTTTTGGTGCTCTTGAT

GGAACCCAGGTGCTTGGACATAGTAAGCACACATAAGACAGAGTAAGACT

GCTGTGTCTCTGGCCTGGAGTAGTCTTTCTTGCTTTTTTTTTTTTTTTT

TTTTTCTCTAGAATGAAAGCAGATGGCCCAGCGAGTTAGGTGCTTCCTAT

GAAAGCATGTGTGCTGGTTTGTCATGCACACAGCCCTGCAGGAGAGAGTA

TGGCAACACAGCCGCTCAGCATCCCAAGATAAAAAGGGAGTTTCTACTGC

CATTTTGAGCTTGGGAGTTTGAAATGTAAAGCCTGTCCATATGTTTTAAG

GATCCATGTATTTCTGTTTTGTTTGTTTTTCAAAACAGGGTTTCTCTGTA

GCCCTGGCTGTCCTGGAACCCACTCTGTATGTAGACCAGGCTGGCCTTGA

ACTCAGAAATCCACCTGCCTCTGGCGATCCATATATTTCTAAGTCCTGTA

CTTAGACGCTGTTTTGGAAAATTCATTTTGGAAGCATTTACTGTTGGTGT

GTTTTGTGGGAATGAATGATAGCTTGGGAATTCTTTTCTGTTTGGTGAG

AGTGAAGCTGTCAGCCCGGTTGTAGCCTGGCTGGTGCTCAAAGGCTTTCT

CTCATTGTCTTCACCTACGTAGCTTTACGTGGGGTAAGGACTTAAGTTAC

TTAAGTTGGGTGCACACTGACCATGTCCACAACCTGTTAACCAACTCTAC

ATGATGAGTACAGATGTACCTTTTTAGAAAGTGTTAATGTGTAGCCCTGG

CTGGCCTCTGCCTCAGGGTATTATGAATAAAGTGTGCAACCTTCATCTGG

TTGATTAAA

*Mus musculus* ribosomal protein S3A (RPS3A)

(SEQ ID NO: 154)
AATCCAGATTTTTAATAGTGACAAATAAAAAGTCCTATTTGTGATCGTT

*Mus musculus* ribosomal protein S4, X- linked (RPS4X)

(SEQ ID NO: 155)
AATGGTCTCTAGGAGACATGCTGGAAAAGTGTTTGTACAAGCCTTTCTAG

GCAACATACATGCTAGATTAAACAGCATGGTGAAACT

*Mus musculus* ribosomal protein S4-like (RPS41)

(SEQ ID NO: 156)
AGTGGACTCTGAGGGACATTGCGGGGAAGGGGCGTTTACGTTTGTTTATA

CTTAAAAGTTTTTTAAGCAGCATGTTGAATTAAAAAAGAAAGCAAGCTTC

*Mus musculus* ribosomal protein S5 (RPS5)

(SEQ ID NO: 157)
TTTCCCAGCTGCTGCCTAATAAACTGTGTCCTTTGGAACAACTAT

*Mus musculus* ribosomal protein S6 (RPS6)

(SEQ ID NO: 158)
GTCTTTAAGAGCAACAAATAAATAATGACCTTGAATCTTTCATTGGCTTT

CATTAATAGTGTAACTAGATAAATGATGGGAAAGATGAGACAGAAGAAGG

AATACATCTATAGGACTGCTAGAATATGGGGAGAGTGATTATTTTCAAAT

TAATATGTATCGAGCTTCTACCCCAAGGTAAATAAATAACATTTGGAGAC

CATTAAAATGTAGGATGGCATAGAAGAGGCCTTTACTAAGATTAATAATT

AAAGAAACACAGCCTTTAAAGTAAAAAACACACTGTGCCTTTGAAACTTG

CTAAAAAGATTAACTTCTGTCCCAAAAGGTATCAGCCATGCGCTACCAGC

CTCCCTGCCCCTACAGTGGCAGTGGCTGCATTCTTGGTGAATGGTAGTGG

AAGGGATTAAACCTAGGCCTCAGTCATGCTTCCCAGTCACTGGTACTGAT

TTGTATGCACCCGCTTAGGTGTGAAGGTAGTTTTGGTGTGTATCACAAGT

TAGCCTGTGTAGCGAAGACAGGTTTTCTCCACCGTGTTTTTTGTTACACA

TGACTATTCACAAATGTGCTGCAGACAGTAAAATGAGAAATACCCTTCCA

AGG

*Mus musculus* ribosomal protein S7 (RPS7)

(SEQ ID NO: 159)
AGAAAATGACTGAATAAAGTGTCATTCATAGTATTTGGTTGTAGTAACTT

GTCAAAATCTCAGGGCCATGGGTGCACGACAGCAGTAGCTTCTTGAATGA

ACTGAAGTTTTCAAGAGGTGCCTGGAAGGTGAAAAACACACTGAAGCCAG

TCATGTTGATATGGGGCATTCTGCTGCTGTGAAACAGACTGGGGTTCAC

ACCCACCTTGCGGGATTAGAACTTCACTGCCCTCCAACTTCTTTCTTTGT

AAACAACTGTCCACATTTT

*Mus musculus* ribosomal protein S8 (RPS8)

(SEQ ID NO: 160)
GCCTCATGTGTAGTGTAATAAAGGTGTCTGCTGTTCTATCTG

*Mus musculus* ribosomal protein S9 (RPS9)

(SEQ ID NO: 161)
TTAATACTTGGCTGAACTGGAGGATTGTCTAGTTTTCCAGCTGAAAAATA

AAAAAGAATTGATACTTGG

*Mus musculus* ribosomal protein S10 (RPS10)

(SEQ ID NO: 162)
AGTTGGAGTTTATGTTGTATTGAATAAACTTTAAAG

*Mus musculus* ribosomal protein S11 (RPS11)

(SEQ ID NO: 163)
GGGGACTCTGGCCAATGCCCTAGAACAAATAAAGTTATTTTCCAACG

*Mus musculus* ribosomal protein S12 (RPS12)

(SEQ ID NO: 164)
ATAAATTTTGGCTGATTTTTCTCTTGTATTTCTTGTTTGCTGGTATAAAA

*Mus musculus* ribosomal protein S13 (RPS13)

(SEQ ID NO: 165)
ATGCTGTTGTGTGCACAAGCAATAAAATCACTTTGAGTAACTT

*Mus musculus* ribosomal protein S15 (RPS15)
(SEQ ID NO: 166)
CCGAGGCCAATAAAGACTGGTTTTGGTCCCTGGA

*Mus musculus* ribosomal protein S15a (RPS15A)
(SEQ ID NO: 167)
ACGTAAAGCATAAATAAAAAGCCTTTGTGGACTGTGCTCAGGGTCAGTCC

TTTTGAATCTCTGCAGCAGAGTAGCTGGCTGTGCTGACTGGTGACACTTC

TGGTGATGCTCAGCTGTGAGGTTTTATGTAGATATTGAAAGCATGACCAT

TGTCTTCACTTCACCTCCAGCTTGGGTTGTATGCCAGTAACATCAGCATA

AGGTGGTTAATGACAGGATGGTCCCTTGAGTGTGCAGTGAGTCTGGTTTA

TTTGCCAATGAGAAGCACAGGCCTCCTGTATGGGTCTTTGCCTACAGCCC

CCTTTCATCACCCAGACTTGGTAGACTTACATTCTGTCACACTGTTGGCT

CTTAATCTCAGCCCTGAAAAATGCCATTTCTTGGGTATCAAGGCTAGTCT

AGATTCAGAAACCATATAAAGGTTGACAGCTGGTTTAAAAAAAAAAGGC

TTGGAGCTTGAGTTGGGTTCGCAGGTTATTCCAGGGTATCTGTCTGCACT

TTGTCTCCCAGATTTAAAGGTAAGTGCCACCATGCCTAGCATGGTGACTT

ATTAGCTTTGTTGCTGTGGAACATACATCAAATGAAACATTGGTATGGCT

CTGGTTTCACTGTCCATGGTTAGTATCTGGTGGGTGGACACCTGGTGGAA

CCAAGCTGCTCATCCCAGAACTAAGGAGCCATTCCCCAGAGACTTGTCTT

CCTACTAAGTTCCATCCCTACAGCTTCTAGTAGTAGCTTCAGAGGTTGTG

AATTGTGGACTTAGTCTGCCATAACATTTAAAATAGGTATTAAATTCAAG

TCATTTGGTCACTCAGCACCCACGTGGCTCTTCAGAACAACAGAAGCCCC

TCGGACTTGTCTGTTGAAAAACCAGTTTGAAATAATGTACCTGCTTTAG

TTGAGAAAACGCTACAACTGGTGCTGTGTCCTGCCATGCTGATGAGCTCT

GCTCTGCGACCTGCCGAACTTGGGGGATCTCTACCCCCAGACTTTGCTCA

GATCTGTTGATGATTTGTCCATGCAGGAAAGTTTACAAGGTCTCTGTGTG

TCTACTACTTACTAGTTGCTGTGACAAAAATACTGAAAGTGTTTACTGTG

TGTGAGGCACAAAGTTTGTGGGAAGCTGTACCCTCCCTCATTTTGGTGCT

GCTCCTGCCTTGACTGACAGGATGAGCTGCCCCAACCATCGTTGCCATCT

TCCATAAGAAGCAGGTGGCTCTATTGAGTTCCCTGGAGGTGATCCCAAGG

GAAGGAGGAGCCTGGGAAAGTGGATCTCAAGTCCCCTAGTCTGGCAGTTG

GCTGTTAGGAAAGTCCAGTGTCAGTGTTTGATATGTTGTAAGGAAACAA

ATTCAGTTTTATTTAGCTTATTGGCTCTGGGGAAATGGCAGTTCCCATTA

ATTGGTGCTGTCTTTCTCTTTGAGGATCAAAATTAGCTTCCTGTTCAGTT

GTTAAGCATATTTCATAGTCAAATAATCCTCTTATCTTTACAAGTGAGGT

TTTCCTTCGAGTGGATATCAGAGTCCCTCCCACGGCTTCTATCCCTCCTA

TCCTTGTGTAGGAAGTTAAGCTTGCTCATTTGTAGATTAGTGGTCGGTTA

CACTGCAATTTAGAGTATCATGTGTACTCTACACATGATTGATTCTAAGC

CCCCTTCCCTTTCCATGTCCTTCAAAAATTTTTTATTCTGAGACAGTGT

TAGGATTTTCCTGGGCTAGCCAAATGCAAGAAGTGTTGGTCCCAGACTTT

GTAATCTTTCTGCCTTAGCCTCCCAAATTCTAGGATTATAGATTTATGTC

ATGTGATGAGTGGTCTTTTAAAGATTATCTTTTATTTTTTTTGAGATGGG

GTTTTTCTGTGTAGTTTTGGCTTTCTTGGGACTTGCTCTGTAGACCCAGG

ATGGTCTTTACTCAGATCTGCTTGCCTCTGCCTCCCAACTGCTAGGATTA

AAGCATGAGCCTGAGCCTTCATGCCTGGCTGACAGGTGAATTCTCAATAC

CTACCTAGCCATAGGGAAAGTGATTGTGTCCCCTTCCTCATAGAGGGGCA

TAGTCACCCAGGCCATACCTTTAGCTTGGGCTTTTGGTCAGTGAAGAAGT

ATGAAGGGACAAGAACACTATCAAGAGCCTAATGTGCTCTGGCCTGGATG

GTCAGCACAAAATGAATAGACTTACCAAATTCTGCTGTCTCCTTGGTAGA

TGTGAAGTTGTTGGAAGAGTCCTAAATTTAGCAGACTATACTGTCAGCCT

ATCAGACTATAGGCTGCCGGAGGGCAAGTCTGCTACCTATTTCCATCTCA

TGCCTGCATTGTTCATCCCCCTATGTAACCCACCTACCTGTCACTCATTC

CTCCATCCAAAAACTATTGTAGGTTCAGTGGAAATTTCAAGCTTGCCTGT

CTCAGCATCTTTCTTACCTTACCCCTAAGGATGGCATCTCTCTTGGCTAC

ATCTTTGGTTTATCTGGAGATCCTTGATTAATTTGAACAAGAGCTACCTT

GGGTTATGCAGTTTATGCCTCCAGTGTCCCAGAGACCGGCATTTGAGAGA

TCCCTGATAGCAAACCCATAGGGTGGCCTTTTTTTCATCCACCCCATTCT

CCCTCCCACCTCCCTCTTTTGACCTTGAGTCCTCACCAGAGAGAAACCAG

GCCCACTTAATTAGTTCTACATGTGTACACTACATGGGTGCAGTGCCCAA

GCAGGAGAGGTGTTAGATTCCCTTTTAACTATAGTTAATAGACAGTTTTT

AAGCCCCAGTGGATGCTGGGAAGCAAACCTACATCCTCTAGAAGAGCAGC

TATTTCTCTGAGCCATTTCTCCAGCACCATTTTCCCCTCTTTTAAAAGCA

GGTCTTGCAGTGTGGCCTAGTCTGGCCCCCTGAGGTGTTTGCATTGCATG

GCAGGCATGTCCACAGGAACACCATAGTTCTCACCACTCGTACAGCACAG

CAAGTGGGGTGCCGCAGGGGATTATCACTTGAGTATAAAATAAGGGTTGC

TTTAGATTGAATAGGATAACCACGCGTTCTCAGAACAATCAAGGAAGGCT

GGGGTGAGCCAGCACCGACCTTAATTGTTTACTTAGTAAACTACTAAATG

TATGCACGTGTAAGCTTTTGCCTTGATTGAGGTCAAGCTGTCGAGAAATG

GTTCTCTTTACAGTGGATCCAGTCAGGATTGGCAGCAAGCACCTTTGCCT

GCTGAGCCTACATGTTGTATAGAATGGCAACGTTGTGTAGAATGGCAGTA

CATTAAATGGGTTTTTCATTTA

*Mus musculus* ribosomal protein S16 (RPS16)
(SEQ ID NO: 168)
GCCCATCTCAAGGATCGGGGTTTACCTTTGTAATAAACATCCTAGGATTT

TAACGTTCC

*Mus musculus* ribosomal protein S19 (RPS19)
(SEQ ID NO: 169)
AACAAAGGATGCTGGGTTAATAAATTGCCTCATTC

*Mus musculus* ribosomal protein S20 (RPS20)
(SEQ ID NO: 170)
GACAACTGAATAAATCGTCTTAATGGTCAAATTTTGCTGGCTTTTGTTCA

GGTTTTTTTTTTTAATTCATGTTTATGAGTGTAAATGTGTGTCACAG

GGGTGTCAGATGTTCTTTGAACCACCATGTAGGTGCTGGAAACCCAACCT

GCATCCTCGGAGAGAACAGGTTCCTTAACCACTGAGCAAGTACTGAAGCA

TTAAACTGCTTTTAAAAATGAAGGTGTGCTAACAGATTGGTCAGGTGAAA

-continued

```
AAGAGACGTTAGGTTTCCTGCAGGGGGCGCTAAGCCAATTTAAAGACTAA

GTTGGGTTAGAAAAGAGCAGATTGCATCCTTGATCTTTTAAGCCTGGGGA

TTTTGTTTTGTTTTGGGATAGGGTCCCAACACAGAACAGGCTGACCTCAT

TAAATATCAATCTTATTTGATTGCCTCTGCTCCCAGAGTACTGGAATTAA

AGGCAGGGACCACTGTATTAGCCATTCTGAGTTATTTGAAATGGACTCTG

CAGGCCATACTTGGTCAAAATTCTGCCTTCTCAATTACAGGCATGAGCCA

CTATGCCTGGTTTACTTACTAATAGATGTCCAAAGACTAGTGTATGAAAA

TTTTGCTTTTCCAGGTGATTTGTGAAAGGCAGGGTGGCCTCTCCCATGTC

ACACTACTTGGGTTACTCATGTTGCAACATATCTGCAACTTTAGGTTGAG

GGGATTTGAGCCTGCATGTGCCACTTTGGCCAACTGAACTAATCTTTAAT

TCCATCTAAAACTTTTAAATCTCAGTCATGTGTTCAACTGGAAATAACC

TAGAGTGTGCTATGTTGACTTCAGGTACACATCAAAGCAGGTTTTAGTGA

TGTAGAAGCTGTGTTTGAGTTGAACTAGTGTTGAGGCTAGGCTTAGGTAC

CATAGAACTTTGGTTTTTCAAGACAGGGTTTCTCTGTGTAGCCCTGGCTG

TCCTGGAACTCACTGTAGACCAGGCTGGCCTTGAACTCAGAAATCTGCCT

GCCTGTGCCTCCCAACACACCCAGCTCTAGCTTTAAATTCCTTGCACCAA

GAGATGCTTTATCCCTCCGCTGAGAATACAGGTGCATGTCAGCATGCTAA

ACTCTAGATAAAATTTCATCTTGTTTGAAAGGACAATAATATAAGAAAAG

TGTATTTGCACTGTATACCATGCCCTTTTGTGTTTAAAGTTAAACTGGCA

ACAGTGTCCCATAGAGGTTCCAGAAGAAACTGCTTCTAAGGGGAGGACCA

TAAAGGGAAATGCTTACCATAGAACTTTTTAAATGTTCCTACAGGTTGTA

CTCTGGATAGGTATATGAACACCTTTCTATTAGAACAGTTTTATAGTAGT

ACTTAGTGAATATGTAAATAATACTATTTGTGAAATAGTTTGAGGTTTCT

CTATAGTCCTGGCTGGCTTGAGCTCTATACCAGATTGGCTTCTAAATCAG

AAATCTGCCTCTATCTCCTGAATGGTTATGATAGAGATGCAAGTTACTTA

ATTTCTTACATGAATTGCACTTTGTACATGCTTTTGGATATGGGCCTAGG

CTTTTGCTTTTGGATTAGACTGTCTTTATTACATTTACTGGCTTGATACT

TTACAGTCTTAAGCCCACTTGCCTGGGTGTGATGCACACCTTTAATCCCA

GCACTTTGGGATTTCTGAGTTCCAGGACAGCCAGGGCTACGCAGAGAAAC

CCTGTCTTGGAGGGGAAAAAAGAAACTTTGGAAATCAAAACTTCTTGGA

AAGCCACTTTTAGAGACTTGAATCTAAGGATAACTAACCAGGTAGTAACC

ACGAGTCATTGATTCTGTGAATCTTGTATGAGTGGGTTACAGGCAGAAAT

TAACTTCCTCTGAGAGCACTGCTGTTTTAGAAATGCGACCTAGTAATTAC

CAAAGGCATTGAAGCCACTTGACTACAGTCTCAGGTTTCTGCATCTGACA

TTGCTGGGACTGTGTGGGTTTATGGGTGTAAAATAAAACAGGCGAAAGG

ATGTTGAGTGGAAAGCTTTGGCTTCAGAATCAAATTCCAAATCAATTACC

AGATCAAATCAAATGCCAGATCAAATTACAAGACTTCCTTATGACTAAAT

TCTTCAGTGACTTAGGATACTAATAGTATCTGCCTCAAAAGTGTATGTGG

TTATTTTGTCCCAGTGAAGCCAAGATTCACATGCTATGGGCATGGATTT

CCTGAGGACATGCTAGCCTATGGTATGAGTTACTTGAAAGGACTCTGAGA

AATCTTAGTCCCCAGCTGTGAGGTTTTTAAAGATCATGCTCAATGGAAAG

TGGGGCAGTAATTTGAGAGCATGGCACAAATGAGGTTTTATCTTTTGAAA

CTAAGTGAATCTATGTCCTTGGACTAGCATATTTTAAATCACACATCAAA

TGAAATTTCTGTTCAATTCCTATAAACAGTTTATTTCATATTTTGTAGTT

ACCATTTTCATTAACAGCATACACCCTTCAATTGTGTTGCTAAAACTGAG

TCACATTATTCTGTAAGAACTTACTCCAGTATCACAACTTGGTGCTCATC

CAATATTTTTATTTTCATTCTATTTTCCCTGTCTAGCCACGTATGGCCCT

ATTCTCTCTTCTTGGATTGACCCTAGCTTCAACACAAGAAAGCTTGCAGT

ATTTTTTTTTGCGCCTGGTTCATTGTTTTGTCCTCAAGTTCTATCCATG

TGTCCAGAAATTCGAGGATTTTTAAAATTTACTTTTCTGCCTAAATACT

GGTATGTGGATAGTCTGTTATTTTACTGTTGGTTGCATATCTGTAGCAT

ATTTCTGTATTTGCAATGACTACATTGAATGTCCCTTAGTTAACCTCATT

CTTCTTAACTATTTTGTAGGCGTTTGCTATTCAAAGCACAATCTCAATTA

AAATGTTTTTAATAGCATCTTTCCACTTGGATGTGTAAAGAAAGTATTTC

TAGAAGTCTGAATTTTTGTTGCATTGTAGATGTGTACACAATAGGGCTGG

GAAAGTAGCTCACAGTGGGTAAAAGCCATTTGTTGCCAATCCTAACAGCC

TGAGTTCAATCCCAGAATCTATAAGGTAGAAGAAAAAAACCCCAGCTCCC

ACAAGTTATCTGGCCCTCTGCACACATATAAATAGTGCAATAAAAATTAA

CCATTTAAAAATATAAA
```

*Mus musculus* ribosomal protein S21 (RPS21)
                                    (SEQ ID NO: 171)
```
GCAGAAGAAATCGGGAATTTGTTACAAATAAAAGTTTTAAGTACCTGTGA

CAGTTAAG
```

*Mus musculus* ribosomal protein S23 (RPS23)
                                    (SEQ ID NO: 172)
```
AATTTGACAATGGAAACACAGTAATAAATTTTCATATTCTGAAAAAATA
```

*Mus musculus* ribosomal protein S25 (RPS25)
                                    (SEQ ID NO: 173)
```
ACAGGTTCAATCAGCTGTACATTTGGAAAAATAAAACTTTATTGAATCAA

ATGAATGGGTGCATCTGTTTCCTAAGGCAGCCGGGGAGGATTTGGTCTTA

GGAATAATAGCTGGAATTGGTTTGTTGGCCATGAAGTCAGATGCAATTGC

GCCTGGGAACCTTCAGCTTTTCCCTTTACGTGGTTGCTTGCTTCTTGTTG

CAGCTTCGGTTTTGAATTGATGCCTGAAAGAAAATAAAAACTTAGCAAGA

CTAATGGTAAATCT
```

*Mus musculus* ribosomal protein S26 (RPS26)
                                    (SEQ ID NO: 174)
```
AGAGGCCGTTTTGTAAGGACGGAAGGAAAATTACCCTGGAAAAATAAAT

GGAAGTTGTACTTTACATGGC
```

*Mus musculus* ribosomal protein S27 (RPS27)
                                    (SEQ ID NO: 175)
```
AAGCCCCTGATTGAAGATGAGTGGGAACCTTCCCAATAAACACGTTTTGG

ATATAT
```

*Mus musculus* ribosomal protein S27a (RPS27a)
                                    (SEQ ID NO: 176)
```
TTGTGTATGCGTTAATAAAAAGAAGGAACTCGTACTTA
```

*Mus musculus* ribosomal protein S28 (RPS28)
                                    (SEQ ID NO: 177)
```
TCTTGCAGCTGGGTTCTGGATATCCACTACTTAGCCCACGGAATGATCTG
```

-continued

CAACTGTTAAATAAAGCATTTATATTAATTCTTGTCTAGAAA

Mus musculus ribosomal protein S29 (RPS29)
(SEQ ID NO: 178)
GCGACCTTGAATGGATTCGACTGACTACTACCAAGTGGAACCGATCATGC

TAGTCTTTGTACACAAAGAATAAAAATGTGAAGAACTTTAA

Mus musculus ribosomal protein L15 (RPL15)
(SEQ ID NO: 179)
TACACGTGATATTTGTAAAATTCATATCCAATAAACAATTTAGGACAGTC

ATTTCTGCTTAAAGGTGTTATTTGTTAAAACTAGTCTACAGATTGTCATG

AGTGTTCTGTGAAAATGTAGAAGTTAAGTGCAATAATTGAAAACTGCAGG

TGATGGCATATCTTGTTTCTGATGTACTTTGCATTATCTGCTTATGAGAT

TAAGTGTATATAGTGTTTGTGCCAAGTGGTGTTCTGTGTGTAAGACCCTG

TAAGAGGTAAAAAGTCCTGAAACTGACCCTGGATGTGTTGGTGCATGAGA

TAGAATCTACAGCTTTACGATGGCATCTTTTGGTTCACTGAAGTGGCTGC

TTGGGAGTTTGATGAGTACAAACTTTATAGAGTTGGATTTTGCTTAGAAA

TGTGTAGGAAGAGAGGGTTTCAAAACCTGTTTTGTGCATAGAAAAGTGAG

ATCAACTATAACCCACATTTTGAGAATTGAATCCAGTGTTATTTTCAGAA

GACCAGGTAAATTTGTTGGAAGAGGTTTCACTTTCTGTTGGATCTAGAGT

ATGGATTTGGAGATGAAGGTTGAACATTGGATGTAGTAGGGCTTATTTAG

GGCAGATTATTTCCATTAGATTTGTAAACTTGGTTGTGGTTGCAAGTTAA

TATCAACCAAGCAAATATAAGTTTGATTAAGCTTGCAGACATTAAGCTTT

TCTAGCAGCTGGTGTGTGCAGAGGCAGATGGCTCTCTGGTTCCAGGACTA

CCTACAATATAGAGAAATTTTCTCTATTCCAGTCAATTCATCATGGGTAA

GAATAGTCCATTTTGGTAGTGTTATTTCATCGTTTACAATCTACCTATGG

GTAGTGGCTGGTAACTGCCTGGATGTTGACATTTCACAAAGGCCATACTT

AACCACACTTTTATTTCTATTTGTGCGATGCCTTGGAGTAGTTTCCCAAA

GTGATTTTGAGTGTGGAAGAAATGGTATTGTCCCCGAACAGCTGGCTTGG

TCTCAAAATCTAATTGATGCTTTTATTAAATTGGTTTTCCTTTGGAGATT

TTAAAAGGATGATTTGATTTCCAGAAAATACTAGACTCAAAATCTTGATA

GCTAAAATTCTTTTCTATTCAGCAAAACAAGTCACTGTATAGAGGTTGTT

CAAATCAACTAAAGTAATAAATGTCTTAAACAAGTGG

Mus musculus ribosomal protein S2 (RPS2)
(SEQ ID NO: 180)
GGGTTTTTATATGAGAAAAATAAAAGAATTAAGTCTGCTGATT Mus musculus ribosomal protein L14 (RPL14)
(SEQ ID NO: 181)
GGCTACACAGAATAATAAAGGTTCTTTTTGACGGTGGTAAATCTCATGTG

TGGACTCTAAGCTTGTCGCCAAGTGGGAAATAGACTGGTGGGATTGTAGA

TAGGATGGGCTACTTAAACTCATTCTACCCAGGCCTTAGTACTTAGCATA

CAGCCAGAGTCAAACTGATCCTTTATACAGGGGGTACCATGACAGTACAA

CAGTGTCGTTAACCCTAACAAATAAATTTCCCACCAACGGGTGGAATTCC

TTCATTTTG

Mus musculus ribosomal protein S14 (RPS14)
(SEQ ID NO: 182)
ACAGGACTTCTCATTATTTTCTGTTAATAAATTGCTTTGTGTAAGCTA Mus musculus ribosomal protein L10 (RPL10)
(SEQ ID NO: 183)
AGGCTTCAATAGTTCTCCTATACCCTACCAAATCGTTCAATAATAAAATC

TCGCATCAAGTTCGCTT

Mus musculus ribosomal protein L10a (RPL10A)
(SEQ ID NO: 184)
GATGCTCCAATAAACCTCACTGCTGCCACTCAG Mus musculus ribosomal protein L35 (RPL35)
(SEQ ID NO: 185)
GATGACAACGACAATAAAGTGCGAGACTGACTGGCT Mus musculus ribosomal protein L13a (RPL13A)
(SEQ ID NO: 186)
ACCCAATAAAGACTGTTTGCCTCATGCCTGCCTGGCCTGCCCTTCCTCCG

CCGCCAACTAGGGAAGTGGGGACCAAAGGTTCCTTAGGCACTGCTCCTGT

GGGTAGAGGGGACATTAGAGAGCTGACAGCGCACCACCTGCATGAGTTTT

TATTAAAGTGCAAACCATGGGATGAATCAGTTGAGCTTCAGTGTTGAAAA

TGAGTAGCAGGGCTGCCCCACCCACCTGACCAAGTACCCTATTCTGCAGC

TATGAAAATGAGATCTGCACATGAGCTGGGGTTCACAAGTGCACACTTGG

AGCACTGCCTTGCTCCTTCCCAGCAGACCACAAAGCAGTATTTTTCTGGA

GGATTTTATGTGCTAATAAATTATTTGACTTAAGTGTG

Mus musculus ribosomal protein L36 (RPL36)
(SEQ ID NO: 187)
TGAACCCTCCCCCAATAAAGATGGTTCCTAC Mus musculus ribosomal protein L36a (RPL36A)
(SEQ ID NO: 188)
GCAGATTTTGTTATGAAGACAATAAAATCTTGACCTTTCAACCCCTTTGA

TTGCAGTTGTTCGTTTGGGAGGGAATACATTAAAAGCTTTCAGAAATTAC

CTG

Mus musculus ribosomal protein L41 (RPL41)
(SEQ ID NO: 189)
GCCAGCCCGTGCACCTACGACGCCTGCAGGAGCAGAAGTGAGGGATGCTG

AGGGCCGGGACAAGCTATCGGACTGTGTGCTGCCATCGGTAATGAGTCTC

AGTAGACCTGGAACGTCACCTCGCCGCGATCGCCTGGAGAAATGACCGCC

TTTCTTACAACCAAAACAGTCCCTCTGCCCTGGACCCCCGGCACTCTGGA

CTAGCTCTGTTCTCTTGTGGCCAAGTGTAGCTCGTGTACAATAAACCCTC

TTGCAGTCAGCTGAAGAATCAAACTGC

Mus musculus ribosomal protein S18 (RPS18)
(SEQ ID NO: 190)
GTCTCTGGGCCTTTGCTGTTAATAAATAGTTTATATACCTATGA Mus musculus ribosomal protein S24 (RPS24)
(SEQ ID NO: 191)
AATACCTAGCAGTGAGTGGAGATTGGATACAGCCAAAGGAGTAGATCTGC

GGTGACTTGATGTTTTGCTGTGATGTGCAGATTTCTGAGAGGACAAATAA

ACTAAAAGCTCCTACACGTCTGCTCTGCTGCTTATTGGGCATTAGAAGA

ATCAGGTGGCTGCTTGGGTGTTGATGCAGTCAAGTGCACTGGGCTTGGTG

AAAAGCCCAGTGTAAGAGGCCGGTACAGATCCTTCCTGGCAGAGGGTGGT

GATGGAGAGAACATAAATAACTACATGGGCAAAGTGTAGGACCAATTACC

CTGTTAGCATCGTCTTTGCTCAACACCTTTCTGTGTCCCTAGACTCTGAG

TTTTTTTCTAATTGATTTTTATTGAACACTGAGTGTTTTGAGGTTTTATT

TTTT

Mus musculus ribosomal protein L8 (RPL8)
(SEQ ID NO: 192)
AGTTCAGGAGCTAATAAAGTACGTCCTTTGGCTAATCCG Mus musculus ribosomal protein L34 (RPL34)
(SEQ ID NO: 193)
ATATGCACATTTTTTAAGTAATAAAAATCAAGACTTGATCTACGCTTC Mus musculus ribosomal protein S17 (RPS17)
(SEQ ID NO: 194)
TCTGTTATGCCATATTTTCAATAAACCTGAAAACAA Mus musculus ribosomal protein SA (RPSA)
(SEQ ID NO: 195)
GCTGCTGTGCAGGTGCCTGAGCAAAGGGAAAAAAGATGGAAGGAAAATAA

AGTTGCTAAAAGCTGTCTTATGGTCCTCACTGCAGACTGTACCTGGATTG

GCATTTGGCTATACAACAGAGGCATGGTCCTACTGACATGTTTTGTGTTG

AATACTTAAGCATGTGAACACATGGGTTTTTTTTTTTTAATGTAAAAT

GTAGTAACACAATGTTTAGGTGGCTTTGGTGTTAGCTCTGGAGACTTCAT

GTGTCATCTAGGTGAGGTGTTCTTTAACACAGGGTCTCTGTTCTGTCATG

CCTCATAGATCCTTCTACCTCCAGATTGGAGAGGGAAAAGGCTTATGTCA

CTGAACCTGGCCAGATTGGGATTTTGTGTCCCAGGAACAAAGTTAATGCT

AAAAAGTTAATGCCTTGGTGAGACTGATAGTCTGATGGTGTGAATTCACA

GTAAGTGGTTGGGATTGCCAGATGGAATTCCCTGAGCTGCCGTGACAGGT

GGCATTGCAGAAGTGAAGGATTCAGGAATTTGAGTGTTGGGTGGGGGCCT

GTGAATAGCACTTGGGCTGGGAGGGGAGACTGCTGCCCCTGAATGTCCTG

GAATTCAAGGACAGTACCTGGTTAAATGTTTTTCTAGCTTTTCTAAAAAG

TTTGTTAGGCCTGGCATTGGCGGCGCACACCTTTAATCCCAGCACTTGGG

AGTCAGGCAGGTGGATTTCTGGCCTGGTCTACAGAGAGTTCCAGGATAGC

CAGGGATACACAGAAATCCTGCCTCAGGAAAAAACCAAAAAGAAGTTTGC

TAAAAATAAGCATTTTTGCTTGATGGTATTGAAGATTGTAAGACATTAAA

TTGTGTCATTACTTCTCCAGGTACT

Mus musculus ubiquitin A-52 residue ribosomal
protein fusion product 1 (UBA52)
(SEQ ID NO: 196)
AGCTGTGGTCATACCTGGCATGTGACCCCGGGACCAAATAAAGTCCCCTT

CCATCCACTGGAGCAGC

Mus musculus Finkel-Biskis-Reilly murine
sarcoma virus (FBR-MuSV) ubiquitously
expressed (FAU)
(SEQ ID NO: 197)
GTCCTATTGCCACCCTGCCATGCTAATAAAGCCACTGTGTCCAGACTTCT Mus musculus ribosomal protein L22-like 1
(RPL22L1)
(SEQ ID NO: 198)
TTGGCCTCTGCTTGTAATACAATGAAAGTATTCTAAAGAAATATAAAATT

GGACTTTATGAGAAAATAAAAGTCATTTCACTCT

Mus musculus ribosomal protein S17 (RPS17)
(SEQ ID NO: 199)
TCTGTTATGCCATATTTTCAATAAACCTGAAAACAA Mus musculus ribosomal protein L39-like (RPL39L)
(SEQ ID NO: 200)
GGAACCACACGTACTTATGCTGTAACTTACTGTAGCGTTTACAGCGTTAC

CGCTGTCTGGACAGCTGAGTGTGTTCTTAGGAATATAAGTTTTCTTTCT

GTGCTTTAGTGAGTTCATTCAGCAGTTCAGTAATAAATATGTGAAACCTT

TTGTTTCGAAAAAAATTGCTTCTGTGTTACAACTTACTTTGTTTTATGGT

TCAGGATCATCTGCATAATAGACAAGTATTCTATCAGTGAGCGATATCCT

GGATCTTGTTTGTGTAGTTTGGGGTTGAGACAAGTCCAGACTGCCCTAAA

ACTCACGATCTTCCTTCCTCGGCCTTCTAAATGATTGGAGGACTCCAAAC

CTAAGTGATGGAAGTAAAAAGAAACTTATATGTCAAGACTCATTTTCTCT

ATCATTTCATGTGACAATTGAAATTAGATTATTTCTTTTTTCAATC

Mus musculus ribosomal protein L10-like (RPL10L)
(SEQ ID NO: 201)
GGACTTTGCTGGCAGAAAAGAAGTACAGATGAGGTTATAGTTTGAAAAAC

GTTAATTCCGTTTATTGACTTTAGAATGTTACTTTGCATAGTATAGACCA

TTACAATGGAAAGTACCTGCCTTAAGAAACAAGAAAACTGCAGTTTATAG

AGAAAGAATTTTCAATTTTGACCCATGTACTTAAAATTTTTGGTGTATAC

TGCAGTGTAGCAAATGTTTTGTGGTGACGGTATAAATGGTACTGTTTGTT

ATCTTGGATTAAGAGTGGCTAGAGAAGTTGGAAGACGTGTGAGAAGTTCT

TTATAGAGAATTAAACATGAAAATTACATCTC

Mus musculus ribosomal protein L36a-like
(RPL36AL)
(SEQ ID NO: 202)
AACTTGTGTTCTCTGAGAGGAAAATACTGAAGCAGTAGAGAAATGACCTG

CTAGAGAATAAAGTTACTGTTAATGATACC

Mus musculus ribosomal protein L3-like
(RPL3L)
(SEQ ID NO: 203)
GATGTCTGGAATGGAGCACACCTGGGATGTAGCACTCTTGCTATCTGTCC

GGTCCTTTTTGTTCAATAAAGTCCTGAGGCAACTCTCTCTGTC

Mus musculus ribosomal protein S27-like
(RPS27L)
(SEQ ID NO: 204)
TGAGCTATGAAGTTCCGGAATTTGTGTTTTTCACAGAAAGCCTTACCAAC

TTCAGTTACTTTACCAAGACAATGTAATTATTGTTTGATTTTATAAAGTC

TACAACAATGATCTCCTATTTTGGTGTCAGTTTTTCAATAAAGTTTTAAT

TA

Mus musculus ribosomal protein L7-like 1
(RPL7L1)
(SEQ ID NO: 205)
AGCAGGAGCAGGTTTTCCAAAAGCACCCCTCGGAAGTGTTTTTGTCGTCG

TTTAAAATTATCAAGTATCTTCAGAGAAGATTATTTTCTGCCTTCAGAAA

CTGAAGGAAGGCTTGGGCCTAGAGAACGACAGTAAGGTGCGAGCACCGGA

GACACTTAACACAGCTCAGTCCATGGAAGGACGAGTTCCCTCATTGGCTG

CCTGTCTCGAAATCCACGCAAGCTGTGGAGGAAAGAATTACCCTGCTCAT

CCTGCCTTCTATCTTGGTGTTTAATGTTGGGTGGGCAACAAGCACAAACC

TCCCTCCCACCCCCTCCAAGACTGTTAGAGCAGTGGGCCAGACCAAGCGG

CGCACTTGAACATGGATCAAGAGGGTCCCGGTTTTACTTTTTATTTTTGT

CAGGGTAGGCAGTCTTGTGTTTGCTTTGTTCAAAGCAGGGTCTCCCTGTT

GGCCCTGGCTGGCCTTATACTCCACAGCAGTCCTGCCTCCTCCTCCTAGG

TGCTGGGATTAAAGGCGTGCGCCACCACGCCCGGCTACAGCCTGCATTTT

TATGCACATTGGTCTGTTAAGCTAGTTGCATTCTGTGCTACCGGAGGGGA

-continued

```
CTGAAGTTTAATCACTTGTCTTCTATTAAAAACTAGTGTTTGCCTGGGCC

TGGTGTGTATACCTTTAGTTGCAGCGCTTGGGAGGCAGAGGCAGGCAGAC

TTCATGAGTTCAGGGACAGGCAAGCCTGCTCTACAGATTTCCAGGATACC

CAGGGCTACACATAGAGAAAATGTTAAAGATAAACAAAAAGCTGGACAGT

GGGGGAGCACACCTTTAATCCCAGCACTCGGGAGGCAGAGGCAGGCGGAT

TTCTGAGTTCGAGGCCAGCCTGGTCTACAGAGTGAGTTCCAGGACAGCCA

GGACTACACAGAGAAACCCTGTCTCAGAAAAAAAACAAAACAAAAACCAA

TGCAGTGATAGATTGTTGTTTCCTAAACCACATGTACCCAGGAAATGCCC

ACTAAATTTCACCTGGATCAGTGTTAACTGATCATTGGGAAATGAGGTGA

CCAAAAATGCATCGCAACCTTGGACAAACAGCATGGCTATTTAACATTCT

GGGATCCTGCAGAATCCTGCATCTTCCTAAGTAGGGAAGCACTGTAGCAT

TGGAGAGAGGCCTGGGCGAGCAGAGCTAAGGCTTCCATTTCTGGCTTGCT

TGGAATTTAAAACAAGCTTTTTTCTATATAGTAAAAGATTGTTTTTAAGA

TTTTTGCGTGTGAGTACATGCCAAAGTAGCCAGGAAGTGTCACTTGCCCT

GGAGCTAGAATTACTGGCAAATGAAGGCTCAGAGGTGGATGCTGGGACCA

ATTCTAGGCCCTCTGAGAAAGCAGGTGCACTTGGCTTGTGCCTCCAGCCC

CAAAGGCGATGGCTTATTGTGAGCCTGAGGCCAGCCAGGGTTACAGAGAC

TCAAGAAACAAGTGGGGTTGTCCATGTTGCTGGAGATGACCCAGGTCTAT

TAGGACCTTGACTACATGGATAGACATTCTGGCAGCTAGTATACTGCCAT

TGGGGCCTATGGAGAAGTAGCCACCGAGCCTATTTAGAAAGAAGGACTGC

TGGCAAGCTTGGTGTCACTATGAAGGCAGACAAAGATCGATGTATTAACG

ACCCCGACTCCAAAAACACTCGAGGGGGCCCAAGGTGGGCTCAGTGGTTA

AGAGCCGTTCGCCCAGGGGCTGGAGAGTTGGCTCAGTGGTACCACATGGT

GGCTCACAACCATCTGTAATGAGATCTGACGCCCTCTTCTGGTGTATCTG

AAGACAGCTACAGTGTACTTACATAAAATAAATAAATCTTT
```

In a preferred embodiment, the at least one 3'-UTR element of the artificial nucleic acid molecule according to the present invention comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the 3'-UTR sequence of ribosomal protein Small 9 (RPS9). Most preferably, the at least one 3'-UTR element of the artificial nucleic acid molecule according to the present invention comprises or consists of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to SEQ ID NO: 1 or SEQ ID NO: 2

```
                                              SEQ ID NO: 1
GTCCACCTGTCCCTCCTGGGCTGCTGGATTGTCTCGTTTTCCTGCCAAAT

AAACAGGATCAGCGCTTTAC

SEQ ID NO: 2
GUCCACCUGUCCCUCCUGGGCUGCUGGAUUGUCUCGUUUUCCUGCCAAAU

AAACAGGAUCAGCGCUUUAC
```

The at least one 3'-UTR element of the artificial nucleic acid molecule according to the present invention may also comprise or consist of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the nucleic acid sequence of the 3'-UTR of a ribosomal protein gene, such as to the 3'-UTR of a sequence according to SEQ ID NOs:10 to 205, wherein the fragment is preferably a functional fragment or a functional variant fragment as described above. Such fragment preferably exhibits a length of at least about 3 nucleotides, preferably of at least about 5 nucleotides, more preferably of at least about 10, 15, 20, 25 or 30 nucleotides, even more preferably of at least about 50 nucleotides, most preferably of at least about 70 nucleotides. In a preferred embodiment, the fragment or variant thereof exhibits a length of between 3 and about 500 nucleotides, preferably of between 5 and about 150 nucleotides, more preferably of between 10 and 100 nucleotides, even more preferably of between 15 and 90, most preferably of between 20 and 70.

Preferably, said variants, fragments or variant fragments are functional variants, functional fragments, or functional variant fragments as described above, exhibiting at least one function of the nucleic acid sequence according to SEQ ID NOs:10 to 205, such as stabilization of the artificial nucleic acid molecule according to the invention, stabilizing and/or prolonging protein expression from the artificial nucleic acid molecule according to the invention, and/or increasing protein production, preferably with an efficiency of at least 40%, more preferably of at least 50%, more preferably of at least 60%, even more preferably of at least 70%, even more preferably of at least 80%, most preferably of at least 90% of the stabilizing efficiency and/or protein production increasing efficiency exhibited by an artificial nucleic acid molecule comprising the nucleic acid sequence according to SEQ ID No. 1 or SEQ ID NO. 2.

Preferably, the at least one 3'-UTR element of the artificial nucleic acid molecule according to the present invention exhibits a length of at least about 3 nucleotides, preferably of at least about 5 nucleotides, more preferably of at least about 10, 15, 20, 25 or 30 nucleotides, even more preferably of at least about 50 nucleotides, most preferably of at least about 70 nucleotides. The upper limit for the length of the 3'-UTR element may be 500 nucleotides or less, e.g. 400, 300, 200, 150 or 100 nucleotides. For other embodiments the upper limit may be chosen within the range of 50 to 100 nucleotides. For example, the fragment or variant thereof may exhibit a length of between 3 and about 500 nucleotides, preferably of between 5 and about 150 nucleotides, more preferably of between 10 and 100 nucleotides, even more preferably of between 15 and 90, most preferably of between 20 and 70.

Furthermore, the artificial nucleic acid molecule according to the present invention may comprise more than one 3'-UTR elements as described above. For example, the artificial nucleic acid molecule according to the present invention may comprise one, two, three, four or more 3'-UTR elements, wherein the individual 3'-UTR elements may be the same or they may be different. For example, the artificial nucleic acid molecule according to the present invention may comprise two essentially identical 3'-UTR elements as described above, e.g. two 3'-UTR elements comprising or consisting of a nucleic acid sequence, which is derived from the 3'-UTR of a ribosomal protein gene, such as from a sequence according to SEQ ID NO: 10 to 205, or from a fragment or variant of the 3'-UTR of a ribosomal protein gene, such as a nucleic acid sequence according to SEQ ID No. 1 or 2, functional variants thereof, functional fragments thereof, or functional variant fragments thereof as described above.

Surprisingly, the inventors found that an artificial nucleic acid molecule comprising a 3'-UTR element as described above may represent or may provide an mRNA molecule, which allows for enhanced, prolonged and/or stabilized protein production. Thus, a 3'-UTR element as described herein may improve stability of protein expression from an mRNA molecule and/or improve translational efficiency.

The artificial nucleic acid molecule according to the present invention may be RNA, such as mRNA, DNA, such as a DNA vector, or may be a modified RNA or DNA molecule. It may be provided as a double-stranded molecule having a sense strand and an anti-sense strand, for example, as a DNA molecule having a sense strand and an anti-sense strand.

The artificial nucleic acid molecule according to the present invention may further comprise optionally a 5'-UTR and/or a 5'-cap. The optional 5'-cap and/or the 5'-UTR are preferably located 5' to the ORF within the artificial nucleic acid molecule according to the present invention.

Preferably, the artificial nucleic acid molecule according to the present invention further comprises a poly(A) sequence and/or a polyadenylation signal. Preferably, the optional poly(A) sequence is located 3' to the at least one 3'-UTR element, preferably the optional poly(A) sequence is connected to the 3'-end of the 3'-UTR element. The connection may be direct or indirect, for example, via a stretch of 2, 4, 6, 8, 10, 20 etc. nucleotides, such as via a linker of 1-50, preferably of 1-20 nucleotides, e.g. comprising or consisting of one or more restriction sites.

In one embodiment, the optional polyadenylation signal is located downstream of the 3' of the 3'-UTR element. Preferably, the polyadenylation signal comprises the consensus sequence NN(U/T)ANA, with N=A or U, preferably AA(U/T)AAA or A(U/T)(U/T)AAA. Such consensus sequence may be recognised by most animal and bacterial cell-systems, for example by the polyadenylation-factors, such as cleavage/polyadenylation specificity factor (CPSF) cooperating with CstF, PAP, PAB2, CFI and/or CFII. Preferably, the polyadenylation signal, preferably the consensus sequence NNUANA, is located less than about 50 nucleotides, more preferably less than about 30 bases, most preferably less than about 25 bases, for example 21 bases, downstream of the 3'-end of the 3'-UTR element.

Transcription of an artificial nucleic acid molecule according to the present invention, e.g. of an artificial DNA molecule, comprising a polyadenylation signal downstream of the 3'-UTR element will result in a premature-RNA containing the polyadenylation signal downstream of its 3'-UTR element. For example, transcription of a DNA molecule comprising a 3'-UTR element according to SEQ ID No. 1 will result in an RNA having a 3'-UTR element according to the sequence SEQ ID No. 2.

Using an appropriate transcription system will then lead to attachment of a poly(A) sequence to the premature-RNA. For example, the inventive artificial nucleic acid molecule may be a DNA molecule comprising a 3'-UTR element as described above and a polyadenylation signal, which may result in polyadenylation of an RNA upon transcription of this DNA molecule. Accordingly, a resulting RNA may comprise a combination of the inventive 3'-UTR element followed by a poly(A) sequence.

Potential transcription systems are in vitro transcription systems or cellular transcription systems etc. Accordingly, transcription of an artificial nucleic acid molecule according to the invention, e.g. transcription of an artificial nucleic acid molecule comprising an open reading frame, a 3'-UTR element and a polyadenylation-signal, may result in an mRNA molecule comprising an open reading frame, a 3'-UTR element and a poly(A) sequence.

Accordingly, the invention also provides an artificial nucleic acid molecule, which is an mRNA molecule comprising an open reading frame, a 3'-UTR element as described above and a poly(A) sequence.

In one embodiment, the invention provides an artificial nucleic acid molecule, which is an artificial DNA molecule comprising an open reading frame and a sequence according to SEQ ID No. 1 or a sequence having an identity of at least about 40% or more to SEQ ID No. 1 or a fragment thereof as described above. Furthermore, the invention provides an artificial nucleic acid molecule which is an artificial RNA molecule comprising an open reading frame and a sequence according to SEQ ID NO. 2 or a sequence having an identity of at least about 40% or more to SEQ ID No. 2 or a fragment thereof as described above.

Accordingly, the invention provides an artificial nucleic acid molecule, which may serve as a template for an RNA molecule, preferably for an mRNA molecule, which is stabilised and optimized with respect to translation efficiency. In other words, the artificial nucleic acid molecule may be a DNA, which may be used as a template for production of an mRNA. The obtainable mRNA, may, in turn, be translated for production of a desired peptide or protein encoded by the open reading frame. If the artificial nucleic acid molecule is a DNA, it may, for example, be used as a double-stranded storage form for continued and repetitive in vitro or in vivo production of mRNA.

In another embodiment, the 3'-UTR of the artificial nucleic acid molecule according to the invention does not comprise a polyadenylation signal or a poly(A) sequence. Further preferably, the artificial nucleic acid molecule according to the invention does not comprise a polyadenylation signal or a poly(A) sequence. More preferably, the 3'-UTR of the artificial nucleic acid molecule, or the inventive artificial nucleic acid molecule as such, does not comprise a polyadenylation signal, in particular it does not comprise the polyadenylation signal AAU/TAAA.

In one embodiment, the artificial nucleic acid molecule according to the present invention further comprises a poly(A) sequence. For example, a DNA molecule comprising an ORF followed by the ribosomal 3' UTR may contain a stretch of thymidine nucleotides which can be transcribed into a poly(A) sequence in the resulting mRNA. The length of the poly(A) sequence may vary. For example, the poly(A) sequence may have a length of about 20 adenine nucleotides up to about 300 adenine nucleotides, preferably of about 40 to about 200 adenine nucleotides, more preferably from about 50 to about 100 adenine nucleotides, such as about 60, 70, 80, 90 or 100 adenine nucleotides. Most preferably, the inventive nucleic acid comprises a poly(A) sequence of about 60 to about 70 nucleotides, most preferably 64 adenine nucleotides.

For example, the artificial nucleic acid molecule according to the present invention may comprise a nucleic acid sequence corresponding to the DNA-sequence (SEQ ID No. 3)
GTCCACCTGTCCCTCCTGGGCTGCTGGATTGTCTCGTTTTCCTGCCAAAT

AAACAGGATCAGCGCTTTACAGATCTAAAAAAAAAAAAAAAAAAAAAAAA

AAAAAAAAAAAAAAAAAAAAAAAAAAAAAAAAAAAAAAAA.

Transcription of such sequences may result in artificial nucleic acid molecules comprising the sequence (SEQ ID No. 4)
GUCCACCUGUCCCUCCUGGGCUGCUGGAUUGUCUCGUUUUCCUGCCAAAU

AAACAGGAUCAGCGCUUUACAGAUCUAAAAAAAAAAAAAAAAAAAAAAAA

AAAAAAAAAAAAAAAAAAAAAAAAAAAAAAAAAAAAAAAA.

Such artificial RNA-molecules, i.e. artificial nucleic acid molecules comprising a sequence according to SEQ ID No. 4 may also be obtainable in vitro by common methods of chemical-synthesis without being necessarily transcribed from a DNA-progenitor.

In a particularly preferred embodiment, the artificial nucleic acid molecule according to the present invention is an RNA molecule, preferably an mRNA molecule comprising in 5'-to-3'-direction an open reading frame, a 3'-UTR element as described above and a poly(A) sequence.

Preferably, the open reading frame does not code for a ribosomal protein. In a preferred embodiment, the open reading frame does not code for a ribosomal protein, from which the 3'-UTR element of the inventive artificial nucleic acid is derived, particularly not for a mammalian ribosomal protein, provided that the 3'-UTR element is identical to the 3'-UTR of a mammalian ribosomal protein gene. In some further preferred embodiments, the open reading frame does not code for RPS9 or variants thereof, provided that the 3'-UTR element is a sequence which is identical to SEQ ID No. 1 or SEQ ID No. 2.

In a preferred embodiment, the ORF does not encode human or plant, in particular *Arabidopsis*, ribosomal proteins, in particular does not encode human ribosomal protein S6 (RPS6), human ribosomal protein L36a-like (RPL36AL) or *Arabidopsis* ribosomal protein S16 (RPS16). In a further preferred embodiment, the open reading frame (ORF) does not encode ribosomal protein S6 (RPS6), ribosomal protein L36a-like (RPL36AL) or ribosomal protein S16 (RPS16) of whatever origin.

In one embodiment, the invention provides an artificial DNA molecule comprising an open reading frame, preferably an open reading frame which encodes a peptide or protein other than the ribosomal protein, from which the 3'-UTR is derived; a 3'-UTR element comprising or consisting of a sequence which has at least about 60%, preferably at least about 70%, more preferably at least about 80%, more preferably at least about 90%, even more preferably at least about 95%; even more preferably at least about 99%; even more preferably 100% sequence identity to SEQ ID No. 1; and a polyadenylation signal and/or a poly(A) sequence. Furthermore, the invention provides an artificial DNA molecule comprising an open reading frame, preferably an open reading frame which encodes any peptide or protein other than the ribosomal protein, from which the 3'-UTR is derived; a 3'-UTR element comprising or consisting of a sequence, which has at least about 60%, preferably at least about 70%, more preferably at least about 80%, more preferably at least about 90%, even more preferably at least about 95%; even more preferably at least 99%; even more preferably 100% sequence identity to SEQ ID No. 3.

Furthermore, the invention provides an artificial RNA molecule, preferably an artificial mRNA molecule or an artificial viral RNA molecule, comprising an open reading frame, preferably an open reading frame which encodes a peptide or protein other than the ribosomal protein, from which the 3'-UTR is derived; a 3'-UTR element comprising or consisting of a sequence which has at least about 60%, preferably at least about 70%, more preferably at least about 80%, more preferably at least about 90%, even more preferably at least about 95%; even more preferably at least 99%; even more preferably 100% sequence identity to SEQ ID No. 2; and a polyadenylation signal and/or a poly(A) sequence. Furthermore, the invention provides an artificial RNA molecule, preferably an artificial mRNA molecule or an artificial viral RNA molecule, comprising an open reading frame, preferably an open reading frame which encodes a peptide or protein other than the ribosomal protein, from which the 3'-UTR is derived; a 3'-UTR element comprising or consisting of a sequence which has at least about 60%, preferably at least about 70%, more preferably at least about 80%, more preferably at least about 90%, even more preferably at least about 95%; even more preferably at least 99%; even more preferably 100% sequence identity to SEQ ID No. 4.

The invention provides an artificial nucleic acid molecule, preferably an artificial mRNA, which may be characterized by enhanced stability and prolonged expression of the encoded peptide or protein. Without being bound by any theory, enhanced stability of protein expression and thus prolonged protein expression may result from reduction in degradation of the artificial nucleic acid molecule, such as an artificial mRNA molecule according to the present invention.

Accordingly, the inventive 3'-UTR element may prevent the artificial nucleic acid from degradation and decay.

In some embodiments, the artificial nucleic acid molecule may comprise a histone stem-loop in addition to the nucleic acid sequence derived from the 3'-UTR of a ribosomal protein gene. Such artificial nucleic acid molecule according to the present invention, for example, may comprise in 5'-to-3'-direction an ORF, an 3'-UTR element, an optional histone stem-loop sequence, an optional poly(A) sequence or polyadenylation signal and an optional poly(C) sequence. It may also comprise in 5'-to-3'-direction an ORF, an 3'-UTR element, an optional poly(A) sequence, an optional poly (C) sequence and an optional histone stem-loop sequence.

In a preferred embodiment, the artificial nucleic acid molecule according to the invention comprises at least one histone stem-loop sequence.

Such histone stem-loop sequences are preferably selected from histone stem-loop sequences as disclosed in WO 2012/019780, whose disclosure is incorporated herewith by reference.

A histone stem-loop sequence, suitable to be used within the present invention, is preferably selected from at least one of the following formulae (I) or (II):

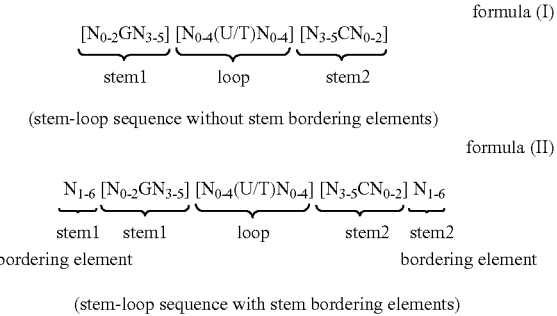

(stem-loop sequence without stem bordering elements)

formula (II)

$N_{1-6}$ [$N_{0-2}GN_{3-5}$] [$N_{0-4}$(U/T)$N_{0-4}$] [$N_{3-5}CN_{0-2}$] $N_{1-6}$ stem1    stem1      loop      stem2    stem2
bordering element                                bordering element (stem-loop sequence with stem bordering elements)

wherein:
stem1 or stem2 bordering elements $N_{1-6}$ is a consecutive sequence of 1 to 6, preferably of 2 to 6, more preferably of 2 to 5, even more preferably of 3 to 5, most preferably of 4 to 5 or 5 N, wherein each N is independently from another selected from a nucleotide selected from A, U, T, G and C, or a nucleotide analogue thereof;
stem1 [$N_{0-2}GN_{3-5}$] is reverse complementary or partially reverse complementary with element stem2, and is a consecutive sequence between of 5 to 7 nucleotides;
  wherein $N_{0-2}$ is a consecutive sequence of 0 to 2, preferably of 0 to 1, more preferably of 1 N, wherein each N is independently from another selected from a nucleotide selected from A, U, T, G and C or a nucleotide analogue thereof;
  wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof, and
  wherein G is guanosine or an analogue thereof, and may be optionally replaced by a cytidine or an analogue thereof, provided that its complementary nucleotide cytidine in stem2 is replaced by guanosine;
loop sequence [$N_{0-4}$(U/T)$N_{0-4}$] is located between elements stem1 and stem2, and is a consecutive sequence of 3 to 5 nucleotides, more preferably of 4 nucleotides;
  wherein each $N_{0-4}$ is independent from another a consecutive sequence of 0 to 4, preferably of 1 to 3, more preferably of 1 to 2 N, wherein each N is independently from another selected from a nucleotide selected from A, U, T, G and C or a nucleotide analogue thereof; and
  wherein U/T represents uridine, or optionally thymidine;
stem2 [$N_{3-5}CN_{0-2}$] is reverse complementary or partially reverse complementary with element stem1, and is a consecutive sequence between of 5 to 7 nucleotides;
  wherein $N_{3-5}$ is a consecutive sequence of 3 to 5, preferably of 4 to 5, more preferably of 4 N, wherein each N is independently from another selected from a nucleotide selected from A, U, T, G and C or a nucleotide analogue thereof;
  wherein $N_{0-2}$ is a consecutive sequence of 0 to 2, preferably of 0 to 1, more preferably of 1 N, wherein each N is independently from another selected from a nucleotide selected from A, U, T, G or C or a nucleotide analogue thereof; and
  wherein C is cytidine or an analogue thereof, and may be optionally replaced by a guanosine or an analogue thereof provided that its complementary nucleoside guanosine in stem1 is replaced by cytidine;

wherein
stem1 and stem2 are capable of base pairing with each other forming a reverse complementary sequence, wherein base pairing may occur between stem1 and stem2, e.g. by Watson-Crick base pairing of nucleotides A and U/T or G and C or by non-Watson-Crick base pairing e.g. wobble base pairing, reverse Watson-Crick base pairing, Hoogsteen base pairing, reverse Hoogsteen base pairing or are capable of base pairing with each other forming a partially reverse complementary sequence, wherein an incomplete base pairing may occur between stem1 and stem2, on the basis that one ore more bases in one stem do not have a complementary base in the reverse complementary sequence of the other stem.

According to a further preferred embodiment the histone stem-loop sequence may be selected according to at least one of the following specific formulae (Ia) or (IIa):

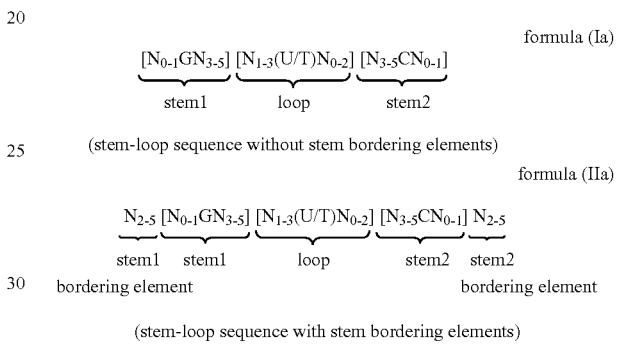

wherein:
N, C, G, T and U are as defined above.

According to a further more particularly preferred embodiment of the first aspect, the artificial nucleic acid molecule sequence may comprise at least one histone stem-loop sequence according to at least one of the following specific formulae (Ib) or (IIb):

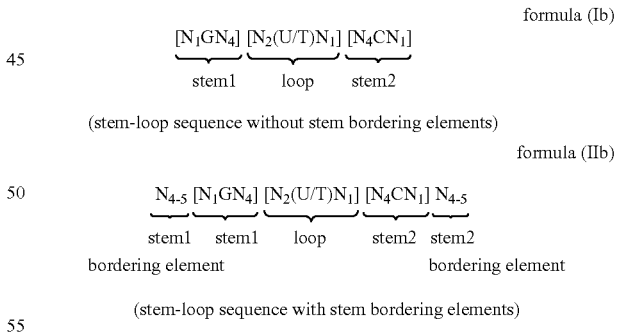

wherein:
N, C, G, T and U are as defined above.

A particular preferred histone stem-loop sequence is the sequence according to SEQ ID NO: 5: CAAAGGCTCTTTTCAGAGCCACCA or more preferably the corresponding RNA sequence of the nucleic acid sequence according to SEQ ID NO: 5.

As an example, the single elements may be present in the artificial nucleic acid molecule in the following order:
5'-cap-5'-UTR-ORF-3'-UTR element-histone stem-loop-poly(A)/(C) sequence;

5'-cap-5'-UTR-ORF-3'-UTR element-poly(A)/(C) sequence-histone stem-loop;
5'-cap-5'-UTR-ORF-IRES-ORF-3'-UTR element-histone stem-loop-poly(A)/(C) sequence;
5'-cap-5'-UTR-ORF-IRES-ORF-3'-UTR element-histone stem-loop-poly(A)/(C) sequence-poly(A)/(C) sequence;
5'-cap-5'-UTR-ORF-IRES-ORF-3'-UTR element-poly(A)/(C) sequence-histone stem-loop;
5'-cap-5'-UTR-ORF-IRES-ORF-3'-UTR element-poly(A)/(C) sequence-poly(A)/(C) sequence-histone stem-loop;
5'-cap-5'-UTR-ORF-3'-UTR element-poly(A)/(C) sequence-poly(A)/(C) sequence;
5'-cap-5'-UTR-ORF-3'-UTR element-poly(A)/(C) sequence-poly(A)/(C) sequence-histone stem loop; etc.

In some embodiments, the artificial nucleic acid molecule comprises further elements such as a 5'-cap, a poly(C) sequence and/or an IRES-motif. A 5'-cap may be added during transcription or post-transcriptionally to the 5'end of an RNA. Furthermore, the inventive artificial nucleic acid molecule, particularly if the nucleic acid is in the form of an mRNA or codes for an mRNA, may be modified by a sequence of at least 10 cytidines, preferably at least 20 cytidines, more preferably at least 30 cytidines (so-called "poly(C) sequence"). In particular, the inventive artificial nucleic acid molecule may contain, especially if the nucleic acid is in the form of an (m)RNA or codes for an mRNA, a poly(C) sequence of typically about 10 to 200 cytidine nucleotides, preferably about 10 to 100 cytidine nucleotides, more preferably about 10 to 70 cytidine nucleotides or even more preferably about 20 to 50 or even 20 to 30 cytidine nucleotides. Most preferably, the inventive nucleic acid comprises a poly(C) sequence of 30 cytidine residues. Thus, preferably the artificial nucleic acid molecule according to the present invention comprises, preferably in 5'-to-3' direction, an ORF, at least one 3'-UTR element as described above, a poly(A) sequence or a polyadenylation signal, and a poly(C) sequence.

An internal ribosome entry site (IRES) sequence or IRES-motif may separate several open reading frames, for example if the artificial nucleic acid molecule encodes for two or more peptides or proteins. An IRES-sequence may be particularly helpful if the artificial nucleic acid molecule is a bi- or multicistronic nucleic acid molecule.

Furthermore, the artificial nucleic acid molecule may comprise additional 5'-elements, preferably a 5'-UTR, a promoter, or a 5'-UTR and a promoter containing-sequence. The promoter may drive and or regulate transcription of the artificial nucleic acid molecule according to the present invention, for example of an artificial DNA-molecule according to the present invention. Furthermore, the 5'-UTR may consist or may comprise the 5'-UTR of a gene as defined herein. Furthermore the 5'-UTR may interact with the inventive 3'-UTR element and thus may support the stabilising effect of the inventive 3'-UTR element. Such elements may further support stability and translational efficiency. Accordingly, in some embodiments, the invention provides artificial nucleic acid molecules, preferably mRNA-molecules, comprising in 5'-to-3'-direction at least one of the following structures 5'-cap-5'-UTR-ORF-3'-UTR element-histone stem-loop-poly(A)/(C) sequence;
5'-cap-5'-UTR-ORF-3'-UTR element-poly(A)/(C) sequence-histone stem-loop;
5'-cap-5'-UTR-ORF-IRES-ORF-3'-UTR element-histone stem-loop-poly(A)/(C) sequence;
5'-cap-5'-UTR-ORF-IRES-ORF-3'-UTR element-histone stem-loop-poly(A)/(C) sequence-poly(A)/(C) sequence;
5'-cap-5'-UTR-ORF-IRES-ORF-3'-UTR element-poly(A)/(C) sequence-histone stem-loop;
5'-cap-5'-UTR-ORF-IRES-ORF-3'-UTR element-poly(A)/(C) sequence-poly(A)/(C) sequence-histone stem-loop;
5'-cap-5'-UTR-ORF-3'-UTR element-poly(A)/(C) sequence-poly(A)/(C) sequence;
5'-cap-5'-UTR-ORF-3'-UTR element-poly(A)/(C) sequence-poly(A)/(C) sequence-histone stem loop.

In a particularly preferred embodiment of the present invention the artificial nucleic acid molecule comprises at least one 5'-untranslated region element (5'UTR element) of a length of less than 500, 400, 300, 250, 200, 150 or 100 nucleotides and/or of more than 20, 30, 40, 50 or 60 nucleotides, which preferably comprises or consists of a nucleic acid sequence which is derived from the 5'UTR of a TOP gene or which is derived from a fragment, homolog or variant of the 5'UTR of a TOP gene.

It is particularly preferred that the 5'UTR element does not comprise a TOP-motif or a 5'TOP, as defined above.

The nucleic acid sequence, which is derived from the 5'UTR of a TOP gene is derived from a eukaryotic TOP gene, preferably a plant or animal TOP gene, more preferably a chordate TOP gene, even more preferably a vertebrate TOP gene, most preferably a mammalian TOP gene, such as a human TOP gene.

For example, the 5'UTR element is preferably selected from 5'-UTR elements comprising or consisting of a nucleic acid sequence, which is derived from a nucleic acid sequence selected from the group consisting of SEQ ID NOs. 1-1363, SEQ ID NO. 1395, SEQ ID NO. 1421 and SEQ ID NO. 1422 of the patent application WO2013/143700 whose disclosure is incorporated herein by reference, from the homologs of SEQ ID NOs. 1-1363, SEQ ID NO. 1395, SEQ ID NO. 1421 and SEQ ID NO. 1422 of the patent application WO2013/143700, from a variant thereof, or preferably from a corresponding RNA sequence. The term "homologs of SEQ ID NOs. 1-1363, SEQ ID NO. 1395, SEQ ID NO. 1421 and SEQ ID NO. 1422 of the patent application WO2013/143700" refers to sequences of other species than *homo sapiens*, which are homologous to the sequences according to SEQ ID NOs. 1-1363, SEQ ID NO. 1395, SEQ ID NO. 1421 and SEQ ID NO. 1422 of the patent application WO2013/143700.

In a preferred embodiment, the 5'UTR element comprises or consists of a nucleic acid sequence, which is derived from a nucleic acid sequence extending from nucleotide position 5 (i.e. the nucleotide that is located at position 5 in the sequence) to the nucleotide position immediately 5' to the start codon (located at the 3' end of the sequences), e.g. the nucleotide position immediately 5' to the ATG sequence, of a nucleic acid sequence selected from SEQ ID NOs. 1-1363, SEQ ID NO. 1395, SEQ ID NO. 1421 and SEQ ID NO. 1422 of the patent application WO2013/143700, from the homologs of SEQ ID NOs. 1-1363, SEQ ID NO. 1395, SEQ ID NO. 1421 and SEQ ID NO. 1422 of the patent application WO2013/143700, from a variant thereof, or a corresponding RNA sequence. It is particularly preferred that the 5' UTR element is derived from a nucleic acid sequence extending from the nucleotide position immediately 3' to the 5'TOP to the nucleotide position immediately 5' to the start codon (located at the 3' end of the sequences), e.g. the nucleotide position immediately 5' to the ATG sequence, of a nucleic acid sequence selected from SEQ ID NOs. 1-1363, SEQ ID NO. 1395, SEQ ID NO. 1421 and SEQ ID NO. 1422 of the patent application WO2013/143700, from the homologs of SEQ ID NOs. 1-1363, SEQ ID NO. 1395, SEQ ID NO. 1421 and SEQ ID NO. 1422 of the patent application WO2013/143700, from a variant thereof, or a corresponding RNA sequence.

In a particularly preferred embodiment, the 5'UTR element comprises or consists of a nucleic acid sequence, which is derived from a 5'UTR of a TOP gene encoding a ribosomal protein or from a variant of a 5'UTR of a TOP gene encoding a ribosomal protein. For example, the 5'UTR element comprises or consists of a nucleic acid sequence which is derived from a 5'UTR of a nucleic acid sequence according to any of SEQ ID NOs: 170, 232, 244, 259, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1346, 1347, 1348, 1349, 1350, 1351, 1352, 1353, 1354, 1355, 1356, 1357, 1358, 1359, or 1360 of the patent application WO2013/143700, a corresponding RNA sequence, a homolog thereof, or a variant thereof as described herein, preferably lacking the 5'TOP motif. As described above, the sequence extending from position 5 to the nucleotide immediately 5' to the ATG (which is located at the 3' end of the sequences) corresponds to the 5'UTR of said sequences.

Preferably, the 5'UTR element comprises or consists of a nucleic acid sequence, which is derived from a 5'UTR of a TOP gene encoding a ribosomal Large protein (RPL) or from a homolog or variant of a 5'UTR of a TOP gene encoding a ribosomal Large protein (RPL). For example, the 5'UTR element comprises or consists of a nucleic acid sequence which is derived from a 5'UTR of a nucleic acid sequence according to any of SEQ ID NOs: SEQ ID NOs: 67, 259, 1284-1318, 1344, 1346, 1348-1354, 1357, 1358, 1421 and 1422 of the patent application WO2013/143700, a corresponding RNA sequence, a homolog thereof, or a variant thereof as described herein, preferably lacking the 5'TOP motif.

In a particularly preferred embodiment, the 5'UTR element comprises or consists of a nucleic acid sequence which is derived from the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, or from a variant of the 5'UTR of a ribosomal protein Large 32 gene, preferably from a vertebrate ribosomal protein Large 32 (L32) gene, more preferably from a mammalian ribosomal protein Large 32 (L32) gene, most preferably from a human ribosomal protein Large 32 (L32) gene, wherein preferably the 5'UTR element does not comprise the 5'TOP of said gene.

Accordingly, in a particularly preferred embodiment, the 5'UTR element comprises or consists of a nucleic acid sequence, which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 6 (5'-UTR of human ribosomal protein Large 32 lacking the 5' terminal oligopyrimidine tract: GGCGCT-GCCTACGGAGGTGGCAGCCATCTCCTTCTCG-GCATC; corresponding to SEQ ID No. 1368 of the patent application WO2013/143700) or preferably to a corresponding RNA sequence, or wherein the at least one 5'UTR element comprises or consists of a fragment of a nucleic acid sequence which has an identity of at least about 40%, preferably of at least about 50%, preferably of at least about 60%, preferably of at least about 70%, more preferably of at least about 80%, more preferably of at least about 90%, even more preferably of at least about 95%, even more preferably of at least about 99% to the nucleic acid sequence according to SEQ ID No. 6 or more preferably to a corresponding RNA sequence, wherein, preferably, the fragment is as described above, i.e. being a continuous stretch of nucleotides representing at least 20% etc. of the full-length 5'UTR. Preferably, the fragment exhibits a length of at least about 20 nucleotides or more, preferably of at least about 30 nucleotides or more, more preferably of at least about 40 nucleotides or more. Preferably, the fragment is a functional fragment as described herein.

In some embodiments, the artificial nucleic acid molecule comprises a 5'UTR element which comprises or consists of a nucleic acid sequence which is derived from the 5'UTR of a vertebrate TOP gene, such as a mammalian, e.g. a human TOP gene, selected from RPSA, RPS2, RPS3, RPS3A, RPS4, RPS5, RPS6, RPS7, RPS8, RPS9, RPS10, RPS11, RPS12, RPS13, RPS14, RPS15, RPS15A, RPS16, RPS17, RPS18, RPS19, RPS20, RPS21, RPS23, RPS24, RPS25, RPS26, RPS27, RPS27A, RPS28, RPS29, RPS30, RPL3, RPL4, RPL5, RPL6, RPL7, RPL7A, RPL8, RPL9, RPL10, RPL10A, RPL11, RPL12, RPL13, RPL13A, RPL14, RPL15, RPL17, RPL18, RPL18A, RPL19, RPL21, RPL22, RPL23, RPL23A, RPL24, RPL26, RPL27, RPL27A, RPL28, RPL29, RPL30, RPL31, RPL32, RPL34, RPL35, RPL35A, RPL36, RPL36A, RPL37, RPL37A, RPL38, RPL39, RPL40, RPL41, RPLP0, RPLP1, RPLP2, RPLP3, RPLP0, RPLP1, RPLP2, EEF1A1, EEF1B2, EEF1D, EEF1G, EEF2, EIF3E, EIF3F, EIF3H, EIF2S3, EIF3C, EIF3K, EIF3EIP, EIF4A2, PABPC1, HNRNPA1, TPT1, TUBB1, UBA52, NPM1, ATP5G2, GNB2L1, NME2, UQCRB or from a homolog or variant thereof, wherein preferably the 5'UTR element does not comprise a TOP-motif or the 5'TOP of said genes, and wherein optionally the 5'UTR element starts at its 5'-end with a nucleotide located at position 1, 2, 3, 4, 5, 6, 7, 8, 9 or 10 downstream of the 5'terminal oligopyrimidine tract (TOP) and wherein further optionally the 5'UTR element which is derived from a 5'UTR of a TOP gene terminates at its 3'-end with a nucleotide located at position 1, 2, 3, 4, 5, 6, 7, 8, 9 or 10 upstream of the start codon (A(U/T)G) of the gene it is derived from.

Preferably, the artificial nucleic acid molecule according to the present invention, preferably the open reading frame, is at least partially G/C modified. Thus, the inventive artificial nucleic acid molecule may be thermodynamically stabilized by modifying the G (guanosine)/C (cytidine) content of the molecule. The G/C content of the open reading frame of an artificial nucleic acid molecule according to the present invention may be increased compared to the G/C content of the open reading frame of a corresponding wild type sequence, preferably by using the degeneration of the genetic code. Thus, the encoded amino acid sequence of the artificial nucleic acid molecule is preferably not modified by the G/C modification compared to the coded amino acid sequence of the particular wild type sequence. The codons of the coding sequence or the whole artificial nucleic acid molecule, e.g. an mRNA, may therefore be varied compared to the wild type coding sequence, such that they include an increased amount of G/C nucleotides while the translated amino acid sequence is maintained. Due to the fact that several codons code for one and the same amino acid (so-called degeneration of the genetic code), it is feasible to alter codons while not altering the encoded peptide/protein sequence (so-called alternative codon usage). Hence, it is possible to specifically introduce certain codons (in exchange for the respective wild-type codons encoding the same amino acid), which are more favourable with respect to stability of RNA and/or with respect to codon usage in a subject (so-called codon optimization).

Depending on the amino acid to be encoded by the coding region of the inventive artificial nucleic acid molecule as defined herein, there are various possibilities for modification of the nucleic acid sequence, e.g. the open reading frame, compared to its wild type coding region. In the case of amino acids, which are encoded by codons which contain exclusively G or C nucleotides, no modification of the codon is necessary. Thus, the codons for Pro (CCC or CCG), Arg (CGC or CGG), Ala (GCC or GCG) and Gly (GGC or GGG) require no modification, since no A or U/T is present.

In contrast, codons which contain A and/or U/T nucleotides may be modified by substitution of other codons which code for the same amino acids but contain no A and/or U/T. For example the codons for Pro can be modified from CC(U/T) or CCA to CCC or CCG;

the codons for Arg can be modified from CG(U/T) or CGA or AGA or AGG to CGC or CGG;

the codons for Ala can be modified from GC(U/T) or GCA to GCC or GCG;

the codons for Gly can be modified from GG(U/T) or GGA to GGC or GGG.

In other cases, although A or (U/T) nucleotides cannot be eliminated from the codons, it is however possible to decrease the A and (U/T) content by using codons which contain a lower content of A and/or (U/T) nucleotides. Examples of these are:

The codons for Phe can be modified from (U/T)(U/T)(U/T) to (U/T) (U/T)C;

the codons for Leu can be modified from (U/T) (U/T)A, (U/T) (U/T)G, C(U/T) (U/T) or C(U/T)A to C(U/T)C or C(U/T)G;

the codons for Ser can be modified from (U/T)C(U/T) or (U/T)CA or AG(U/T) to (U/T)CC, (U/T)CG or AGC;

the codon for Tyr can be modified from (U/T)A(U/T) to (U/T)AC;

the codon for Cys can be modified from (U/T)G(U/T) to (U/T)GC;

the codon for His can be modified from CA(U/T) to CAC;

the codon for Gln can be modified from CAA to CAG;

the codons for Ile can be modified from A(U/T)(U/T) or A(U/T)A to A(U/T)C;

the codons for Thr can be modified from AC(U/T) or ACA to ACC or ACG;

the codon for Asn can be modified from AA(U/T) to AAC;

the codon for Lys can be modified from AAA to AAG;

the codons for Val can be modified from G(U/T)(U/T) or G(U/T)A to G(U/T)C or G(U/T)G;

the codon for Asp can be modified from GA(U/T) to GAC;

the codon for Glu can be modified from GAA to GAG;

the stop codon (U/T)AA can be modified to (U/T)AG or (U/T)GA.

In the case of the codons for Met (A(U/T)G) and Trp ((U/T)GG), on the other hand, there is no possibility of sequence modification without altering the encoded amino acid sequence.

The substitutions listed above can be used either individually or in all possible combinations to increase the G/C content of the open reading frame of the inventive artificial nucleic acid molecule as defined herein, compared to its particular wild type open reading frame (i.e. the original sequence). Thus, for example, all codons for Thr occurring in the wild type sequence can be modified to ACC (or ACG).

Preferably, the G/C content of the open reading frame of the inventive artificial nucleic acid molecule as defined herein is increased by at least 7%, more preferably by at least 15%, particularly preferably by at least 20%, compared to the G/C content of the wild type coding region without altering the encoded amino acid sequence, i.e. using the degeneracy of the genetic code. According to a specific embodiment at least 5%, 10%, 20%, 30%, 40%, 50%, 60%, more preferably at least 70%, even more preferably at least 80% and most preferably at least 90%, 95% or even 100% of the substitutable codons in the open reading frame of the inventive artificial nucleic acid molecule or a fragment, variant or derivative thereof are substituted, thereby increasing the G/C content of said open reading frame.

In this context, it is particularly preferable to increase the G/C content of the open reading frame of the inventive artificial nucleic acid molecule as defined herein, to the maximum (i.e. 100% of the substitutable codons), compared to the wild type open reading frame, without altering the encoded amino acid sequence.

Furthermore, the open reading frame is preferably at least partially codon-optimized. Codon-optimization is based on the finding that the translation efficiency may be determined by a different frequency in the occurrence of transfer RNAs (tRNAs) in cells. Thus, if so-called "rare codons" are present in the coding region of the inventive artificial nucleic acid molecule as defined herein, to an increased extent, the translation of the corresponding modified nucleic acid sequence is less efficient than in the case where codons coding for relatively "frequent" tRNAs are present.

Thus, the open reading frame of the inventive artificial nucleic acid molecule is preferably modified compared to the corresponding wild type coding region such that at least one codon of the wild type sequence which codes for a tRNA, which is relatively rare in the cell, is exchanged for a codon, which codes for a tRNA, which is comparably frequent in the cell and carries the same amino acid as the relatively rare tRNA. By this modification, the open reading frame of the inventive artificial nucleic acid molecule as defined herein, is modified such that codons, for which frequently occurring tRNAs are available may replace codons, which correspond to rare tRNAs. In other words, according to the invention, by such a modification all codons of the wild type open reading frame, which code for a rare tRNA, may be exchanged for a codon, which codes for a tRNA, which is more frequent in the cell and which carries the same amino acid as the rare tRNA. Which tRNAs occur relatively frequently in the cell and which, in contrast, occur relatively rarely is known to a person skilled in the art; cf. e.g. Akashi, Curr. Opin. Genet. Dev. 2001, 11(6): 660-666. Accordingly, preferably, the open reading frame is codon-optimized, preferably with respect to the system in which the artificial nucleic acid molecule according to the present invention is to be expressed, preferably with respect to the system in which the artificial nucleic acid molecule according to the present invention is to be translated. Preferably, the codon usage of the open reading frame is codon-optimized according to mammalian codon usage, more preferably according to human codon usage. Preferably, the open reading frame is codon-optimized and G/C-content modified.

For further improving degradation resistance, e.g. resistance to in vivo degradation by an exo- or endonuclease, and/or for further improving stability of protein expression from the artificial nucleic acid molecule according to the present invention, the artificial nucleic acid molecule may further comprise modifications, such as backbone modifications, sugar modifications and/or base modifications, e.g., lipid-modifications or the like. Preferably, the transcription and/or the translation of the artificial nucleic acid molecule according to the present invention is not significantly impaired by said modifications.

Generally, the artificial nucleic acid molecule of the present invention may comprise any native (=naturally occurring) nucleotide, e.g. guanosine, uracil, adenosine, and/or cytosine or an analogue thereof. In this respect, nucleotide analogues are defined as natively and non-natively occurring variants of the naturally occurring nucleotides adenosine, cytosine, thymidine, guanosine and uridine. Accordingly, analogues are e.g. chemically derivatized nucleotides with non-natively occurring functional groups, which are preferably added to or deleted from the naturally occurring nucleotide or which substitute the naturally occurring functional groups of a nucleotide. Accordingly, each component of the naturally occurring nucleotide may be modified, namely the base component, the sugar (ribose) component and/or the phosphate component forming the backbone (see above) of the RNA sequence. Analogues of guanosine, uridine, adenosine, thymidine and cytosine include, without implying any limitation, any natively occurring or non-natively occurring guanosine, uridine, adenosine, thymidine or cytosine that has been altered e.g. chemically, for example by acetylation, methylation, hydroxylation, etc., including 1-methyl-adenosine, 1-methyl-guanosine, 1-methyl-inosine, 2,2-dimethyl-guanosine, 2,6-diaminopurine, 2'-Amino-2'-deoxyadenosine, 2'-Amino-2'-deoxycytidine, 2'-Amino-2'-deoxyguanosine, 2'-Amino-2'-deoxyuridine, 2-Amino-6-chloropurineriboside, 2-Aminopurine-riboside, 2'-Araadenosine, 2'-Aracytidine, 2'-Arauridine, 2'-Azido-2'-deoxyadenosine, 2'-Azido-2'-deoxycytidine, 2'-Azido-2'-deoxyguanosine, 2'-Azido-2'-deoxyuridine, 2-Chloroadenosine, 2'-Fluoro-2'-deoxyadenosine, 2'-Fluoro-2'-deoxycytidine, 2'-Fluoro-2'-deoxyguanosine, 2'-Fluoro-2'-deoxyuridine, 2'-Fluorothymidine, 2-methyl-adenosine, 2-methyl-guanosine, 2-methyl-thio-N6-isopenenyl-adenosine, 2'-O-Methyl-2-aminoadenosine, 2'-O-Methyl-2'-deoxyadenosine, 2'-O-Methyl-2'-deoxycytidine, 2'-O-Methyl-2'-deoxyguanosine, 2'-O-Methyl-2'-deoxyuridine, 2'-O-Methyl-5-methyluridine, 2'-O-Methylinosine, 2'-O-Methylpseudouridine, 2-Thiocytidine, 2-thio-cytosine, 3-methyl-cytosine, 4-acetyl-cytosine, 4-Thiouridine, 5-(carboxyhydroxymethyl)-uracil, 5,6-Dihydrouridine, 5-Aminoallylcytidine, 5-Aminoallyl-deoxy-uridine, 5-Bromouridine, 5-carboxymehtylaminomethyl-2-thio-uracil, 5-carboxymethylamonomethyl-uracil, 5-Chloro-Ara-cytosine, 5-Fluoro-uridine, 5-Iodouridine, 5-methoxycarbonylmethyl-uridine, 5-methoxy-uridine, 5-methyl-2-thio-uridine, 6-Azacytidine, 6-Azauridine, 6-Chloro-7-deaza-guanosine, 6-Chloropurineriboside, 6-Mercapto-guanosine, 6-Methyl-mercaptopurine-riboside, 7-Deaza-2'-deoxy-guanosine, 7-Deazaadenosine, 7-methyl-guanosine, 8-Azaadenosine, 8-Bromo-adenosine, 8-Bromo-guanosine, 8-Mercapto-guanosine, 8-Oxoguanosine, Benzimidazole-riboside, Beta-D-mannosyl-queosine, Dihydro-uracil, Inosine, N1-Methyladenosine, N6-([6-Aminohexyl]carbamoylmethyl)-adenosine, N6-isopentenyl-adenosine, N6-methyl-adenosine, N7-Methyl-xanthosine, N-uracil-5-oxyacetic acid methyl ester, Puromycin, Queosine, Uracil-5-oxyacetic acid, Uracil-5-oxyacetic acid methyl ester, Wybutoxosine, Xanthosine, and Xylo-adenosine. The preparation of such analogues is known to a person skilled in the art, for example from U.S. Pat. Nos. 4,373,071, 4,401,796, 4,415,732, 4,458,066, 4,500,707, 4,668,777, 4,973,679, 5,047,524, 5,132,418, 5,153,319, 5,262,530 and 5,700,642. In the case of an analogue as described above, particular preference may be given according to certain embodiments of the invention to those analogues that increase the protein expression of the encoded peptide or protein or that increase the immunogenicity of the artificial nucleic acid molecule of the invention and/or do not interfere with a further modification of the artificial nucleic acid molecule that has been introduced.

According to a particular embodiment, the artificial nucleic acid molecule of the present invention can contain a lipid modification.

In a preferred embodiment, the artificial nucleic acid molecule comprises, preferably from 5' to 3' direction, the following elements:
a 5'-UTR;
at least one open reading frame (ORF), wherein the ORF preferably comprises at least one modification with respect to the wildtype sequence;
a 3'-UTR derived from the 3'-UTR of a ribosomal protein, preferably from a nucleic acid sequence according to any of SEQ ID NOs: 10 to 115, more preferably of the 3'-UTR of RPS9, more preferably of the 3'-UTR of human RPS9;
a poly(A) sequence, preferably comprising 64 adenylates;
a poly(C) sequence, preferably comprising 30 cytidylates;
a histone stem-loop sequence.

In another preferred embodiment, the artificial nucleic acid molecule comprises or consists of a nucleotide sequence as shown according to SEQ ID NO: 7 (see FIG. 3) or the complementary DNA sequence.

In a particularly preferred embodiment, the artificial nucleic acid molecule according to the invention may further comprise one or more of the modifications described in the following:

Chemical Modifications:

The term "modification" as used herein with regard to the artificial nucleic acid molecule may refer to chemical modifications comprising backbone modifications as well as sugar modifications or base modifications.

In this context, the artificial nucleic acid molecule, preferably an RNA molecule, as defined herein may contain nucleotide analogues/modifications, e.g. backbone modifications, sugar modifications or base modifications. A backbone modification in connection with the present invention is a modification, in which phosphates of the backbone of the nucleotides contained in a nucleic acid molecule as defined herein are chemically modified. A sugar modification in connection with the present invention is a chemical modification of the sugar of the nucleotides of the nucleic acid molecule as defined herein. Furthermore, a base modification in connection with the present invention is a chemical modification of the base moiety of the nucleotides of the nucleic acid molecule of the nucleic acid molecule. In this context, nucleotide analogues or modifications are preferably selected from nucleotide analogues which are applicable for transcription and/or translation.

Sugar Modifications:

The modified nucleosides and nucleotides, which may be incorporated into the artificial nucleic acid molecule, preferably an RNA, as described herein, can be modified in the sugar moiety. For example, the 2' hydroxyl group (OH) of an RNA molecule can be modified or replaced with a number of different "oxy" or "deoxy" substituents. Examples of "oxy"-2' hydroxyl group modifications include, but are not limited to, alkoxy or aryloxy (—OR, e.g., R=H, alkyl, cycloalkyl, aryl, aralkyl, heteroaryl or sugar); polyethyleneglycols (PEG), -0(CH2CH2o)nCH2CH2OR; "locked" nucleic acids (LNA) in which the 2' hydroxyl is connected, e.g., by a methylene bridge, to the 4' carbon of the same ribose sugar; and amino groups (—O-amino, wherein the amino group, e.g., NRR, can be alkylamino, dialkylamino, heterocyclyl, arylamino, diarylamino, heteroarylamino, or diheteroaryl amino, ethylene diamine, polyamino) or aminoalkoxy.

"Deoxy" modifications include hydrogen, amino (e.g. NH2; alkylamino, dialkylamino, heterocyclyl, arylamino, diaryl amino, heteroaryl amino, diheteroaryl amino, or amino acid); or the amino group can be attached to the sugar through a linker, wherein the linker comprises one or more of the atoms C, N, and O.

The sugar group can also contain one or more carbons that possess the opposite stereochemical configuration than that of the corresponding carbon in ribose. Thus, a modified nucleic acid molecule can include nucleotides containing, for instance, arabinose as the sugar.

Backbone Modifications:

The phosphate backbone may further be modified in the modified nucleosides and nucleotides, which may be incorporated into the artificial nucleic acid molecule, preferably an RNA, as described herein. The phosphate groups of the backbone can be modified by replacing one or more of the oxygen atoms with a different substituent. Further, the modified nucleosides and nucleotides can include the full replacement of an unmodified phosphate moiety with a modified phosphate as described herein. Examples of modified phosphate groups include, but are not limited to, phosphorothioate, phosphoroselenates, borano phosphates, borano phosphate esters, hydrogen phosphonates, phosphoroamidates, alkyl or aryl phosphonates and phosphotriesters. Phosphorodithioates have both non-linking oxygens replaced by sulfur. The phosphate linker can also be modified by the replacement of a linking oxygen with nitrogen (bridged phosphoroamidates), sulfur (bridged phosphorothioates) and carbon (bridged methylene-phosphonates).

Base Modifications:

The modified nucleosides and nucleotides, which may be incorporated into the artificial nucleic acid molecule, preferably an RNA molecule, as described herein, can further be modified in the nucleobase moiety. Examples of nucleobases found in RNA include, but are not limited to, adenine, guanine, cytosine and uracil. For example, the nucleosides and nucleotides described herein can be chemically modified on the major groove face. In some embodiments, the major groove chemical modifications can include an amino group, a thiol group, an alkyl group, or a halo group.

In particularly preferred embodiments of the present invention, the nucleotide analogues/modifications are selected from base modifications, which are preferably selected from 2-amino-6-chloropurineriboside-5'-triphosphate, 2-Aminopurine-riboside-5'-triphosphate; 2-aminoadenosine-5'-triphosphate, 2'-Amino-2'-deoxycytidine-triphosphate, 2-thiocytidine-5'-triphosphate, 2-thiouridine-5'-triphosphate, 2'-Fluorothymidine-5'-triphosphate, 2'-O-Methyl inosine-5'-triphosphate 4-thiouridine-5'-triphosphate, 5-aminoallylcytidine-5'-triphosphate, 5-aminoallyluridine-5'-triphosphate, 5-bromocytidine-5'-triphosphate, 5-bromouridine-5'-triphosphate, 5-Bromo-2'-deoxycytidine-5'-triphosphate, 5-Bromo-2'-deoxyuridine-5'-triphosphate, 5-iodocytidine-5'-triphosphate, 5-Iodo-2'-deoxycytidine-5'-triphosphate, 5-iodouridine-5'-triphosphate, 5-Iodo-2'-deoxyuridine-5'-triphosphate, 5-methylcytidine-5'-triphosphate, 5-methyluridine-5'-triphosphate, 5-Propynyl-2'-deoxycytidine-5'-triphosphate, 5-Propynyl-2'-deoxyuridine-5'-triphosphate, 6-azacytidine-5'-triphosphate, 6-azauridine-5'-triphosphate, 6-chloropurineriboside-5'-triphosphate, 7-deazaadenosine-5'-triphosphate, 7-deazaguanosine-5'-triphosphate, 8-azaadenosine-5'-triphosphate, 8-azidoadenosine-5'-triphosphate, benzimidazole-riboside-5'-triphosphate, N1-methyladenosine-5'-triphosphate, N1-methylguanosine-5'-triphosphate, N6-methyladenosine-5'-triphosphate, O6-methylguanosine-5'-triphosphate, pseudouridine-5'-triphosphate, or puromycin-5'-triphosphate, xanthosine-5'-triphosphate. Particular preference is given to nucleotides for base modifications selected from the group of base-modified nucleotides consisting of 5-methylcytidine-5'-triphosphate, 7-deazaguanosine-5'-triphosphate, 5-bromocytidine-5'-triphosphate, and pseudouridine-5'-triphosphate.

In some embodiments, modified nucleosides include pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyluridine, 1-carboxymethyl-pseudouridine, 5-propynyluridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In some embodiments, modified nucleosides include 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In other embodiments, modified nucleosides include 2-aminopurine, 2, 6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In other embodiments, modified nucleosides include inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some embodiments, the nucleotide can be modified on the major groove face and can include replacing hydrogen on C-5 of uracil with a methyl group or a halo group.

In specific embodiments, a modified nucleoside is 5'-O-(1-Thiophosphate)-Adenosine, 5'-O-(1-Thiophosphate)-Cytidine, 5'-O-(1-Thiophosphate)-Guanosine, 5'-O-(1-Thiophosphate)-Uridine or 5'-O-(1-Thiophosphate)-Pseudouridine.

In further specific embodiments the artificial nucleic acid molecule, preferably an RNA molecule, may comprise nucleoside modifications selected from 6-aza-cytidine, 2-thio-cytidine, alpha-thio-cytidine, Pseudo-iso-cytidine, 5-aminoallyl-uridine, 5-iodo-uridine, N1-methyl-pseudouridine, 5,6-dihydrouridine, alpha-thio-uridine, 4-thio-uridine, 6-aza-uridine, 5-hydroxy-uridine, deoxy-thymidine, 5-methyl-uridine, Pyrrolo-cytidine, inosine, alpha-thio-guanosine, 6-methyl-guanosine, 5-methyl-cytdine, 8-oxo-guanosine, 7-deaza-guanosine, N1-methyl-adenosine, 2-amino-6-Chloro-purine, N6-methyl-2-amino-purine, Pseudo-iso-cytidine, 6-Chloro-purine, N6-methyl-adenosine, alpha-thio-adenosine, 8-azido-adenosine, 7-deaza-adenosine.

Lipid Modification:

According to a further embodiment, the artificial nucleic acid molecule, preferably an RNA, as defined herein can contain a lipid modification. Such a lipid-modified RNA typically comprises an RNA as defined herein. Such a lipid-modified RNA molecule as defined herein typically further comprises at least one linker covalently linked with that RNA molecule, and at least one lipid covalently linked with the respective linker. Alternatively, the lipid-modified RNA molecule comprises at least one RNA molecule as defined herein and at least one (bifunctional) lipid covalently linked (without a linker) with that RNA molecule. According to a third alternative, the lipid-modified RNA molecule comprises an artificial nucleic acid molecule, preferably an RNA molecule, as defined herein, at least one linker covalently linked with that RNA molecule, and at least one lipid covalently linked with the respective linker, and also at least one (bifunctional) lipid covalently linked (without a linker) with that RNA molecule. In this context, it is particularly preferred that the lipid modification is present at the terminal ends of a linear RNA sequence.

Modification of the 5'-End of the Modified RNA:

According to another preferred embodiment of the invention, the artificial nucleic acid molecule, preferably an RNA molecule, as defined herein, can be modified by the addition of a so-called "5' CAP" structure.

A 5'-cap is an entity, typically a modified nucleotide entity, which generally "caps" the 5'-end of a mature mRNA. A 5'-cap may typically be formed by a modified nucleotide, particularly by a derivative of a guanine nucleotide. Preferably, the 5'-cap is linked to the 5'-terminus via a 5'-5'-triphosphate linkage. A 5'-cap may be methylated, e.g. m7GpppN, wherein N is the terminal 5' nucleotide of the nucleic acid carrying the 5'-cap, typically the 5'-end of an RNA. m7GpppN is the 5'-CAP structure which naturally occurs in mRNA transcribed by polymerase II and is therefore not considered as modification comprised in the modified RNA according to the invention. This means the artificial nucleic acid molecule, preferably an RNA molecule, according to the present invention may comprise a m7GpppN as 5'-CAP, but additionally the artificial nucleic acid molecule, preferably an RNA molecule, comprises at least one further modification as defined herein.

Further examples of 5'cap structures include glyceryl, inverted deoxy abasic residue (moiety), 4',5' methylene nucleotide, 1-(beta-D-erythrofuranosyl) nucleotide, 4'-thio nucleotide, carbocyclic nucleotide, 1,5-anhydrohexitol nucleotide, L-nucleotides, alpha-nucleotide, modified base nucleotide, threo-pentofuranosyl nucleotide, acyclic 3',4'-seco nucleotide, acyclic 3,4-dihydroxybutyl nucleotide, acyclic 3,5 dihydroxypentyl nucleotide, 3'-3'-inverted nucleotide moiety, 3'-3'-inverted abasic moiety, 3'-2'-inverted nucleotide moiety, 3'-2'-inverted abasic moiety, 1,4-butanediol phosphate, 3'-phosphoramidate, hexylphosphate, aminohexyl phosphate, 3'-phosphate, 3'phosphorothioate, phosphorodithioate, or bridging or non-bridging methylphosphonate moiety. These modified 5'-CAP structures are regarded as at least one modification comprised in the artificial nucleic acid molecule, preferably in an RNA molecule, according to the present invention.

Particularly preferred modified 5'-CAP structures are CAP1 (methylation of the ribose of the adjacent nucleotide of m7G), CAP2 (methylation of the ribose of the $2^{nd}$ nucleotide downstream of the m7G), CAP3 (methylation of the ribose of the $3^{rd}$ nucleotide downstream of the m7G), CAP4 (methylation of the ribose of the $4^{th}$ nucleotide downstream of the m7G), ARCA (anti-reverse CAP analogue, modified ARCA (e.g. phosphothioate modified ARCA), inosine, N1-methyl-guanosine, 2'-fluoro-guanosine, 7-deaza-guanosine, 8-oxo-guanosine, 2-amino-guanosine, LNA-guanosine, and 2-azido-guanosine.

In a preferred embodiment, the at least one open reading frame encodes a therapeutic protein or peptide. In another embodiment, an antigen is encoded by the at least one open reading frame, such as a pathogenic antigen, a tumour antigen, an allergenic antigen or an autoimmune antigen. Therein, the administration of the artificial nucleic acid molecule encoding the antigen is used in a genetic vaccination approach against a disease involving said antigen.

In an alternative embodiment, an antibody is encoded by the at least one open reading frame of the artificial nucleic acid molecule according to the invention.

Antigens:
Pathogenic Antigens:

The artificial nucleic acid molecule according to the present invention may encode a protein or a peptide, which comprises a pathogenic antigen or a fragment, variant or derivative thereof. Such pathogenic antigens are derived from pathogenic organisms, in particular bacterial, viral or protozoological (multicellular) pathogenic organisms, which evoke an immunological reaction in a subject, in particular a mammalian subject, more particularly a human. More specifically, pathogenic antigens are preferably surface antigens, e.g. proteins (or fragments of proteins, e.g. the exterior portion of a surface antigen) located at the surface of the virus or the bacterial or protozoological organism.

Pathogenic antigens are peptide or protein antigens preferably derived from a pathogen associated with infectious disease which are preferably selected from antigens derived from the pathogens *Acinetobacter baumannii, Anaplasma* genus, *Anaplasma phagocytophilum, Ancylostoma braziliense, Ancylostoma duodenale, Arcanobacterium haemolyticum, Ascaris lumbricoides, Aspergillus* genus, Astroviridae, *Babesia* genus, *Bacillus anthracis, Bacillus cereus, Bartonella henselae*, BK virus, *Blastocystis hominis, Blastomyces dermatitidis, Bordetella pertussis, Borrelia burgdorferi, Borrelia* genus, *Borrelia* spp, *Brucella* genus, *Brugia malayi*, Bunyaviridae family, *Burkholderia cepacia* and other *Burkholderia* species, *Burkholderia mallei, Burkholderia pseudomallei*, Caliciviridae family, *Campylobacter* genus, *Candida albicans, Candida* spp, *Chlamydia trachomatis, Chlamydophila pneumoniae, Chlamydophila psittaci*, CJD prion, *Clonorchis sinensis, Clostridium botulinum, Clostridium difficile, Clostridium perfringens, Clostridium perfringens, Clostridium* spp, *Clostridium tetani, Coccidioides* spp, coronaviruses, *Corynebacterium diphtheriae, Coxiella burnetii*, Crimean-Congo hemorrhagic fever virus, *Cryptococcus neoformans, Cryptosporidium* genus, Cytomegalovirus (CMV), *Dengue* viruses (DEN-1, DEN-2, DEN-3 and DEN-4), *Dientamoeba fragilis*, Ebolavirus (EBOV), *Echinococcus* genus, *Ehrlichia chaffeensis, Ehrlichia ewingii, Ehrlichia* genus, *Entamoeba histolytica, Enterococcus* genus, *Enterovirus* genus, Enteroviruses, mainly Coxsackie A virus and Enterovirus 71 (EV71), *Epidermophyton* spp, Epstein-Barr Virus (EBV), *Escherichia coli* O157:H7, O111 and O104:H4, *Fasciola hepatica* and *Fasciola gigantica*, FFI prion, Filarioidea superfamily, Flaviviruses, *Francisella tularensis, Fusobacterium* genus, *Geotrichum candidum, Giardia intestinalis, Gnathostoma* spp, GSS prion, Guanarito virus, *Haemophilus ducreyi, Haemophilus influenzae, Helicobacter pylori*, Henipavirus (Hendra virus Nipah virus), Hepatitis A Virus, Hepatitis B Virus (HBV), Hepatitis C Virus (HCV), Hepatitis D Virus, Hepatitis E Virus, Herpes simplex virus 1 and 2 (HSV-1 and HSV-2), *Histoplasma capsulatum*, HIV (Human immunodeficiency virus), *Hortaea werneckii*, Human bocavirus (HBoV), Human herpesvirus 6 (HHV-6) and Human herpesvirus 7 (HHV-7), Human metapneumovirus (hMPV), Human papillomavirus (HPV), Human parainfluenza viruses (HPIV), Japanese encephalitis virus, JC virus, Junin virus, *Kingella kingae, Klebsiella granulomatis, Kuru prion*, Lassa virus, *Legionella pneumophila, Leishmania* genus, *Leptospira* genus, *Listeria monocytogenes*, Lymphocytic choriomeningitis virus (LCMV), Machupo virus, *Malassezia* spp, Marburg virus, Measles virus, *Metagonimus yokagawai*, Microsporidia phylum, Molluscum contagiosum virus (MCV), Mumps virus, *Mycobacterium leprae* and *Mycobacterium lepromatosis, Mycobacterium tuberculosis, Mycobacterium ulcerans, Mycoplasma pneumoniae, Naegleria fowleri, Necator americanus, Neisseria gonorrhoeae, Neisseria meningitidis, Nocardia asteroides, Nocardia* spp, *Onchocerca volvulus, Orientia tsutsugamushi*, Orthomyxoviridae family (Influenza), *Paracoccidioides brasiliensis, Paragonimus* spp, *Paragonimus westermani*, Parvovirus B19, *Pasteurella* genus, *Plasmodium* genus, *Pneumocystis jirovecii*, Poliovirus, Rabies virus, Respiratory syncytial virus (RSV), Rhinovirus, rhinoviruses, *Rickettsia akari, Rickettsia* genus, *Rickettsia prowazekii, Rickettsia rickettsii, Rickettsia typhi*, Rift Valley fever virus, Rotavirus, Rubella virus, Sabia virus, *Salmonella* genus, *Sarcoptes scabiei*, SARS coronavirus, *Schistosoma* genus, *Shigella* genus, Sin Nombre virus, Hantavirus, *Sporothrix schenckii, Staphylococcus* genus, *Staphylococcus* genus, *Streptococcus agalactiae, Streptococcus pneumoniae, Streptococcus pyogenes, Strongyloides stercoralis, Taenia* genus, *Taenia solium*, Tick-borne encephalitis virus (TBEV), *Toxocara canis* or *Toxocara cati, Toxoplasma gondii, Treponema pallidum, Trichinella spiralis, Trichomonas vaginalis, Trichophyton* spp, *Trichuris trichiura, Trypanosoma brucei, Trypanosoma cruzi, Ureaplasma urealyticum*, Varicella zoster virus (VZV), Varicella zoster virus (VZV), Variola major or Variola minor, vCJD prion, Venezuelan equine encephalitis virus, *Vibrio cholerae*, West Nile virus, Western equine encephalitis virus, *Wuchereria bancrofti*, Yellow fever virus, *Yersinia enterocolitica, Yersinia pestis*, and *Yersinia pseudotuberculosis.*

In this context particularly preferred are antigens from the pathogens selected from Influenza virus, respiratory syncytial virus (RSV), Herpes simplex virus (HSV), human Papilloma virus (HPV), Human immunodeficiency virus (HIV), *Plasmodium, Staphylococcus aureus, Dengue virus, Chlamydia trachomatis*, Cytomegalovirus (CMV), Hepatitis B virus (HBV), *Mycobacterium tuberculosis*, Rabies virus, and Yellow Fever Virus.

Tumour Antigens:

In a further embodiment the artificial nucleic acid molecule according to the present invention may encode a protein or a peptide, which comprises a peptide or protein comprising a tumour antigen, a fragment, variant or derivative of said tumour antigen, preferably, wherein the tumour antigen is a melanocyte-specific antigen, a cancer-testis antigen or a tumour-specific antigen, preferably a CT-X antigen, a non-X CT-antigen, a binding partner for a CT-X antigen or a binding partner for a non-X CT-antigen or a tumour-specific antigen, more preferably a CT-X antigen, a binding partner for a non-X CT-antigen or a tumour-specific antigen or a fragment, variant or derivative of said tumour antigen; and wherein each of the nucleic acid sequences encodes a different peptide or protein; and wherein at least one of the nucleic acid sequences encodes for 5T4, 707-AP, 9D7, AFP, AlbZIP HPG1, alpha-5-beta-1-integrin, alpha-5-beta-6-integrin, alpha-actinin-4/m, alpha-methylacyl-coenzyme A racemase, ART-4, ARTC1/m, B7H4, BAGE-1, BCL-2, bcr/abl, beta-catenin/m, BING-4, BRCA1/m, BRCA2/m, CA 15-3/CA 27-29, CA 19-9, CA72-4, CA125, calreticulin, CAMEL, CASP-8/m, cathepsin B, cathepsin L, CD19, CD20, CD22, CD25, CDE30, CD33, CD4, CD52, CD55, CD56, CD80, CDC27/m, CDK4/m, CDKN2A/m, CEA, CLCA2, CML28, CML66, COA-1/m, coactosin-like protein, collage XXIII, COX-2, CT-9/BRD6, Cten, cyclin B1, cyclin D1, cyp-B, CYPB1, DAM-10, DAM-6, DEK-CAN, EFTUD2/m, EGFR, ELF2/m, EMMPRIN, EpCam, EphA2, EphA3, ErbB3, ETV6-AML1, EZH2, FGF-5, FN, Frau-1, G250, GAGE-1, GAGE-2, GAGE-3, GAGE-4, GAGE-5, GAGE-6, GAGE7b, GAGE-8, GDEP, GnT-V, gp100, GPC3, GPNMB/m, HAGE, HAST-2, hepsin, Her2/neu, HERV-K-MEL, HLA-A*0201-R17I, HLA-A11/m, HLA-A2/m, HNE, homeobox NKX3.1, HOM-TES-14/SCP-1, HOM-TES-85, HPV-E6, HPV-E7, HSP70-2M, HST-2, hTERT, iCE, IGF-1R, IL-13Ra2, IL-2R, IL-5, immature laminin receptor, kallikrein-2, kallikrein-4, Ki67, KIAA0205, KIAA0205/m, KK-LC-1, K-Ras/m, LAGE-A1, LDLR-FUT, MAGE-A1, MAGE-A2, MAGE-A3, MAGE-A4, MAGE-A6, MAGE-A9, MAGE-A10, MAGE-A12, MAGE-B1, MAGE-B2, MAGE-B3, MAGE-B4, MAGE-B5, MAGE-B6, MAGE-B10, MAGE-B16, MAGE-B17, MAGE-C1, MAGE-C2, MAGE-C3, MAGE-D1, MAGE-D2, MAGE-D4, MAGE-E1, MAGE-E2, MAGE-F1, MAGE-H1, MAGEL2, mammaglobin A, MART-1/melan-A, MART-2, MART-2/m, matrix protein 22, MC1R, M-CSF, ME1/m, mesothelin, MG50/PXDN, MMP11, MN/CA IX-antigen, MRP-3, MUC-1, MUC-2, MUM-1/m, MUM-2/m, MUM-3/m, myosin class I/m, NA88-A, N-acetylglucosaminyltransferase-V, Neo-PAP, Neo-PAP/m, NFYC/m, NGEP, NMP22, NPM/ALK, N-Ras/m, NSE, NY-ESO-1, NY-ESO-B, OA1, OFA-iLRP, OGT, OGT/m, OS-9, OS-9/m, osteocalcin, osteopontin, p15, p190 minor bcr-abl, p53, p53/m, PAGE-4, PAI-1, PAI-2, PAP, PART-1, PATE, PDEF, Pim-1-Kinase, Pin-1, Pml/PARalpha, POTE, PRAME, PRDX5/m, prostein, proteinase-3, PSA, PSCA, PSGR, PSM, PSMA, PTPRK/m, RAGE-1, RBAF600/m, RHAMM/CD168, RU1, RU2, S-100, SAGE, SART-1, SART-2, SART-3, SCC, SIRT2/m, Sp17, SSX-1, SSX-2/HOM-MEL-40, SSX-4, STAMP-1, STEAP-1, survivin, survivin-2B, SYT-SSX-1, SYT-SSX-2, TA-90, TAG-72, TARP, TEL-AML1, TGFbeta, TGFbetaRII, TGM-4, TPI/m, TRAG-3, TRG, TRP-1, TRP- 2/6b, TRP/INT2, TRP-p8, tyrosinase, UPA, VEGFR1, VEGFR-2/FLK-1, WT1 and a immunoglobulin idiotype of a lymphoid blood cell or a T cell receptor idiotype of a lymphoid blood cell, or a fragment, variant or derivative of said tumour antigen; preferably survivin or a homologue thereof, an antigen from the MAGE-family or a binding partner thereof or a fragment, variant or derivative of said tumour antigen. Particularly preferred in this context are the tumour antigens NY-ESO-1, 5T4, MAGE-C1, MAGE-C2, Survivin, Muc-1, PSA, PSMA, PSCA, STEAP and PAP.

In a preferred embodiment, the artificial nucleic acid molecule encodes a protein or a peptide, which comprises a therapeutic protein or a fragment, variant or derivative thereof.

Therapeutic proteins as defined herein are peptides or proteins, which are beneficial for the treatment of any inherited or acquired disease or which improves the condition of an individual. Particularly, therapeutic proteins play an important role in the creation of therapeutic agents that could modify and repair genetic errors, destroy cancer cells or pathogen infected cells, treat immune system disorders, treat metabolic or endocrine disorders, among other functions. For instance, Erythropoietin (EPO), a protein hormone can be utilized in treating patients with erythrocyte deficiency, which is a common cause of kidney complications. Furthermore adjuvant proteins, therapeutic antibodies are encompassed by therapeutic proteins and also hormone replacement therapy which is e.g. used in the therapy of women in menopause. In more recent approaches, somatic cells of a patient are used to reprogram them into pluripotent stem cells, which replace the disputed stem cell therapy. Also these proteins used for reprogramming of somatic cells or used for differentiating of stem cells are defined herein as therapeutic proteins. Furthermore, therapeutic proteins may be used for other purposes, e.g. wound healing, tissue regeneration, angiogenesis, etc. Furthermore, antigen-specific B cell receptors and fragments and variants thereof are defined herein as therapeutic proteins.

Therefore therapeutic proteins can be used for various purposes including treatment of various diseases like e.g. infectious diseases, neoplasms (e.g. cancer or tumour diseases), diseases of the blood and blood-forming organs, endocrine, nutritional and metabolic diseases, diseases of the nervous system, diseases of the circulatory system, diseases of the respiratory system, diseases of the digestive system, diseases of the skin and subcutaneous tissue, diseases of the musculoskeletal system and connective tissue, and diseases of the genitourinary system, independently if they are inherited or acquired.

In this context, particularly preferred therapeutic proteins, which can be used inter alia in the treatment of metabolic or endocrine disorders, are selected from (in brackets the particular disease for which the therapeutic protein is used in the treatment): Acid sphingomyelinase (Niemann-Pick disease), Adipotide (obesity), Agalsidase-beta (human galactosidase A) (Fabry disease; prevents accumulation of lipids that could lead to renal and cardiovascular complications), Alglucosidase (Pompe disease (glycogen storage disease type II)), alpha-galactosidase A (alpha-GAL A, Agalsidase alpha) (Fabry disease), alpha-glucosidase (Glycogen storage disease (GSD), Morbus Pompe), alpha-L-iduronidase (mucopolysaccharidoses (MPS), Hurler syndrome, Scheie syndrome), alpha-N-acetylglucosaminidase (Sanfilippo syndrome), Amphiregulin (cancer, metabolic disorder), Angiopoietin ((Ang1, Ang2, Ang3, Ang4, ANGPTL2, ANGPTL3, ANGPTL4, ANGPTL5, ANGPTL6, ANGPTL7) (angiogenesis, stabilize vessels), Betacellulin (metabolic disorder), Beta-glucuronidase (Sly syndrome), Bone morphogenetic protein BMPs (BMP1, BMP2, BMP3, BMP4, BMP5, BMP6, BMP7, BMP8a, BMP8b, BMP10, BMP15) (regenerative effect, bone-related conditions, chronic kidney disease (CKD)), CLN6 protein (CLN6 disease—Atypical Late Infantile, Late Onset variant, Early Juvenile, Neuronal Ceroid Lipofuscinoses (NCL)), Epidermal growth factor (EGF) (wound healing, regulation of cell growth, proliferation, and differentiation), Epigen (metabolic disorder), Epiregulin (metabolic disorder), Fibroblast Growth Factor (FGF, FGF-1, FGF-2, FGF-3, FGF-4, FGF-5, FGF-6, FGF-7, FGF-8, FGF-9, FGF-10, FGF-11, FGF-12, FGF-13, FGF-14, FGF-16, FGF-17, FGF-17, FGF-18, FGF-19, FGF-20, FGF-21, FGF-22, FGF-23) (wound healing, angiogenesis, endocrine disorders, tissue regeneration), Galsulphase (Mucopolysaccharidosis VI), Ghrelin (irritable bowel syndrome (IBS), obesity, Prader-Willi syndrome, type II diabetes mellitus), Glucocerebrosidase (Gaucher's disease), GM-CSF (regenerative effect, production of white blood cells, cancer), Heparin-binding EGF-like growth factor (HB-EGF) (wound healing, cardiac hypertrophy and heart development and function), Hepatocyte growth factor HGF (regenerative effect, wound healing), Hepcidin (iron metabolism disorders, Beta-thalassemia), Human albumin (Decreased production of albumin (hypoproteinaemia), increased loss of albumin (nephrotic syndrome), hypovolaemia, hyperbilirubinaemia), Idursulphase (Iduronate-2-sulphatase) (Mucopolysaccharidosis II (Hunter syndrome)), Integrins αVβ3, αVβ5 and α5β1 (Bind matrix macromolecules and proteinases, angiogenesis), Iuduronate sulfatase (Hunter syndrome), Laronidase (Hurler and Hurler-Scheie forms of mucopolysaccharidosis I), N-acetylgalactosamine-4-sulfatase (rhASB; galsulfase, Arylsulfatase A (ARSA), Arylsulfatase B (ARSB)) (arylsulfatase B deficiency, Maroteaux-Lamy syndrome, mucopolysaccharidosis VI), N-acetylglucosamine-6-sulfatase (Sanfilippo syndrome), Nerve growth factor (NGF, Brain-Derived Neurotrophic Factor (BDNF), Neurotrophin-3 (NT-3), and Neurotrophin 4/5 (NT-4/5) (regenerative effect, cardiovascular diseases, coronary atherosclerosis, obesity, type 2 diabetes, metabolic syndrome, acute coronary syndromes, dementia, depression, schizophrenia, autism, Rett syndrome, anorexia nervosa, bulimia nervosa, wound healing, skin ulcers, corneal ulcers, Alzheimer's disease), Neuregulin (NRG1, NRG2, NRG3, NRG4) (metabolic disorder, schizophrenia), Neuropilin (NRP-1, NRP-2) (angiogenesis, axon guidance, cell survival, migration), Obestatin (irritable bowel syndrome (IBS), obesity, Prader-Willi syndrome, type II diabetes mellitus), Platelet Derived Growth factor (PDGF (PDFF-A, PDGF-B, PDGF-C, PDGF-D) (regenerative effect, wound healing, disorder in angiogenesis, Arteriosclerosis, Fibrosis, cancer), TGF beta receptors (endoglin, TGF-beta 1 receptor, TGF-beta 2 receptor, TGF-beta 3 receptor) (renal fibrosis, kidney disease, diabetes, ultimately end-stage renal disease (ESRD), angiogenesis), Thrombopoietin (THPO) (Megakaryocyte growth and development factor (MGDF)) (platelets disorders, platelets for donation, recovery of platelet counts after myelosuppressive chemotherapy), Transforming Growth factor (TGF (TGF-alpha, TGF-beta (TGFbeta1, TGFbeta2, and TGFbeta3))) (regenerative effect, wound healing, immunity, cancer, heart disease, diabetes, Marfan syndrome, Loeys-Dietz syndrome), VEGF (VEGF-A, VEGF-B, VEGF-C, VEGF-D, VEGF-E, VEGF-F und PIGF) (regenerative effect, angiogenesis, wound healing, cancer, permeability), Nesiritide (Acute decompensated congestive heart failure), Trypsin (Decubitus ulcer, varicose ulcer, debridement of eschar, dehiscent wound, sunburn, meconium ileus), adrenocorticotrophic hormone (ACTH) ("Addison's disease, Small cell carcinoma, Adrenoleukodystrophy, Congenital adrenal hyperplasia, Cushing's syndrome, Nelson's syndrome, Infantile spasms), Atrialnatriuretic peptide (ANP) (endocrine disorders), Cholecystokinin (diverse), Gastrin (hypogastrinemia), Leptin (Diabetes, hypertriglyceridemia, obesity), Oxytocin (stimulate breastfeeding, non-progression of parturition), Somatostatin (symptomatic treatment of carcinoid syndrome, acute variceal bleeding, and acromegaly, polycystic diseases of the liver and kidney, acromegaly and symptoms caused by neuroendocrine tumors), Vasopressin (antidiuretic hormone) (diabetes insipidus), Calcitonin (Postmenopausal osteoporosis, Hypercalcaemia, Paget's disease, Bone metastases, Phantom limb pain, Spinal Stenosis), Exenatide (Type 2 diabetes resistant to treatment with metformin and a sulphonylurea), Growth hormone (GH), somatotropin (Growth failure due to GH deficiency or chronic renal insufficiency, Prader-Willi syndrome, Turner syndrome, AIDS wasting or cachexia with antiviral therapy), Insulin (Diabetes mellitus, diabetic ketoacidosis, hyperkalaemia), Insulin-like growth factor 1 IGF-1 (Growth failure in children with GH gene deletion or severe primary IGF1 deficiency, neurodegenerative disease, cardiovascular diseases, heart failure), Mecasermin rinfabate, IGF-1 analog (Growth failure in children with GH gene deletion or severe primary IGF1 deficiency, neurodegenerative disease, cardiovascular diseases, heart failure), Mecasermin, IGF-1 analog (Growth failure in children with GH gene deletion or severe primary IGF1 deficiency, neurodegenerative disease, cardiovascular diseases, heart failure), Pegvisomant (Acromegaly), Pramlintide (Diabetes mellitus, in combination with insulin), Teriparatide (human parathyroid hormone residues 1-34) (Severe osteoporosis), Becaplermin (Debridement adjunct for diabetic ulcers), Dibotermin-alpha (Bone morphogenetic protein 2) (Spinal fusion surgery, bone injury repair), Histrelin acetate (gonadotropin releasing hormone; GnRH) (Precocious puberty), Octreotide (Acromegaly, symptomatic relief of VIP-secreting adenoma and metastatic carcinoid tumours), and Palifermin (keratinocyte growth factor; KGF) (Severe oral mucositis in patients undergoing chemotherapy, wound healing).

These and other proteins are understood to be therapeutic, as they are meant to treat the subject by replacing its defective endogenous production of a functional protein in sufficient amounts. Accordingly, such therapeutic proteins are typically mammalian, in particular human proteins.

For the treatment of blood disorders, diseases of the circulatory system, diseases of the respiratory system, cancer or tumour diseases, infectious diseases or immunedeficiencies following therapeutic proteins may be used: Alteplase (tissue plasminogen activator; tPA) (Pulmonary embolism, myocardial infarction, acute ischaemic stroke, occlusion of central venous access devices), Anistreplase (Thrombolysis), Antithrombin III (AT-III) (Hereditary AT-III deficiency, Thromboembolism), Bivalirudin (Reduce blood-clotting risk in coronary angioplasty and heparin-induced thrombocytopaenia), Darbepoetin-alpha (Treatment of anaemia in patients with chronic renal insufficiency and chronic renal failure (+/−dialysis)), Drotrecogin-alpha (activated protein C) (Severe sepsis with a high risk of death), Erythropoietin, Epoetin-alpha, erythropoetin, erthropoyetin (Anaemia of chronic disease, myleodysplasia, anaemia due to renal failure or chemotherapy, preoperative preparation), Factor IX (Haemophilia B), Factor VIIa (Haemorrhage in patients with haemophilia A or B and inhibitors to factor VIII or factor IX), Factor VIII (Haemophilia A), Lepirudin (Heparin-induced thrombocytopaenia), Protein C concentrate (Venous thrombosis, Purpura fulminans), Reteplase (deletion mutein of tPA) (Management of acute myocardial infarction, improvement of ventricular function), Streptokinase (Acute evolving transmural myocardial infarction, pulmonary embolism, deep vein thrombosis, arterial thrombosis or embolism, occlusion of arteriovenous cannula), Tenecteplase (Acute myocardial infarction), Urokinase (Pulmonary embolism), Angiostatin (Cancer), Anti-CD22 immunotoxin (Relapsed CD33+ acute myeloid leukaemia), Denileukin diftitox (Cutaneous T-cell lymphoma (CTCL)), Immunocyanin (bladder and prostate cancer), MPS (Metallopanstimulin) (Cancer), Aflibercept (Non-small cell lung cancer (NSCLC), metastatic colorectal cancer (mCRC), hormone-refractory metastatic prostate cancer, wet macular degeneration), Endostatin (Cancer, inflammatory diseases like rheumatoid arthritis as well as Crohn's disease, diabetic retinopathy, psoriasis, and endometriosis), Collagenase (Debridement of chronic dermal ulcers and severely burned areas, Dupuytren's contracture, Peyronie's disease), Human deoxy-ribonuclease I, dornase (Cystic fibrosis; decreases respiratory tract infections in selected patients with FVC greater than 40% of predicted), Hyaluronidase (Used as an adjuvant to increase the absorption and dispersion of injected drugs, particularly anaesthetics in ophthalmic surgery and certain imaging agents), Papain (Debridement of necrotic tissue or liquefication of slough in acute and chronic lesions, such as pressure ulcers, varicose and diabetic ulcers, burns, postoperative wounds, pilonidal cyst wounds, carbuncles, and other wounds), L-Asparaginase (Acute lymphocytic leukaemia, which requires exogenous asparagine for proliferation), Peg-asparaginase (Acute lymphocytic leukaemia, which requires exogenous asparagine for proliferation), Rasburicase (Paediatric patients with leukaemia, lymphoma, and solid tumours who are undergoing anticancer therapy that may cause tumour lysis syndrome), Human chorionic gonadotropin (HCG) (Assisted reproduction), Human follicle-stimulating hormone (FSH) (Assisted reproduction), Lutropin-alpha (Infertility with luteinizing hormone deficiency), Prolactin (Hypoprolactinemia, serum prolactin deficiency, ovarian dysfunction in women, anxiety, arteriogenic erectile dysfunction, premature ejaculation, oligozoospermia, asthenospermia, hypofunction of seminal vesicles, hypoandrogenism in men), alpha-1-Proteinase inhibitor (Congenital antitrypsin deficiency), Lactase (Gas, bloating, cramps and diarrhoea due to inability to digest lactose), Pancreatic enzymes (lipase, amylase, protease) (Cystic fibrosis, chronic pancreatitis, pancreatic insufficiency, post-Billroth II gastric bypass surgery, pancreatic duct obstruction, steatorrhoea, poor digestion, gas, bloating), Adenosine deaminase (pegademase bovine, PEG-ADA) (Severe combined immunodeficiency disease due to adenosine deaminase deficiency), Abatacept (Rheumatoid arthritis (especially when refractory to TNFalpha inhibition)), Alefacept (Plaque Psoriasis), Anakinra (Rheumatoid arthritis), Etanercept (Rheumatoid arthritis, polyarticular-course juvenile rheumatoid arthritis, psoriatic arthritis, ankylosing spondylitis, plaque psoriasis, ankylosing spondylitis), Interleukin-1 (IL-1) receptor antagonist, Anakinra (inflammation and cartilage degradation associated with rheumatoid arthritis), Thymulin (neurodegenerative diseases, rheumatism, anorexia nervosa), TNF-alpha antagonist (autoimmune disorders such as rheumatoid arthritis, ankylosing spondylitis, Crohn's disease, psoriasis, hidradenitis suppurativa, refractory asthma), Enfuvirtide (HIV-1 infection), and Thymosin α1 (Hepatitis B and C).

(in brackets is the particular disease for which the therapeutic protein is used in the treatment)

In a further aspect, the present invention provides a vector comprising a. an open reading frame (ORF) and/or a cloning site, e.g. for insertion of an open reading frame or a sequence comprising an open reading frame; and
b. at least one 3'-untranslated region element (3'-UTR element) comprising a nucleic acid sequence which is derived from the 3'-UTR of a ribosomal protein gene.

The at least one 3'-UTR element and the ORF are as described above for the artificial nucleic acid molecule according to the present invention. The cloning site may be any sequence that is suitable for introducing an open reading frame or a sequence comprising an open reading frame, such as one or more restriction sites. Thus, the vector comprising a cloning site is preferably suitable for inserting an open reading frame into the vector, preferably for inserting an open reading frame 5' to the 3'-UTR element. Preferably, the cloning site or the ORF is located 5' to the 3'-UTR element, preferably in close proximity to the 5'-end of the 3'-UTR element. For example, the cloning site or the ORF may be directly connected to the 5'-end of the 3'-UTR element or they may be connected via a stretch of nucleotides, such as by a stretch of 2, 4, 6, 8, 10, 20 etc. nucleotides as described above for the artificial nucleic acid molecule according to the present invention.

Preferably, the vector according to the present invention is suitable for producing the artificial nucleic acid molecule according to the present invention, preferably for producing an artificial mRNA according to the present invention, for example, by optionally inserting an open reading frame or a sequence comprising an open reading frame into the vector and transcribing the vector. Thus, preferably, the vector comprises elements needed for transcription, such as a promoter, e.g. an RNA polymerase promoter. Preferably, the vector is suitable for transcription using eukaryotic, prokaryotic, viral or phage transcription systems, such as eukaryotic cells, prokaryotic cells, or eukaryotic, prokaryotic, viral or phage in vitro transcription systems. Thus, for example, the vector may comprise a promoter sequence, which is recognized by a polymerase, such as by an RNA polymerase, e.g. by a eukaryotic, prokaryotic, viral, or phage RNA polymerase. In a preferred embodiment, the vector comprises a phage RNA polymerase promoter such as an SP6, T3 or T7, preferably a T7 promoter. Preferably, the vector is suitable for in vitro transcription using a phage based in vitro transcription system, such as a T7 RNA polymerase based in vitro transcription system.

In another preferred embodiment, the vector may be used directly for expression of the encoded peptide or protein in cells or tissue. For this purpose, the vector comprises particular elements, which are necessary for expression in those cells/tissue e.g. particular promoter sequences, such as a CMV promoter.

The vector may further comprise a poly(A) sequence and/or a polyadenylation signal as described above for the artificial nucleic acid molecule according to the present invention.

The vector may be an RNA vector or a DNA vector. Preferably, the vector is a DNA vector. The vector may be any vector known to the skilled person, such as a viral vector or a plasmid vector. Preferably, the vector is a plasmid vector, preferably a DNA plasmid vector.

In a preferred embodiment, the vector according to the present invention comprises the artificial nucleic acid molecule according to the present invention.

In one embodiment, a DNA vector according to the invention comprises a nucleic acid sequence, which has an identity of at least about 1, 2, 3, 4, 5, 10, 15, 20, 30 or 40%, preferably of at least about 50%, preferably of at least about 60%, preferably of at least about 70%, more preferably of at least about 80%, more preferably of at least about 90%, even more preferably of at least about 95%, even more preferably of at least about 99%, most preferably of 100% to the nucleic acid sequence of a 3'-UTR of a ribosomal protein gene, such as to the nucleic acid sequences according to SEQ ID NOs:10 to 115.

Preferably, a DNA vector according to the present invention comprises a sequence according to SEQ ID No. 1, SEQ ID No. 3, a sequence complementary to SEQ ID No. 7 or a sequence having an identity of at least about 40%, preferably of at least about 50%, preferably of at least about 60%, preferably of at least about 70%, more preferably of at least about 80%, more preferably of at least about 90%, even more preferably of at least about 95%; even more preferably of at least about 99% sequence identity to the nucleic acid sequence according to SEQ ID No. 1, SEQ ID No. 3, SEQ ID No. 7 or a fragment thereof as described above, preferably a functional fragment thereof.

Preferably, an RNA vector according to the present invention comprises a sequence according to SEQ ID No. 2, SEQ ID No. 4, SEQ ID No. 7 or a sequence having an identity of at least about 40%, preferably of at least about 50%, preferably of at least about 60%, preferably of at least about 70%, more preferably of at least about 80%, more preferably of at least about 90%, even more preferably of at least about 95%; even more preferably of at least about 99% sequence identity to the nucleic acid sequence according to SEQ ID No. 2, SEQ ID No. 4, SEQ ID No. 7 or a fragment thereof, preferably a functional fragment thereof.

Preferably, the vector is a circular molecule. Preferably, the vector is a double-stranded molecule, such as a double-stranded DNA molecule. Such circular, preferably double stranded DNA molecule may be used conveniently as a storage form for the inventive artificial nucleic acid molecule. Furthermore, it may be used for transfection of cells, for example, cultured cells. Also it may be used for in vitro transcription for obtaining an artificial RNA molecule according to the invention.

Preferably, the vector, preferably the circular vector, is linearizable, for example, by restriction enzyme digestion. In a preferred embodiment, the vector comprises a cleavage site, such as a restriction site, preferably a unique cleavage site, located immediately 3' to the 3'-UTR element, or—if present—located 3' to the poly(A) sequence or polyadenylation signal, or—if present—located 3' to the poly(C) sequence, or—if present—located 3' to the histone stem-loop. Thus, preferably, the product obtained by linearizing the vector terminates at the 3' end with the 3'-end of the 3'-UTR element, or—if present—with the 3'-end of the poly(A) sequence or polyadenylation signal, or—if present—with the 3'-end of the poly(C) sequence. In the embodiment, wherein the vector according to the present invention comprises the artificial nucleic acid molecule according to the present invention, a restriction site, preferably a unique restriction site, is preferably located immediately 3' to the 3'-end of the artificial nucleic acid molecule.

In a further aspect, the present invention relates to a cell comprising the artificial nucleic acid molecule according to the present invention or the vector according to present invention. The cell may be any cell, such as a bacterial cell, insect cell, plant cell, vertebrate cell, e.g. a mammalian cell. Such cell may be, e.g., used for replication of the vector of the present invention, for example, in a bacterial cell. Furthermore, the cell may be used for transcribing the artificial nucleic acid molecule or the vector according to the present invention and/or translating the open reading frame of the artificial nucleic acid molecule or the vector according to the present invention. For example, the cell may be used for recombinant protein production.

The cells according to the present invention are, for example, obtainable by standard nucleic acid transfer methods, such as standard transfection, transduction or transformation methods. For example, the artificial nucleic acid molecule or the vector according to the present invention may be transferred into the cell by electroporation, lipofection, e.g. based on cationic lipids and/or liposomes, calcium phosphate precipitation, nanoparticle based transfection, virus based transfection, or based on cationic polymers, such as DEAE-dextran or polyethylenimine etc.

Preferably, the cell is a mammalian cell, such as a cell of human subject, a domestic animal, a laboratory animal, such as a mouse or rat cell. Preferably the cell is a human cell. The cell may be a cell of an established cell line, such as a CHO, BHK, 293T, COS-7, HELA, HEK, etc. or the cell may be a primary cell, such as a human dermal fibroblast (HDF) cell etc., preferably a cell isolated from an organism. In a preferred embodiment, the cell is an isolated cell of a mammalian subject, preferably of a human subject. For example, the cell may be an immune cell, such as a dendritic cell, a cancer or tumor cell, or any somatic cell etc., preferably of a mammalian subject, preferably of a human subject.

In a further aspect, the present invention provides a pharmaceutical composition comprising the artificial nucleic acid molecule according to the present invention, the vector according the present invention, or the cell according to the present invention. The pharmaceutical composition according to the invention may be used, e.g., as a vaccine, for example, for genetic vaccination. Thus, the ORF may, e.g., encode an antigen to be administered to a patient for vaccination. Thus, in a preferred embodiment, the pharmaceutical composition according to the present invention is a vaccine. Furthermore, the pharmaceutical composition according to the present invention may be used, e.g., for gene therapy.

Preferably, the pharmaceutical composition further comprises one or more pharmaceutically acceptable vehicles, diluents and/or excipients and/or one or more adjuvants. In the context of the present invention, a pharmaceutically acceptable vehicle typically includes a liquid or non-liquid basis for the inventive pharmaceutical composition. In one embodiment, the pharmaceutical composition is provided in liquid form. In this context, preferably, the vehicle is based on water, such as pyrogen-free water, isotonic saline or buffered (aqueous) solutions, e.g phosphate, citrate etc. buffered solutions. The buffer may be hypertonic, isotonic or hypotonic with reference to the specific reference medium, i.e. the buffer may have a higher, identical or lower salt content with reference to the specific reference medium, wherein preferably such concentrations of the afore mentioned salts may be used, which do not lead to damage of mammalian cells due to osmosis or other concentration effects. Reference media are e.g. liquids occurring in "in vivo" methods, such as blood, lymph, cytosolic liquids, or other body liquids, or e.g. liquids, which may be used as reference media in "in vitro" methods, such as common buffers or liquids. Such common buffers or liquids are known to a skilled person. Ringer-Lactate solution is particularly preferred as a liquid basis.

One or more compatible solid or liquid fillers or diluents or encapsulating compounds suitable for administration to a patient may be used as well for the inventive pharmaceutical composition. The term "compatible" as used herein preferably means that these components of the inventive pharmaceutical composition are capable of being mixed with the inventive artificial nucleic acid, vector or cells as defined herein in such a manner that no interaction occurs which would substantially reduce the pharmaceutical effectiveness of the inventive pharmaceutical composition under typical use conditions.

The pharmaceutical composition according to the present invention may optionally further comprise one or more additional pharmaceutically active components. A pharmaceutically active component in this context is a compound that exhibits a therapeutic effect to heal, ameliorate or prevent a particular indication or disease. Such compounds include, without implying any limitation, peptides or proteins, nucleic acids, (therapeutically active) low molecular weight organic or inorganic compounds (molecular weight less than 5000, preferably less than 1000), sugars, antigens or antibodies, therapeutic agents already known in the prior art, antigenic cells, antigenic cellular fragments, cellular fractions, cell wall components (e.g. polysaccharides), modified, attenuated or de-activated (e.g. chemically or by irradiation) pathogens (virus, bacteria etc.).

Furthermore, the inventive pharmaceutical composition may comprise a carrier for the artificial nucleic acid molecule or the vector. Such a carrier may be suitable for mediating dissolution in physiological acceptable liquids, transport and cellular uptake of the pharmaceutical active artificial nucleic acid molecule or the vector. Accordingly, such a carrier may be a component, which may be suitable for depot and delivery of an artificial nucleic acid molecule or vector according to the invention. Such components may be, for example, cationic or polycationic carriers or compounds, which may serve as transfection or complexation agent.

Particularly preferred transfection or complexation agents, in this context, are cationic or polycationic compounds, including protamine, nucleoline, spermine or spermidine, or other cationic peptides or proteins, such as poly-L-lysine (PLL), poly-arginine, basic polypeptides, cell penetrating peptides (CPPs), including HIV-binding peptides, HIV-1 Tat (HIV), Tat-derived peptides, Penetratin, VP22 derived or analog peptides, HSV VP22 (Herpes simplex), MAP, KALA or protein transduction domains (PTDs), PpT620, proline-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, pIsl, FGF, Lactoferrin, Transportan, Buforin-2, Bac715-24, SynB, SynB(1), pVEC, hCT-derived peptides, SAP, or histones.

Furthermore, such cationic or polycationic compounds or carriers may be cationic or polycationic peptides or proteins, which preferably comprise or are additionally modified to comprise at least one —SH moiety. Preferably, a cationic or polycationic carrier is selected from cationic peptides having the following sum formula (I):

$$\{(Arg)_l;(Lys)_m;(His)_n;(Orn)_o;(Xaa)_x\}; \qquad \text{formula (I)}$$

wherein l+m+n+o+x=3-100, and l, m, n or o independently of each other is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90 and 91-100 provided that the overall content of Arg (Arginine), Lys (Lysine), His (Histidine) and Orn (Ornithine) represents at least 10% of all amino acids of the oligopeptide; and Xaa is any amino acid selected from native (=naturally occurring) or non-native amino acids except of Arg, Lys, His or Orn; and x is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80, 81-90, provided, that the overall content of Xaa does not exceed 90% of all amino acids of the oligopeptide. Any of amino acids Arg, Lys, His, Orn and Xaa may be positioned at any place of the peptide. In this context cationic peptides or proteins in the range of 7-30 amino acids are particular preferred.

Further, the cationic or polycationic peptide or protein, when defined according to formula $\{(Arg)_l;(Lys)_m;(His)_n;(Orn)_o;(Xaa)_x\}$ (formula (I)) as shown above and which comprise or are additionally modified to comprise at least one —SH moeity, may be, without being restricted thereto, selected from subformula (Ia):

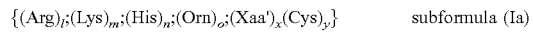

$\{(Arg)_l;(Lys)_m;(His)_n;(Orn)_o;(Xaa')_x(Cys)_y\}$  subformula (Ia)

wherein $(Arg)_l;(Lys)_m;(His)_n;(Orn)_o$; and x are as defined herein, Xaa' is any amino acid selected from native (=naturally occurring) or non-native amino acids except of Arg, Lys, His, Orn or Cys and y is any number selected from 0, 1, 2, 3, 4, 5, 6, 7, 8, 9, 10, 11, 12, 13, 14, 15, 16, 17, 18, 19, 20, 21-30, 31-40, 41-50, 51-60, 61-70, 71-80 and 81-90, provided that the overall content of Arg (Arginine), Lys (Lysine), His (Histidine) and Orn (Ornithine) represents at least 10% of all amino acids of the oligopeptide. Further, the cationic or polycationic peptide may be selected from subformula (Ib):

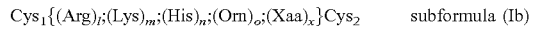

$Cys_1\{(Arg)_l;(Lys)_m;(His)_n;(Orn)_o;(Xaa)_x\}Cys_2$  subformula (Ib)

wherein empirical formula $\{(Arg)_l;(Lys)_m;(His)_n;(Orn)_o;(Xaa)_x\}$ (formula (III)) is as defined herein and forms a core of an amino acid sequence according to (semiempirical) formula (III) and wherein $Cys_1$ and $Cys_2$ are Cysteines proximal to, or terminal to $(Arg)_l;(Lys)_m;(His)_n;(Orn)_o;(Xaa)_x$.

Further preferred cationic or polycationic compounds, which can be used as transfection or complexation agent may include cationic polysaccharides, for example chitosan, polybrene, cationic polymers, e.g. polyethyleneimine (PEI), cationic lipids, e.g. DOTMA: [1-(2,3-sioleyloxy)propyl)]-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicylspermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(α-trimethylammonioacetyl) diethanolamine chloride, CLIP1: rac-[(2,3-dioctadecyloxypropyl)(2-hydroxyethyl)]-dimethylammonium chloride, CLIP6: rac-[2(2,3-dihexadecyloxypropyl-oxymethyloxy)ethyl]-trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as β-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, chitosan, etc., silan backbone based polymers, such as PMOXA-PDMS copolymers, etc., blockpolymers consisting of a combination of one or more cationic blocks (e.g. selected from a cationic polymer as mentioned above) and of one or more hydrophilic or hydrophobic blocks (e.g polyethyleneglycole); etc.

According to another embodiment, the pharmaceutical composition according to the invention may comprise an adjuvant in order to enhance the immunostimulatory properties of the pharmaceutical composition. In this context, an adjuvant may be understood as any compound, which is suitable to support administration and delivery of the components such as the artificial nucleic acid molecule or vector comprised in the pharmaceutical composition according to the invention. Furthermore, such an adjuvant may, without being bound thereto, initiate or increase an immune response of the innate immune system, i.e. a non-specific immune response. With other words, when administered, the pharmaceutical composition according to the invention typically initiates an adaptive immune response directed to the antigen encoded by the artificial nucleic acid molecule. Additionally, the pharmaceutical composition according to the invention may generate an (supportive) innate immune response due to addition of an adjuvant as defined herein to the pharmaceutical composition according to the invention.

Such an adjuvant may be selected from any adjuvant known to a skilled person and suitable for the present case, i.e. supporting the induction of an immune response in a mammal. Preferably, the adjuvant may be selected from the group consisting of, without being limited thereto, TDM, MDP, muramyl dipeptide, pluronics, alum solution, aluminium hydroxide, ADJUMER™ (polyphosphazene); aluminium phosphate gel; glucans from algae; algammulin; aluminium hydroxide gel (alum); highly protein-adsorbing aluminium hydroxide gel; low viscosity aluminium hydroxide gel; AF or SPT (emulsion of squalane (5%), Tween 80 (0.2%), Pluronic L121 (1.25%), phosphate-buffered saline, pH 7.4); AVRIDINE™ (propanediamine); BAY R1005™ ((N-(2-deoxy-2-L-leucylamino-b-D-glucopyranosyl)-N-octadecyl-dodecanoyl-amide hydroacetate); CALCITRIOL™ (1-alpha,25-dihydroxy-vitamin D3); calcium phosphate gel; CAP™ (calcium phosphate nanoparticles); cholera holotoxin, cholera-toxin-A1-protein-A-D-fragment fusion protein, sub-unit B of the cholera toxin; CRL 1005 (block copolymer P1205); cytokine-containing liposomes; DDA (dimethyldioctadecylammonium bromide); DHEA (dehydroepiandrosterone); DMPC (dimyristoylphosphatidylcholine); DMPG (dimyristoylphosphatidylglycerol); DOC/alum complex (deoxycholic acid sodium salt); Freund's complete adjuvant; Freund's incomplete adjuvant; gamma inulin; Gerbu adjuvant (mixture of: i) N-acetylglucosaminyl-(P1-4)-N-acetylmuramyl-L-alanyl-D-glutamine (GMDP), ii) dimethyldioctadecylammonium chloride (DDA), iii) zinc-L-proline salt complex (ZnPro-8); GM-CSF); GMDP (N-acetylglucosaminyl-(beta-1-4)-N-acetylmuramyl-L-alanyl-D-isoglutamine); imiquimod (1-(2-methylpropyl)-1H-imidazo[4,5-c]quinoline-4-amine); ImmTher™ (N-acetylglucosaminyl-N-acetylmuramyl-L-Ala-D-isoGlu-L-Ala-glycerol dipalmitate); DRVs (immunoliposomes prepared from dehydration-rehydration vesicles); interferon-gamma; interleukin-1beta; interleukin-2; interleukin-7; interleukin-12; ISCOMS™; ISCOPREP 7.0.3.™; liposomes; LOXORIBINE™ (7-allyl-8-oxoguanosine); LT oral adjuvant (*E. coli* labile enterotoxin-protoxin); microspheres and microparticles of any composition; MF59™; (squalene-water emulsion); MONTANIDE ISA 51™ (purified incomplete Freund's adjuvant); MONTANIDE ISA 720™ (metabolisable oil adjuvant); MPL™ (3-Q-desacyl-4'-monophosphoryl lipid A); MTP-PE and MTP-PE liposomes ((N-acetyl-L-alanyl-D-isoglutaminyl-L-alanine-2-(1,2-dipalmitoyl-sn-glycero-3-(hydroxyphosphoryloxy))-ethylamide, monosodium salt); MURAMETIDE™ (Nac-Mur-L-Ala-D-Gln-OCH3); MURAPALMITINE™ and D-MURAPALMITINE™ (Nac-Mur-L-Thr-D-isoGln-sn-glyceroldipalmitoyl); NAGO (neuraminidase-galactose oxidase); nanospheres or nanoparticles of any composition; NISVs (non-ionic surfactant vesicles); PLEURAN™ (beta-glucan); PLGA, PGA and PLA (homo- and co-polymers of lactic acid and glycolic acid; microspheres/nanospheres); PLURONIC L121™; PMMA (polymethyl methacrylate); PODDS™ (proteinoid microspheres); polyethylene carbamate derivatives; poly-rA: poly-rU (polyadenylic acid-polyuridylic acid complex); polysorbate 80 (Tween 80); protein cochleates (Avanti Polar Lipids, Inc., Alabaster, Ala.); STIMULON™ (QS-21); Quil-A (Quil-A saponin); S-28463 (4-amino-otec-dimethyl-2-ethoxymethyl-1H-imidazo[4,5 c]quinoline-1-ethanol); SAF-1™ ("Syntex adjuvant formulation"); Sendai proteoliposomes and Sendai-containing lipid matrices; Span-85 (sorbitan trioleate); Specol (emulsion of Marcol 52, Span 85 and Tween 85); squalene or Robane® (2,6,10,15,19,23-hexamethyltetracosan and 2,6,10,15,19,23-hexamethyl-2,6,10,14,18,22-tetracosahexane); stearyltyrosine (octadecyltyrosine hydrochloride); Theramid® (N-acetylglucosaminyl-N-acetylmuramyl-L-Ala-D-isoGlu-L-Ala-dipalmitoxypropylamide); Theronyl-MDP (Termurtide™ or [thr 1]-MDP; N-acetylmuramyl-L-threonyl-D-isoglutamine); Ty particles (Ty-VLPs or virus-like particles); Walter-Reed liposomes (liposomes containing lipid A adsorbed on aluminium hydroxide), and lipopeptides, including Pam3Cys, in particular aluminium salts, such as Adju-phos, Alhydrogel, Rehydragel; emulsions, including CFA, SAF, IFA, MF59, Provax, TiterMax, Montanide, Vaxfectin; copolymers, including Optivax (CRL1005), L121, Poloaxmer4010), etc.; liposomes, including Stealth, cochleates, including BIORAL; plant derived adjuvants, including QS21, Quil A, Iscomatrix, ISCOM; adjuvants suitable for costimulation including Tomatine, biopolymers, including PLG, PMM, Inulin,; microbe derived adjuvants, including Romurtide, DETOX, MPL, CWS, Mannose, CpG nucleic acid sequences, CpG7909, ligands of human TLR 1-10, ligands of murine TLR 1-13, ISS-1018, IC31, Imidazoquinolines, Ampligen, Ribi529, IMOxine, IRIVs, VLPs, cholera toxin, heat-labile toxin, Pam3Cys, Flagellin, GPI anchor, LNFPIII/Lewis X, antimicrobial peptides, UC-1V150, RSV fusion protein, cdiGMP; and adjuvants suitable as antagonists including CGRP neuropeptide.

Suitable adjuvants may also be selected from cationic or polycationic compounds wherein the adjuvant is preferably prepared upon complexing the artificial nucleic acid molecule or the vector of the pharmaceutical composition with the cationic or polycationic compound. Association or complexing the artificial nucleic acid molecule or the vector of the pharmaceutical composition with cationic or polycationic compounds as defined herein preferably provides adjuvant properties and confers a stabilizing effect to the artificial nucleic acid molecule or the vector of the pharmaceutical composition. Particularly such preferred, such cationic or polycationic compounds are selected from cationic or polycationic peptides or proteins, including protamine, nucleoline, spermin or spermidine, or other cationic peptides or proteins, such as poly-L-lysine (PLL), poly-arginine, basic polypeptides, cell penetrating peptides (CPPs), including HIV-binding peptides, Tat, HIV-1 Tat (HIV), Tat-derived peptides, Penetratin, VP22 derived or analog peptides, HSV VP22 (Herpes simplex), MAP, KALA or protein transduction domains (PTDs, PpT620, prolin-rich peptides, arginine-rich peptides, lysine-rich peptides, MPG-peptide(s), Pep-1, L-oligomers, Calcitonin peptide(s), Antennapedia-derived peptides (particularly from *Drosophila antennapedia*), pAntp, pIsl, FGF, Lactoferrin, Transportan, Buforin-2, Bac715-24, SynB, SynB(1), pVEC, hCT-derived peptides, SAP, protamine, spermine, spermidine, or histones. Further preferred cationic or polycationic compounds may include cationic polysaccharides, for example chitosan, polybrene, cationic polymers, e.g. polyethyleneimine (PEI), cationic lipids, e.g. DOTMA: □1-(2,3-sioleyloxy)propyl□-N,N,N-trimethylammonium chloride, DMRIE, di-C14-amidine, DOTIM, SAINT, DC-Chol, BGTC, CTAP, DOPC, DODAP, DOPE: Dioleyl phosphatidylethanol-amine, DOSPA, DODAB, DOIC, DMEPC, DOGS: Dioctadecylamidoglicyl-spermin, DIMRI: Dimyristo-oxypropyl dimethyl hydroxyethyl ammonium bromide, DOTAP: dioleoyloxy-3-(trimethylammonio)propane, DC-6-14: O,O-ditetradecanoyl-N-(□-trimethylammonioacetyl)diethanolamine chloride, CLIP 1: rac-[(2,3-dioctadecyloxypropyl)(2-hydroxyethyl)]-dimethylammonium chloride, CLIP6: rac-[2(2,3-dihexadecyloxy-propyl-oxymethyloxy)ethyl]-trimethylammonium, CLIP9: rac-[2(2,3-dihexadecyloxypropyl-oxysuccinyloxy)ethyl]-trimethylammonium, oligofectamine, or cationic or polycationic polymers, e.g. modified polyaminoacids, such as □-aminoacid-polymers or reversed polyamides, etc., modified polyethylenes, such as PVP (poly(N-ethyl-4-vinylpyridinium bromide)), etc., modified acrylates, such as pDMAEMA (poly(dimethylaminoethyl methylacrylate)), etc., modified Amidoamines such as pAMAM (poly(amidoamine)), etc., modified polybetaaminoester (PBAE), such as diamine end modified 1,4 butanediol diacrylate-co-5-amino-1-pentanol polymers, etc., dendrimers, such as polypropylamine dendrimers or pAMAM based dendrimers, etc., polyimine(s), such as PEI: poly(ethyleneimine), poly(propyleneimine), etc., polyallylamine, sugar backbone based polymers, such as cyclodextrin based polymers, dextran based polymers, Chitosan, etc., silan backbone based polymers, such as PMOXA-PDMS copolymers, etc., Blockpolymers consisting of a combination of one or more cationic blocks (e.g. selected of a cationic polymer as mentioned above) and of one or more hydrophilic- or hydrophobic blocks (e.g polyethyleneglycole); etc.

Additionally, preferred cationic or polycationic proteins or peptides, which can be used as an adjuvant by complexing the artificial nucleic acid molecule or the vector, preferably an RNA, of the composition, may be selected from following proteins or peptides having the following total formula (I): $(Arg)_l;(Lys)_m;(His)_n;(Orn)_o;(Xaa)_x$, wherein $l+m+n+o+x=8-15$, and l, m, n or o independently of each other may be any number selected from 0, 1, 2, 3, 4, 5, 6, 7, 8, 9, 10, 11, 12, 13, 14 or 15, provided that the overall content of Arg, Lys, His and Orn represents at least 50% of all amino acids of the oligopeptide; and Xaa may be any amino acid selected from native (=naturally occurring) or non-native amino acids except of Arg, Lys, His or Orn; and x may be any number selected from 0, 1, 2, 3 or 4, provided, that the overall content of Xaa does not exceed 50% of all amino acids of the oligopeptide. Particularly preferred oligoarginines in this context are e.g. Arg7, Arg8, Arg9, Arg7, H3R9, R9H3, H3R9H3, YSSR9SSY, (RKH)4, Y(RKH)2R, etc.

The ratio of the artificial nucleic acid or the vector to the cationic or polycationic compound may be calculated on the basis of the nitrogen/phosphate ratio (N/P-ratio) of the entire nucleic acid complex. For example, 1 µg RNA typically contains about 3 nmol phosphate residues, provided the RNA exhibits a statistical distribution of bases. Additionally, 1 µg peptide typically contains about x nmol nitrogen residues, dependent on the molecular weight and the number of basic amino acids. When exemplarily calculated for (Arg)9 (molecular weight 1424 g/mol, 9 nitrogen atoms), 1 µg (Arg)9 contains about 700 pmol (Arg)9 and thus 700× 9=6300 pmol basic amino acids=6.3 nmol nitrogen atoms. For a mass ratio of about 1:1 RNA/(Arg)9 an N/P ratio of about 2 can be calculated. When exemplarily calculated for protamine (molecular weight about 4250 g/mol, 21 nitrogen atoms, when protamine from salmon is used) with a mass ratio of about 2:1 with 2 µg RNA, 6 nmol phosphate are to be calculated for the RNA; 1 µg protamine contains about 235 pmol protamine molecules and thus 235×21=4935 pmol basic nitrogen atoms=4.9 nmol nitrogen atoms. For a mass ratio of about 2:1 RNA/protamine an N/P ratio of about 0.81 can be calculated. For a mass ratio of about 8:1 RNA/protamine an N/P ratio of about 0.2 can be calculated. In the context of the present invention, an N/P-ratio is preferably in the range of about 0.1-10, preferably in a range of about 0.3-4 and most preferably in a range of about 0.5-2 or 0.7-2 regarding the ratio of nucleic acid:peptide in the complex, and most preferably in the range of about 0.7-1.5.

Patent application WO2010/037539, the disclosure of which is incorporated herein by reference, describes an immunostimulatory composition and methods for the preparation of an immunostimulatory composition. Accordingly, in a preferred embodiment of the invention, the composition is obtained in two separate steps in order to obtain both, an efficient immunostimulatory effect and efficient translation of the artificial nucleic acid molecule according to the invention. Therein, a so called "adjuvant component" is prepared by complexing —in a first step—the artificial nucleic acid molecule or vector, preferably an RNA, of the adjuvant component with a cationic or polycationic compound in a specific ratio to form a stable complex. In this context, it is important, that no free cationic or polycationic compound or only a negligibly small amount remains in the adjuvant component after complexing the nucleic acid. Accordingly, the ratio of the nucleic acid and the cationic or polycationic compound in the adjuvant component is typically selected in a range that the nucleic acid is entirely complexed and no free cationic or polycationic compound or only a neclectably small amount remains in the composition. Preferably the ratio of the adjuvant component, i.e. the ratio of the nucleic acid to the cationic or polycationic compound is selected from a range of about 6:1 (w/w) to about 0.25:1 (w/w), more preferably from about 5:1 (w/w) to about 0.5:1 (w/w), even more preferably of about 4:1 (w/w) to about 1:1 (w/w) or of about 3:1 (w/w) to about 1:1 (w/w), and most preferably a ratio of about 3:1 (w/w) to about 2:1 (w/w).

According to a preferred embodiment, the artificial nucleic acid molecule or vector, preferably an RNA molecule, according to the invention is added in a second step to the complexed nucleic acid molecule, preferably an RNA, of the adjuvant component in order to form the (immunostimulatory) composition of the invention. Therein, the artificial acid molecule or vector, preferably an RNA, of the invention is added as free nucleic acid, i.e. nucleic acid, which is not complexed by other compounds. Prior to addition, the free artificial nucleic acid molecule or vector is not complexed and will preferably not undergo any detectable or significant complexation reaction upon the addition of the adjuvant component.

Suitable adjuvants may furthermore be selected from nucleic acids having the formula (II): GlXmGn, wherein: G is guanosine, uracil or an analogue of guanosine or uracil; X is guanosine, uracil, adenosine, thymidine, cytosine or an analogue of the above-mentioned nucleotides; l is an integer from 1 to 40, wherein when l=1 G is guanosine or an analogue thereof, when l>1 at least 50% of the nucleotides are guanosine or an analogue thereof; m is an integer and is at least 3; wherein when m=3 X is uracil or an analogue thereof, when m>3 at least 3 successive uracils or analogues of uracil occur; n is an integer from 1 to 40, wherein when n=1 G is guanosine or an analogue thereof, when n>1 at least 50% of the nucleotides are guanosine or an analogue thereof.

Other suitable adjuvants may furthermore be selected from nucleic acids having the formula (III): ClXmCn, wherein: C is cytosine, uracil or an analogue of cytosine or uracil; X is guanosine, uracil, adenosine, thymidine, cytosine or an analogue of the above-mentioned nucleotides; l is an integer from 1 to 40, wherein when l=1 C is cytosine or an analogue thereof, when l>1 at least 50% of the nucleotides are cytosine or an analogue thereof; m is an integer and is at least 3; wherein when m=3 X is uracil or an analogue thereof, when m>3 at least 3 successive uracils or analogues of uracil occur; n is an integer from 1 to 40, wherein when n=1 C is cytosine or an analogue thereof, when n>1 at least 50% of the nucleotides are cytosine or an analogue thereof.

The pharmaceutical composition according to the present invention preferably comprises a "safe and effective amount" of the components of the pharmaceutical composition, particularly of the inventive artificial nucleic acid molecule, the vector and/or the cells as defined herein. As used herein, a "safe and effective amount" means an amount sufficient to significantly induce a positive modification of a disease or disorder as defined herein. At the same time, however, a "safe and effective amount" preferably avoids serious side-effects and permits a sensible relationship between advantage and risk. The determination of these limits typically lies within the scope of sensible medical judgment.

In a further aspect, the present invention provides the artificial nucleic acid molecule according to the present invention, the vector according to the present invention, the cell according to the present invention, or the pharmaceutical composition according to the present invention for use as a medicament, for example, as vaccine (in genetic vaccination) or in gene therapy.

The artificial nucleic acid molecule according to the present invention, the vector according to the present invention, the cell according to the present invention, or the pharmaceutical composition according to the present invention are particularly suitable for any medical application which makes use of the therapeutic action or effect of peptides, polypeptides or proteins, or where supplementation of a particular peptide or protein is needed. Thus, the present invention provides the artificial nucleic acid molecule according to the present invention, the vector according to the present invention, the cell according to the present invention, or the pharmaceutical composition according to the present invention for use in the treatment or prevention of diseases or disorders amenable to treatment by the therapeutic action or effect of peptides, polypeptides or proteins or amenable to treatment by supplementation of a particular peptide, polypeptide or protein. For example, the artificial nucleic acid molecule according to the present invention, the vector according to the present invention, the cell according to the present invention, or the pharmaceutical composition according to the present invention may be used for the treatment or prevention of genetic diseases, autoimmune diseases, cancerous or tumour-related diseases, infectious diseases, chronic diseases or the like, e.g., by genetic vaccination or gene therapy.

In particular, such therapeutic treatments which benefit from a stable and prolonged presence of therapeutic peptides, polypeptides or proteins in a subject to be treated are especially suitable as medical application in the context of the present invention, since the inventive 3'-UTR element provides for a stable and prolonged expression of the encoded peptide or protein of the inventive artificial nucleic acid molecule or vector. Thus, a particularly suitable medical application for the artificial nucleic acid molecule according to the present invention, the vector according to the present invention, the cell according to the present invention, or the pharmaceutical composition according to the present invention is vaccination. Thus, the present invention provides the artificial nucleic acid molecule according to the present invention, the vector according to the present invention, the cell according to the present invention, or the pharmaceutical composition according to the present invention for vaccination of a subject, preferably a mammalian subject, more preferably a human subject. Preferred vaccination treatments are vaccination against infectious diseases, such as bacterial, protozoal or viral infections, and anti-tumour-vaccination. Such vaccination treatments may be prophylactic or therapeutic.

Depending on the disease to be treated or prevented, the ORF may be selected. For example, the open reading frame may code for a protein that has to be supplied to a patient suffering from total lack or at least partial loss of function of a protein, such as a patient suffering from a genetic disease. Additionally the open reading frame may be chosen from an ORF coding for a peptide or protein, which beneficially influences a disease or the condition of a subject. Furthermore, the open reading frame may code for a peptide or protein which effects down-regulation of a pathological overproduction of a natural peptide or protein or elimination of cells expressing pathologically a protein or peptide. Such lack, loss of function or overproduction may, e.g., occur in the context of tumour and neoplasia, autoimmune diseases, allergies, infections, chronic diseases or the like. Furthermore, the open reading frame may code for an antigen or immunogen, e.g. for an epitope of a pathogen or for a tumour antigen. Thus, in preferred embodiments, the artificial nucleic acid molecule or the vector according to the present invention comprises an ORF encoding an amino acid sequence comprising or consisting of an antigen or immunogen, e.g. an epitope of a pathogen or a tumour-associated antigen, a 3'-UTR element as described above, and optional further components, such as a poly(A) sequence etc.

In the context of medical application, in particular, in the context of vaccination, it is preferred that the artificial nucleic acid molecule according to the present invention is RNA, preferably mRNA, since DNA harbours the risk of eliciting an anti-DNA immune response and tends to insert into genomic DNA. However, in some embodiments, for example, if a viral delivery vehicle, such as an adenoviral delivery vehicle is used for delivery of the artificial nucleic acid molecule or the vector according to the present invention, e.g., in the context of gene therapeutic treatments, it may be desirable that the artificial nucleic acid molecule or the vector is a DNA molecule.

The artificial nucleic acid molecule according to the present invention, the vector according to the present invention, the cell according to the present invention, or the pharmaceutical composition according to the present invention may be administered orally, parenterally, by inhalation spray, topically, rectally, nasally, buccally, vaginally, via an implanted reservoir or via jet injection. The term parenteral as used herein includes subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, and sublingual injection or infusion techniques. In a preferred embodiment, the artificial nucleic acid molecule according to the present invention, the vector according to the present invention, the cell according to the present invention, or the pharmaceutical composition according to the present invention is administered via needle-free injection (e.g. jet injection).

Preferably, the artificial nucleic acid molecule according to the present invention, the vector according to the present invention, the cell according to the present invention, or the pharmaceutical composition according to the present invention is administered parenterally, e.g. by parenteral injection, more preferably by subcutaneous, intravenous, intramuscular, intra-articular, intra-synovial, intrasternal, intrathecal, intrahepatic, intralesional, intracranial, transdermal, intradermal, intrapulmonal, intraperitoneal, intracardial, intraarterial, sublingual injection or via infusion techniques. Particularly preferred is intradermal and intramuscular injection. Sterile injectable forms of the inventive pharmaceutical composition may be aqueous or oleaginous suspension. These suspensions may be formulated according to techniques known in the art using suitable dispersing or wetting agents and suspending agents. Preferably, the solutions or suspensions are administered via needle-free injection (e.g. jet injection).

The artificial nucleic acid molecule according to the present invention, the vector according to the present invention, the cell according to the present invention, or the pharmaceutical composition according to the present invention may also be administered orally in any orally acceptable dosage form including, but not limited to, capsules, tablets, aqueous suspensions or solutions.

The artificial nucleic acid molecule according to the present invention, the vector according to the present invention, the cell according to the present invention, or the pharmaceutical composition according to the present invention may also be administered topically, especially when the target of treatment includes areas or organs readily accessible by topical application, e.g. including diseases of the skin or of any other accessible epithelial tissue. Suitable topical formulations are readily prepared for each of these areas or organs. For topical applications, the artificial nucleic acid molecule according to the present invention, the vector according to the present invention, the cell according to the present invention, or the pharmaceutical composition according to the present invention may be formulated in a suitable ointment suspended or dissolved in one or more carriers.

In one embodiment, the use as a medicament comprises the step of transfection of mammalian cells, preferably in vitro or ex vivo transfection of mammalian cells, more preferably in vitro transfection of isolated cells of a subject to be treated by the medicament. If the use comprises the in vitro transfection of isolated cells, the use as a medicament may further comprise the readministration of the transfected cells to the patient. The use of the inventive artificial nucleic acid molecules or the vector as a medicament may further comprise the step of selection of successfully transfected isolated cells. Thus, it may be beneficial if the vector further comprises a selection marker. Also, the use as a medicament may comprise in vitro transfection of isolated cells and purification of an expression-product, i.e. the encoded peptide or protein from these cells. This purified peptide or protein may subsequently be administered to a subject in need thereof.

The present invention also provides a method for treating or preventing a disease or disorder as described above comprising administering the artificial nucleic acid molecule according to the present invention, the vector according to the present invention, the cell according to the present invention, or the pharmaceutical composition according to the present invention to a subject in need thereof.

Furthermore, the present invention provides a method for treating or preventing a disease or disorder comprising transfection of a cell with an artificial nucleic acid molecule according to the present invention or with the vector according to the present invention. Said transfection may be performed in vitro, ex vivo or in vivo. In a preferred embodiment, transfection of a cell is performed in vitro and the transfected cell is administered to a subject in need thereof, preferably to a human patient. Preferably, the cell which is to be transfected in vitro is an isolated cell of the subject, preferably of the human patient. Thus, the present invention provides a method of treatment comprising the steps of isolating a cell from a subject, preferably from a human patient, transfecting the isolated cell with the artificial nucleic acid according to the present invention or the vector according to the present invention, and administering the transfected cell to the subject, preferably the human patient.

The method of treating or preventing a disorder according to the present invention is preferably a vaccination method or a gene therapy method as described above.

As described above, the inventive 3'-UTR element is capable of stabilizing an mRNA molecule and/or of enhancing, stabilizing and/or prolonging the protein production from an mRNA molecule. Thus, in a further aspect, the present invention relates to a method for stabilizing an RNA molecule, preferably an mRNA molecule, comprising the step of associating the RNA molecule, preferably the mRNA molecule, or a vector encoding the RNA molecule, with a 3'-UTR element comprising or consisting of a nucleic acid sequence which is derived from the 3'-UTR of a ribosomal protein gene or from a variant of the 3'-UTR of a ribosomal protein gene, preferably with the 3'-UTR element as described above.

Furthermore, the present invention relates to a method for enhancing, stabilizing and/or prolonging protein production from an artificial nucleic acid molecule or from a vector, preferably from an mRNA molecule, and/or for stabilizing and/or prolonging protein production from an artificial nucleic acid molecule or from a vector, preferably from an mRNA molecule, the method comprising the step of associating the artificial nucleic acid molecule or the vector, preferably the mRNA molecule, with a 3'-UTR element which comprises or consists of a nucleic acid sequence which is derived from the 3'-UTR of a ribosomal protein gene or from a variant of the 3'-UTR of a ribosomal protein gene, preferably with the 3'-UTR element as described above.

The term "associating the artificial nucleic acid molecule or the vector with a 3'-UTR element" in the context of the present invention preferably means functionally associating or functionally combining the artificial nucleic acid molecule or the vector with the 3'-UTR element. This means that the artificial nucleic acid molecule or the vector and the 3'-UTR element, preferably the 3'-UTR element as described above, are associated or coupled such that the function of the 3'-UTR element, e.g., the RNA and/or protein production stabilizing function, is exerted. Typically, this means that the 3'-UTR element is integrated into the artificial nucleic acid molecule or the vector, preferably the mRNA molecule, 3' to an open reading frame, preferably immediately 3' to an open reading frame, preferably between the open reading frame and a poly(A) sequence or a polyadenylation signal. Preferably, the 3'-UTR element is integrated into the artificial nucleic acid molecule or the vector, preferably the mRNA, as 3'-UTR, i.e. such that the 3'-UTR element is the 3'-UTR of the artificial nucleic acid molecule or the vector, preferably the mRNA, i.e., such that it extends from the 3'-side of the open reading frame to the 5'-side of a poly(A) sequence or a polyadenylation signal, optionally connected via a short linker, such as a sequence comprising or consisting of one or more restriction sites. Thus, preferably, the term "associating the artificial nucleic acid molecule or the vector with a 3'-UTR element" means functionally associating the 3'-UTR element with an open reading frame located within the artificial nucleic acid molecule or the vector, preferably within the mRNA molecule. The 3'-UTR and the ORF are as described above for the artificial nucleic acid molecule according to the present invention, for example, preferably the ORF and the 3'-UTR are heterologous, e.g. derived from different genes, as described above.

In a further aspect, the present invention provides the use of a 3'-UTR element, preferably the 3'-UTR element as described above, for increasing the stability of an RNA molecule, preferably of an mRNA molecule, wherein the 3'-UTR element comprises or consists of a nucleic acid sequence, which is derived from the 3'-UTR of a ribosomal protein gene or from a variant of the 3'-UTR of a ribosomal protein gene.

Furthermore, the present invention provides the use of a 3'-UTR element, preferably the 3'-UTR element as described above, for increasing protein production from an artificial nucleic acid molecule or a vector, preferably from an mRNA molecule, and/or for stabilizing and/or prolonging protein production from an artificial nucleic acid molecule or a vector molecule, preferably from an mRNA molecule, wherein the 3'-UTR element comprises or consists of a nucleic acid sequence which is derived from the 3'-UTR of a ribosomal protein gene or from a variant of the 3'-UTR of a ribosomal protein gene as described above.

The uses according to the present invention preferably comprise associating the artificial nucleic acid molecule, the vector, or the RNA with the 3'-UTR element as described above.

The compounds and ingredients of the inventive pharmaceutical composition may also be manufactured and traded separately of each other. Thus, the invention relates further to a kit or kit of parts comprising an artificial nucleic acid molecule according to the invention, a vector according to the invention, a cell according to the invention, and/or a pharmaceutical composition according to the invention. Preferably, such kit or kits of parts may, additionally, comprise instructions for use, cells for transfection, an adjuvant, a means for administration of the pharmaceutical composition, a pharmaceutically acceptable carrier and/or a pharmaceutically acceptable solution for dissolution or dilution of the artificial nucleic acid molecule, the vector, the cells or the pharmaceutical composition.

BRIEF DESCRIPTION OF THE DRAWINGS

The following Figures, Sequences and Examples are intended to illustrate the invention further. They are not intended to limit the subject matter of the invention thereto.

FIGS. 1 to 3 show sequences encoding mRNAs that can be obtained by in vitro transcription. The following abbreviations are used:

rpl32: 5'-UTR of human ribosomal protein Large 32 lacking the 5' terminal oligopyrimidine tract PpLuc (GC): GC-enriched mRNA sequence coding for *Photinus pyralis* luciferase A64: poly(A)-sequence with 64 adenylates ag: center, α-complex-binding portion of the 3'-UTR of human α-globin rps9: 3'-UTR element derived from the 3'-UTR of human ribosomal protein Small 9

C30: poly(C)-sequence with 30 cytidylates histoneSL: A histone stem-loop sequence taken from (Cakmakci, Lerner, Wagner, Zheng, & William F Marzluff, 2008. Mol. Cell. Biol. 28(3):1182-94);

albumin: 3'-UTR of human albumin.

FIG. 1: shows the sequence encoding the mRNA rpl32-PpLuc(GC)-A64-C30-histoneSL (SEQ ID NO:8)

FIG. 2: shows the sequence encoding the mRNA rpl32-PpLuc(GC)-ag-A64-C30-histoneSL (SEQ ID NO:9). The center, α-complex-binding portion of the 3'-UTR of human α-globin was inserted between ORF and poly(A). The PpLuc(GC) ORF is highlighted in italics. The 3'-UTR element derived from □-globin is underlined.

FIG. 3: mRNA sequence of rpl32-PpLuc(GC)-rps9-A64-C30-hSL (SEQ ID NO:7). The 3'-UTR of human ribosomal protein Small 9 was inserted between ORF and poly(A). The PpLuc(GC) ORF is highlighted in italics, the 3' UTR element derived from rps9 is underlined.

Figure 4:
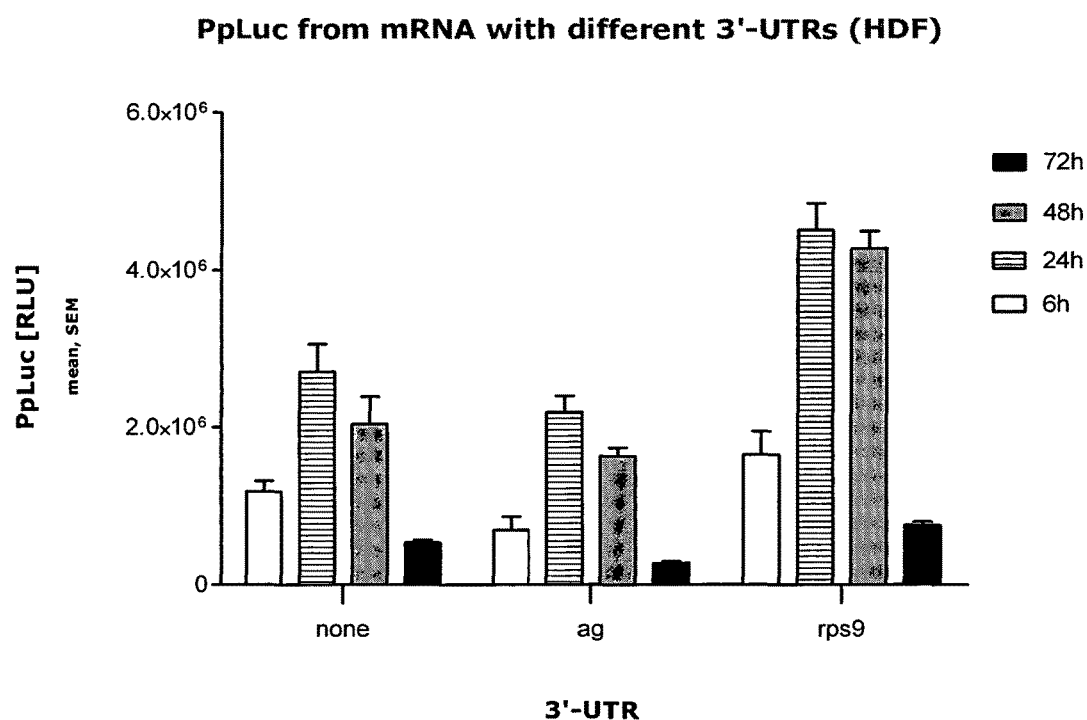

FIG. 4: shows that the 3'-UTR of ribosomal protein Small 9 markedly increases protein expression from mRNA.

The effect of the inventive 3'-UTR of human ribosomal protein Small 9 on luciferase expression from mRNA was examined, compared to luciferase expression from mRNA lacking a 3'-UTR or containing the human α-globin 3'-UTR. Therefore different mRNAs were transfected into human dermal fibroblasts (HDF) by lipofection. Luciferase levels were measured at 6, 24, 48, and 72 hours after transfection. Luciferase was clearly expressed from mRNA lacking a 3'-UTR. However, luciferase expression was not increased by the well-known α-globin 3'-UTR. In contrast, the 3'-UTR of ribosomal protein Small 9 increased luciferase expression markedly. Data are graphed as mean RLU±SEM (relative light units±standard error) for triplicate transfections. RLU are summarized in Example 5.1.

FIG. 5: shows the sequence encoding the mRNA rpl32-PpLuc(GC)-albumin-A64-C30-histoneSL (SEQ ID NO: 206). The 3'-UTR of human albumin was inserted between ORF and poly(A). The PpLuc(GC) ORF is highlighted in italics. The 3'-UTR element derived from albumin is underlined.

Figure 6:
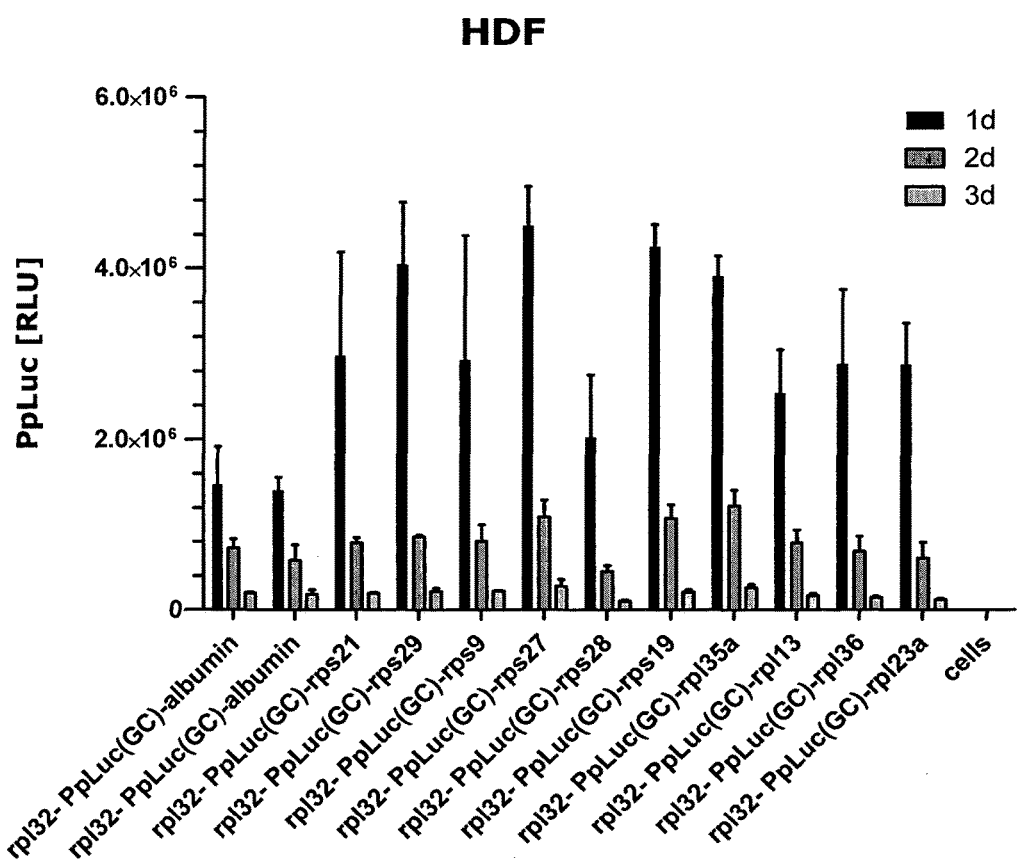

FIG. 6: shows that the 3'-UTRs derived from the murine ribosomal protein genes rps21, rps29, rps9, rps27, rps28, rps19, rpl35a, rpl13, rpl36 and rpl23a increase protein expression from mRNA in HDF cells (human dermal fibroblasts) at least to the same extent as an mRNA comprising the 3'-UTR of the albumin gene, which was already shown to increase protein expression from mRNA (WO2013143698).

Figure 7:
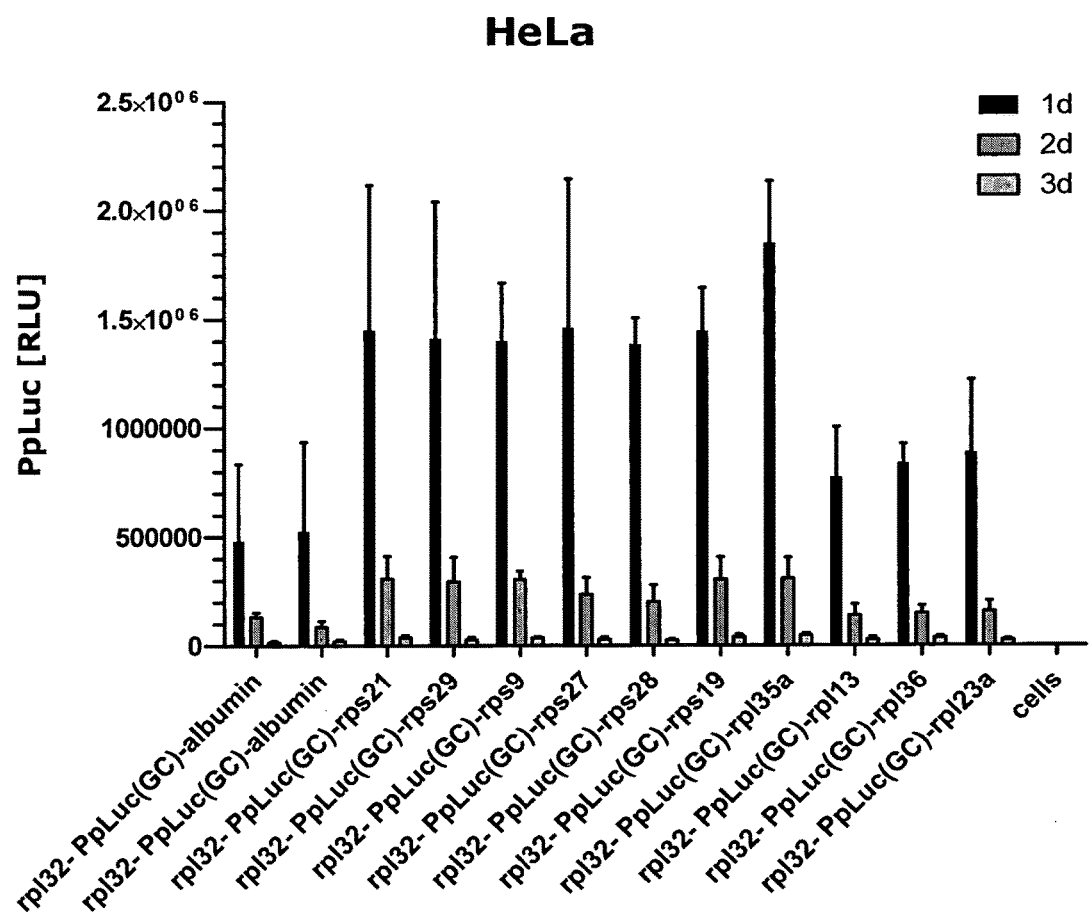

FIG. 7: shows that the 3'-UTRs derived from the murine ribosomal protein genes rps21, rps29, rps9, rps27, rps28, rps19, rpl35a, rpl13, rpl36 and rpl23a increase protein expression from mRNA in HeLa cells at least to the same extent as an mRNA comprising the 3'-UTR of the albumin gene, which was already shown to increase protein expression from mRNA (WO2013143698).

Figure 8:
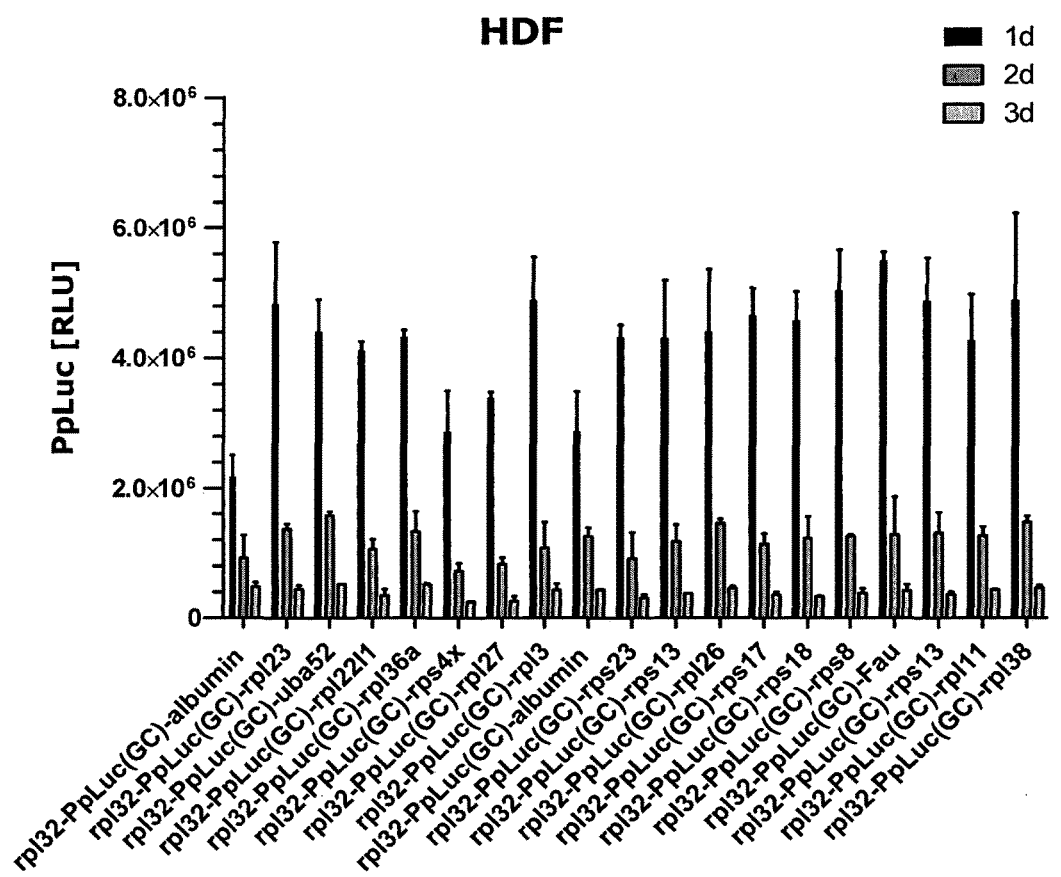

FIG. 8: shows that the 3'-UTRs derived from the murine ribosomal protein genes rpl23, uba52, rpl22l1, rpl36a, rps4x, rpl27, rpl3, rps23, rps13, rpl26, rps17, rps18, rps8, Fau, rps13, rpl11 and rpl38 increase protein expression from mRNA in HDF cells (human dermal fibroblasts) at least to the same extent as an mRNA comprising the 3'-UTR of the albumin gene, which was already shown to increase protein expression from mRNA (WO2013143698).

Figure 9:
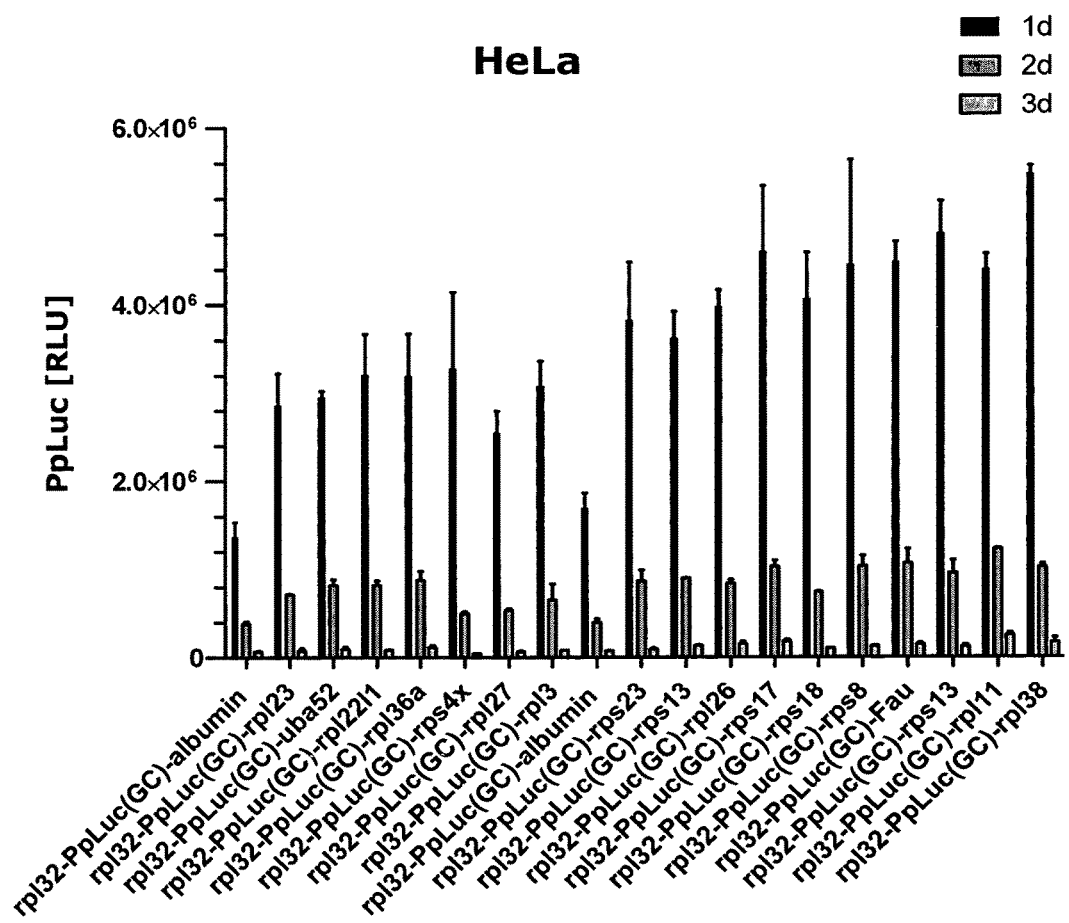

FIG. 9: shows that the 3'-UTRs derived from the murine ribosomal protein genes rpl23, uba52, rpl22l1, rpl36a, rps4x, rpl27, rpl3, rps23, rps13, rpl26, rps17, rps18, rps8, Fau, rps13, rpl11 and rpl38 increase protein expression from mRNA in HeLa cells at least to the same extent as an mRNA comprising the 3'-UTR of the albumin gene, which was already shown to increase protein expression from mRNA (WO2013143698).

EXAMPLES

1. Preparation of DNA-templates

A vector for in vitro transcription was constructed containing a T7 promoter and a GC-enriched sequence coding for *Photinus pyralis* luciferase (PpLuc(GC)). The 5' untranslated region (5'-UTR) of ribosomal protein Large 32 was inserted 5' of PpLuc(GC). An A64 poly(A) sequence, followed by C30 and a histone stem-loop sequence, was inserted 3' of PpLuc(GC). The histone stem-loop sequence was followed by a restriction site used for linearization of the vector before in vitro transcription. mRNA obtained from this vector accordingly by in vitro transcription is designated as "rpl32-PpLuc(GC)-A64-C30-histoneSL".

This vector was modified to include untranslated sequences 3' of the open reading frame (3'-UTR). In summary, vectors comprising the following mRNA encoding sequences have been generated (some of the mRNA encoding sequences are depicted as examples in FIGS. 1 to 3):

rpl32-PpLuc(GC)-A64-C30-histoneSL (SEQ ID NO:8, FIG. 1)
rpl32-PpLuc(GC)-ag-A64-C30-histoneSL (SEQ ID NO:9, FIG. 2)
rpl32-PpLuc(GC)-rps9-A64-C30-histoneSL (SEQ ID NO:7, FIG. 3)
rpl32-PpLuc(GC)-rps21-A64-C30-histoneSL
rpl32-PpLuc(GC)-rps29-A64-C30-histoneSL
rpl32-PpLuc(GC)-rps9-A64-C30-histoneSL
rpl32-PpLuc(GC)-rps27-A64-C30-histoneSL
rpl32-PpLuc(GC)-rps28-A64-C30-histoneSL
rpl32-PpLuc(GC)-rps19-A64-C30-histoneSL
rpl32-PpLuc(GC)-rpl35a-A64-C30-histoneSL
rpl32-PpLuc(GC)-rpl13-A64-C30-histoneSL
rpl32-PpLuc(GC)-rpl36-A64-C30-histoneSL
rpl32-PpLuc(GC)-rpl23a-A64-C30-histoneSL
rpl32-PpLuc(GC)-rpl23-A64-C30-histoneSL
rpl32-PpLuc(GC)-uba52-A64-C30-histoneSL
rpl32-PpLuc(GC)-rpl22l1-A64-C30-histoneSL
rpl32-PpLuc(GC)-rpl36a-A64-C30-histoneSL
rpl32-PpLuc(GC)-rps4x-A64-C30-histoneSL
rpl32-PpLuc(GC)-rpl27-A64-C30-histoneSL
rpl32-PpLuc(GC)-rpl3-A64-C30-histoneSL
rpl32-PpLuc(GC)-rps23-A64-C30-histoneSL rpl32-PpLuc(GC)-rps13-A64-C30-histoneSL
rpl32-PpLuc(GC)-rpl26-A64-C30-histoneSL
rpl32-PpLuc(GC)-rps17-A64-C30-histoneSL
rpl32-PpLuc(GC)-rps18-A64-C30-histoneSL
rpl32-PpLuc(GC)-Fau-A64-C30-histoneSL
rpl32-PpLuc(GC)-rps13-A64-C30-histoneSL
rpl32-PpLuc(GC)-rpl11-A64-C30-histoneSL
rpl32-PpLuc(GC)-rpl38-A64-C30-histoneSL 2. In vitro Transcription The DNA-template according to Example 1 was linearized and transcribed in vitro using T7-RNA polymerase. The DNA template was then digested by DNase-treatment. mRNA transcripts contained a 5'-CAP structure obtained by adding an excess of N7-Methyl-Guanosine-5'-Triphosphate-5'-Guanosine to the transcription reaction. mRNA thus obtained was purified and resuspended in water.

3. Luciferase Expression by mRNA Lipofection

Human dermal fibroblasts (HDF) or HeLa cells were seeded in 24 well plates three days before transfection at a density of $3\times10^4$ cells per well in medium (RPMI 1640 medium with L-glutamine and 25 mM Hepes (Lonza, Basel, Switzerland) to which 10% FCS, 1% Pen/Strep, 1% Glutamine were added). Immediately before lipofection, cells were washed in Opti-MEM. Cells were lipofected with 25 ng of PpLuc-encoding mRNA per well complexed with Lipofectamine2000. mRNA coding for *Renilla reniformis* luciferase (RrLuc) was transfected together with PpLuc mRNA to control for transfection efficiency (2.5 ng of RrLuc mRNA per well). 90 minutes after start of transfection, Opti-MEM was exchanged for medium. 6, 24, 48, and 72 hours after transfection, medium was aspirated and cells were lysed in 100 µl of lysis buffer (Passive Lysis Buffer, Promega). Lysates were stored at −80° C. until luciferase activity was measured.

4. Luciferase Measurement

Luciferase activity was measured as relative light units (RLU) in a Hidex Chameleon plate reader. PpLuc activity was measured at 2 seconds measuring time using 20 µl of lysate and 50 µl of luciferin buffer (Beetle-Juice, PJK GmbH). RrLuc activity was measured at 2 seconds measuring time using 20 µl of lysate and 50 µl of coelenterazin buffer (*Renilla*-Juice, PJK GmbH).

5. Results 5.1 the 3'-UTR of Ribosomal Protein Genes Increases Protein Expression To investigate the effect of the 3'-UTR of ribosomal protein genes on protein expression from mRNA, mRNAs with different UTRs were synthesized: mRNAs either lacked a 3'-UTR, or contained the center, α-complex-binding portion of the 3'-UTR of human α-globin (ag), or contained the 3'-UTR of human ribosomal protein Small 9 (rps9). Luciferase-encoding mRNAs were transfected into human dermal fibroblasts (HDF). Luciferase levels were measured at 6, 24, 48, and 72 hours after transfection. From these data, total protein expressed from 0 to 72 hours was calculated as the area under the curve (AUC) (see following Table 1 and FIG. 4).

TABLE 1

| 3'-UTR | RLU at 6 hours | RLU at 24 hours | RLU at 48 hours | RLU at 72 hours | AUC |
|---|---|---|---|---|---|
| none | 1183752 | 2703805 | 2040979 | 536076 | 126400000 |
| ag | 696317 | 2188117 | 1630769 | 273142 | 96720000 |
| rps9 | 1650962 | 4513651 | 4273634 | 755401 | 226200000 |

Luciferase was clearly expressed from mRNA lacking a 3'-UTR. However, luciferase expression was not increased by the well-known α-globin 3'-UTR. In contrast, the 3'-UTR of ribosomal protein Small 9 increased luciferase expression markedly.

5.2 the 3'-UTRs of Murine Ribosomal Protein Genes Increase Protein Expression

To investigate the effect of 3'-UTRs of murine ribosomal protein genes on protein expression from mRNA, mRNAs with different UTRs were synthesized: mRNAs contained the 3'-UTR of different murine ribosomal proteins (rps21, rps29, rps9, rps27, rps28, rps19, rpl35a, rpl13, rpl36 and rpl23a) and for comparison the 3'-UTR of albumin, which is known to increase protein expression from mRNA (WO2013143698). Luciferase-encoding mRNAs were transfected into human dermal fibroblasts (HDF). Luciferase levels were measured at 24, 48, and 72 hours after transfection. (see following Table 2 and FIG. 6).

TABLE 2

| | RLU at 24 hours | RLU at 48 hours | RLU at 72 hours |
|---|---|---|---|
| rpl32-PpLuc(GC)-albumin | 1468876 | 720609 | 199437 |
| rpl32-PpLuc(GC)-albumin | 1407897 | 580822 | 181030 |
| rpl32-PpLuc(GC)-rps21 | 2974366 | 779239 | 191021 |
| rpl32-PpLuc(GC)-rps29 | 4040760 | 856996 | 216321 |
| rpl32-PpLuc(GC)-rps9 | 2930305 | 802405 | 219681 |
| rpl32-PpLuc(GC)-rps27 | 4503067 | 1090230 | 274320 |
| rpl32-PpLuc(GC)-rps28 | 2026219 | 448372 | 103269 |
| rpl32-PpLuc(GC)-rps19 | 4249503 | 1075621 | 206846 |
| rpl32-PpLuc(GC)-rpl35a | 3907863 | 1223672 | 262108 |
| rpl32-PpLuc(GC)-rpl13 | 2543231 | 782597 | 165374 |
| rpl32-PpLuc(GC)-rpl36 | 2880198 | 683174 | 143539 |
| rpl32-PpLuc(GC)-rpl23a | 2872413 | 606451 | 120915 |
| cells | 118 | 213 | 191 |

The results show that more Luciferase was expressed from mRNA comprising a 3'-UTR of murine ribosomal proteins compared to mRNA comprising the 3'-UTR of albumin, which has already been described to increase protein production.

5.3 the 3'-UTRs of Murine Ribosomal Protein Genes Increase Protein Expression

To investigate the effect of 3'-UTRs of murine ribosomal protein genes on protein expression from mRNA, mRNAs with different UTRs were synthesized: mRNAs contained the 3'-UTR of different murine ribosomal proteins (rps21, rps29, rps9, rps27, rps28, rps19, rpl35a, rpl13, rpl36 and rpl23a) and for comparison the 3'-UTR of albumin. Luciferase-encoding mRNAs were transfected into HeLa cells. Luciferase levels were measured at 24, 48, and 72 hours after transfection. (see following Table 3 and FIG. 7).

TABLE 3

| | RLU at 24 hours | RLU at 48 hours | RLU at 72 hours |
|---|---|---|---|
| rpl32-PpLuc(GC)-albumin | 482053 | 131028 | 16580 |
| rpl32-PpLuc(GC)-albumin | 525908 | 86636 | 21971 |
| rpl32-PpLuc(GC)-rps21 | 1452649 | 307127 | 38317 |
| rpl32-PpLuc(GC)-rps29 | 1413088 | 293924 | 27114 |
| rpl32-PpLuc(GC)-rps9 | 1399948 | 304061 | 36627 |
| rpl32-PpLuc(GC)-rps27 | 1460812 | 235486 | 28608 |

TABLE 3-continued

|  | RLU at 24 hours | RLU at 48 hours | RLU at 72 hours |
|---|---|---|---|
| rpl32-PpLuc(GC)-rps28 | 1384794 | 201359 | 25787 |
| rpl32-PpLuc(GC)-rps19 | 1446100 | 303612 | 40591 |
| rpl32-PpLuc(GC)-rpl35a | 1848259 | 307848 | 47293 |
| rpl32-PpLuc(GC)-rpl13 | 772371 | 138186 | 27188 |
| rpl32-PpLuc(GC)-rpl36 | 837643 | 147108 | 36641 |
| rpl32-PpLuc(GC)-rpl23a | 887643 | 157330 | 24916 |
| cells | 97 | 193 | 117 |

The results show that more Luciferase was expressed from mRNA comprising a 3'-UTR of murine ribosomal proteins compared to mRNA comprising the 3'-UTR of albumin, which has already been described to increase protein production.

5.4 the 3'-UTRs of Murine Ribosomal Protein Genes Increase Protein Expression

To investigate the effect of 3'-UTRs of murine ribosomal protein genes on protein expression from mRNA, mRNAs with different UTRs were synthesized: mRNAs contained the 3'-UTR of different murine ribosomal proteins (rpl23, uba52, rpl22l1, rpl36a, rps4x, rpl27, rpl3, rps23, rps13, rpl26, rps17, rps18, rps8, Fau, rps13, rpl11 and rpl38) and for comparison the 3'-UTR of albumin. Luciferase-encoding mRNAs were transfected into human dermal fibroblasts (HDF). Luciferase levels were measured at 24, 48, and 72 hours after transfection. (see following Table 4 and FIG. 8).

TABLE 4

|  | RLU at 24 hours | RLU at 48 hours | RLU at 72 hours |
|---|---|---|---|
| rpl32-PpLuc(GC)-albumin | 2181914 | 921116 | 474521 |
| rpl32-PpLuc(GC)-rpl23 | 4836067 | 1365445 | 444623 |
| rpl32-PpLuc(GC)-uba52 | 4404508 | 1572170 | 517874 |
| rpl32-PpLuc(GC)-rpl22l1 | 4124152 | 1057264 | 346186 |
| rpl32-PpLuc(GC)-rpl36a | 4326843 | 1328764 | 510755 |
| rpl32-PpLuc(GC)-rps4x | 2879407 | 724050 | 246616 |
| rpl32-PpLuc(GC)-rpl27 | 3391506 | 830016 | 254254 |
| rpl32-PpLuc(GC)-rpl3 | 4889331 | 1074353 | 427856 |
| rpl32-PpLuc(GC)-albumin | 2870659 | 1252124 | 437208 |
| rpl32-PpLuc(GC)-rps23 | 4321886 | 911262 | 308560 |
| rpl32-PpLuc(GC)-rps13 | 4313724 | 1173245 | 373579 |
| rpl32-PpLuc(GC)-rpl26 | 4405685 | 1450797 | 455755 |
| rpl32-PpLuc(GC)-rps17 | 4661966 | 1138370 | 359931 |
| rpl32-PpLuc(GC)-rps18 | 4580492 | 1224085 | 329321 |
| rpl32-PpLuc(GC)-rps8 | 5043669 | 1255188 | 380314 |
| rpl32-PpLuc(GC)-Fau | 5495042 | 1277753 | 416901 |
| rpl32-PpLuc(GC)-rps13 | 4879517 | 1307823 | 361588 |
| rpl32-PpLuc(GC)-rpl11 | 4273583 | 1264210 | 436367 |
| rpl32-PpLuc(GC)-rpl38 | 4891163 | 1477135 | 464923 |

The results show that more Luciferase was expressed from mRNA comprising a 3'-UTR of murine ribosomal proteins compared to mRNA comprising the 3'-UTR of albumin, which has already been described to increase protein production.

5.5 the 3'-UTRs of Murine Ribosomal Protein Genes Increase Protein Expression

To investigate the effect of 3'-UTRs of murine ribosomal protein genes on protein expression from mRNA, mRNAs with different UTRs were synthesized: mRNAs contained the 3'-UTR of different murine ribosomal proteins (rpl23, uba52, rpl22l1, rpl36a, rps4x, rpl27, rpl3, rps23, rps13, rpl26, rps17, rps18, rps8, Fau, rps13, rpl11 and rpl38) and for comparison the 3'-UTR of albumin. Luciferase-encoding mRNAs were transfected into HeLa cells. Luciferase levels were measured at 24, 48, and 72 hours after transfection. (see following Table 5 and FIG. 9).

TABLE 5

|  | RLU at 24 hours | RLU at 48 hours | RLU at 72 hours |
|---|---|---|---|
| rpl32-PpLuc(GC)-albumin | 1370770 | 383733 | 69772 |
| rpl32-PpLuc(GC)-rpl23 | 2860370 | 711666 | 78196 |
| rpl32-PpLuc(GC)-uba52 | 2954670 | 820157 | 97648 |
| rpl32-PpLuc(GC)-rpl22l1 | 3211757 | 822579 | 86780 |
| rpl32-PpLuc(GC)-rpl36a | 3198982 | 878820 | 115778 |
| rpl32-PpLuc(GC)-rps4x | 3282181 | 500040 | 45538 |
| rpl32-PpLuc(GC)-rpl27 | 2544927 | 533978 | 66691 |
| rpl32-PpLuc(GC)-rpl3 | 3081117 | 653787 | 83858 |
| rpl32-PpLuc(GC)-albumin | 1692963 | 397629 | 73285 |
| rpl32-PpLuc(GC)-rps23 | 3828806 | 864761 | 94624 |
| rpl32-PpLuc(GC)-rps13 | 3627626 | 898377 | 135420 |
| rpl32-PpLuc(GC)-rpl26 | 3981814 | 839608 | 149750 |
| rpl32-PpLuc(GC)-rps17 | 4607487 | 1029902 | 182204 |
| rpl32-PpLuc(GC)-rps18 | 4071557 | 742337 | 101819 |
| rpl32-PpLuc(GC)-rps8 | 4459446 | 1032970 | 125825 |
| rpl32-PpLuc(GC)-Fau | 4486972 | 1066363 | 147843 |
| rpl32-PpLuc(GC)-rps13 | 4811136 | 955703 | 123026 |
| rpl32-PpLuc(GC)-rpl11 | 4405071 | 1231676 | 252711 |
| rpl32-PpLuc(GC)-rpl38 | 5485224 | 1023424 | 170059 |

The results show that more Luciferase was expressed from mRNA comprising a 3'-UTR of murine ribosomal proteins compared to mRNA comprising the 3'-UTR of albumin, which has already been described to increase protein production.

The invention claimed is:

1. A method for enhancing, stabilizing or prolonging protein production from an artificial nucleic acid molecule in a cell, the method comprising transferring into the cell the artificial nucleic acid molecule comprising an open reading frame (ORF) encoding the protein, a 5'-UTR sequence from a TOP gene, and a 3'-UTR element that comprises a 3'-UTR sequence from a ribosomal protein gene, wherein the 5'-UTR sequence lacks a TOP motif.

2. The method according to claim 1, wherein the cell is a mammalian cell.

3. The method of claim 1, wherein the artificial nucleic acid is comprised in a pharmaceutical composition further comprising one or more pharmaceutically acceptable vehicles, diluents and/or excipients and/or one or more adjuvants.

4. The method according to claim 1, wherein the cell is an in vitro or ex vivo cell.

5. The method according to claim 4, wherein the cell is a human cell.

6. The method according to claim 1, wherein the 3'-UTR element comprises a nucleic acid sequence from the 3'-UTR of a eukaryotic ribosomal protein gene.

7. The method according to claim 1, wherein the 3'-UTR element comprises a nucleic acid sequence from the 3'-UTR of a human ribosomal protein gene.

8. The method according to claim 1, wherein the artificial nucleic acid molecule is a mRNA.

9. The method according to claim 8, wherein the mRNA is complexed with a cationic or polycationic component.

10. The method according to claim 8, wherein the mRNA is complexed with a cationic or polycationic lipid.

11. The method according to claim 1, wherein the artificial nucleic acid molecule further comprises a poly(A) sequence and/or a polyadenylation signal.

12. The method according to claim 1, wherein the 3'-UTR element comprises a nucleic acid sequence from ribosomal protein L9(RPL9), ribosomal protein L3 (RPL3), ribosomal protein L4 (RPL4), ribosomal protein L5 (RPL5), ribosomal protein L6 (RPL6), ribosomal protein L7 (RPL7), ribosomal prohtein L7a (RPL7A), ribosomal protein L11 (RPL11), ribosomal protein L12 (RPL12), ribosomal protein L13 (RPL13), ribosomal protein L23 (RPL23), ribosomal protein L18 (RPL18), ribosomal protein L18a (RPL18A), ribosomal protein L19 (RPL19), ribosomal protein L21 (RPL21), ribosomal protein L22 (RPL22), ribosomal protein L23a (RPL23A), ribosomal protein L17 (RPL17), ribosomal protein L24 (RPL24), ribosomal protein L26 (RPL26), ribosomal protein L27(RPL27), ribosomal protein L30 (RPL30), ribosomal protein L27a (RPL27A), ribosomal protein L28 (RPL28), ribosomal protein L29 (RPL29), ribosomal protein L31 (RPL31), ribosomal protein L32 (RPL32), ribosomal protein L35a (RPL35A), ribosomal protein L37 (RPL37), ribosomal protein L37a (RPL37A), ribosomal protein L38 (RPL38), ribosomal protein L39 (RPL39), ribosomal protein, large, PO (RPLPO), ribosomal protein, large, P1 (RPLP1), ribosomal protein, large, P2 (RPLP2), ribosomal protein S3 (RPS3), ribosomal protein S3A (RPS3A), ribosomal protein S4, X-linked (RPS4X), ribosomal protein S4, Y-linked 1 (RPS4Y1), ribosomal protein S5 (RPS5), ribosomal protein S6 (RPS6), ribosomal protein S7 (RPS7), ribosomal protein S8 (RPS8), ribosomal protein S9 (RPS9), ribosomal protein S10 (RPS10), ribosomal protein S11 (RPS11), ribosomal protein S12 (RPS12), ribosomal protein S13 (RPS13), ribosomal protein S15 (RPS15), ribosomal protein S15a (RPS15A), ribosomal protein S16 (RPS16), ribosomal protein S19 (RPS19), ribosomal protein S20 (RPS20), ribosomal protein S21 (RPS21), ribosomal protein S23 (RPS23), ribosomal protein S25 (RPS25), ribosomal protein S26 (RPS26), ribosomal protein S27 (RPS27), ribosomal protein S27a (RPS27a), ribosomal protein S28 (RPS28), ribosomal protein S29 (RPS29), ribosomal protein L15 (RP15), ribosomal protein S2 (RPS2), ribosomal protein L14 (RPL14), ribosomal protein S14 (RPS14), ribosomal protein L10 (RPL10), ribosomal protein L10a (RPL10A), ribosomal protein L35 (RPL35), ribosomal protein L13a (RPL13A), ribosomal protein L36 (RPL36), ribosomal protein L36a (RPL36A), ribosomal protein L41 (RP41), ribosomal protein S18 (RPS18), ribosomal protein S24 (RPS24), ribosomal protein L8 (RPL8), ribosomal protein L34 (RPL34), ribosomal protein S17 (RPS17), ribosomal protein SA (RPSA), ubiquitin A-52 residue ribosomal protein fusion product 1 (UBA52), Finkel-Biskis-Reilly murine sarcoma virus (FBR-MuSV) ubiquitously expressed (FAU), ribosomal protein L22-like 1 (RPL22L1), ribosomal protein S17 (RPS17), ribosomal protein L39-like (RPL39L), ribosomal protein L10-like (RPL10L), ribosomal protein L36a-like (RPL36AL), ribosomal protein L3-like (RPL3L), ribosomal protein S27-like (RPS27L), ribosomal protein L26-like 1 (RPL26L1), ribosomal protein L7-like 1 (RPL7L1), ribosomal protein L13a pseudogene (RPL13AP), ribosomal protein L37a pseudogene 8 (RPL37AP8), ribosomal protein S10 pseudogene 5 (RPS10P5), ribosomal protein S26 pseudogene 11 (RPS26P11), ribosomal protein L39 pseudogene 5 (RPL39P5), ribosomal protein, large, P0 pseudogene 6 (RPLP0P6) or ribosomal protein L36 pseudogene 14 (RPL36P14).

13. The method according to claim 1, wherein the artificial nucleic acid molecule further comprises a 5'-cap structure, a poly(C) sequence, a histone stem-loop, and/or an IRES-motif.

14. The method according to claim 13, wherein the histone stem-loop comprises a sequence according to SEQ ID NO:5.

15. The method according to claim 1, wherein the open reading frame is at least partially G/C modified, such that the G/C content of the open reading frame is increased compared to a corresponding wild type open reading frame.

16. The method according to claim 1, wherein the artificial nucleic acid molecule comprises a 5'-UTR sequence from a rpl32 5'-UTR.

17. The method according to claim 1, wherein the cell is a cell comprised in an animal.

18. The method according to claim 1, wherein the ORF encodes an antigen or a therapeutic protein.

\* \* \* \* \*

UNITED STATES PATENT AND TRADEMARK OFFICE
CERTIFICATE OF CORRECTION

PATENT NO.         : 10,047,375 B2
APPLICATION NO.    : 15/195934
DATED              : August 14, 2018
INVENTOR(S)        : Andreas Thess Page 1 of 1

It is certified that error appears in the above-identified patent and that said Letters Patent is hereby corrected as shown below:

In the Claims

In Claim 12, Column 242, Line 25, delete "PO (RPLPO)" and insert --P0 (RPLP0)-- therefor.

In Claim 12, Column 242, Line 49, delete "RP41" and insert --RPL41-- therefor.

Signed and Sealed this
Fourth Day of December, 2018

Andrei Iancu
*Director of the United States Patent and Trademark Office*

SEQUENCE LISTING

<160> NUMBER OF SEQ ID NOS: 206

<210> SEQ ID NO 1
<211> LENGTH: 70
<212> TYPE: DNA
<213> ORGANISM: Artificial Sequence
<220> FEATURE:
<223> OTHER INFORMATION: 3-UTR element of Homo sapiens ribosomal protein
      S9 (RPS9)

<400> SEQUENCE: 1

```
gtccacctgt ccctcctggg ctgctggatt gtctcgtttt cctgccaaat aaacaggatc    60
agcgctttac                                                            70

<210> SEQ ID NO 2
<211> LENGTH: 70
<212> TYPE: RNA
<213> ORGANISM: Artificial Sequence
<220> FEATURE:
<223> OTHER INFORMATION: 3-UTR element of Homo sapiens ribosomal protein
      S9 (RPS9)

<400> SEQUENCE: 2
guccaccugu cccuccuggg cugcuggauu gucucguuuu ccugccaaau aaacaggauc    60
agcgcuuuac                                                            70

<210> SEQ ID NO 3
<211> LENGTH: 140
<212> TYPE: DNA
<213> ORGANISM: Artificial Sequence
<220> FEATURE:
<223> OTHER INFORMATION: 3-UTR element of Homo sapiens ribosomal protein
      S9 (RPS9) + poly A

<400> SEQUENCE: 3
gtccacctgt ccctcctggg ctgctggatt gtctcgtttt cctgccaaat aaacaggatc    60
agcgctttac agatctaaaa aaaaaaaaaa aaaaaaaaaa aaaaaaaaaa aaaaaaaaaa   120
aaaaaaaaaa aaaaaaaaaa                                                140

<210> SEQ ID NO 4
<211> LENGTH: 140
<212> TYPE: RNA
<213> ORGANISM: Artificial Sequence
<220> FEATURE:
<223> OTHER INFORMATION: 3-UTR element of Homo sapiens ribosomal protein
      S9 (RPS9) + poly A

<400> SEQUENCE: 4
guccaccugu cccuccuggg cugcuggauu gucucguuuu ccugccaaau aaacaggauc    60
agcgcuuuac agaucuaaaa aaaaaaaaaa aaaaaaaaaa aaaaaaaaaa aaaaaaaaaa   120
aaaaaaaaaa aaaaaaaaaa                                                140

<210> SEQ ID NO 5
<211> LENGTH: 24
<212> TYPE: DNA
<213> ORGANISM: Artificial Sequence
<220> FEATURE:
<223> OTHER INFORMATION: A particular preferred histone stem-loop
      sequence

<400> SEQUENCE: 5
caaaggctct tttcagagcc acca                                            24

<210> SEQ ID NO 6
<211> LENGTH: 42
<212> TYPE: DNA
<213> ORGANISM: Artificial Sequence
<220> FEATURE:
<223> OTHER INFORMATION: 5-UTR of human ribosomal protein Large 32
      lacking the 5 terminal oligopyrimidine tract

<400> SEQUENCE: 6
ggcgctgcct acggaggtgg cagccatctc cttctcggca tc                        42
```

<210> SEQ ID NO 7
<211> LENGTH: 1918
<212> TYPE: DNA
<213> ORGANISM: Artificial Sequence
<220> FEATURE:
<223> OTHER INFORMATION: rpl32  PpLuc(GC)  rps9  A64  C30  histoneSL

<400> SEQUENCE: 7

```
ggggcgctgc ctacggaggt ggcagccatc tccttctcgg catcaagctt gaggatggag      60
gacgccaaga acatcaagaa gggcccggcg cccttctacc cgctggagga cgggaccgcc     120
ggcgagcagc tccacaaggc catgaagcgg tacgccctgg tgccgggcac gatcgccttc     180
accgacgccc acatcgaggt cgacatcacc tacgcggagt acttcgagat gagcgtgcgc     240
ctggccgagg ccatgaagcg gtacggcctg aacaccaacc accggatcgt ggtgtgctcg     300
gagaacagcc tgcagttctt catgccggtg ctgggcgccc tcttcatcgg cgtggccgtc     360
gccccggcga cgacatcta caacgagcgg gagctgctga acagcatggg gatcagccag     420
ccgaccgtgg tgttcgtgag caagaagggc ctgcagaaga tcctgaacgt gcagaagaag     480
ctgcccatca tccagaagat catcatcatg acagcaagaa ccgactacca gggcttccag     540
tcgatgtaca cgttcgtgac cagccacctc ccgccgggct caacgagta cgacttcgtc     600
ccggagagct tcgaccggga caagaccatc gccctgatca tgaacagcag cggcagcacc     660
ggcctgccga aggggtggc cctgccgcac cggaccgcct gcgtgcgctt ctcgcacgcc     720
cgggacccca tcttcggcaa ccagatcatc ccggacaccg ccatcctgag cgtggtgccg     780
ttccaccacg gcttcggcat gttcacgacc ctgggctacc tcatctgcgg cttccgggtg     840
gtcctgatgt accggttcga ggaggagctg ttcctgcgga gcctgcagga ctacaagatc     900
cagagcgcgc tgctcgtgcc gaccctgttc agcttcttcg ccaagagcac cctgatcgac     960
aagtacgacc tgtcgaacct gcacgagatc gccagcgggg gcgccccgct gagcaaggag    1020
gtgggcgagg ccgtggccaa gcggttccac ctccccgggca tccgccaggg ctacggcctg    1080
accgagacca cgagcgcgat cctgatcacc cccgaggggg acgacaagcc gggcgccgtg    1140
ggcaaggtgg tcccgttctt cgaggccaag gtggtggacc tggacaccgg caagaccctg    1200
ggcgtgaacc agcggggcga gctgtgcgtg cggggggccga tgatcatgag cggctacgtg    1260
aacaacccgg aggccaccaa cgccctcatc gacaaggacg gctggctgca cagcggcgac    1320
atcgcctact gggacgagga cgagcacttc ttcatcgtcg accggctgaa gtcgctgatc    1380
aagtacaagg gctaccaggt ggcgccggcc gagctggaga gcatcctgct ccagcacccc    1440
aacatcttcg acgccggcgt ggccgggctg ccggacgacg acgccggcga gctgccggcc    1500
gcggtggtgg tgctggagca cggcaagacc atgacggaga aggagatcgt cgactacgtg    1560
gccagccagg tgaccaccgc caagaagctg cggggcggcg tggtgttcgt ggacgaggtc    1620
ccgaagggcc tgaccgggaa gctcgacgcc cggaagatcc gcgagatcct gatcaaggcc    1680
aagaagggcg gcaagatcgc cgtgtaagac tagtgtccac ctgtccctcc tgggctgctg    1740
gattgtctcg ttttcctgcc aaataaacag gatcagcgct ttacagatct aaaaaaaaaa    1800
aaaaaaaaaa aaaaaaaaaa aaaaaaaaaa aaaaaaaaaa aaaaaaaaaa aaaatgcatc    1860
cccccccccc cccccccccc cccccccccc aaaggctctt tcagagcca ccagaatt     1918
```

<210> SEQ ID NO 8
<211> LENGTH: 1848
<212> TYPE: DNA
<213> ORGANISM: Artificial Sequence
<220> FEATURE:
<223> OTHER INFORMATION: rpl32 PpLuc(GC) A64 C30 histoneSL

<400> SEQUENCE: 8

```
ggggcgctgc ctacggaggt ggcagccatc tccttctcgg catcaagctt gaggatggag      60
gacgccaaga acatcaagaa gggcccggcg cccttctacc cgctggagga cgggaccgcc     120
ggcgagcagc tccacaaggc catgaagcgg tacgccctgg tgccgggcac gatcgccttc     180
accgacgccc acatcgaggt cgacatcacc tacgcggagt acttcgagat gagcgtgcgc     240
ctggccgagg ccatgaagcg gtacggcctg aacaccaacc accggatcgt ggtgtgctcg     300
gagaacagct gcagttctt catgccgtg ctgggcgccc tcttcatcgg cgtggccgtc       360
gccccggcga acgacatcta caacgagcgg gagctgctga acagcatggg gatcagccag     420
ccgaccgtgg tgttcgtgag caagaagggc ctgcagaaga tcctgaacgt gcagaagaag     480
ctgcccatca tccagaagat catcatcatg gacagcaaga ccgactacca gggcttccag     540
tcgatgtaca cgttcgtgac cagccacctc ccgccgggct tcaacgagta cgacttcgtc     600
ccggagagct tcgaccggga caagaccatc gccctgatca tgaacagcag cggcagcacc     660
ggcctgccga agggggtggc cctgccgcac cggaccgcct gcgtgcgctt ctcgcacgcc     720
cgggacccca tcttcggcaa ccagatcatc ccggacaccg ccatcctgag cgtggtgccg     780
ttccaccacg gcttcggcat gttcacgacc ctgggctacc tcatctgcgg cttccgggtg     840
gtcctgatgt accggttcga ggaggagctg ttcctgcgga gcctgcagga ctacaagatc     900
cagagcgcgc tgctcgtgcc gaccctgttc agcttcttcg ccaagagcac cctgatcgac     960
aagtacgacc tgtcgaacct gcacgagatc gccagcgggg gcgccccgct gagcaaggag    1020
gtgggcgagg ccgtgccaa gcggttccac ctccccgggca tccgccaggg ctacggcctg    1080
accgagacca cgagcgcgat cctgatcacc cccgaggggg acgacaagcc gggcgccgtg    1140
ggcaaggtgg tcccgttctt cgaggccaag gtggtggacc tggacaccgg caagaccctg    1200
ggcgtgaacc agcggggcga gctgtgcgtg cggggggccga tgatcatgag cggctacgtg    1260
aacaacccgg aggccaccaa cgccctcatc gacaaggacg gctggctgca cagcggcgac    1320
atcgcctact gggacgagga cgagcacttc ttcatcgtcg accggctgaa gtcgctgatc    1380
aagtacaagg ctaccaggt ggcgccggcc gagctggaga gcatcctgct ccagcacccc    1440
aacatcttcg acgccggcgt ggccgggctg ccggacgacg acgccggcga gctgccggcc    1500
gcggtggtgg tgctggagca cggcaagacc atgacggaga aggagatcgt cgactacgtg    1560
gccagccagg tgaccaccgc caagaagctg cggggcggcg tggtgttcgt ggacgaggtc    1620
ccgaagggcc tgaccgggaa gctcgacgcc cggaagatcc gcgagatcct gatcaaggcc    1680
aagaagggcg gcaagatcgc cgtgtaagac tagtagatct aaaaaaaaaa aaaaaaaaaa    1740
aaaaaaaaaa aaaaaaaaaa aaaaaaaaaa aaaaaaaaa aaaatgcatc cccccccccc     1800
cccccccccc cccccccccc aaaggctctt ttcagagcca ccagaatt                 1848
```

<210> SEQ ID NO 9
<211> LENGTH: 1914
<212> TYPE: DNA
<213> ORGANISM: Artificial Sequence
<220> FEATURE:
<223> OTHER INFORMATION: rpl32 PpLuc(GC) ag A64 C30 histoneSL

<400> SEQUENCE: 9

```
ggggcgctgc ctacggaggt ggcagccatc tccttctcgg catcaagctt gaggatggag      60
```

```
gacgccaaga acatcaagaa gggcccggcg cccttctacc cgctggagga cgggaccgcc    120
ggcgagcagc tccacaaggc catgaagcgg tacgccctgg tgccgggcac gatcgccttc    180
accgacgccc acatcgaggt cgacatcacc tacgcggagt acttcgagat gagcgtgcgc    240
ctggccgagg ccatgaagcg gtacggcctg aacaccaacc accggatcgt ggtgtgctcg    300
gagaacagcc tgcagttctt catgccggtg ctgggcgccc tcttcatcgg cgtggccgtc    360
gccccggcga cgacatcta caacgagcgg gagctgctga acagcatggg gatcagccag    420
ccgaccgtgg tgttcgtgag caagaagggc ctgcagaaga tcctgaacgt gcagaagaag    480
ctgcccatca tccagaagat catcatcatg gacagcaaga ccgactacca gggcttccag    540
tcgatgtaca cgttcgtgac cagccacctc ccgccgggct tcaacgagta cgacttcgtc    600
ccggagagct tcgaccggga caagaccatc gccctgatca tgaacagcag cggcagcacc    660
ggcctgccga aggggtggc cctgccgcac cggaccgcct gcgtgcgctt ctcgcacgcc    720
cgggacccca tcttcggcaa ccagatcatc ccggacaccg ccatcctgag cgtggtgccg    780
ttccaccacg gcttcggcat gttcacgacc ctgggctacc tcatctgcgg cttccgggtg    840
gtcctgatgt accggttcga ggaggagctg ttcctgcgga gcctgcagga ctacaagatc    900
cagagcgcgc tgctcgtgcc gaccctgttc agcttcttcg ccaagagcac cctgatcgac    960
aagtacgacc tgtcgaacct gcacgagatc gccagcgggg cgccccgct gagcaaggag   1020 gtgggcgagg ccgtggccaa gcggttccac ctccccggca tccgccaggg ctacggcctg   1080
accgagacca cgagcgcgat cctgatcacc cccgaggggg acgacaagcc gggcgccgtg   1140
ggcaaggtgg tcccgttctt cgaggccaag gtggtggacc tggacaccgg caagaccctg   1200
ggcgtgaacc agcggggcga gctgtgcgtg cgggggccga tgatcatgag cggctacgtg   1260
aacaacccgg aggccaccaa cgccctcatc gacaaggacg ctggctgca cagcggcgac   1320 atcgcctact gggacgagga cgagcacttc ttcatcgtcg accggctgaa gtcgctgatc   1380
aagtacaagg ctaccaggt ggcgccggcc gagctggaga catcctgct ccagcacccc   1440 aacatcttcg acgccggcgt ggccgggctg ccggacgacg acgccggcga gctgccggcc   1500
gcggtggtgg tgctggagca cggcaagacc atgacggaga aggagatcgt cgactacgtg   1560
gccagccagg tgaccaccgc caagaagctg cggggcggcg tggtgttcgt ggacgaggtc   1620
ccgaagggcc tgaccgggaa gctcgacgcc cggaagatcc gcgagatcct gatcaaggcc   1680
aagaagggcg gcaagatcgc cgtgtaagac tagttataag actgactagc ccgatgggcc   1740
tcccaacggg ccctcctccc ctccttgcac cgagattaat agatctaaaa aaaaaaaaaa   1800 aaaaaaaaa aaaaaaaaa aaaaaaaaa aaaaaaaaa aaaaaaaaa tgcatccccc   1860 ccccccccc ccccccccc cccccaaag gctcttttca gagccaccag aatt          1914
```

<210> SEQ ID NO 10
<211> LENGTH: 109
<212> TYPE: DNA
<213> ORGANISM: Homo sapiens

<400> SEQUENCE: 10

```
gatctaagag ttacctggct acagaaagaa gatgccagat gacacttaag acctacttgt     60
gatatttaaa tgatgcaata aaagacctat tgatttggac cttcttctt                109
```

<210> SEQ ID NO 11
<211> LENGTH: 57
<212> TYPE: DNA
<213> ORGANISM: Homo sapiens

<400> SEQUENCE: 11
tgccaggaac agattttgca gttggtgggg tctcaataaa agttattttc cactgac      57

<210> SEQ ID NO 12
<211> LENGTH: 91
<212> TYPE: DNA
<213> ORGANISM: Homo sapiens

<400> SEQUENCE: 12
actcttaaat ttgattattc cataaaggtc aaatcatttt ggacagcttc ttttgaataa      60
agacctgatt atacaggcag tgagaaacat g      91

<210> SEQ ID NO 13
<211> LENGTH: 58
<212> TYPE: DNA
<213> ORGANISM: Homo sapiens

<400> SEQUENCE: 13
acccagcaat tttctatgat tttttcagat atagataata aacttatgaa cagcaact      58

<210> SEQ ID NO 14
<211> LENGTH: 33
<212> TYPE: DNA
<213> ORGANISM: Homo sapiens

<400> SEQUENCE: 14
atgtcttaag aacctaatta aatagctgac tac      33

<210> SEQ ID NO 15
<211> LENGTH: 67
<212> TYPE: DNA
<213> ORGANISM: Homo sapiens

<400> SEQUENCE: 15
ggtgtctacc atgattattt ttctaagctg gttggttaat aaacagtacc tgctctcaaa      60
ttgaaat      67

<210> SEQ ID NO 16
<211> LENGTH: 59
<212> TYPE: DNA
<213> ORGANISM: Homo sapiens

<400> SEQUENCE: 16
atgtacactg ttgagttttc tgtacataaa aataattgaa ataatacaaa ttttccttc      59

<210> SEQ ID NO 17
<211> LENGTH: 50
<212> TYPE: DNA
<213> ORGANISM: Homo sapiens

<400> SEQUENCE: 17
attcccgttt ctatccaaaa gagcaataaa aagttttcag tgaaatgtgc      50

<210> SEQ ID NO 18
<211> LENGTH: 46
<212> TYPE: DNA
<213> ORGANISM: Homo sapiens

<400> SEQUENCE: 18
gcacaaagga aaacatttca ataaaggatc atttgacaac tggtgg      46

<210> SEQ ID NO 19
<211> LENGTH: 3787
<212> TYPE: DNA
<213> ORGANISM: Homo sapiens

<400> SEQUENCE: 19

| | | | | | |
|---|---|---|---|---|---|
| agccctcctg | gggacttgga | atcagtcggc | agtcatgctg | ggtctccacg | tggtgtgttt | 60 |
| cgtgggaaca | actgggcctg | ggatggggct | tcactgctgt | gacttcctcc | tgccagggga | 120 |
| tttggggctt | tcttgaaaga | cagtccaagc | cctggataat | gctttacttt | ctgtgttgaa | 180 |
| gcactgttgg | ttgtttggtt | agtgactgat | gtaaaacggt | tttcttgtgg | ggaggttaca | 240 |
| gaggctgact | tcagagtgga | cttgtgtttt | ttcttttaa | agaggcaagg | ttgggctggt | 300 |
| gctcacagct | gtaatcccag | cactttgagg | ttggctggga | gttcaagacc | agcctggcca | 360 |
| acatgtcaga | actactaaaa | ataaagaaat | cagccatgct | tggtgctgca | cacttgtagt | 420 |
| tgcagctcct | gggaggcaga | ggtgagggat | cacttaaccc | aggaggcaga | ggctgcactg | 480 |
| agccaggatc | acgccactgc | actctagcct | gggcaacagt | gagactgtct | caaaaaaaaa | 540 |
| aaaagagaca | gggtcttcgg | cacccaggct | ggagtacagt | gccacaatca | tggctcactg | 600 |
| cagtcttgaa | ctcatggcct | caagcagtcc | tccctcagcc | tcccaagtag | aggggttat | 660 |
| aggcacgaga | ccctgcaccc | aacctagagt | tgccttttt | aagcaaagca | gtttctagtt | 720 |
| aatgtagcat | cttggacttt | ggggcgtcat | tcttaagctt | gttgtgcccg | gtaaccatgg | 780 |
| tcctcttgct | ctgattaacc | cttccttcaa | tgggcttctt | cacccagaca | ccaaggtatg | 840 |
| agatggccct | gccaagtgtc | ggcctctcct | gttaaacaaa | aacattctaa | agccattgtt | 900 |
| cttgcttcat | ggacaagagg | cagccagaga | gagtgccagg | gtgccctggt | ctgagctggc | 960 |
| atccccatgt | cttctgtgtc | cgagggcagc | atggtttctc | gtgcagtgct | cagacacagc | 1020 |
| ctgccctagt | cctaccagct | cacagcagca | cctgctctcc | ttggcagcta | tggccatgac | 1080 |
| aaccccagag | aagcagcttc | agggaccgag | tcagattctg | ttttgtctac | atgcctctgc | 1140 |
| cgggtgccgg | tattgaggca | cccagggagc | tgttactggc | gtggaaatag | gtgatgctgc | 1200 |
| tacctctgct | gctgcactca | cagccacact | tgatacacga | tgacaccttg | cttgttttga | 1260 |
| aacatctaaa | catctagtag | atgacttgca | ggctgttggc | taccagtttc | ctgtctgagg | 1320 |
| tgtatatgtt | aacttcgtga | tcagtttgta | tgtttgggac | tcttgtccta | tgtaaagtta | 1380 |
| aggtgggccg | ggtgcagtgg | ctcacgcctg | taatcctaac | actgggaggc | cgaggcgggt | 1440 |
| ggatcacctg | atggtgaaac | ctcatctcta | ctgaaaatac | aaaaattagc | tgagtggtga | 1500 |
| cacacgcctg | taatcccagc | tacttggtag | gcttgaaccc | aggaggcaga | gattgcagtg | 1560 |
| agccgagctg | caccactgtg | ctccagcctg | ggtgacagcg | agactcagtc | tcaaaaaaag | 1620 |
| ttgtacaagg | tggatggttg | gaagcttgag | cctaggctcg | aatccctctc | acgtgagagg | 1680 |
| gcctgaagat | ttctggtgga | ttccaacctg | gctgaagact | ggccgtgggg | ggtgcagggg | 1740 |
| tctccagcgc | tctgccctcc | agcctgcttc | ctccctgccc | acaccgcact | agggaaggg | 1800 |
| cctttcctgc | tgcctgcggg | gccgcacctg | gagtaggtaa | tgccatgtgg | tgacgtgaat | 1860 |
| ggagcagagg | tctgtgcccc | atcacaccgc | cttgctgttt | ttactgtggg | acaaaagcac | 1920 |
| tctgatctgc | gtgttccggg | ggccctccta | ccagccgact | tgacgggaag | tcagggttca | 1980 |
| ggtatcatct | gtgcacctgg | ggcgggtag | tctgcactga | acctgccaga | gtccctcct | 2040 |
| catttcactg | aaagtcacag | tctccagggc | tgtgttgcta | accttacgtt | ctctccgttt | 2100 |
| gcttaatcta | ttaagagccc | taacaggaga | ggatgggctt | tctctgttgt | ctggggccct | 2160 |

```
gctgttggcc ggtgctctta gcaagaggtc atttttctag gttgcgctgg gacattgtga    2220
gtttggtgag ggtcatggat gtgggctggg ctgggctggg ctgggccggg ctgcctgctg    2280
cctgctgctc ccctacctga aatgcagcta gtgcggctct gcccttcctg gggctgagga    2340
aggcttctgc aggatagctg gggggctggg caggtgggtg aggcagcctc ctgctgaca    2400 ctcagtcctt gtagctggag caagatctcc tgatccaggt acgggcctgt ctgctccaag    2460
aaagactctg ccaccagatg caaagggcc ctttgtttta acttagtccc tggggaccgc     2520
ctgattcagc acctgtcggc ccaggatacc ccgctggtgg ggacaagtgc ctgagtgtgg    2580
gccgtgcccg agtgtggcca tccctgagtg gggccgtcct gactaggaag tggcttttca    2640
gttgtgatgt gtgggcctga cctagggggc gctgtggaac ccgggctgga accagccctc    2700
tgtgccaggc cgcagacagg ttccgccggc cctgaggggc agctgccatg gcgtgggtca    2760
ctgggagctg agaggaaggg cccccaccgc acctcaggca aagcggctct gggaacacct    2820
tgatttcgtc catgtgagcc gtcccaggga gggcagccaa gctgtgaagc ctgagaaact    2880
gacctgtgtg ccacgagctt gtggtctgct gcccggtgga ggaagtgcag gtgcgcccag    2940
gctcctcatt ccgttttgca ggattccttc ggggtgtgag catttcctat tcagcctgtc    3000
gcccccgggg agcacgggct ggctctgtgg tgcccgtggc cttttgtaga agcgttggtt    3060
ttacggcagg ttcatctctg gggcagcctc ccacagtggg tggggctttg ccagcagtgc    3120 ccacggggt catgggcca ggcgcgctcc ggcgcctgca gaactgatcg gggatagtct      3180
caggaggcgc tagtcacgtg ccccggtgat cgggatagt ctcagaaggc gctagtctcc     3240
tgccccggtg atcggggata gtctcaggag gcacgagtcg cctgcctcgg tgatgcaccg    3300
tttctcacac cggctgctct ggcccgagct aaagggaag acgtgtgcgg ataggagctg     3360
cacacaattt tcctccatgt attgtttatt ttgctttttc ttttggctag acattaggaa    3420
tttcagtttt cccaagttgt attttttcctt ttctattta aaattatcat gcagggctgg    3480
gtgaggtcgc tcacgcctat agtctcaaaa ctttgggagg ctgaggggg aggatggcat     3540 gagcccagga gtttaaggct gcagtgagcc gagatcgctc cactgtcctc cagcctgcat    3600
gacagagcga gaccctatct caggaaaaaa aaaacaaaa ctattatgca gtagtttcga    3660
ccctggaaga cgagtgtgca tctttgagtt gtaacacgtg tacctcgccc atccaggcgt    3720
agtttcattt ggaatctggt tatcctgtag ttgctttgtt aaaaatatat gtaattgcaa    3780
atcattt                                                              3787

<210> SEQ ID NO 20
<211> LENGTH: 63
<212> TYPE: DNA
<213> ORGANISM: Homo sapiens

<400> SEQUENCE: 20
ttctccagta tatttgtaaa aaataaaaaa aaaaactaaa cccattaaaa agtatttgtt    60
tgc                                                                  63

<210> SEQ ID NO 21
<211> LENGTH: 45
<212> TYPE: DNA
<213> ORGANISM: Homo sapiens

<400> SEQUENCE: 21
ccctggatcc tactctctta ttaaaaagat ttttgctgac agtgc                    45
```

<210> SEQ ID NO 22
<211> LENGTH: 61
<212> TYPE: DNA
<213> ORGANISM: Homo sapiens

<400> SEQUENCE: 22
gtgcagggcc ctcgtccggg tgtgccccaa ataaactcag gaacgccccg gtgctcgccg    60
c                                                                   61

<210> SEQ ID NO 23
<211> LENGTH: 79
<212> TYPE: DNA
<213> ORGANISM: Homo sapiens

<400> SEQUENCE: 23
aacctcccac tttgtctgta catactggcc tctgtgatta catagatcag ccattaaaat    60
aaaacaagcc ttaatctgc                                                79

<210> SEQ ID NO 24
<211> LENGTH: 38
<212> TYPE: DNA
<213> ORGANISM: Homo sapiens

<400> SEQUENCE: 24
taggtgttaa aaaaaaaaat aaaggacctc tgggctac                            38

<210> SEQ ID NO 25
<211> LENGTH: 1651
<212> TYPE: DNA
<213> ORGANISM: Homo sapiens

<400> SEQUENCE: 25
atttcattta tctggaaaat tttgtatgag ttcttgaata aaacttggga accaaaatgg    60
tggtttatcc ttgtatctct gcagtgtgga ttgaacagaa aattggaaat catagtcaaa   120
gggcttccct tggttcgcca ctcatttatt tgtaacttga cttcttttt tttctgctta   180
aaaatttcaa ttctcgtggt aataccagag tagaaggaga gggtgacttt accgaactga   240
cagccattgg ggaggcagat gcgggtgtgg aggtgtgggc tgaaggtagt gactgtttga   300
ttttaaaaag tgtgactgtc agttgtatct gttgcttttc tcaatgattc agggatacaa   360
atgggcttct ctcattcatt aaaagaaaac gcgacatctt tctaagattc tctgtgggaa   420
aatgactgtc aataaaatgc gggtttctgg gccattcgtc ttactttcat ttttttgatta   480
caaatttctc ttgacgcaca caattatgtc tgctaatcct cttcttccta gagagagaaa   540
ctgtgctcct tcagtgttgc tgccataaag gggtttgggg aatcgattgt aaaagtccca   600
ggttctaaat taactaaatg tgtacagaaa tgaacgtgta agtaatgttt ctacaggtct   660
ttgcaacaaa ctgtcacttt cgtctccagc agagggagct gtaggaatag tgcttccaga   720
tgtggtctcc cgtgtggggc ccagcaatgg gggccctga tgccaagagc tctggaggtt   780
cttgaaagag gggacacgaa ggaggagtga ctgggaagcc tcccatgcca aggaggtggg   840
aggtgccctg gaaatagctg cctcatgcca cttaggccat gactggattt aatgtcagtg   900
gtgtgccaca gtgcagaggc tagacaactg aaggggcta ccaaggctgg gaaaaaatg    960
caattgttgc tgtgagtgac tttgaaagac tctggtgcct tgtggtgccc ttctgaaatt  1020
caaacagtaa tgcaaaagtg tctgcattag aatttacggt gtctaaaatt catgttttta  1080
aaagagcttg cctacagatg gtttccacac ttgaaattgt gccctgcgag ttgcatagct  1140

```
ggaagttcaa tgctcagtcc taccttggct cccattaaac atttggtgct ctgtggattg    1200
agttgaacgt gttgaggctt tgcaatttca cttgtgttaa aggctctggc attttttccat   1260 ttctatgcaa atttctttga agcagaattg cttgcatatt tcttctctgc cgtcacagaa    1320
agcagagttt ctttcaaact tcactgaggc atcagttgct ctttggcaat gtcccttaac    1380
catgattatt aactaagttt gtggcttgag tttacaaatt ctacttgttg cattgatgtt    1440
cccatgtagt aagtcatttt tagtttggtt gtgaaaaaac cctgggctga agttggcatt    1500
tcagttaaaa gaaaaaagaa aactagtccc agatttgaaa acttgtaata aaattgaaac    1560
tcactggttt tctatgtctt tttgaactct tgtaatcgag ttttgatcat attttctatt    1620
aaagtggcta acacctggct actcttactg t                                   1651

<210> SEQ ID NO 26
<211> LENGTH: 474
<212> TYPE: DNA
<213> ORGANISM: Homo sapiens

<400> SEQUENCE: 26
actgagtcca gctgcctaat tctgaatata tatatatata tatcttttca ccatatacat      60
gcctgtctgt caatttctgg ttgggctggg aggccacaca cacacactga catgacaggg    120
cttgggcaag actcctgttc tacttatcct tttgaaatac ctcaccctgc cactccacca    180
tgtatgatca ttccagagat cttgtgact agagttagtg tcctaggaaa accagaactc    240
agaacttgcc tccatggttg agtaacaagc tgtacaagaa ccccttttat ccctggaaga    300
ggctgtgtat gaaaccaatg cccagggttt gaagggtgtt agcatccatt tcaggggagt    360
gtggattggc tggctctctg gtagcatttt gtcctcacac acccatctac tatgtccaac    420
cggtctgtct gcttccctca ccccttgccc aataaaggac aaggacttca gagg          474

<210> SEQ ID NO 27
<211> LENGTH: 36
<212> TYPE: DNA
<213> ORGANISM: Homo sapiens

<400> SEQUENCE: 27
attcagcatt aaaataaatg taattaaaag gaaaag                                36

<210> SEQ ID NO 28
<211> LENGTH: 45
<212> TYPE: DNA
<213> ORGANISM: Homo sapiens

<400> SEQUENCE: 28
actggcagat tagattttta aataaagatt ggattataac tctag                      45

<210> SEQ ID NO 29
<211> LENGTH: 48
<212> TYPE: DNA
<213> ORGANISM: Homo sapiens

<400> SEQUENCE: 29
agtaatctta tatacaagct ttgattaaaa cttgaaacaa agagcctg                   48

<210> SEQ ID NO 30
<211> LENGTH: 32
<212> TYPE: DNA
<213> ORGANISM: Homo sapiens
```

<400> SEQUENCE: 30
atgctttgtt ttgatcatta aaaattataa ag                                32

<210> SEQ ID NO 31
<211> LENGTH: 90
<212> TYPE: DNA
<213> ORGANISM: Homo sapiens

<400> SEQUENCE: 31
accttttcac ctacaaaatt tcacctgcaa accttaaacc tgcaaaattt tccttttaata    60 aaatttgctt gttttaaaaa cattgtatct                                     90

<210> SEQ ID NO 32
<211> LENGTH: 4065
<212> TYPE: DNA
<213> ORGANISM: Homo sapiens

<400> SEQUENCE: 32
agccacatgg agggagtttc attaaatgct aactactttt tccttgtggt gtgagtgtag     60
gttcttcagt ggcacctcta catcctgtgt gcattgggag cccaggttct agtacttagg    120
gtatgaagac atggggtcct ctcctgactt ccctcaaata tatggtaaac gtaagaccaa    180
cacagacgtt ggccagttaa acatttctgt ttataaagtc agaataatac ctgttgatca    240
ctgaaaggcc tgcatgtatt gtactctgaa ttttacagtg aatgagagaa tgtaccctaa    300
ttgttcaaca gggctcaaaa ggaaagattc cattttgatg ggtcacattc taaagagggg    360
cagtgtgata ggaatgagat ggtcccttag gacttaagtt ctcagcccaa ggtttttcca    420 cgtggcccc tcatcttttt ttttttttta aacggagtct ctcttgccag gctggagtgc     480
agtggcacga tctcggctca ctgcagcctc cgcctcccag gttaagcgat tctcctgcct    540
cagcttcctg actaactggg attacaggcg cccaccacca tgcccagcta attttttgtat   600 tttcagtaga gatggggttt caccatgttg gccatgctgg tctctaactc ctaacctcaa    660
gtgatctgcc cacatcggcc tccaaaagtt ctgggattat agtgtgagcc actgcgcccg    720
gccatggctc cttaatcttg atccaaatta ttgttcacatc cagaatgtga tgaatcaaaa   780
tctcgagatg ggggtccagc aatctgaaat tcagtatgc cagggctttt ctgtatgtca     840
aagtgggttt gaaatagtta attttttcttc tagtctgaaa tgtatcggga aaatttggaa    900
atcctgaagg ctggaaattg aaataagttt ttctaggatt tgtgtctctt gctattggaa   960
aactgatggt gaccaattca tgtttacaaa taagatcctc atagatctcg gtaaattata   1020
atttgctaca gttttatggt tcttcctgtg attttgagct ttttttgacc caaaataata    1080
cagtctaaaa ctatagacaa ataagatggc acttagactc ctgggttta gttagtggag     1140 gtttccttag tgcactgtgg ggtcataata agccgagaac catggctgtc tatgggacac   1200
atctgtcagg acaaccttta gaggatgttg gggatcaaat agaaggcaca gagaagcact   1260
gaattggctt acataagaat aggctagaat tacaagtagt gaaacctcga ttcagctgga   1320
caattttaaa caaatgtatc atttggcttg tatcttctgt tgtgctggag aagttagaaa   1380
taagggctct ccagaccagc ctgaccaacc tggagaaacc ttgtctctac taaatacaca   1440
aaattagcca ggcgtggtgg cacatgcctg taatcccagc tactttggag gctgagccag   1500
gagaatctcc aggaggcgga ggttgctgtg agccgagatc gtgccattgc actccagctt   1560
gggcaacaag agtgaaactc tgtccacccc cccaaaaaa agtaagggct ctccattagg    1620
gcccatagag gacttgtaat atggaacctg aatccaagga tcccacaata agtggtcagt   1680

```
agttcatgat gaattaaaag actcaatatt tggtcttcac ccaatacctg tgtgactttt    1740
agtcctaatt tcctcatctt taaaatttca gtgaaagtgc ctacctgagg attgtgtaga    1800
ttaaaatgga aaccgtgcac ttaattttt  gttttgtttt gagacggagt ctcgctctgt    1860
cgcccaggct ggagtgcagt ggtgcgatct cagatcactg caagctccgc ctcctaggtt    1920
cagaccattc tcctgcctca gcttcccaag tagctgggac tacaggcgcc cgccactgcg    1980
cccggctaat ttttgcatt  tttagtagag acagggtttc accgtgttag ccaggatggt    2040
ctcgatctcc tgatctgccc gcctcagcct cccaaagtgc tgggattaca ggcatgagcc    2100
accgcgcccg gccaggcac  ttaattttg  tgtttgactt agtaacttaa gtgcaaacta    2160
ttacgggagc agatggagtc aattggcctt catgtgattg tcagtgggaa attggtccaa    2220
gcagagggaa tactggttca ggaaactggt ttgggaaggt taggcaaacg ggaagtgcta    2280
tggtggagag aaagattact ctggccgggc tgtaaaggac ggctacaatg ggaggctgaa    2340
ggcagaacca agaaaatggg agtgagtatg gaaaaggtac gattcagacg cataatgga     2400
cgggacttgg agactgaatt gtagtgggcc gaccacaaaa tgataaggca tggaaggaag    2460
tagagtttgg ggggaaggat ccctagtccc ttaatggcta ccttcttccc caggagttgt    2520
taggccatcc gatcccctgg cctgggaaag aaacactgat ttcgttgctg gcttgttcac    2580
tcaccgaaag ctacagctac taacagttct aaaaactgtt tcatgtgatg aggaacagac    2640
gaaaatagtt ttgagcccta agtccgccga ttccagtgct ttcttgaacc cgcatttact    2700
aaaatatttt catgactgcc aagctttgaa tagcctgctg tgttcatgga ggctcatact    2760
ggcgatctct agtggctggc taaagcttga attgcaaaag atctaatttc tggtctaatg    2820
tatatatgcc ttaaatatag ttgcgttcaa acgtgggagc tgcaggtgca acttgatttt    2880
atgacaaatg gctgccacat aatttgcaca agcagtgctc gtcaagggca gctaaatcag    2940
gcgagctttc aatcaaaata aatgtactac taaaccctac ttagcggcta actagcccaa    3000
gagcagacag cccacggacg gactgcaagt cggaagcgcg ggcggaagct gtgcagcgcc    3060
cacctggtgg ctccatcggc cgcgttcatc agtcagcacg acccgacctc agtggcgtcc    3120
tcacaacaca gaccggacct tgggtcttac cccggcacct gagaaccact tccggtgagt    3180
agcttctact tccggagacg atgactcccc cgcgtcccag accggaagaa gcccggcgga    3240
gaccggcctc gctcggccac ttccggcaag ggcggagccg gccagtggtg cgcgagcgca    3300
gataactccc ctggagaggc gggatgttca actccacccc tggtccttgg gcggccgtgg    3360
gtccccttcg aagcggagga atggccaacc tcgccgcact tcgagcccct ttagggtgcg    3420
tttaagaaca gtgggcgtgg cctttacgta aatcttcgag atgggaacct ccagaatttg    3480
tctcaattgt ctaaaggta  atgagcgtca gcgacattca agggcacttt gggctaaaaa    3540
agaaagtgct tgtacacgga tggaaatatt ctagaagaac ataaaaggaa tttcctctta    3600
ggaggttagg gaaatgagca cgaagtatgt tttggtgcag ttttttgttc aacccaatgc    3660
gtattttcat attgagaggc aatataaatg gagcgaaagt atcttgagaa aaaaaaaaa    3720
actaccagaa cttgccgttg ctgaaaagta atattttctc tttcgagagt tttcatggcc    3780
ttttaaatta caccccacc  tccacaggca ataaatttg  ttttggaatg cataccacat    3840
catctggctc tagaaacgta ttttgtgtag ctcccctagc aagaatatag gttaaagcgt    3900
aaatttaatt cctggctcta ttttacatcc caatttttat tttcctctca ttcccacttt    3960
acgttgtttc aaataaccta gtttgtgtat ccctgtaagt catttggta  taaagtaggt    4020
```
tataagtgta catgcgaaaa gatgttttta acaaaaatgt aactg        4065

<210> SEQ ID NO 33
<211> LENGTH: 3865
<212> TYPE: DNA
<213> ORGANISM: Homo sapiens

<400> SEQUENCE: 33

```
gccttgctct gctcccccgc ccccaggcag ccatccgcag ggccagcgcc atcctgcgca      60
gccagaagcc tgtgatggtg aagaggaagc ggacccgccc caccaagagc tcctgagccc     120
cctgccccca gagcaataaa gtcagctggc tttctcacct gcctcgactg ggcctccctt     180
tttgaaacgc tctggggagc tctggccctg tgtgttgtca ttcaggccat gtcatcaaaa     240
ctctgcatgt caccttgtcc atctggaggt gatgtcaatg ctggccatg caggaggggt      300
ggggtagctg ccttgtccct ggtgagggca agggtcactg tcttcacaga aaaagtttgc     360
tgacttgtga ttgagaccta ctgtcccatt gtgaggtggc ctgaagaatc ccagctgggg     420
cagtggcttc cattcagaag aagaaaggcc ttttctagcc cagaagggtg caggctgagg     480
gctgggccct gggccctggt gctgtagcac ggtttgggga cttggggtgt cccaagacc      540
tggggggacga cagacatcac gggaggaaga tgagatgact tttgcatcca gggagtgggt     600
gcagccacat ttggagggga tgggctttac ttgatgcaac ctcatctctg agatgggcaa     660
cttggtgggt ggtggcttat aactgtaagg agatgtgcag ccccagggta cagccagcag    720
gcattgagca gccttagcat tgtcccccta ctcccgtcct ccaggtgtcc ccatccctcc    780
cctgtctctt tgagctggct cttgtcactt aggtctcatc tcagtggccg ctcctgggcc    840
accctgtcac ccaagctttc ctgattgccc agccctcttg tttcctttgg cctgtttgct    900
ccctagtgtt tattacagct tgtgaggcca ggagtttgag accatcctag caacataat     960
gagacaccgt ctctaaaata aaattagctg ggtgtggtgg tgcaccgcct gtggtcccag    1020
ctcctcagag gttgagtaga ggctgaggtg agcggagcac ttgagccaag agtatgaggc    1080
tgcagtgagc ccatgagccc caccactaca ctccagcctg aagacaccta tgacacacag    1140
tgaggcctgg atggggaaag agtcctgctg ttgatcctca catgtttcct gggcacctaa    1200
ctctgtcagc cactgccagg gaccaaggat ccagcatcca tggcaccct ggttcctgcc     1260
atcctggggt acccgattca agaaggact ctgctccctg tctgagacca ccccggctc     1320
tgactgagag taagggact gtcagggcct cgacttgcca ttggttgggg tcgtacgggg    1380
ctgggagccc tgcgttttga ggcagaccac tgcccttccg acctcagtcc tgtctgctcc    1440
agtcttgccc agctcgaagg agagcagatc tgaccacttg ccagcccctg tctgctgtga    1500
attaccattt cctttgtcct tcccttagtt gggtctatta gctcagattg agaggtgttg    1560
ccttaaaact gagttgggtg acttggtacc tgctcaggac cccccgcact gtcccaatcc    1620
cactcaggcc cacctccagc tggcctcact ccgctggtga cttcgtacct gctcaggagc    1680
ccccactgtc ccagtcccac tcaggcccat ctctggctgg cctcactgcg ctgggactcc    1740
gccttcataa ggagagctca ctgctcacgt tagtagatgg ccccttctcg tgaggcctct    1800
cccctggcac ctgcttcagt tgtcctccac agcactgatt gcagcccac aagctggcag     1860
gtttatctgt ctcatgtttg tcttgtgctg gtgggcaagg ggtttgtcta gcacaccagc    1920
atataatgag atgcttgatg aatggtgcat attgaatgta taaagcccac cggtcctgag    1980
agtttgctca ctggagactt tctggagatg gagtctcgct ctgttgccca ggctggcgag    2040
tgcaatggcg cgatcttggc tcactgcagc ctccacctcc tgggttcaag cgattctcct    2100
```

```
gcctcagcct cccgagtagc tgggattaca ggtgggtgtc accacaccca gctcagtatt    2160 gtattttttag cagagatggg gtttcaccat tttgcccagg ctggtttgga actcctgact    2220
tcaaattacc cacctgcctc agcctcccaa agtgctggca ttacaggcgc tcgaggcttt    2280
ctgatgtggc tgctgctgct cagaaggcct tgtccttaac cacctccttg cctgccctgg    2340
aggcttgtgc ctctaggccc cacccctgt ggagtcctgc tggctttctc catccctatc    2400
tgaatcctcc ctgctgtgtg gcctccctg gtctcatccg taacacagcc cagcttagtg    2460
ggcctctgtt cctgcgggtg gccagcctgt ctgtgtggct gggctgggga ggccacgtct    2520
ggtatctgaa tgctatcggt gggttggggt ggaggaacca ggagagggct ggagggaggg    2580
agatggtctc agccccacag agtttggagt cctcagtgtg ctgagcaaac gtggagacac    2640
catttccctc ctctagacct catcttggag agagagatgt tggatggggc catctattcc    2700
agctttattc acacaaatca tgtctgttgg cctggaaatt ggaaaccag ttaaaccaaa    2760 aacatgatat taagaaaaca ggcaggctca ccatagtaaa aatgctgaaa gccaaagaca    2820
aaattgggag aacaaaagaa aagcgtcttg tcacatacag aaggtccctg ataaagttag    2880
tagctgccct catcagaaac caggcccagg cagtggggac acatccagag tgctgaaaga    2940
acctccccca ggtcatccta tccccaagag tgatgcccgg cagcattccc agctcagggc    3000
taatggttca cggaagccag gaatcaaact gcctgggttc cagtcccagc tctgccagtt    3060
atgcccagct gtggggactt gggcagctcg tttagtagca ccgtgcctca gtttcccata    3120
tgtaaaaggc cattttgagt gcctttcaca gccctgcata aggcaggtgt tcagtgttc    3180 actgctgtct ctccagctct tagtccagta gctgcatggt gagtgagcgt agggcgcacc    3240
ctggaaggct gccaagccca aagttgtgca gagcgctggg gactccagac tccccacagc    3300
agcagagact cgggactgag gcatcctctg ttcacaggac atgctggcat ctactgggtc    3360
agggctctgc tgctcggtgg ctgtgcaacc ttgggcaagt tcctcaacct ctctgtgtct    3420
tcgtaccctc atctgtaaca tgcgtgtcga tagaccctac tactcagggt tgatgagaag    3480
attaaatgtg caaaacctgc ttgactgtgc ccacaaatcc tgattgtagg aataaattaa    3540 tgactttttta taaatatttt gatcagatgg actcatgatc acagatgtct tcacatgcct    3600
atgactaatt tgtacacaaa ctaatgctcg tgtttcccaa gcacctggaa gacatgccag    3660
atccatgtgc agtaatgcct ggtggctcca ggtctgcccc gccgtcctgt ggggctgtga    3720
gctttcccag cctcctgccc gtgtttgtga atatcattct gtcctcagct gcatttccag    3780
cccaggctgt ttggcgctgc ccaggaatgg tatcaattcc cctgtttctc ttgtagccag    3840
ttactagaat aaaatcatct acttt                                          3865
```

<210> SEQ ID NO 34
<211> LENGTH: 288
<212> TYPE: DNA
<213> ORGANISM: Homo sapiens

<400> SEQUENCE: 34

```
ttttttactg tcaggcagga agagcggtaa ctgccatcgc ggcgggcatc cctggcgcca      60
gggtgttggt ctgggtaccg gcttccctct cggccgactt gtcagctctg tgagccgcgc     120
gcgtctgagc ccgtgtcctc acctgtaaag tggagaaatg aaaaaggacc tgaacttcct     180
cggtggttgt tgagagttaa ggcacggggt tgatgttttc agatgaaatt ctcaaagcaa     240
gtcagggtgg ggatggatgg tttcatccca caggtgggaa gattgagg                  288
```

```
<210> SEQ ID NO 35
<211> LENGTH: 430
<212> TYPE: DNA
<213> ORGANISM: Homo sapiens

<400> SEQUENCE: 35
gtttttctca ggtccttgat tggaactgcc tcagagccaa gggtcctttt actcagtggc      60
agcaacaaac gcagtctgtt ggctagtgat cctcctgtct cagggacacg tagtccaggg     120
agcagccaat tgcttggcac ttggggaccc cgttctgggg agtcctgaaa gctttcacct     180
cttggattgc cgaatacatg ggtggcccct cctagactaa gggactggcc tgagtgaggc     240
tgggcctctc agccaagctg atgttgaacc actgctgtgg ggatgggcct ggggttcctg     300
ggaagctgtt catacccatt gccaggagcg tgggctctgg ctggacctgg atcagatcct     360
aactgaagcg gcagctttct ggcatgagaa aggagtgttt tcatggtgga cagaattggg     420
ctatgagtgt                                                            430

<210> SEQ ID NO 36
<211> LENGTH: 120
<212> TYPE: DNA
<213> ORGANISM: Homo sapiens

<400> SEQUENCE: 36
atatctctgc caacatgagg acagaaggac tggtgcgacc ccccaccccc gccctgggc       60 taccatctgc atggggctgg ggtcctcctg tgctatttgt acaaataaac ctgaggcagg     120

<210> SEQ ID NO 37
<211> LENGTH: 655
<212> TYPE: DNA
<213> ORGANISM: Homo sapiens

<400> SEQUENCE: 37
agggagccct cctggaagtg gatgaggcct tgggtctcgg ctcttcattg cttcctgagc      60
tgcagcagat gcctttacaa ccaagctcac cgaggacgtc tgtctcccat attaccctgg     120
cagagggcca ggcctgttct acacggccgg ggtttcaaca aggtactgat gtcttctgcc     180
cttgcctctt cgacaggcaa gtaataagac ttaagtgaag agaattcttt aggcacacaa     240
attcacattt gatgtaatct cattatactt cctgatctgt gattgaaaac tttcatttcg     300
taactagtat gtctgtccca cctttaaaaa gttttcatt atgaaagtaa gtatttgtta     360
gaattaagtc tatttaaatg aaaaaaactt agatatgagt ctgcatggcc tcaggaaaat     420
gatgttttaa aatagagatt ttaggttgtc tgcactctag cttttttgtc gttttcttaa     480
ggctttttta actgcatcaa aaattcagat acgaaacata cactaaaaaa taatacatca     540
tatcttaatt tccactgaac ttgatttaaa ttcagagtta cacagtatga atatcacaat     600
cagatatgtt caaaaggtc tgaacaattg attttctgaa accatgaagg actac           655

<210> SEQ ID NO 38
<211> LENGTH: 331
<212> TYPE: DNA
<213> ORGANISM: Homo sapiens

<400> SEQUENCE: 38
agccatttaa attcattaga aaaatgtcct tacctcttaa aatgtgaatt catctgttaa      60
gctaggggtg acacacgtca ttgtacccct tttaaattgt tggtgtggga agatgctaaa     120
gaatgcaaaa ctgatcccata tctgggatgt aaaaaggttg tggaaaatag aatgcccaga    180
```

```
cccgtctaca aaaggttttt agagttgaaa tatgaaatgt gatgtgggta tggaaattga    240
ctgttacttc ctttacagat ctacagacag tcaatgtgga tgagaactaa tcgctgatcg    300
tcagatcaaa taaagttata aaattgcctt c                                  331
```

<210> SEQ ID NO 39
<211> LENGTH: 1152
<212> TYPE: DNA
<213> ORGANISM: Homo sapiens

<400> SEQUENCE: 39

```
gcagctcatg tgcacgtttt ctgtttaaat aaatgtaaaa actgccatct ggcatcttcc     60
ttccttgatt ttaagtcttc agcttcttgg ccaacttagt ttgccacaga gattgttctt    120
ttgcttaagc ccctttggaa tctcccattt ggagggggatt tgtaaaggac actcagtcct    180
tgaacagggg aatgtggcct caagtgcaca gactagcctt agtcatctcc agttgaggct    240
gggtatgagg ggtacagact tggccctcac accaggtagg ttctgagaca cttgaagaag    300
cttgtggctc ccaagccaca agtagtcatt cttagccttg cttttgtaaa gttaggtgac    360
aagttattcc atgtgatgct tgtgagaatt gagaaaatat gcatggaaat atccagatga    420
atttcttaca cagattctta cgggatgcct aaattgcatc ctgtaacttc tgtccaaaaa    480
gaacaggatg atgtacaaat tgctcttcca ggtaatccac cacggttaac tggaaaagca    540 cttttcagtct cctataaccc tcccaccagc tgctgcttca ggtataatgt tacagcagtt    600
tgccaaggcg gggacctaac tggtgacaat tgagcctctt gactggtact cagaatttag    660
tgacacgtgg tcctgatttt ttttggagac ggggtcttgc tctcacccag gctgggagtg    720
cagtggcaca ctgactacag ccttgacctc ccaggctca ggtgatcttc ccacctcagc     780
cttccaagta gctgggacta cagatgcaca cctccaaacc tgggtagttt ttgaagtttt    840
tttgtagagg tggtctagcc atgttgccta ggctcccgaa ctcctgagct caagcaatcc    900
tgcttcagcc tcccaaagta ctgggattac aggcatcttc tgtagtatat aggtcatgag    960
ggatatggga tgtggtactt atgagacaga atgcttaca ggatgttttt ctgtaaccat    1020
cctggtcaac ttagcagaaa tgctgcgctg ggtataataa agcttttcta cttctagtct    1080
agacaggaat cttacagatt gtctcctgtt caaaacctag tcataaatat ttataatgca    1140
aactggtcct tc                                                      1152
```

<210> SEQ ID NO 40
<211> LENGTH: 75
<212> TYPE: DNA
<213> ORGANISM: Homo sapiens

<400> SEQUENCE: 40

```
actaacgaaa aatcaataaa taaatgtgga tttgtgctct tgtatttta agtggattaa      60 aaaacttact acctt                                                      75
```

<210> SEQ ID NO 41
<211> LENGTH: 1176
<212> TYPE: DNA
<213> ORGANISM: Homo sapiens

<400> SEQUENCE: 41

```
gaatgtcaac gattagtcat gcaataaatg ttctggtttt aaaaaataca tatctggttt     60
tggtaaggta tttttaatca attaggcttg tagtatcagt gaaatactgt aggtttaggg    120
```

```
actgggctag cttcatatca gatttacttg ttaagtgact gttttggaat gtttactttt      180
ggactgggtt tgtaacacgg ttaaaggcaa tgagaaacaa gcagaattcc aggagtcctt      240
gaagcagagg gcactggaag acaatatagc agattaaaat agcacagctc atgtggcata      300
ggtgggtatt ttagatgttt gagtaaattt gaaagagtat gatgtttaaa ttacctttag      360
caacatgttc atctgctatg ctgtcatgac tagggggatg attattagtc acatagagct      420
tgggagtacc actggaaacg tatgggtagg agtttaggtg gcttctgttt ttcaaaagat      480
gatcttatcc tagtatctgt aatgctcact tggcacacct gacttgtggg ctgtgtgtaa      540
ggtggctagc taagtgaaaa aagcctgcta ggtgtgagtc aacttaagaa tatgtaaata      600
ggtttgagaa aaagtagggc ttgggtgcaa gtaaagattg agcaggaaat aaggaaaat       660
caagtataat ccctgagatt tgtagactaa aggcaatgat gtgggactac ttggtcgaat      720
ttttttagcc ctcaacttgg taattgggtg tttctgtgtt aaagcactga aacttgctgt      780
cgtgccttcc tagttttcgt ggtttattga cagggttggg ggttttttt gttttttaa        840
aatgaaggga caaagtcaac tggactgctg agtgagaggg caggggcagt tgaagggaac      900
atgaattgct ggaacagcta cataaaatag tgatgtagcc aagtcatgct atttaaatta      960
taattctcca ctgtgtttag aataacatct gaggttctta acctggcctt ggaagggtat     1020
cacttttact tgtaacctgg aatggcttta taatgtgcta gctaattgct actctcatct     1080
tgtattttaa ctcctaattt acccttcagg tctcagcttc agaacattca cttataaaga     1140
aaccctgctg attaaatctc tcttgggctt cctccc                              1176
```

<210> SEQ ID NO 42
<211> LENGTH: 59
<212> TYPE: DNA
<213> ORGANISM: Homo sapiens

<400> SEQUENCE: 42

```
acgctcctct actctttgag acatcactgg cctataataa atgggttaat ttatgtaac       59
```

<210> SEQ ID NO 43
<211> LENGTH: 49
<212> TYPE: DNA
<213> ORGANISM: Homo sapiens

<400> SEQUENCE: 43

```
accagacaca ctgattggaa ctgtattata ttaaaatact aaaaatcct                  49
```

<210> SEQ ID NO 44
<211> LENGTH: 178
<212> TYPE: DNA
<213> ORGANISM: Homo sapiens

<400> SEQUENCE: 44

```
ggaattgcac atgagatggc acacatattt atgctgtctg aaggtcacga tcatgttacc      60
atatcaagct gaaaatgtca ccactatctg gagatttcga cgtgttttcc tctctgaatc     120
tgttatgaac acgttggttg gctggattca gtaataaata tgtaaggcct ttcttttt       178
```

<210> SEQ ID NO 45
<211> LENGTH: 73
<212> TYPE: DNA
<213> ORGANISM: Homo sapiens

<400> SEQUENCE: 45

```
tcaccaaaaa gcaaccaact tagccagttt tatttgcaaa acaaggaaat aaaggcttac      60
```
ttctttaaaa agt                                                73

<210> SEQ ID NO 46
<211> LENGTH: 38
<212> TYPE: DNA
<213> ORGANISM: Homo sapiens

<400> SEQUENCE: 46
acctctttta taacatgttc aataaaaagc tgaacttt                      38

<210> SEQ ID NO 47
<211> LENGTH: 40
<212> TYPE: DNA
<213> ORGANISM: Homo sapiens

<400> SEQUENCE: 47
attcctgctc ccctgcaaat aaagccttttt tacacatctc                   40

<210> SEQ ID NO 48
<211> LENGTH: 1301
<212> TYPE: DNA
<213> ORGANISM: Homo sapiens

<400> SEQUENCE: 48
cagggtctcc ttggcagctg tattctggag tctggatgtt gctctctaaa gacctttaat    60
aaaattttgt acaaagacac aaggtctgac tagactgttc agtattcaga ctgaggggca   120
tgttggcctc tggagcatta catatcttct tggttttaac catacttgtg gtatttgcaa   180
gggccagaac agtaagaccc aagcagagcc aaccagagaa ataatatttg tgtgatagag   240
aaggctgata gcaagcaagg cagcaccttg attcgttgtc ctgtagttca ggattgtagg   300
tttagaagag ggatatgttt gagttttttcc tatgcataag gcgatccacg ttgcacatag   360
aaagtgaata taaatggcca ttatattttg tgtcatgctg tgctctaagt gttctttaca   420
tatgtactcg ttaatcaacc tctctaaagt gtaaaggaaa tttgcttgca ccactgaagg   480
cacataaggc tcagaagtaa atttgcctaa gcagtataaa gctatcatta gaatccacat   540
tcctaagttg tgttctctta ggggatcatg gaaccagtca ttggtactac aggctattat   600
gttctggaga actgtgaaga acatttaaat tgtctctgat tttatctatc aatgttttga   660
agtattttct accagtgtct gtacttcaca agaaattcgg cactattttt tcaggcaaaa   720
ctagtgaggg acaggttggc ttgaaaatca tgagactgtt gttaaatcag atgctggttg   780
atcacagagg ggacttccag ggaaagctgt tatcaggtgg ctgcttcctg gtgatgcagc   840
ctggctgatg agataaccct ggctccacag atggcttagc aggtgctgtg atgatttggt   900
tttcttctca attagactga gctgcacatg gtgtttatat tgcttggcac atggtaaggg   960
cttaatattt gaggtaatta tgtagggcgt acactgacaa gtatctgacc ccccttcct  1020 ttttgactca taaattggtc atcttaacca tttaagtgta cacttctata gtgacagagt  1080
tagccctctg tccaagggat tgcatctgt ggattcaacc aactttgggt caaaaataat   1140
caaaaaggat ggttgtgtgt gtattgaaca tgtagactta ttttttctta tttcaaaata  1200 ctatatttc ttgtcactta ttttcttgta cactgcagtt gtaacagcta tgtagcatgt   1260
acattaggta ttaaaagtaa tccagtgaag attgaaagtc t                    1301

<210> SEQ ID NO 49
<211> LENGTH: 576
<212> TYPE: DNA

```
<213> ORGANISM: Homo sapiens

<400> SEQUENCE: 49
cagcctcttc catgagtggg gagcccgctg cttgtctcca gctcctagca gtgagtcctg      60
ataatctcaa atttaaggac agtaactttg tctgggatga gtgtgggaaa ggatgtgttt     120
gggaacagac gcgagcctgc agaggtgttt gtaaccatct ctttctaagt ggtgggaagc     180
agacatttta ttctttaact gttaatatat atagtgtgtg ttttttatgc atgaaatatt     240
ttatagtttt taaaaatgcc cacactacta ttttgaaagt aaatgaggta atgtatgtgt     300
cagaacccaa tacccaaagc gatcgtagta agaggtgggg cctttgggaa ggcattaaat     360
tgcttaggga atgagggtgg aaccctcatg aatgagatta gagccttata ggagaggttg     420
gagggagttg cctggcctcc ctctcccatg tgaagactca gcaagaaaac attatttagg     480
aagcagagag ccctcatcaa acaccagatc tgctggccac ctgatctggc actttccagc     540
cttcagaact gtgagaaata aatttctgtt gtctat                               576

<210> SEQ ID NO 50
<211> LENGTH: 57
<212> TYPE: DNA
<213> ORGANISM: Homo sapiens

<400> SEQUENCE: 50
agttcagact tcaaatagtg gcaaataaaa agtgctattt gtgatggttt gcttctg         57

<210> SEQ ID NO 51
<211> LENGTH: 1324
<212> TYPE: DNA
<213> ORGANISM: Homo sapiens

<400> SEQUENCE: 51
agctcacgtt gatgtcaaga ctaccgatgg ttacttgctt cgtctgttct gtgttggttt      60
tactaaaaaa cgcaacaatc agatacggaa gacctcttat gctcagcacc aacaggtccg     120
ccaaatccgg aagaagatga tggaaatcat gacccgagag gtgcagacaa atgacttgaa     180
agaagtggtc aataaaattg taagtgtttct ttgcttcctc acacaacaca accttgagta     240
ttggattatt cctgagatga gagaacgcat atgagacaag gtaaaggtct gttgaaatcc     300
tgtctgtgaa tccttctagc tatatctctt taagtgaaag agtgttaagt actcagtaaa     360
tatgattatt attactatta ttatttgagt cagagtcttg ctctgttgcc caggctcgag     420
tgcagtattg tgatcctcct tggctcactg taaccactgc ttcctgggtt caagcagttc     480
ttgagcctca gcctcctgag tatctgggaa tacagggac tgccaccata cccagctaat      540
ttttttaaat tttagtagag atggggtttt catcatgttg gccaggctgg tcttgaactc     600
ctgacttcag gtgatctgcc agtactctaa atgataacag tttttcgtg tttatttatt      660
ttgaatgaag ctgtctcaca gtagatggag ttgaaggaca ggaaatgttt ttcccctact     720
tggaaaatac actgaataag ttgagtgggg tgggatgtgc ctggagtccc agctactcag     780
gaggctgagg tggtaggatt gtttgagccc aggagtttga ggccagcctg gcaatatag      840
ggagaccctg tcccaaaaaa taaaaatat acgtatatat atatacacac acaaagaaaa     900
aatacactga atagacaaaa cctttcatga ttaatgatgc acgggaataa gtgatgaaaa     960
aagtttcggt cccagatgat ggccagtgat aacaacattt ttctgatgtt cccatgcaat    1020
atacagttag ctaagagggt gtaatggaaa agcataagg cttggactca gaagactcta     1080
ctaactttgc cactagctag ctatgtaatt cagatcatct atcctttaca tgtgaaaggt    1140
```

```
aaataatggc ttatcttaac aggaggattt atgcaggtta aatgaggtag gtgttatgtg    1200
taggtttatt ccaaggcttc tctacttta aaggaaatgg cttatatctg agaactagga     1260
cttttagaaa aaaatttact gttactggtt tgcaggattc cagacagcat tggaaaagac    1320
atag                                                                 1324
```

<210> SEQ ID NO 52
<211> LENGTH: 68
<212> TYPE: DNA
<213> ORGANISM: Homo sapiens

<400> SEQUENCE: 52

```
aatgggtccc tgggtgacat gtcagatctt tgtacgtaat taaaaatatt gtggcaggat    60
taatagca                                                             68
```

<210> SEQ ID NO 53
<211> LENGTH: 60
<212> TYPE: DNA
<213> ORGANISM: Homo sapiens

<400> SEQUENCE: 53

```
attgcagtag cagcatatct tttttctt gcacaaataa acagtgaatt ctcgtttctt      60
```

<210> SEQ ID NO 54
<211> LENGTH: 53
<212> TYPE: DNA
<213> ORGANISM: Homo sapiens

<400> SEQUENCE: 54

```
ttttcccagc tgctgcccaa taaacctgtc tgcccttgg ggcagtccca gcc            53
```

<210> SEQ ID NO 55
<211> LENGTH: 37
<212> TYPE: DNA
<213> ORGANISM: Homo sapiens

<400> SEQUENCE: 55

```
gattttttga gtaacaaata aataagatca gactctg                             37
```

<210> SEQ ID NO 56
<211> LENGTH: 36
<212> TYPE: DNA
<213> ORGANISM: Homo sapiens

<400> SEQUENCE: 56

```
acaaaaatga ctaaataaaa agtatatatt cacagt                              36
```

<210> SEQ ID NO 57
<211> LENGTH: 55
<212> TYPE: DNA
<213> ORGANISM: Homo sapiens

<400> SEQUENCE: 57

```
atccttgttt tgtcttcacc catgtaataa aggtgtttat tgttttgttc ccaca          55
```

<210> SEQ ID NO 58
<211> LENGTH: 70
<212> TYPE: DNA
<213> ORGANISM: Homo sapiens

<400> SEQUENCE: 58

```
gtccacctgt ccctcctggg ctgctggatt gtctcgtttt cctgccaaat aaacaggatc    60
agcgctttac                                                           70
```

<210> SEQ ID NO 59
<211> LENGTH: 50
<212> TYPE: DNA
<213> ORGANISM: Homo sapiens

<400> SEQUENCE: 59

```
aattggagag gattcttttg cattgaataa acttacagcc aaaaaacctt              50
```

<210> SEQ ID NO 60
<211> LENGTH: 77
<212> TYPE: DNA
<213> ORGANISM: Homo sapiens

<400> SEQUENCE: 60

```
ggctggacat cggcccgctc cccacaatga aataaagtta ttttctcatt cccaggccag    60
acttgggatc ttccgcg                                                   77
```

<210> SEQ ID NO 61
<211> LENGTH: 21
<212> TYPE: DNA
<213> ORGANISM: Homo sapiens

<400> SEQUENCE: 61

```
agaaataaat ctttggctca c                                              21
```

<210> SEQ ID NO 62
<211> LENGTH: 41
<212> TYPE: DNA
<213> ORGANISM: Homo sapiens

<400> SEQUENCE: 62

```
atttgtctgt gtactcaagc aataaaatga ttgtttaact a                        41
```

<210> SEQ ID NO 63
<211> LENGTH: 31
<212> TYPE: DNA
<213> ORGANISM: Homo sapiens

<400> SEQUENCE: 63

```
tggctcagct aataaaggcg cacatgactc c                                   31
```

<210> SEQ ID NO 64
<211> LENGTH: 53
<212> TYPE: DNA
<213> ORGANISM: Homo sapiens

<400> SEQUENCE: 64

```
ggatgtaata catatattta caaataaaat gcctcatgga ctctggtgct tcc            53
```

<210> SEQ ID NO 65
<211> LENGTH: 64
<212> TYPE: DNA
<213> ORGANISM: Homo sapiens

<400> SEQUENCE: 65

```
gcccatcgtg actcaaaact cacttgtata ataaacagtt tttgagggat tttaaagttt    60
caag                                                                 64
```

```
<210> SEQ ID NO 66
<211> LENGTH: 37
<212> TYPE: DNA
<213> ORGANISM: Homo sapiens

<400> SEQUENCE: 66
aacaaaccat gctgggttaa taaattgcct cattcgt                              37

<210> SEQ ID NO 67
<211> LENGTH: 386
<212> TYPE: DNA
<213> ORGANISM: Homo sapiens

<400> SEQUENCE: 67
ctgcattctc ctccgccaaa aaagtgacca agcagagtct ttctctgtca cccaggctgg     60
agtgcaatgg cgtgatctca gctcactgca acctctgcct cctgggttca agtgattctc    120
gtgtctcagc ctcctgagta gctgagacta caggtgtgca ccagtgttcc cagctgattt    180
ttgtatttta tgtagagatg gggttatgcc attttggcca ggctagtctc gaactcctga    240
gctcaggtga tacacacacc tcagcaaatc ttttaaatta tacattctgt gatatttcct    300
tgactttctt atccagcact tgtattgatt atttttcatt ttgataatgt tgggttttta    360
aaaactcctt tatgatggaa aatttc                                        386

<210> SEQ ID NO 68
<211> LENGTH: 281
<212> TYPE: DNA
<213> ORGANISM: Homo sapiens

<400> SEQUENCE: 68
gtcaactatt ttaataaatt gatgaccagt tgttaacttc tgttggtttt tattcagaat     60
actggcagat tttaggaata taaggtgta ctatgagact tccactttc aggtggaata    120 tatgggtatc ttagagtggt ctatcctgtt ttcgttgtcg tttgagtcat ttgaaaactg    180
gattccgtta actacataat atgtgagacc tgactggttt tattggacac tggcagttta    240
taactttggc atactctaga taaattctga ttggtatggg g                        281

<210> SEQ ID NO 69
<211> LENGTH: 53
<212> TYPE: DNA
<213> ORGANISM: Homo sapiens

<400> SEQUENCE: 69
ctggagagaa tcacagatgt ggaatatttg tcataaataa ataatgaaaa cct            53

<210> SEQ ID NO 70
<211> LENGTH: 2785
<212> TYPE: DNA
<213> ORGANISM: Homo sapiens

<400> SEQUENCE: 70
atattaatgg tgaaaacact gtagtaataa attttcatat gccaaaaaat gtttgtatct     60
tactgtcccc tgttctcacc acgaagatca tgttcattac caccaccacc cccccttatt    120 tttttatcc taaaccagca aacgcaggac ctgtaccaat tttaggagac aataagacag    180
ggttgtttca ggattctcta gagttaataa catttgtaac ctggcacagt ttccctcatc    240
ctgtggaata agaaatggg atagatctgg aataaatgtg cagtattgta gtattacttt    300
aagaacttta agggaacttc aaaaactcac tgaaattcta gtgagatact ttcttttta    360
```

```
ttcttggtat tttccatatc gggtgcaaca cttcagttac caaatttcat tgcacataga    420
ttatcttagg taccettgga aatgcacatt cttgtatcca tcttacaggg gcccaagatg    480
ataaatagta aactcaaaat tgctccccac tctgtttatt atttaaaggt gtcaggatct    540
gtgttgtaat gtgtctacat taatgtgttt aggagaatac aggcattgga tcatttagtt    600
gatggaagta tatgccaggc aagggagata aggtatacga caagactgat gttttcagta    660
tcttctcatg aggttgtcag agaccttcat gtcttcaaag actagtcagc aaatgaagtg    720
gtttagtgta gagacaagat tggttgtgtt ttgataattt aagctaggta ttgagtacat    780
gtggattttg ctgtccacaa atacttgttt cagagttttc atggatacag tggcatggtt    840
gaaatgaagc tgtgagcctt ctgctttaaa tctgatgtaa gaaactcctg ttaacaaata    900
gtaagtatgg gttaattagc cctttgatca aagcctagct ttacattgtt taggatcttt    960
ggaaaacaat tggtttggtt gcccactttc cgtaggatca agagcagaac ctttcacatg   1020
gcacagaaga acccaggttg cgcttcatac ctgcatattc cagccttagc ctgccatttc   1080
tctccttggc actttgtgct ccagcaacac tggtctcagt tggtcatcct caaacttggg   1140
ttccatatcc agcctcagga cctctgttcc tgttactatg gttccttgca tgtcgcctgc   1200
tcttactaaa gagctcgtgt gttttccagc acacttcggt ttatctcttg atgatgatgc   1260
tagtctctcc ctccgcaagg gcggaaaggc tgcctgttgg tttgtaccag tgtttcctaa   1320
cgtgtagctg cagtcagtat ttggctaagc tgttcccagg ggctcaacag atgctttcgg   1380
atgagcctta actgacccaa tcctttgtga tgcgggagag attgctaggc ctcgctcacc   1440
tggccagaac cagggaaaga ggccgcggtt gcagcgcgat tccaggccct gggcgtcagg   1500
cgcggggtgg gcagctctcc ccgggcggtg gggcccttgt gaccgcgagg cggggcgcac   1560
caggaaggga gtgggacagc gcgggcgccc agggatgtgg cctggttacc tgccttctct   1620
gatacgtcaa gacaccttca acaatggctt gcagctgtac cctgttggct gcacccagga   1680
cgccctttcc actgctaagc agtcctacct gaggcccagg ggctgccaga ttgacccata   1740
aataatctcc ggcgcctcag atccagaagc tgctgagcct gatcttagtg ccttctcctt   1800
tctctgtgtg gccccccagc ccctttcccc actgccttgt gtccaaggcc ctttccttca   1860
tgtatccatg gaggagagac aaaaatacac atcaataaaa taagataggg aatccataaa   1920
tagacattca gaagtatggc caacggattt atcttaaaac caatggagga agaagagttt   1980
caataaatgt tgtggacttc catttgtcaa agaccaaaac aaaggaaccc caaccttaca   2040
tgtaatacaa acttaactca aaatggatca tatatctaaa tgtaaaatgg aaagctataa   2100
aactgaaaac agactatctt tacaacctag gcgtaggtat agttttttaga cattacacca   2160 aaagcacatg ccgtaaaaga aaaaatagat aaattggtgg atttcattaa aattaaaaaa   2220
ctttttctct ctgaaaaatc ctgttaagct gggcgctgtg gttcatgcct gtaatcccag   2280
cactttggga ggctgagttg ggaagaaatt aatagcttga ggccaggagt tcaagatcat   2340
cctgggcagc aaagtcatac actcttgagg gaagagagag accttctcat attgttttat   2400
attgttttat actcagtacc tgttttaaga aaaaacaag gaagtgaaat caaagacagg   2460
cagcccggca ccaggcctga aaccagccct gggcctgcct ggcctaaacc tagtagttaa   2520
aaatcaactt acgacttaga acctgatgtt atccgtagat tccaagcatt gtataaaaaa   2580
attgtgaaac tccctgttgt gttctgtacc agtgcatgaa accctgtcaa catatcccct   2640
agattgctca atcaatcacg acccctttcat gtgaaatctt tagtgttgtg agcccttaaa   2700
agggacagaa attgtgcact tgaggagctc agattttaag gctgtagctt gccgatgctc   2760
```

```
ccagctgaat aaagcccttc cttct                                       2785

<210> SEQ ID NO 71
<211> LENGTH: 48
<212> TYPE: DNA
<213> ORGANISM: Homo sapiens

<400> SEQUENCE: 71
ataggtccaa ccagctgtac atttggaaaa ataaaacttt attaaatc              48

<210> SEQ ID NO 72
<211> LENGTH: 67
<212> TYPE: DNA
<213> ORGANISM: Homo sapiens

<400> SEQUENCE: 72
ggagctgagt tcttaaagac tgaagacagg ctattctctg agaaaaata aaatggaaat  60 tgtactt                                                           67

<210> SEQ ID NO 73
<211> LENGTH: 62
<212> TYPE: DNA
<213> ORGANISM: Homo sapiens

<400> SEQUENCE: 73
aagcactctg agtcaagatg agtgggaaac catctcaata aacacatttt ggataaatcc  60
tg                                                                62

<210> SEQ ID NO 74
<211> LENGTH: 276
<212> TYPE: DNA
<213> ORGANISM: Homo sapiens

<400> SEQUENCE: 74
ctgtatgagt taataaaaga catgaactaa catttattgt tgggttttat tgcagtaaaa  60
agaatggttt ttaagcacca aattgatggt cacaccattt cctttagta gtgctactgc  120 tatcgctgtg tgaatgttgc ctctgggggat tatgtgaccc agtggttctg tatacctgcc  180
aggtgccaac cacttgtaaa ggtcttgata ttttcaattc ttagactacc tatactttgg  240
cagaagttat atttaatgta agttgtctaa atataa                           276

<210> SEQ ID NO 75
<211> LENGTH: 139
<212> TYPE: DNA
<213> ORGANISM: Homo sapiens

<400> SEQUENCE: 75
gcttggctgc tcgctgggtc ttggatgtcg ggttcgacca cttggccgat gggaatggtc  60
tgtcacagtc tgctcctttt ttttgtccgc cacacgtaac tgagatgctc ctttaaataa  120
agcgtttgtg tttcaagtt                                             139

<210> SEQ ID NO 76
<211> LENGTH: 94
<212> TYPE: DNA
<213> ORGANISM: Homo sapiens

<400> SEQUENCE: 76
atgctcttcc ttcagaggat tatccggggc atctactcaa tgaaaaacca tgataattct  60
```

```
ttgtatataa aataaacatt tgaaaaaacc cttc                                94
```

<210> SEQ ID NO 77
<211> LENGTH: 1355
<212> TYPE: DNA
<213> ORGANISM: Homo sapiens

<400> SEQUENCE: 77

```
tataagtaaa gtttgtaaaa ttcatactta ataaacaatt taggacagtc atgtctgctt    60
acaggtgtta tttgtctgtt aaaactagtc tgcagatgtt tcttgaatgc tttgtcaaat   120
taagaaagtt aaagtgcaat aatgtttgaa gacaataagt ggtggtgtat cttgtttcta   180
ataagataaa cttttttgtc tttgctttat cttattaggg agttgtatgt cagtgtataa   240
aacatactgt gtggtataac aggcttaata aattctttaa aaggagagaa ctgaaactag   300
ccctgtagat ttgtctggtg catgtgatga aacctgcagc tttatcggag tgatggcaat   360
gctctgctgg tttatttca agtggctgcg ttttttttag tttggcaggt gtagactttt    420
taagttgggc tttagaaaat ctgggttagc ctgaagaaaa ttgcctcagc ctccacagta   480
ccattttaaa ttcacataaa aggtgaaagc tcctggttca gtgccatggc ttcatggcat   540
tcagtgatta gtggtaatgg taaacactgg tgtgttttga agttgaatgt gcgataaaat   600
tattagcctt aagattggta agctagcaat gaatgctagg gtgggaagct ggtgagccag   660
tggccattag ataaataccct ttcaagtgtg agcttagacg tcaaccctaa atacttaac   720
cgtaatgcta attgtgatca ttatgaatcc cttcagtcac attagggga aagtagttgg    780
ctataagtac gtcattctta gtccagtcag tcttaaaaac atcttgggtt acccactctg   840
tccactccca taggctacag aaaaagtcac aagcgcatgg tttccaacca tatgtgtttt   900
ctgcagttat ttctcttgtt ctggccaaac aaccctaaaa atccttacca ttccacaaag   960
ttggaccatc acttgtgcac ccactttgac tatgagtata ccaccacatt gcatttctgt  1020
ttgcaccatg tcttccagga gactagacta ctgttgtcca gggtcaattt gagtgtaaag  1080
aaaatgtaga caaggaattg cccaattta aattctgact ttgctgactt aatttaaatg   1140
ctcgttctga accaattttc tcctatcttc tctaggggtt tcaaaagact cagttaattg  1200
atttccagga agtactcata gcaagttcat aaaagttctt gagacctaaa tttcttcaca  1260
aaaaagaaa agatcttaag tcatacattt taattgtgta gaggttgttc aactgaagga  1320
ataaatgtct attaaactaa acaaatggga ccttc                             1355
```

<210> SEQ ID NO 78
<211> LENGTH: 2017
<212> TYPE: DNA
<213> ORGANISM: Homo sapiens

<400> SEQUENCE: 78

```
gcaattcttc tgcctcggcc tcccaaatag ccaggactac aggcgcacac tgccatgccc    60
agctaagttt tgtattttta gtagagactg ggtttcacta tgttggccag gctggtctcg   120
aactcctgac ctcaagtgat ccacctgcct tggcctccca aagtgctggg attacaggcg   180
tgagccacca cccccagccc aattttatt ttttgtacag acaggatctc actatgttgc    240
ccaggttggt ctcaaactac tggcctcaag caatcctgcc ttggcctccc aaagtgctgg   300
aattatagga atgagccacc acccgggcc caaatttact ttagtaataa caacaattgg   360
ctgggtgcgg tggctcacgc ctgcaatccc aacactttcg gtaaccaagg tgggcttgag   420
ctcatgagtt agagagcagc ctgagcaacg tggtgagagc ccatctcaca aaaaataaca   480
```

```
aatcagctgg gcatggtgtt gcacgcctgt agtctccgaa atcacaccac tgcactccca      540
tcttgggtga tagagccaga acttgtctca aaaataacaa ttggtttctt acaatcccaa      600
aaggtgcagt tactagtatt aatccttttt tgccaatgag gaaacacaaa gatgaagcaa      660
cttgctcaaa gtcatacagt gacagtctga attcaaatcc tatacactta aagtttattt      720
gttttgtttt ggttttttttt gagatggagt ctcactgtgt cgcaaggctg gagtgcagtg      780
gcacgatctc agctcactgc aacccgggtt caagcgattc tcctgcctca gcctcccgag      840
tagctgggac tacaggcacg caccaccaca cccagctaat ttttgtattt ttagtagaga      900
cggtttcacc atgttggcca ggatggtctc gagctcctga cctcaggtga tcctcccgcc      960
ttggcctccc aaagtgccgg gattacaggt gtcagccact gcacgtggcc aacttaaagt     1020
ttttgataga taatacatta acgttaaaaa ttcaaaagat aagtataggc tctacagtac     1080
aaacccttct gcctcctagt tcctctccct ggaggcaagg tgatcagttt aacaatattt     1140
ttttattttg agacagggtc tcactgttgc ccaggctgga gtgtagtggc gcgttcacaa     1200
cttactgtag cctcaacctc ctggctcaag caatcctccc acctcagcct gtcgagtagc     1260
tggaaccaca ggtgcacacc accatgccag gctaattttt gtattttttg tagagacagg     1320
gtttcaccat gttgttcagg ctggtctcaa agtcctgggc tcaagcaatc ttcctgtctc     1380
tgcttcccaa agtgctggga ttacagatgt gggccacggt gcctggccta catatgtatt     1440
ttttcctttt cttccccaag tggtaggata tgatacacat tgttgatttt tttgtttagt     1500
tatgtatctc agagcttatt ctttatcagc tcatgaggaa cttcattttt tttttttttt     1560
ttgagatgta gttttgctct tatagcccag gttggagtac agtaacacaa tcttggctcg     1620
cagcaacttc tgcctcccag gttcaagcga ttctcctgcc tcagcctccg agtagctagg     1680
attacaggtg cctgccacta catccagcta tttttgtatt ttcagtagag acggggtttc     1740
accattttgg ccaagctggt ctcgaactcc tgacctcagg tgatccgccc atctcagcct     1800
cccaaagtag tgggattaca ggcatgagca accgtgcccg gctggaactt cattcttttg     1860
gtataactgc atggtatccc atcatgtgga tgtaccatga ttcattggat gtggaccctc     1920
ctgatggaca tttaaatttc ttccaatctg ttgctattac aaaaagaaaa atgtgtgcat     1980
acatctttat tcatctgtag aataaattct tagaagt                              2017
```

<210> SEQ ID NO 79
<211> LENGTH: 37
<212> TYPE: DNA
<213> ORGANISM: Homo sapiens

<400> SEQUENCE: 79

```
ggtttttata caagaaaaat aaagtgaatt aagcgtg                                37
```

<210> SEQ ID NO 80
<211> LENGTH: 140
<212> TYPE: DNA
<213> ORGANISM: Homo sapiens

<400> SEQUENCE: 80

```
gtggcaatca taaaaagtaa taaaggttct ttttgacctg ttgacaaatg tatttaagcc       60
tttggattta aagcctgttg aggctggagt taggaggcag attgatagta ggattataat      120
aaacattaaa taatcagttc                                                  140
```

<210> SEQ ID NO 81

<211> LENGTH: 55
<212> TYPE: DNA
<213> ORGANISM: Homo sapiens

<400> SEQUENCE: 81

```
acaagattcc tcaaaatatt ttctgttaat aaattgcctt catgtaaact gtttc         55
```

<210> SEQ ID NO 82
<211> LENGTH: 1485
<212> TYPE: DNA
<213> ORGANISM: Homo sapiens

<400> SEQUENCE: 82

```
gggcttccaa tgtgctgccc ccctcttaat actcaccaat aaattctact tcctgtccac    60
ctatgtcttt gtatctacat tcttgacggg gaaggaactt cctctgggaa cctttgggtc   120
attgcccttt cacttcagaa acaggttgac aactcagccc tgctcatgag gcagcaaacc   180
ctgcaaaggg ctgggactgg tggccttatg tcagttgtct actctggagc ttgacttgga   240
cctccccagg tcctaggcag taggttgaaa aacactgaag tgcttttcat gaagcacagc   300
tgcagcaaag ccttgcaatc ccaggctggg gtcagcctac agttgtgttg cttattacaa   360
cacatgcgga ccaagagggg cttgtgggct agaggctgac cagcagcgtt tatttagcaa   420
gggtaggtgt gcatcacatt gggcttgttc tcacccatct ggtttggcca ttcctccttg   480
gtgggaatca tccaggtact gctgaggtca cctgcgattt gccccatttc ctatctctag   540
caacctcctg ggccccatgc ccccaccct tctagaacct gcattccag ggccttcacc    600
acctgaccaa aggtctaggc taaccttgg tcatttgtaa caagacctcg aacagacac    660
gtgtgtggca tggtttggcc tggggatctt agatgtctga cctgaactat tgtagaacag   720
cgctggcttt tgggggagca gcaaaaatga gaggagtgct aggtgggtgg cctgagcatc   780
tgtatccagg acaggactc caaaggcttt tggtcccaga gctggggtat gttggcccca    840
gcccccagcc tgtggctccc aaaaggcctc tggttttttg taatctcagt ttacagccat   900
ttcttaggtt tttaattacc tttatttat tttgccaaac atacctggga ataccttta    960
ttttttttt accttggggt gatggttcca aaccataaat gtgattatag ttaacacatg  1020
accccttctag cgtcccagcc agtgtttttc ctgacctctg ttctttggag aggaggatgg  1080
aagggagggg tccggcacgc tgctggcatt ttgctgtgtc ctgcagcccc tttccgggac  1140
acctgggttc acacagcttt ttagcttaca taactggtgc agattttctg tgtggagatg  1200
ttgccttgac cagccttggc tggacttac caggcatgca gaagcctgta ccaacacaga  1260
ctacagcacc caggaggtgc gagtgtggct gctcagcggt tataacaggc ctgactgcat  1320
tgttcaccgg attataatga gccaaaatgt tccccggtgt ttgctggttt cagggaagga  1380
gtttgatata gcagattaac caccctcctt gtagctattg gggcttaatg gtttcctggt  1440
gattcttacc aatccacaat aaacatggcc cattggcata tctgc                  1485
```

<210> SEQ ID NO 83
<211> LENGTH: 31
<212> TYPE: DNA
<213> ORGANISM: Homo sapiens

<400> SEQUENCE: 83

```
ggcacatttg aataaattct attaccagtt c                                   31
```

<210> SEQ ID NO 84
<211> LENGTH: 39

```
<212> TYPE: DNA
<213> ORGANISM: Homo sapiens

<400> SEQUENCE: 84
ggggcgcatt gtcaataaag cacagctggc tgagactgc                          39

<210> SEQ ID NO 85
<211> LENGTH: 486
<212> TYPE: DNA
<213> ORGANISM: Homo sapiens

<400> SEQUENCE: 85
gcccaataaa gactgttaat tcctcatgcg ttgcctgccc ttcctccatt gttgccctgg   60
aatgtacggg acccaggggc agcagcagtc caggtgccac aggcagccct gggacatagg  120
aagctgggag caaggaaagg gtcttagtca ctgcctcccg aagttgcttg aaagcactcg  180
gagaattgtg caggtgtcat ttatctatga ccaataggaa gagcaaccag ttactatgag  240
tgaaagggag ccagaagact gattggaggg ccctatcttg tgagtggggc atctgttgga  300 cttttccacct ggtcatatac tctgcagctg ttagaatgtg caagcacttg gggacagcat  360
gagcttgctg ttgtacacag ggtatttcta gaagcagaaa tagactggga agatgcacaa  420
ccaaggggtt acaggcatcg cccatgctcc tcacctgtat tttgtaatca gaaataaatt  480
gcttttt                                                            486

<210> SEQ ID NO 86
<211> LENGTH: 44
<212> TYPE: DNA
<213> ORGANISM: Homo sapiens

<400> SEQUENCE: 86
gcccctcccc tgccctctcc ctgaaataaa gaacagcttg acag                    44

<210> SEQ ID NO 87
<211> LENGTH: 406
<212> TYPE: DNA
<213> ORGANISM: Homo sapiens

<400> SEQUENCE: 87
gtgtcatctt ttattatgaa gacaataaaa tcttgagttt atgttcactt catttgtttg   60
ctgttcatct tttgggaggg aataagctag agccatcaat acaattccgc ttgtggggaa  120
atttatgcct cttactggta ctacttgttt tgcattgaag ctgactggtt gagttcacat  180
catatgttgc aattttctaa tttggcactt caatcactag gggccttatg aggcagtttg  240
tcattatgca atggttattg gttatcatgt gagtagacac atttcaggct aatagggaga  300
agtcagtaac acattcatag tgaatatgag atgtctttgc taagagttaa gtgtcagatc  360
tttgttataa cagttaattt aataaagaat tttggcattg ttcttc                 406

<210> SEQ ID NO 88
<211> LENGTH: 1994
<212> TYPE: DNA
<213> ORGANISM: Homo sapiens

<400> SEQUENCE: 88
ttgccgtaag gatatgcact tgtctctagt ccacacactt catgatatag gtatagcgtt   60
agtttagcga agttttcact gcactgatat atctagtagg tgatggagct gggaatgcaa  120
ctcatgtctg actagtccac aatactgcac tatttcagtg tttacgattt tttatccttt  180
```

```
cccttctgaa gaggcaaaaa attgaggaat gtgccctgct ttcctaagaa ctgaagtgtg      240
agtacactgg taaatccttt catttgcctt gttccttatc tgtcaatatg tctgaatcct      300
cgcttgttgg ttgcactaag aattgttctg ttgtttctca tcacagaaat ctgcagtcaa      360
ctacctgttc tcgtgaagtc ttaaaactct tatagaatag ccatttaggc ctttctgcta      420
gcctcctgaa ttctgtattc tcaggctgag cgagtttctg tttactctca aaccttaggt      480
gatttggcta actcttaaag taattagcac gatgattgga acggagcatt ctctccaaca      540
cagcatttct tttggcactt tgcttcttgt gcagtttagc tccagaaagt attaaggaat      600
gactttagtg ctcatttgga tgcagtaagt ggtttgatct cagggtggca aaagaatgc       660 ttttttttata ccttttcaca ttcggataac ttgtttagaa acagaggtt ctaactaggt      720 tttggcctat taagaactgc aaactagcag cagcagaact ctggctaaag gggcaagctt      780
attaggaaat tgagtattta aaagttgagc taccatatga tccaacaatc ccactgctgg      840
gtatataccc agaagaaaat cggtatatca aagagatatc tgcactccta tgtttgttgt      900
agcactgttt ataatagcta agatttagaa gcaaccttag tgtccatcgg gatgaatgga      960
taaagaaaat gtacctatac gcggccaggc acggtggctt gtgcctagca ctttggaaag     1020
ccgaggcggg tggatcacct gaggtcagga gttcgagacc agcctggcca agatagtgaa     1080
accccgtctc tagtaaaaat acaaaaatta gccgggcttg tggtgtgggc ctgtaatctc     1140
agccacccgg gaggctgagg caggagaatc gctggaacct gggaggcaga ggctgcagtg     1200
agccgagatc acgccactgt actccagcct gggcgacaga gcaagactcc atctcaaaaa     1260
aaaaaaaaaa aaaagggaa aaagaaaatg cacctataca cagtggtact attcagccat     1320
aaaaagaatg agatccagtc atttacaaca acatgggtgg aactggagat cgttatgtta     1380
agtgaaatag gcacacaaag acaagcatca catgttcttg tttgtgggat ctaaaaatca     1440
aaacaagtgg acttgtcata tagagagtag aaggatggtt accagaagct gagaacttct     1500
ggtggcggga ggtggggatg gttaatgggt acaaaaagaa aaagaatga attagaccaa      1560 ctatttgata gcacgacagc gtgactaaag tcaataactt agttacatat tttaaaataa     1620
cttagagtgt aattggattg tttgtacctc aaagaaaaaa tgcaataaaa ctttacagtg     1680
gagaaaccta acaagcacta cctcagccag gtaatcaagg ttaacatcaa cagtcacgag     1740
tcatgttgat atatacccct gataaggtgt gatgaaaatg cacttaaaac ctaaaaatcc     1800 ataccctat ctaatgagaa aaataacaaa tcccaagagg ggcatttttac aaaatacttg     1860 accagtagtg cggaaattgt caaggtcatc aaaaaagtct gagaaattgc cacagccaaa     1920
ggagtctaga gacatgatga ctaaatgtta ggtggtgtcc tgcgtggggt cctagaacag     1980
aaaaaggaca ttag                                                         1994
```

<210> SEQ ID NO 89
<211> LENGTH: 307
<212> TYPE: DNA
<213> ORGANISM: Homo sapiens

<400> SEQUENCE: 89

```
accgctagct tgttgcaccg tggaggccac aggagcagaa acatggaatg ccagacgctg       60
gggatgctgg tacaagttgt gggactgcat gctactgtct agagcttgtc tcaatggatc      120
tagaacttca tcgccctctg atcgccgatc acctctgaga cccaccttgc tcataaacaa      180
aatgcccatg ttggtcctct gccctggacc tgtgacattg tggactattt ctgtgtttat      240
ttgtggccga gtgtaacaac catataataa atcacctctt ccgctgtttt agctgaagaa      300
```

```
ttaaatc                                                              307
```

<210> SEQ ID NO 90
<211> LENGTH: 38
<212> TYPE: DNA
<213> ORGANISM: Homo sapiens

<400> SEQUENCE: 90

```
gtctgtaggc cttgtctgtt aataaatagt ttatatac                             38
```

<210> SEQ ID NO 91
<211> LENGTH: 133
<212> TYPE: DNA
<213> ORGANISM: Homo sapiens

<400> SEQUENCE: 91

```
agtgtctagc agtgagctgg agattggatc acagccgaag gagtaaaggt gctgcaatga     60
tgttagctgt ggccactgtg gattttcgc aagaacatta ataaactaaa aacttcatgt     120
gtctggttgt ttg                                                       133
```

<210> SEQ ID NO 92
<211> LENGTH: 1802
<212> TYPE: DNA
<213> ORGANISM: Homo sapiens

<400> SEQUENCE: 92

```
tgtcactgcc atggccgcct tgctgcattt ctgaggatgc ttcatctctc caccttcttc     60
tccactcagc agccagcagg gcactgtgga aatcggagtc acatgagctg gcacctctgt    120
tcagaaccct ccagggctcc acatctctct cacccaaatg ccaaagacct ccccacgccc    180
ccacaatccc ccacgacctg gccactggcc tcccaccacc ttccagctcc agcggctcct    240
accacattta aggcttttcct tcctagtttt aattttttcct cgtcagcagt tgattttatt    300
attttcttgt ttattggtat tttcccacta gaaatgaagc tgcgtgaagt tagagatttt    360 ttttttttggt ctgtgttcct aattagctca ttgctatacc cctggcgccc agaacaatgc    420
cttggacaca gtacgcagta gactaaataa atacttgttg aatgactgac tgacggaatg    480
acggctgtgt ggggagtgga ttgggtcgtg aggcagaggc tgcggtggaa actcaggcag    540
gaggtgatgg tggttcttgg ggctgcgaa tgccaagttt agaagctctt cctctgctgt    600
ggcacatgaa ccggtcactc gagaaggctt ttagatttac tttgcctaat cccctcttag    660
tgcatgtggg gaaactgagg tacacaaaag gaattcccca ccaagttagg ggcagaacct    720
agcccccttg tctcccagat ggatatcttc tttttttttt gagacggagt cttgctctgt    780
tgcccaggct ggagtgcagt ggtaccatct ggctcactg caacctctgc ttcccaggtt    840
caagcgattc tcctgcctca gcctcctgag tgtctgcgat tacaggtgca cacaaccacg    900
cctggctaat ttttgtattt ttagtagaga cggggtttca ccgtgttggt cagggtgacc    960
tcaaactcct gacctcatga tccacccagc tcagcctccc aacgtgctgg gattacaggc   1020
atgagccacc gtgcctggct ggacatcttg ttattaaagc ttcttctctc tttgtagggg   1080
agggggagat gcctctggtg gagaagacca gtgtggcagt gactgtgtct gttagtgaac   1140
ctggtggctg gttgagggtc tgtcgtggtg actgaggaca catacaaagt gcttttctca   1200
gtggtcacct tggtgttggt gaataagggt cagaagatgg ctcctgtcct agggcactgc   1260
cagtcggttt ggaagctgaa atgcctgctt agcagtttga ggaaacacag accttggagg   1320
```

```
atcttctggt tgcctcttca agaattcatt ctattcccct tctgctcccc aaatttgctt    1380
ttcttggggt gggtcttggt tggcctaagc caagaaagta tggcatctac tccttccata    1440
gcaatagctc aggaataggc agtgacccag acctgaacca atcagtgcat ggaattaccc    1500
ctggccaaag tggttgattg aggctgggtg caagcagagt tgtgagaagg ctcccatttg    1560
gtggttggag agatcgcact tgctccagag gtcataatgt gcagatctga ggcttggaac    1620
tgctgcagac attttgctac cacaagtgaa gccaccctga cgacacagtt gacaatttgg    1680
agcagggcag agctgagaga acagcaggga acagccaga gtcttgctca agcctccctg     1740
aagtatctat accccctggac tctagttatg ggggctaata aatgttatat actgtttaag    1800
gt                                                                    1802
```

<210> SEQ ID NO 93
<211> LENGTH: 34
<212> TYPE: DNA
<213> ORGANISM: Homo sapiens

<400> SEQUENCE: 93

```
tgctgagggc ctcaataaag tttgtgttta tgcc                                 34
```

<210> SEQ ID NO 94
<211> LENGTH: 502
<212> TYPE: DNA
<213> ORGANISM: Homo sapiens

<400> SEQUENCE: 94

```
aaaaatgaaa cttttttgag taataaaaat gaaaagacgc tgtccaatag aaaaagttgg    60
tgtgctggag ctacctcacc tcagcttgag agagccagtt gtgtgcatct ctttccagtt    120
ttgcatccag tgacgtctgc ttggcatctt gagattgtta tggtgagagt atttacacct    180
cagcaaatgc tgcaaaatcc tgttttcccc cagagagctg gaggttaaat actaccagca    240
catccctaga tactactcaa gttacagtat atgatcacta atatagtatg ctcttggtac    300
caggagctct gatatatatc tggtacatgt ttgataatga cttgattgtt attataagta    360
cttattaata cttcgattct gtaaagagtt tagggtttga ttttataaaa tccaaaatga    420
gccttttatt gaatccagtt ctctatgtga ccagttctct gtatgaatgg aagggaaaag    480
aattaaaaat cttgcaaagg gg                                              502
```

<210> SEQ ID NO 95
<211> LENGTH: 502
<212> TYPE: DNA
<213> ORGANISM: Homo sapiens

<400> SEQUENCE: 95

```
aaaaatgaaa cttttttgag taataaaaat gaaaagacgc tgtccaatag aaaaagttgg    60
tgtgctggag ctacctcacc tcagcttgag agagccagtt gtgtgcatct ctttccagtt    120
ttgcatccag tgacgtctgc ttggcatctt gagattgtta tggtgagagt atttacacct    180
cagcaaatgc tgcaaaatcc tgttttcccc cagagagctg gaggttaaat actaccagca    240
catccctaga tactactcaa gttacagtat atgatcacta atatagtatg ctcttggtac    300
caggagctct gatatatatc tggtacatgt ttgataatga cttgattgtt attataagta    360
cttattaata cttcgattct gtaaagagtt tagggtttga ttttataaaa tccaaaatga    420
gccttttatt gaatccagtt ctctatgtga ccagttctct gtatgaatgg aagggaaaag    480
aattaaaaat cttgcaaagg gg                                              502
```

<210> SEQ ID NO 96
<211> LENGTH: 48
<212> TYPE: DNA
<213> ORGANISM: Homo sapiens

<400> SEQUENCE: 96

```
attttttctg tagtgctgta ttattttcaa taaatctggg acaacagc                48
```

<210> SEQ ID NO 97
<211> LENGTH: 171
<212> TYPE: DNA
<213> ORGANISM: Homo sapiens

<400> SEQUENCE: 97

```
gctgttcttg cataggctct taagcagcat ggaaaaatgg ttgatggaaa ataaacatca    60
gtttctaaaa gttgtcttca tttagtttgc ttttactcc agatcagaat acctgggatt   120
gcatatcaaa gcataataat aaatacatgt ctcgacatga gttgtacttc t            171
```

<210> SEQ ID NO 98
<211> LENGTH: 2309
<212> TYPE: DNA
<213> ORGANISM: Homo sapiens

<400> SEQUENCE: 98

```
ggtggttctt tccttgaagg gcagcctcct gcccaggccc cgtggccctg gagcctcaat    60
aaagtgtccc tttcattgac tggagcagca attggtgtcc tcatggctga tctgtccagg   120
gaggtggctg aagagtgggc atctccctta ggactctac tcagcactcc attctgtgcc   180
acctgtgggg tcttctgtcc tagattctgt cacatcggca ttggtccctg ccctatgccc   240
ctgactctgg atttgtcatc tgtaaaactg gagtaaaaac ctcagtcgtg taattggtgg   300
gactgaggat cagttttgtc attgctggga tcctgtcagg cactttgagg tgtccctcag   360
gccttggccc tgaagtgtct aggtgtgtgg agatgggtag aaaattaggt acacccaatg   420
gtgtagaacg ttgattctca aattttttta ttttatacaa atggggtctc actatgttgt   480
ccaggctggt cttgaactcc tgggctcaag ccatccgccc atctcagccc ctcaaagtgt   540
tgggattaca agcaagaact gccatgcctg acccagttct cagttttttg tttgtttgtt   600
tgtttgtttg ttttgagacg gagtcttgct ctgtcgccca ggctggagtg cagtggcgca   660
gtctcggctt actacaacct gcctccgg ggttcacatc cttctcctgc ctcagcctcc   720
cgagtagctg ggactacagg tgcccgccac aactcctggc taattttttg tattttagt   780
agagacgggg tttcactggg ttagccaggt tggtctcgat ctcctgacct tgtgatccat   840
cgccttggc ctcccagaat gctggtatta caggcgtgag ccagcacgcc tggcccagtt   900
actcagtttt gaatctgagg ccgtgacatc actcatggtc tgcagtcagt gctctgcccc   960
tgagctgtac cctctcctat gataatcact cttaagaagg caacccttg gtgttttccc   1020
cttaaggtca cccaggctgg aatgcagtgg tgtggtcatg gctccctgta ccctggaact   1080
caggcttggg tgatcctctc tccttttgcct ccgaagtagc caggactaca ggtgtgcacc   1140
caccaccaca ctcagataat tgctttggtg ttttaaagc ttgtaatgat cagtaggctg   1200
aggtgggcaa atcataaggt caagagttt ttagatgggg tgagcacaga ccaattcctg   1260
ttttatttac tgatttaaaa ttttgagaca gtctcactgt cacccaggtt ggggtgcagt   1320
ggtaggatca tagcttgctg cagccttgat ctcccaggat cttgcctcag cctcccgagt   1380
```

| | |
|---|---|
| agctgggact gcatgcttgt gccaccacac tcggttaata ttttgtagag atggggtctt | 1440 |
| gctatgttgc ccaggctggc ttcaaactcc tgaacttaaa agcctcctgt ttagttttgg | 1500 |
| ttttttatca cttttttttt tttttttga gatggagcct tgctcccatc gtgcaggctg | 1560 |
| gagtgcggtg gcgcagtctc ggctcactgc agcttctgcc tctcgggttc aagcgattct | 1620 |
| cctttctcag cctcttgagt agctggaatt accagtgtgc gccaccacca ccacgcctgg | 1680 |
| ctagttttc tgttttagt agagacaggg ttttgctatg ttggccaggc tggtcttgaa | 1740 |
| ctactgacct cttgtgatct acctgtcttg gccttccaaa gtgctaggat tacaagcgta | 1800 |
| agccacagcg cctggccttg ctacattttt tttttttttt tttttttac agacatggtc | 1860 |
| tcgctatgtt gcccagaatg gttttgcact gggtccaagc agttctgccg cagcctccca | 1920 |
| aagtgctggg attacagggg tgaggcacct tgctggcccc tgttttgatt agggtgcagt | 1980 |
| gctggtgaag ccggtgcacg aggccagtga tgcatcctaa tgaggggtgg agttggcggg | 2040 |
| acttcctggg ccagtttggg gactttcaca aaagaccccc atgactcagg gttttgagtt | 2100 |
| cttaactgat cgaatgaagg attcaaaatt aaccactcca aggggggatt gaaggaagaa | 2160 |
| ccactcttaa tggacaaaaa gaaagaaagg ggagggagta acagggatat gagctctagc | 2220 |
| cgcccaagct agcaatggca acccttctgg gtccccttcc agcatgtgga agctttcctt | 2280 |
| tcgcttcatt caataaacag ctgctgctc | 2309 |

<210> SEQ ID NO 99
<211> LENGTH: 58
<212> TYPE: DNA
<213> ORGANISM: Homo sapiens

<400> SEQUENCE: 99

| | |
|---|---|
| gtcttttgta attctggctt tctctaataa aaaagccact tagttcagtc atcgaaaa | 58 |

<210> SEQ ID NO 100
<211> LENGTH: 1502
<212> TYPE: DNA
<213> ORGANISM: Homo sapiens

<400> SEQUENCE: 100

| | |
|---|---|
| gcaaaggctc cccttacagg gctttgctta ttaataaaat aaatgaagta tacatgagaa | 60 |
| ataccaagaa attggctttt agtttatcag tgaataaaaa atattatact cttgaacttt | 120 |
| tgtctcattt ttttgagtat gctgtttata tgattttgat ttccctctga taactatcaa | 180 |
| cagtatttaa atagcttata gctggtataa ttttttccca cgatttccaa aatcttttat | 240 |
| gtactcaggt aaaagtagcg ttatatagga aatctttttt ttagacactc tcgttctgtc | 300 |
| acccaggctg gagtgcagtg actcagcttc ctaaatagct ggaattacag gtgtgagcca | 360 |
| ccatgcccgg ctaatttttt gtacttttag tagagtaggg tttggccatg ttggccaggc | 420 |
| tggtttcaaa ctcctgacct caagtgatct acccacctcg gcttcccaaa gtgctgatta | 480 |
| tagctgtgaa ccaccatgcc cggccaggaa atcttactgt agaacaattt tttatatagc | 540 |
| tgtataaaat gtatatgatt gtcttgacag tctcaaatac tgttttaat agcttgtaaa | 600 |
| tgtaatctca agtgcttaga acagttctta catataagtt gctctgtagt ttgctcttat | 660 |
| agttagccca aagactctgg gtgtgaggcc tgctgtaaac caatgttaaa ctgcttatta | 720 |
| gaaagcccta accacctgct tgtaggcac cagaaactca aaccaaatc tcaactcagc | 780 |
| tacagaatct actgtggtcc ttgtctgaaa aaattagttc actcggttgg aatcttgtct | 840 |
| cagagcatcc tcatctcttt ctcaaaagcc cctaccccaa caccggcgtg ttggttgtct | 900 |

-continued

```
attgaaactt acaagtggat ggacccttc tcccgaataa actggccttt gaaagctcta    960
atcgaaatgg tttggcaaaa tccatactgc aggagattag ggaggacaag aatgatgtgc   1020
cttttttgtac tgctgagcct gatggtggtg ccactacttc aggtacttag atgagtcttg  1080
atgctaatag aattgtgtcg ccaaacatat ctggacagtt acaacctaat ctatgcatta  1140
attggtttgg gaattgcttg aaattattgt ttaattcaat gttttaattc gttttcctaa  1200
aaatttaagt gccccatca tcgtgcaata cctcagtgca gcaactcctt gattcttgga   1260
tgactgaact tcctaacttg gctctgcccc attgttccca ttttcatgt tttcacaaa    1320
tagttaacca ggtacctact actgtgcacc gctgcagagc attgaggatg tatgtgatga  1380
gtaaaaacac ccagcctgct ctgctgtgtt agtattatga cggaaactga tcaaatcaca  1440
tgtgaacaaa tttactgcta caaagggag ggcttaataa aggaatttc atctgggaag    1500
gc                                                                  1502
```

<210> SEQ ID NO 101
<211> LENGTH: 48
<212> TYPE: DNA
<213> ORGANISM: Homo sapiens

<400> SEQUENCE: 101

```
attttttctg tagtgctgta ttatttcaa taaatctggg acaacagc                48
```

<210> SEQ ID NO 102
<211> LENGTH: 193
<212> TYPE: DNA
<213> ORGANISM: Homo sapiens

<400> SEQUENCE: 102

```
ggaattgcac atgagatggc acacatattt atgctgtatc aagttcacga tcatcttacg   60
atatcaagct gaaaatgtca ccactacctg gacagttgca catgttttac tgggaatatt  120
tttttctgtt tttctgtatg ctctgtgcta gtagggtgga ttcagtaata aatatgtgaa  180
agcttttgtt tcc                                                     193
```

<210> SEQ ID NO 103
<211> LENGTH: 73
<212> TYPE: DNA
<213> ORGANISM: Homo sapiens

<400> SEQUENCE: 103

```
aggttttggc agtactgtct ccttgggcca tgctggtctg acttatgctt actaataaat   60
tctgtttact ggc                                                     73
```

<210> SEQ ID NO 104
<211> LENGTH: 93
<212> TYPE: DNA
<213> ORGANISM: Homo sapiens

<400> SEQUENCE: 104

```
actttgggat atttttcttc aattttgaag agaaaatggt gaagccatag aaaagttacc   60
cgagggaaaa taaatacagt gatattctta cgc                               93
```

<210> SEQ ID NO 105
<211> LENGTH: 257
<212> TYPE: DNA
<213> ORGANISM: Homo sapiens

```
<400> SEQUENCE: 105
gctgtgtggg gtggatgaac cctgaagcgc accgcactgt ctgccccaat gtctaacaaa    60
ggccggaggc gactcttcct gcgaggtctc agagcgctgt gtaaccgccc aagggggttca  120 ccttgcctgc tgcctagaca agccgattc attaagacag gggaattgca atagagaaag    180
agtaattcac acagagctgg ctgtgcggga gaccggagtt ttatgtttta ttattactca   240
aatcgatctc tttgagc                                                   257

<210> SEQ ID NO 106
<211> LENGTH: 692
<212> TYPE: DNA
<213> ORGANISM: Homo sapiens

<400> SEQUENCE: 106
tgattcaaac agcttcctga atttttaattt tgtgttgtct cacagaaagc cttatcataa    60
attccataat tctaattaat ttaccaagat aatgtaatta catttggttt tgtaaggtat   120
acagcagtaa tctcctattt tggtgtcagt ttttcaataa agttttgatt atgggcaaat   180
cccctctttt tctttttta aaatatattt gagtatgcca tacatttata tatatggtgt    240
atatgaattt ggtttaaaca ttttaaaatt tattctgatt agtttgtgtc ttttttttt    300 tttttgagag agagagtcct gctctgtcac tcaagctgga gtgcagtggt gcgatctcgg   360
ctcactgcaa cctccgcctc ccaggtccaa gcaattctct tgccttgtcc tcccaagtag   420
ctgggattat aggcacacac caccatgcct ggctaattg tgtctcattt tcaagagtag    480
aaaccctaaa tattttattt tcattccttt tccaaattgc tatgaatggg attaaaggat   540
tacagatgta aagtctatta tttgtgaatt ctaaatgtag ttctgctgtt gtacctgtgg   600
aaacatctta aagaagtaca tatttttgcac gtcctgcacg tgtaccccag aacttaaact  660
ataattaaaa agaatagttt caaaaaaata ca                                  692

<210> SEQ ID NO 107
<211> LENGTH: 228
<212> TYPE: DNA
<213> ORGANISM: Homo sapiens

<400> SEQUENCE: 107
atagaacctg ttgtgcaacc acggtttaac cggagatttt gaggctaggg tgtgtttctt    60
tcgaactttt cggaatgtct ggaacatttc atttcctgtt ttgttacctg tgcctctgta   120
aatctacttt tgcaatttta agtaataatt ttatgaataa aaatgggaaa tgcttcctaa   180
ttccacatag tatttgcatt gttttataaa taaattccac ttactatc                228

<210> SEQ ID NO 108
<211> LENGTH: 529
<212> TYPE: DNA
<213> ORGANISM: Homo sapiens

<400> SEQUENCE: 108
acccaggtga ggcagggctg aaaactgccc ttgggctgac ttttgatagg ccatgccttg    60
ccactttaca agttcttttt gcatttacta gtatttaaga gtaaccttga gattgggagg   120
aatagaggag gctggtacaa atagatggag acctgctggg atcagtgaat gcctgattag   180
gacatggggc tatgcatagc ctaagagtta taggcttaaa gatgtcgagt aactaaaaac   240
tgtattgctg gccgggcgcg gtggctcacg cctgtaatcc cagcactttg ggaggccaag   300
gcgggcagac catgaggtca ggagattgag accatcctgg ccaacatggt gaaaccctgt   360
```

```
ctctactaaa aatacaaaaa tgagctgggt gtggtggcac gtgcctgtag tcccagctac    420
tcgagaggct aaggcaggaa aatcgcttga acccaggagg cagagattgc agtgagccaa    480
gattgcacca gtgcactcca gctgggcgac agagcgagac tccatctcg               529

<210> SEQ ID NO 109
<211> LENGTH: 174
<212> TYPE: DNA
<213> ORGANISM: Homo sapiens

<400> SEQUENCE: 109
gtggaaaaga acatgaaaaa gaaaactgac aaatacacac aggtctcctc aagatccatg    60
gacttctggt ctgagcctaa taaagactgt ttgtttattc ctcaaaaaca aacaaacaaa    120
aaaaaaccct ctgtattata aattattctg tgtaatggtg tgttaccata catt          174

<210> SEQ ID NO 110
<211> LENGTH: 156
<212> TYPE: DNA
<213> ORGANISM: Homo sapiens

<400> SEQUENCE: 110
atgctcctct actctttgag acatctctgg cctataacaa atgggttaat ttatgttaaa    60
aaaaaaaaaa gagagagaga gtgaaacaac aatctacaca atcagagaaa atatttgcaa    120
atcttatatc tgattagaaa ttagtatctg gaacat                             156

<210> SEQ ID NO 111
<211> LENGTH: 46
<212> TYPE: DNA
<213> ORGANISM: Homo sapiens

<400> SEQUENCE: 111
aattggagag gattatttca cattgaataa acttacagcc aaaaaa                   46

<210> SEQ ID NO 112
<211> LENGTH: 67
<212> TYPE: DNA
<213> ORGANISM: Homo sapiens

<400> SEQUENCE: 112
ggagctgagt tcttaaagac tgaagacagg ctattctctg gagaaaaata aaatggaaat    60
tgtactt                                                             67

<210> SEQ ID NO 113
<211> LENGTH: 294
<212> TYPE: DNA
<213> ORGANISM: Homo sapiens

<400> SEQUENCE: 113
ggaattgaac atgagatggc acacatattt atgctgtcta aaggtcacaa tcatgttacc    60
atatcaagct gaaaatgtca ccactatctg gacagttgga catgttttttt tgggaatata   120 cttttttctct ctgaatctgt taggaacttt ctggttggct gggttccgta ataaatacat    180
gagacctttc atttcaaaaa aaagaaaaat aggcctcctt cccagggct ccggatttca     240 tcagccttct gtgcatgccc agccatacaa accacgcagg gatggctcca agtg          294

<210> SEQ ID NO 114
<211> LENGTH: 171
<212> TYPE: DNA
```

<213> ORGANISM: Homo sapiens

<400> SEQUENCE: 114

| | | | | | |
|---|---|---|---|---|---|
| tcaccaaaaa | gcaaccaact | tagccagctt | tatttgcaaa | acaaggaaat | aaaggcttac | 60 |
| ttctttaaaa | aataaataaa | taaataaata | aataaataat | aaataaataa | ataaataaat | 120 |
| aaatagataa | ataaataaaa | agttttctac | tcacactgaa | gtgacgaagt | c | 171 |

<210> SEQ ID NO 115
<211> LENGTH: 49
<212> TYPE: DNA
<213> ORGANISM: Homo sapiens

<400> SEQUENCE: 115 gccccttcc cctgccctct ccctgaaata agaatagct tgacagaaa        49

<210> SEQ ID NO 116
<211> LENGTH: 88
<212> TYPE: DNA
<213> ORGANISM: Mus musculus

<400> SEQUENCE: 116
ggaggcctca gttcctggcc ccagaaacga gatcctgacc acatgaacaa tttgggctct    60
tttgggagaa taaaagactt atatattg                                       88

<210> SEQ ID NO 117
<211> LENGTH: 69
<212> TYPE: DNA
<213> ORGANISM: Mus musculus

<400> SEQUENCE: 117
ttccaggacc actttgtgca gatggtgggg tctcaccaat aaaatatttc tactcacact    60
ggttttccc                                                            69

<210> SEQ ID NO 118
<211> LENGTH: 118
<212> TYPE: DNA
<213> ORGANISM: Mus musculus

<400> SEQUENCE: 118
actattaaaa attgttaaat tccagagagc aagtagagac cgcatatttc aataaatcaa    60
acatgtggtg acaaacccct tgtgtgactct taaattgtgg atgtttccaa gccccttg    118

<210> SEQ ID NO 119
<211> LENGTH: 1008
<212> TYPE: DNA
<213> ORGANISM: Mus musculus

<400> SEQUENCE: 119
agcagttttc tatgaagatt ttttcataaa gacaataaac atattgatca agcagctttt    60
tctgtgttaa gctgttatta atgagactat aggaaatagt gtgaaattac aaaagcaaag    120
aagtagatag ttatttaatt aattaaatta attttacctt ttgtgttgca ccataaccta    180
ccactggtgg gattaagggc aagtattacc atgcctagct gagagtcttt ctccaggaaa    240
aaccagctta catgggttcc tgcaaatctc atgagtgttt cttgggtttc tagtcttcct    300
gggaggtgtc cttatctttc agattttcag atctggtaat tagcatgatc atcaggacat    360
ttattacaaa caaattgatt agtgggaaga aagtatctca aggtcaatct ggaagtgaa    420
caactggtgc taatccatgg ctttaaagat ttgagaacaa cggtgaaatt tggtttgagg    480

```
agaaggggt gtctaggacg tttcattttt atggtacatg ccagacatga atgtacatag    540 gaaataact tgaaagggtc aaatattaaa ccttgaatat caggttcact tgggaaagca    600
ttaggtgctt atgcctctta gtaaatagcc cttcatccca gaaggagcaa gaattgtctt    660
cctgacttaa tccagtctta gctgaggtgc tgtgcatctt tatcatcttt gccttgcctc    720
acagtgtcag gctctgtggt actggggcta cacaggtcag gtaaacagtt aactgcttac    780
ctacatcccc agcaaagata atgtgacgat actaagatga acctatcaga gcttaaagat    840
aatgagtttc agtcacagtg ataactgcat gctaacttca gcatgtagaa tatatgccga    900
agctaaaagc cattccacag ttgactccat ctgaagttaa agtgtgtaag tacacagtaa    960
atcatgctat attaactgaa ctttttaata aatgagtcat ttgaattt               1008
```

<210> SEQ ID NO 120
<211> LENGTH: 306
<212> TYPE: DNA
<213> ORGANISM: Mus musculus

<400> SEQUENCE: 120

```
attgttaacc taattaaaca gcttcatagg ttcttttggt gtccttttg tgtgttgtgt      60 gtgcacatgt tgttgggtg ggtgttttgc tggtgtcttt tcctctgtgt cttcctctgg    120 cccttctgg aaagacctgc ttaatctgaa gcatgtgagc taggctagtc cactgggtcc    180
tgctctctgc ccatccccag ctggctttgg attagaggca catacactgc catggctgcc    240
ttttactgtg gctgtggttt tgcccttttt ttttaagcaa atagaaaatg ctgctgacta    300
tactgg                                                                306
```

<210> SEQ ID NO 121
<211> LENGTH: 63
<212> TYPE: DNA
<213> ORGANISM: Mus musculus

<400> SEQUENCE: 121

```
ggtgtcaccc attgtatttt tgtaatctgg tcagttaata aacagtcaca gcttggcaaa     60
ttg                                                                    63
```

<210> SEQ ID NO 122
<211> LENGTH: 49
<212> TYPE: DNA
<213> ORGANISM: Mus musculus

<400> SEQUENCE: 122

```
atgtacacta aattttctgt acctaaatat aattacaaaa ttatcttga                 49
```

<210> SEQ ID NO 123
<211> LENGTH: 39
<212> TYPE: DNA
<213> ORGANISM: Mus musculus

<400> SEQUENCE: 123

```
acttgatcca aaaagctaat aaaatttct cagaaatgc                             39
```

<210> SEQ ID NO 124
<211> LENGTH: 47
<212> TYPE: DNA
<213> ORGANISM: Mus musculus

<400> SEQUENCE: 124
gaagcaacaa gaaaatattc aataaaaga ctatctgata accagtg        47

<210> SEQ ID NO 125
<211> LENGTH: 42
<212> TYPE: DNA
<213> ORGANISM: Mus musculus

<400> SEQUENCE: 125
ttctgtgttg gagagctgca ataaattttc cataaagcaa aa        42

<210> SEQ ID NO 126
<211> LENGTH: 556
<212> TYPE: DNA
<213> ORGANISM: Mus musculus

<400> SEQUENCE: 126
ttctccagtg tatttgtaaa atatattcat taaagtctct gctctgagag ctggtcttct        60
tgacaccttt tccaatatca gctttgcaga aggaaactta aatttcagtt cagggcatga       120
ccttcatgac cttgcagaac ttcttcactt tccaggttaa gtaaaggcga tctttagggg       180
ctgtccagat ggatcagcta taaagattca attgtagaag gttcacgtct caatgcccac       240
gtggtagctg taacttcaat taaaaaacaa aaacagccgg gcgtggtggt gcacgccttt       300
aatcccagca cttgggaggc agaggcaggc ggatttctga ggccagcctg atctacagag       360
tgagttccag acagccagg aatacacaga gaaacccttg tctccaaaaa ccaaaaaaa        420
caaaacacgc attcttttca ggtctttgct gggaccaggt acacataaca cagataaata       480
ttagagcaaa ccatgcacat atggtaaatt atctttgggt tttgggtccc taaaataaag       540
tggtgtgttc attgtg                                                       556

<210> SEQ ID NO 127
<211> LENGTH: 47
<212> TYPE: DNA
<213> ORGANISM: Mus musculus

<400> SEQUENCE: 127
ccctggatct taactgttaa taaaaaaaac attggatgat gatggta        47

<210> SEQ ID NO 128
<211> LENGTH: 693
<212> TYPE: DNA
<213> ORGANISM: Mus musculus

<400> SEQUENCE: 128
acacagagac ccactgaata aaaacttgag actgtccttg cttgtttgct tctatgtccc        60
tggagaggtc ccagttggtc ccgtccctaa caacatgcta gccctgctca cctgcctgtc       120
agccttgctc agtggcatct ttccataggt gtgtatcccc ttagattagc ttcagcccca       180
ctacgatttg tctaggacat agcctgagcc ctgcctgtga cactgagggg tagcagtctg       240
tttctggact ccagggtgct gctgtctcag gcctaagaat tccagacatg actataatcc       300
aagcctgggg acctggttga gcttttatc ctgctggctc taagcttcag ctaggtggaa       360
atgaggccag ccaagcccca cagtgagctt gcaagcttta gatggggaca gggttacgct       420
ttggtgaatg atggaggaaa catggggtt cctttgttg ggtgcagcca gcacggcatc       480
atcatggtgc ccaatcttga aagggcacag gcctgaagct tcctgggact gttctgtcac       540
agggaggaac ctactgcagt tgcctacaat tgctacctct gagggacttg cctctggccc       600
cttgtagaca tttccatgtc tacacatggc ccagagtact ttcagggata gcaatgtgtg       660

```
aatggcactt agaagataac atgtgaaagc cat                                 693
```

<210> SEQ ID NO 129
<211> LENGTH: 98
<212> TYPE: DNA
<213> ORGANISM: Mus musculus

<400> SEQUENCE: 129

```
agcttccctc gtgtctgtac atagcggcct ggctgtggcc tcatgtggat cagtctttaa    60
aataaaacaa gcctttgtct gttgccctct tgtttagc                            98
```

<210> SEQ ID NO 130
<211> LENGTH: 1077
<212> TYPE: DNA
<213> ORGANISM: Mus musculus

<400> SEQUENCE: 130

```
tgtacacaaa gaaataaaat accagcacca ggactgtgaa gtgttttcct tagactgtag    60
tgtggggttt gctcattggc tttcttgttc agattttact aattgttcta aatgatacag   120
cttagtgtgc agaaaatatc ctcttgattg gaaaatagcc aaatatttac aaaacaggta   180
tactagtttg aagaggctct atatgggggg agggggtgct ggaaaacatt agtgggtgac   240
cagtaatggt ggtacagctc taactcctag caccaggagt ccgaggcagg gggatcttca   300
ggctgcatga tgtgcatagt agcatgctgg tattagggag tgggtatctg tggttcccac   360
tttgaaaata accaaaattc tccaaagtgg gcagacctaa gccaggagag ggctggccac   420
agacatttgg tactgcttgc tgagaaagca ctgattgttt tcctaaccta agattatat    480 atggcccacc ataccatctt tgaaacaatg tgtactggcc tttggttcac ctttcttgtc   540
tttgaagttg tacttggtgg gtgcatttaa ccttgccaca gagtggggag gatagagtct   600
aatggacctt aagtggtctc tggtggccat gtcggcagtg cttaggttgt agcccagggt   660
tggagtcggc agtgacaagc aaataactat attcttgctt gctgtggcag ctatacagaa   720
atttacggta taggtaagag ggttctctag aagtactacc tgtcttagtg aaagagattg   780
cttggttaac atcctgttat gtagtggggc tacttttaaa ctgtgtgaag tccccattag   840
ccacctccat aggcaatgga gctaacattc ttgctacagt ggccgcagct cattaacacc   900
taatgatgtg tttaacatgt gtccacatgg tgtgaatgtg ggtacgcatg tgcccagtat   960
tcagttcaca gaattgtcat catcttccat catgtcttca gtgagggact ctgcagatgc  1020
ccaccccagt ccttggttgt ggtgattctg ttagcattaa atgcactgga gagcttc     1077
```

<210> SEQ ID NO 131
<211> LENGTH: 1658
<212> TYPE: DNA
<213> ORGANISM: Mus musculus

<400> SEQUENCE: 131

```
gacacattgg tctgcaatgt tttgtattaa ttcataaata aaatttagga acaaaaccgg    60
tggtttatcc ttgcatctct gcagtgtgga ttggacagga agttggaaat gacagggact   120
ttaactgggc tgctgctcct ttgtatatag acactttttt cctgctcaga aacttgagtt   180
ctccagtagc aatggccaaa cagaagaacc aggctagggg gctgcatctg acagagcaag   240
tagacgagag gctgggtggt gggctccggc cagcccgagt cttagagctg gtggttggtt   300
atatctggtg cctgtctcga ggagggcttg agacacagtg tggtgctcct cagaagcaga   360
```

```
caggtgattt ctttgtgtga tttttctttt ccctgggac aatgacagtc agtaagacag    420
gtttcaggga cttttgtgtc caggtctgag cactagtcgc tcacagttgt gtgtactaac    480
cttcttcctt cctattgaaa tggcaggggt ctttgagtct cactgctgca tgttctgcct    540
tcatagggat ctgtaagtat gctgggcatc tgggcttta gggggctctc tatagggtgt     600
ctgagataga ggtcaacaag ggcttataga caactcaaac aaagcccatg cttgagcaa     660
gtctgcaaca agctgtttgt ctagcctcca gcagagggcg agggagacag cttccagatg    720
ttcccagtag gtggagcccc tccaagccca gggctcagga ggcttacagg gtgggaactc    780
caatactggt ggagggagga gggcgtttga tgggaagata gggaagttgc tgcttcctaa    840
actgtcacaa ctgggcttgg ataggagtca tagtctggga ccacagccct gtggtagaat    900
gctagcctgg tgtgctccag gtttaatctc catcactgca gaaatgagtc caagctgtgt    960
gtacctccag ggcactgggc atgggttcc cttgccattg tgtgtgcccg agaactggc     1020
aggcgggaaa tgtctttatc aagggttacc ttggaagagg tcccaacact gtagggtgct   1080
cctgttgtca aaacctatgc agaggcatct gcttgctctc taataacagt atgcaatgct   1140
aaagggctcg cttacagccg gtggccacac tggaggcctg cacatcaggt ggccacaagt   1200
tctgctgctg cgcctccgag aaacacttg gtcctccgat cgattttaac ctgttgaggc    1260
tttgcaatcc ccctgtggca aaggctccag tgttttctat ttctatgcaa atttcttgaa   1320
gcagaactgt tactgtcttt ctcctctgcc ctggaggag cgctagcgt ttccttccaa     1380
cttcaggtgc agccccctc gtggttagcg gtcttaagtt cgtgacttgg gtttgcagat    1440
cttttttgtt acatcgccgg accatgtggt ggtctttagc tgtaaacaac attaaccctg   1500
ggttgattag catatgcttc taaaagatgg tcccagattc tgcgacttgt aataaaatgg   1560
aaacttgctg gtttttatgc cttctctaact cttgtatttg aatgaatgtt gatcactttt   1620
tgtattaaag tggctgacac atggctactg tcactgtg                          1658

<210> SEQ ID NO 132
<211> LENGTH: 1795
<212> TYPE: DNA
<213> ORGANISM: Mus musculus

<400> SEQUENCE: 132
aatatctcac caaaaaatat ttgaagaaga acaacctccg agactggctg cgtgttgtcg    60
ccaacagcaa agagagttac gagctgcgtt acttccagat taaccaggat gaagaggagg   120
aggaagacga ggattaggac acattggtct gcaatgtttt gtattaattc ataaataaaa   180
tttaggaaca aaaccggtgg tttatccttg catctctgca gtgtggattg acaggaagt    240
tggaaatgac agggacttta actgggctgc tgctccttg tatatagaca cttttttcct    300
gctcagaaac ttgagttctc cagtagcaat ggccaaacag aagaaccagg ctaggggct    360
gcatctgaca gagcaagtag acgagaggct gggtggtggg ctccggccag cccgagtctt    420
agagctggtg gttggttata tctggtgcct gtctcgagga gggcttgaga cacagtgtgg    480
tgctcctcag aagcagacag gtgatttctt tgtgtgattt ttcttttccc ctgggacaat    540
gacagtcagt aagacaggtt tcagggactt ttgtgtccag gtctgagcac tagtcgctca    600
cagttgtgtg tactaacctt cttccttcct attgaaatgg caggggtctt tgagtctcac    660
tgctgcatgt tctgccttca tagggatctg taagtatgct gggcatctgg gcttttaggg    720
ggctctctat agggtgtctg agatagaggt caacaagggc ttatagacaa ctcaaacaaa    780
gcccatggct tgagcaagtc tgcaacaagc tgtttgtcta gcctccagca gagggcgagg    840
```

```
gagacagctt ccagatgttc ccagtaggtg gagcccctcc aagcccaggg ctcaggaggc    900
ttacagggtg ggaactccaa tactggtgga gggaggaggg cgtttgatgg gaagataggg    960
aagttgctgc ttcctaaact gtcacaactg ggcttggata ggagtcatag tctgggacca   1020
cagcccgtgt gtagaatgct agcctggtgt gctccaggtt taatctccat cactgcagaa   1080
atgagtccaa gctgtgtgta cctccagggc actgggcatg gggttcccct gccattgtgt   1140
gtgcccggag aactggcagg cgggaaatgt ctttatcaag ggttaccttg aagaggtcc    1200 caacactgta gggtgctcct gttgtcaaaa cctatgcaga ggcatctgct tgctctctaa   1260
taacagtatg caatgctaaa gggctcgctt acagccggtg ccacactgg aggcctgcac    1320 atcaggtggc cacaagttct gctgctgcgc ctccgaggaa acacttggtc ctccgatcga   1380
ttttaacctg ttgaggcttt gcaatccccc tgtggcaaag gctccagtgt tttctatttc   1440
tatgcaaatt tcttgaagca gaactgttac tgtctttctc ctctgccctg ggaggaggcg   1500
ctagcgtttc cttccaactt caggtgcagc cccctcgtg gttagcggtc ttaagttcgt    1560
gacttgggtt tgcagatctt ttttgttaca tcgccggacc atgtggtggt ctttagctgt   1620
aaacaacatt aaccctgggt tgattagcat atgcttctaa aagatggtcc cagattctgc   1680
gacttgtaat aaaatggaaa cttgctggtt tttatgcctt tctaactctt gtatttgaat   1740
gaatgttgat cacttttgt attaaagtgg ctgacacatg gctactgtca ctgtg         1795
```

<210> SEQ ID NO 133
<211> LENGTH: 48
<212> TYPE: DNA
<213> ORGANISM: Mus musculus

<400> SEQUENCE: 133

```
actgagtcca gatggctaat tctaaatata tacttttttc accataaa                  48
```

<210> SEQ ID NO 134
<211> LENGTH: 140
<212> TYPE: DNA
<213> ORGANISM: Mus musculus

<400> SEQUENCE: 134

```
attcagcata aaataaaggc agataaagtt aaaggtcttc tggtggtctt taatgagccc     60
tgttgggagt gaggtgcttt aacatggaga agcatgttat taaacagtga aatagatggt    120
tcaaaaccac gtgaccatgt                                                140
```

<210> SEQ ID NO 135
<211> LENGTH: 46
<212> TYPE: DNA
<213> ORGANISM: Mus musculus

<400> SEQUENCE: 135

```
tgtggtagag cagagttgga aataaagctc tatctttaac tctagg                    46
```

<210> SEQ ID NO 136
<211> LENGTH: 40
<212> TYPE: DNA
<213> ORGANISM: Mus musculus

<400> SEQUENCE: 136

```
agacatctcg tgcacggctt tcattaaaga ctgcttaagt                           40
```

<210> SEQ ID NO 137

```
<211> LENGTH: 109
<212> TYPE: DNA
<213> ORGANISM: Mus musculus

<400> SEQUENCE: 137
gtatattttt gttttggtca ttaaaaatta aaaaaaaaaa aatacaagtg tctgcctatt    60
gcatttgtgt gggaagagac tggggaaata aaacaggtgt gctgttgtg              109

<210> SEQ ID NO 138
<211> LENGTH: 45
<212> TYPE: DNA
<213> ORGANISM: Mus musculus

<400> SEQUENCE: 138
acaagaaagt tttcctttaa taaaactttg ccagagctcc ttttg                  45

<210> SEQ ID NO 139
<211> LENGTH: 640
<212> TYPE: DNA
<213> ORGANISM: Mus musculus

<400> SEQUENCE: 139
aagccacacc ggaggttaat taaatgctaa catttccat gtggtctttg catccttcct    60
tgtctgcatg ttggaaatct gcctaacatt ctaggaagag gtgaggtgtg ggcccttgag  120
agtcagtctg tgggaataag tgtagcccaa ctatgcacag ttgtaaattc ctacatcccc  180
gtgtgtattg gtcttgatat tcaaagaatt gatgaatgcc attactttca gtccaaagtg  240
aagaaacctg gtctcaaaaa atcccgagga ccagaaatga gatgggtttt cctgaaaatc  300
taaagttctt gaaaaacctt gccatccaga ttgctagcaa ctgcctagct ttgtaagctt  360
actgtgatgg acaggtagct caggacgact ggtcacttaa tactgacag attagcatgg   420 aaaacttaag gggaggagga ggtagtaggt tccatccagc ttcgctttgt tggtggcatc  480
taggtgttgt tccaagggag catgcctacc tgcaacagga catcactggt tgggaatact  540
gtagaaccag agctgtgacc tttgaactac tagaaagatg aaattttatg taaagagtac  600
cttggagtaa ataaataaag cccaagatcc tgattgtcta                        640

<210> SEQ ID NO 140
<211> LENGTH: 40
<212> TYPE: DNA
<213> ORGANISM: Mus musculus

<400> SEQUENCE: 140
gccccacacg cccgaagcaa taaagagtcc actgacttcc                        40

<210> SEQ ID NO 141
<211> LENGTH: 124
<212> TYPE: DNA
<213> ORGANISM: Mus musculus

<400> SEQUENCE: 141
aaaaggctcc tgccagtgtg aagacagacg gactgctgtg acacacctcc ccacacacta   60
tttgcagatg accagtgtcc tatgctgttc ttacaaataa actcaggcaa gatctgttag  120
cttg                                                               124

<210> SEQ ID NO 142
<211> LENGTH: 575
<212> TYPE: DNA
<213> ORGANISM: Mus musculus
```

<400> SEQUENCE: 142

| | | | | | |
|---|---|---|---|---|---|
| cctgctcgtg | tcaaataaag | ttgcagaact | gccttcaggg | tttggttttc | ctttctgttg | 60 |
| tctgcctcat | gggtggaatt | tttgggtcta | cagggtgttg | gaaattaatc | tgagaatctc | 120 |
| tgttctgggt | acatgggaaa | ttagaaatac | gtgaaacatt | cttttcacag | aagtcacttt | 180 |
| attaggattg | tggatttggg | ttggttttga | acagggtttc | cttgtggcac | tgcttgttct | 240 |
| atagaatagg | gtggccttga | actcagaaat | ccacctgcct | tttcctccct | agtattggca | 300 |
| attaaatgcc | cagcttgttt | gtaagctctc | attttcagtt | ccaggtttat | gtgtgagcct | 360 |
| aagattaggt | aaagattgag | gttataactt | aaacgtactg | aattaactta | tgttgtgtgg | 420 |
| gtcccaggaa | ttggacctgg | gacatcaact | ctgcctttcc | agccatcttt | gccaaccagt | 480 |
| agctcatctc | tgggatgtgt | ctgccctcaa | aatgacattt | taaaaaagtc | agtacaaaag | 540 |
| aacgattttt | attaaaaacc | ttgaggacaa | acatt | | | 575 |

<210> SEQ ID NO 143
<211> LENGTH: 54
<212> TYPE: DNA
<213> ORGANISM: Mus musculus

<400> SEQUENCE: 143

| | | | | | |
|---|---|---|---|---|---|
| atggcttgtg | tgcatgtttt | atgtttaaat | aaaatcacaa | aacctgccgt | cgta | 54 |

<210> SEQ ID NO 144
<211> LENGTH: 68
<212> TYPE: DNA
<213> ORGANISM: Mus musculus

<400> SEQUENCE: 144

| | | | | | |
|---|---|---|---|---|---|
| actaatggag | agtaaataaa | taaaagtaga | tttgtgctct | tgtattttttt | tttcacatct | 60 |
| gtcctaaa | | | | | | 68 |

<210> SEQ ID NO 145
<211> LENGTH: 504
<212> TYPE: DNA
<213> ORGANISM: Mus musculus

<400> SEQUENCE: 145

| | | | | | |
|---|---|---|---|---|---|
| ggatttcaat | cagtcataaa | ataaatgttc | tgctttcaaa | aattctgtgg | tgatctaagg | 60 |
| tactttaaca | tcggttcaga | gttcggttat | atgattgctc | tgggatccta | cgcttcttcc | 120 |
| ttcatagttc | ctgtgggtcc | gaagctggga | ggggctgggt | ggactctcgg | gaaagatact | 180 |
| ctgagcctgt | ctcggtcccc | atcgtgtttg | cttggccctg | gcatggaag | tgggtgagtg | 240 |
| atgagctgaa | cgagcaggct | tgctagagat | gaggacagtt | actggtgtgg | ttatatcact | 300 |
| accatgccta | cagtgtctta | agacgcttac | agtctgtaag | ggacttaaat | gatttgagct | 360 |
| cttacttatc | ctgtagtttc | tgatttttaa | catttacttg | aataaagcca | agcaagataa | 420 |
| gcctttattc | ccagcacttg | gtgacaggtg | gatctatgag | ttggggatca | gagctacaca | 480 |
| ttaaaactct | taattcatct | tact | | | | 504 |

<210> SEQ ID NO 146
<211> LENGTH: 306
<212> TYPE: DNA
<213> ORGANISM: Mus musculus

<400> SEQUENCE: 146

```
ggatttcaat cagtcataaa ataaatgttc tgctttcaaa aaaaaaaaaa attaatcctc    60
tgtgatggcc agcagttaac attcaacagt ttctctctag gctcttgatt ctctgactat   120
tgtagggatt cgatcagcac tcgcatacca gaagtgtgag atggtccgtc cttttttcaag 180 acaagatttc tctgtgtagc cctggctgtc ctggaaccca ctctgtagac caggctggcc   240
ttgaatttac agagatcccc ttgcctccgc ttgctgagtg ctaggattaa aggcatgcgc   300
actatg                                                              306

<210> SEQ ID NO 147
<211> LENGTH: 246
<212> TYPE: DNA
<213> ORGANISM: Mus musculus

<400> SEQUENCE: 147
aagccctgct gtctgagact tgcctagcct gcaataaacg ggttatttac gtaactttttt  60 tttttttgcc ttgtttgtgg ttaattaaaa catttggtgt gtgttctatt ttttattttc  120
gaaagatgct tgttttgaga catactgtgt gaccctggct ggccttgagt gcctggttct  180
ccttacaagt gtagatacat ctggcttaag attttagtct ttcagaaata aaaatgttgc  240
taagac                                                              246

<210> SEQ ID NO 148
<211> LENGTH: 41
<212> TYPE: DNA
<213> ORGANISM: Mus musculus

<400> SEQUENCE: 148
accagccctc tgcgtgtgac tattaaaaac cctgaaaagt g                        41

<210> SEQ ID NO 149
<211> LENGTH: 181
<212> TYPE: DNA
<213> ORGANISM: Mus musculus

<400> SEQUENCE: 149
ggattcacac aatggcaaga ctgaggattt atactgaatt gtcatcaatc agtcctacca   60
gatggatttc aacatttaaa cctggagact cttcgtgtct tgaattagga tgtttgtcca  120
gtaataaaat atagaacctt tcaaaatgct tttctggttt ataaagtact gaattgccct  180
t                                                                   181

<210> SEQ ID NO 150
<211> LENGTH: 285
<212> TYPE: DNA
<213> ORGANISM: Mus musculus

<400> SEQUENCE: 150
tcccgccaaa gcaaccaagt cagcctgctt aatttgagaa agatggaaat aaaggcttac   60
ttctcttaaa actccggtct ggatttattt agtttgttca cttaagcagg atgaaaaagc  120
aaaaccgcta ctgtttactt tgtgttggca tctttgtttc taaaattaaa gctcctagtg  180
tttttgtggg ctttgtttgt tttttgagac agtctcttga cttggtgcca tagctagtct  240
gggacaaaga ttttccaggt gtgaattaaa ggtgtatgtc atcaa                   285

<210> SEQ ID NO 151
<211> LENGTH: 40
<212> TYPE: DNA
<213> ORGANISM: Mus musculus
```

<400> SEQUENCE: 151
actgcttttg ttaagttggc taataaagag ctgaacctgt                                40

<210> SEQ ID NO 152
<211> LENGTH: 42
<212> TYPE: DNA
<213> ORGANISM: Mus musculus

<400> SEQUENCE: 152
attcctgctc ccctgcaaat aaagtctttt tatgtatctt ga                            42

<210> SEQ ID NO 153
<211> LENGTH: 1059
<212> TYPE: DNA
<213> ORGANISM: Mus musculus

<400> SEQUENCE: 153
cagggtcttg gcagctgcat ctggaggcat ttaataaaat aaagacattt aataaaatct         60
tgaacaaaga caaggcctga ctggattgtg tccagtattc aactgagtta tgttgtctat        120
ggagccatgc ttattctgtt ggtttaagct ggagggcatg agcagagctg accagagaag        180
tcatgaagtt ggtgaccctg tgttgaacaa ttgagggtta aagagcagt ttggttttgg         240 tgctcttgat ggaacccagg tgcttggaca tagtaagcac acataagaca gagtaagact        300
gctgtgtctc tggcctggag tagtctttct tgcttttttt tttttttttt tttttctcta        360
gaatgaaagc agatggccca gcgagttagg tgcttcctat gaaagcatgt gtgctggttt        420
gtcatgcaca cagccctgca ggagagagta tggcaacaca gccgctcagc atcccaagat        480
aaaaagggag tttctactgc cattttgagc ttgggagttt gaaatgtaaa gcctgtccat        540
atgttttaag gatccatgta tttctgtttt gtttgttttt caaaacaggg tttctctgta        600
gccctggctg tcctggaacc cactctgtat gtagaccagg ctggccttga actcagaaat        660
ccacctgcct ctgcgatcc atatatttct aagtcctgta cttagacgct gttttggaaa         720
attcattttg gaagcattta ctgttggtgt gttttgtggg gaatgaatga tagcttggga        780
attcttttct gtttggtgag agtgaagctg tcagcccggt tgtagcctgg ctggtgctca        840
aaggctttct ctcattgtct tcacctacgt agctttacgt ggggtaagga cttaagttac        900
ttaagttggg tgcacactga ccatgtccac aacctgttaa ccaactctac atgatgagta        960
cagatgtacc tttttagaaa gtgttaatgt gtagccctgg ctggcctctg cctcagggta       1020
ttatgaataa agtgtgcaac cttcatctgg ttgattaaa                              1059

<210> SEQ ID NO 154
<211> LENGTH: 49
<212> TYPE: DNA
<213> ORGANISM: Mus musculus

<400> SEQUENCE: 154
aatccagatt tttaatagtg acaaataaaa agtcctattt gtgatcgtt                     49

<210> SEQ ID NO 155
<211> LENGTH: 87
<212> TYPE: DNA
<213> ORGANISM: Mus musculus

<400> SEQUENCE: 155
aatggtctct aggagacatg ctggaaaagt gtttgtacaa gcctttctag gcaacataca         60

```
tgctagatta aacagcatgg tgaaact                                          87
```

<210> SEQ ID NO 156
<211> LENGTH: 100
<212> TYPE: DNA
<213> ORGANISM: Mus musculus

<400> SEQUENCE: 156

```
agtggactct gagggacatt gcggggaagg ggcgtttacg tttgtttata cttaaaagtt     60
ttttaagcag catgttgaat taaaaaagaa agcaagcttc                          100
```

<210> SEQ ID NO 157
<211> LENGTH: 45
<212> TYPE: DNA
<213> ORGANISM: Mus musculus

<400> SEQUENCE: 157

```
tttcccagct gctgcctaat aaactgtgtc ctttggaaca actat                     45
```

<210> SEQ ID NO 158
<211> LENGTH: 603
<212> TYPE: DNA
<213> ORGANISM: Mus musculus

<400> SEQUENCE: 158

```
gtctttaaga gcaacaaata aataatgacc ttgaatcttt cattggcttt cattaatagt     60
gtaactagat aaatgatggg aaagatgaga cagaagaagg aatacatcta taggactgct    120
agaatatggg gagagtgatt attttcaaat taatatgtat cgagcttcta ccccaaggta    180
aataaataac atttggagac cattaaaatg taggatggca tagaagaggc ctttactaag    240
attaataatt aaagaaacac agcctttaaa gtaaaaaaca cactgtgcct ttgaaacttg    300
ctaaaaagat taacttctgt cccaaaaggt atcagccatg cgctaccagc ctccctgccc    360
ctacagtggc agtggctgca ttcttggtga atggtagtgg aagggattaa acctaggcct    420
cagtcatgct tcccagtcac tggtactgat ttgtatgcac ccgcttaggt gtgaaggtag    480
ttttggtgtg tatcacaagt tagcctgtgt agcgaagaca ggttttctcc accgtgtttt    540
ttgttacaca tgactattca caaatgtgct gcagacagta aaatgagaaa tacccttcca    600
agg                                                                 603
```

<210> SEQ ID NO 159
<211> LENGTH: 269
<212> TYPE: DNA
<213> ORGANISM: Mus musculus

<400> SEQUENCE: 159

```
agaaaatgac tgaataaagt gtcattcata gtatttggtt gtagtaactt gtcaaaatct     60
cagggccatg ggtgcacgac agcagtagct tcttgaatga actgaagttt tcaagaggtg    120
cctggaaggt gaaaaacaca ctgaagccag tcatgttgat atggggcat tctgctgctg     180 tgaaacagac tgggggttcac acccaccttg cgggattaga acttcactgc cctccaactt    240
cttctcttgt aaacaactgt ccacatttt                                     269
```

<210> SEQ ID NO 160
<211> LENGTH: 42
<212> TYPE: DNA
<213> ORGANISM: Mus musculus

<400> SEQUENCE: 160

```
gcctcatgtg tagtgtaata aaggtgtctg ctgttctatc tg                    42
```

<210> SEQ ID NO 161
<211> LENGTH: 69
<212> TYPE: DNA
<213> ORGANISM: Mus musculus

<400> SEQUENCE: 161

```
ttaatacttg gctgaactgg aggattgtct agttttccag ctgaaaaata aaaagaatt  60 gatacttgg                                                        69
```

<210> SEQ ID NO 162
<211> LENGTH: 36
<212> TYPE: DNA
<213> ORGANISM: Mus musculus

<400> SEQUENCE: 162

```
agttggagtt tatgttgtat tgaataaact ttaaag                           36
```

<210> SEQ ID NO 163
<211> LENGTH: 47
<212> TYPE: DNA
<213> ORGANISM: Mus musculus

<400> SEQUENCE: 163

```
ggggactctg gccaatgccc tagaacaaat aaagttattt tccaacg               47
```

<210> SEQ ID NO 164
<211> LENGTH: 50
<212> TYPE: DNA
<213> ORGANISM: Mus musculus

<400> SEQUENCE: 164

```
ataaattttg gctgattttt ctcttgtatt tcttgtttgc tggtataaaa            50
```

<210> SEQ ID NO 165
<211> LENGTH: 43
<212> TYPE: DNA
<213> ORGANISM: Mus musculus

<400> SEQUENCE: 165

```
atgctgttgt gtgcacaagc aataaaatca ctttgagtaa ctt                   43
```

<210> SEQ ID NO 166
<211> LENGTH: 34
<212> TYPE: DNA
<213> ORGANISM: Mus musculus

<400> SEQUENCE: 166

```
ccgaggccaa taaagactgg ttttggtccc tgga                             34
```

<210> SEQ ID NO 167
<211> LENGTH: 3272
<212> TYPE: DNA
<213> ORGANISM: Mus musculus

<400> SEQUENCE: 167

```
acgtaaagca taaataaaaa gcctttgtgg actgtgctca gggtcagtcc ttttgaatct  60
ctgcagcaga gtagctggct gtgctgactg gtgacacttc tggtgatgct cagctgtgag 120
gttttatgta gatattgaaa gcatgaccat tgtcttcact tcacctccag cttgggttgt 180
```

| | |
|---|---|
| atgccagtaa catcagcata aggtggttaa tgacaggatg gtcccttgag tgtgcagtga | 240 |
| gtctggttta tttgccaatg agaagcacag gcctcctgta tgggtctttg cctacagccc | 300 |
| cctttcatca cccagacttg gtagacttac attctgtcac actgttggct cttaatctca | 360 |
| gccctgaaaa atgccatttc ttgggtatca aggctagtct agattcagaa accatataaa | 420 |
| ggttgacagc tggtttaaaa aaaaaaggc ttggagcttg agttgggttc gcaggttatt | 480 |
| ccagggtatc tgtctgcact tgtctccca gatttaaagg taagtgccac catgcctagc | 540 |
| atggtgactt attagctttg ttgctgtgga acatacatca aatgaaacat tggtatggct | 600 |
| ctggtttcac tgtccatggt tagtatctgg tgggtggaca cctggtggaa ccaagctgct | 660 |
| catcccagaa ctaaggagcc attccccaga gacttgtctt cctactaagt tccatcccta | 720 |
| cagcttctag tagtagcttc agaggttgtg aattgtggac ttagtctgcc ataacattta | 780 |
| aaataggtat taaattcaag tcatttggtc actcagcacc cacgtggctc ttcagaacaa | 840 |
| cagaagcccc tcggacttgt ctgttggaaa accagtttg aaataatgta cctgctttag | 900 |
| ttgagaaaac gctacaactg gtgctgtgtc ctgccatgct gatgagctct gctctgcgac | 960 |
| ctgccgaact tgggggatct ctaccccag actttgctca gatctgttga tgatttgtcc | 1020 |
| atgcaggaaa gtttacaagg tctctgtgtg tctactactt actagttgct gtgacaaaaa | 1080 |
| tactgaaagt gtttactgtg tgtgaggcac aaagtttgtg ggaagctgta ccctccctca | 1140 |
| ttttggtgct gctcctgcct tgactgacag gatgagctgc cccaaccatc gttgccatct | 1200 |
| tccataagaa gcaggtggct ctattgagtt ccctggaggt gatcccaagg gaaggaggag | 1260 |
| cctgggaaag tggatctcaa gtcccctagt ctggcagttg gctgtttagg aaagtccagt | 1320 |
| gtcagtgttt gatatgttgt aaggaaacaa attcagtttt atttagctta ttggctctgg | 1380 |
| ggaaatggca gttcccatta attggtgctg tctttctctt tgaggatcaa aattagcttc | 1440 |
| ctgttcagtt gttaagcata tttcatagtc aaataatcct cttatcttta caagtgaggt | 1500 |
| tttccttcga gtggatatca gagtccctcc cacggcttct atccctccta tccttgtgta | 1560 |
| ggaagttaag cttgctcatt tgtagattag tggtcggtta cactgcaatt tagagtatca | 1620 |
| tgtgtactct acacatgatt gattctaagc ccccttccct ttccatgtcc ttcaaaaatt | 1680 |
| tttttattct gagacagtgt taggattttt cctgggctag ccaaatgcaa gaagtgttgg | 1740 |
| tcccagactt gtaatctttc tgccttagcc tcccaaattc taggattata gatttatgtc | 1800 |
| atgtgatgag tggtctttta aagattatct tttattttt ttgagatggg gttttctgt | 1860 |
| gtagttttgg cttcttggg acttgctctg tagacccagg atggtcttta ctcagatctg | 1920 |
| cttgcctctg cctcccaact gctaggatta aagcatgagc ctgagccttc atgcctggct | 1980 |
| gacaggtgaa ttctcaatac ctacctagcc atagggaaag tgattgtgtc cccttcctca | 2040 |
| tagaggggca tagtcaccca ggccatacct ttagcttggg cttttggtca gtgaagaagt | 2100 |
| atgaagggac aagaacacta tcaagagcct aatgtgctct ggcctggatg gtcagcacaa | 2160 |
| aatgaataga cttaccaaat tctgctgtct ccttggtaga tgtgaagttg ttggaagagt | 2220 |
| cctaaattta gcagactata ctgtcagcct atcagactat aggctgccgg agggcaagtc | 2280 |
| tgctacctat ttccatctca tgcctgcatt gttcatcccc ctatgtaacc cacctacctg | 2340 |
| tcactcattc ctccatccaa aaactattgt aggttcagtg gaaatttcaa gcttgcctgt | 2400 |
| ctcagcatct ttcttacctt accctaagg atggcatctc tcttggctac atctttggtt | 2460 |
| tatctggaga tccttgatta atttgaacaa gagctacctt gggttatgca gtttatgcct | 2520 |
| ccagtgtccc agagaccggc atttgagaga tccctgatag caaacccata gggtggcctt | 2580 |

| | |
|---|---|
| tttttcatcc accccattct ccctcccacc tccctctttt gaccttgagt cctcaccaga | 2640 |
| gagaaaccag gcccacttaa ttagttctac atgtgtacac tacatgggtg cagtgcccaa | 2700 |
| gcaggagagg tgttagattc ccttttaact atagttaata gacagttttt aagccccagt | 2760 |
| ggatgctggg aagcaaacct acatcctcta gaagagcagc tatttctctg agccatttct | 2820 |
| ccagcaccat tttcccctct tttaaaagca ggtcttgcag tgtggcctag tctggccccc | 2880 |
| tgaggtgttt gcattgcatg gcaggcatgt ccacaggaac accatagttc tcaccactcg | 2940 |
| tacagcacag caagtggggt gccgcagggg attatcactt gagtataaaa taagggttgc | 3000 |
| tttagattga ataggataac cacgcgttct cagaacaatc aaggaaggct ggggtgagcc | 3060 |
| agcaccgacc ttaattgttt acttagtaaa ctactaaatg tatgcacgtg taagcttttg | 3120 |
| ccttgattga ggtcaagctg tcgagaaatg gttctcttta cagtggatcc agtcaggatt | 3180 |
| ggcagcaagc acctttgcct gctgagccta catgttgtat agaatggcaa cgttgtgtag | 3240 |
| aatggcagta cattaaatgg ttttttcatt ta | 3272 |

<210> SEQ ID NO 168
<211> LENGTH: 59
<212> TYPE: DNA
<213> ORGANISM: Mus musculus

<400> SEQUENCE: 168

| | |
|---|---|
| gcccatctca aggatcgggg tttacctttg taataaacat cctaggattt taacgttcc | 59 |

<210> SEQ ID NO 169
<211> LENGTH: 35
<212> TYPE: DNA
<213> ORGANISM: Mus musculus

<400> SEQUENCE: 169

| | |
|---|---|
| aacaaaggat gctgggttaa taaattgcct cattc | 35 |

<210> SEQ ID NO 170
<211> LENGTH: 3167
<212> TYPE: DNA
<213> ORGANISM: Mus musculus

<400> SEQUENCE: 170

| | |
|---|---|
| gacaactgaa taaatcgtct taatggtcaa attttgctgg cttttgttca ggtttttttt | 60 |
| ttttaattca tgtttatgag tgtaaatgtg tgtgtcacag gggtgtcaga tgttctttga | 120 |
| accaccatgt aggtgctgga aacccaacct gcatcctcgg agagaacagg ttccttaacc | 180 |
| actgagcaag tactgaagca ttaaactgct tttaaaaatg aaggtgtgct aacagattgg | 240 |
| tcaggtgaaa aagagacgtt aggtttcctg caggggcgc taagccaatt taaagactaa | 300 |
| gttgggttag aaaagagcag attgcatcct tgatctttta agcctgggga ttttgttttg | 360 |
| ttttgggata gggtcccaac acagaacagg ctgacctcat taaatatcaa tcttatttga | 420 |
| ttgcctctgc tcccagagta ctggaattaa aggcagggac cactgtatta gccattctga | 480 |
| gttatttgaa atggactctg caggccatac ttggtcaaaa ttctgccttc tcaattacag | 540 |
| gcatgagcca ctatgcctgg tttacttact aatagatgtc caaagactag tgtatgaaaa | 600 |
| ttttgctttt ccaggtgatt tgtgaaaggc agggtggcct ctcccatgtc acactacttg | 660 |
| ggttactcat gttgcaacat atctgcaact ttaggttgag gggatttgag cctgcatgtg | 720 |
| ccactttggc caactgaact aatctttaat tccatctaaa acttttaaat ctcagtcatg | 780 |

```
tgttcaactg gaaaataacc tagagtgtgc tatgttgact tcaggtacac atcaaagcag    840
gttttagtga tgtagaagct gtgtttgagt tgaactagtg ttgaggctag cttaggtac    900 catagaactt tggttttca agacagggtt tctctgtgta gccctggctg tcctggaact    960
cactgtagac caggctggcc ttgaactcag aaatctgcct gcctgtgcct cccaacacac   1020
ccagctctag ctttaaattc cttgcaccaa gagatgcttt atccctccgc tgagaataca   1080
ggtgcatgtc agcatgctaa actctagata aaatttcatc ttgtttgaaa ggacaataat   1140
ataagaaaag tgtatttgca ctgtatacca tgccctttg tgtttaaagt taaactggca   1200
acagtgtccc atagaggttc cagaagaaac tgcttctaag gggaggacca taagggaaa   1260 tgcttaccat agaactttt aaatgttcct acaggttgta ctctggatag gtatatgaac   1320
acctttctat tagaacagtt ttatagtagt acttagtgaa tatgtaaata atactatttg   1380
tgaaatagtt tgaggtttct ctatagtcct ggctggcttg agctctatac cagattggct   1440
tctaaatcag aaatctgcct ctatctcctg aatggttatg atagagatgc aagttactta   1500
atttcttaca tgaattgcac tttgtacatg cttttggata tgggcctagg cttttgcttt   1560
tggattagac tgtctttatt acatttactg gcttgatact ttacagtctt aagcccactt   1620
gcctgggtgt gatgcacacc tttaatccca gcactttggg attctgagt tccaggacag   1680 ccagggctac gcagagaaac cctgtcttgg aggggaaaaa agaaactttt ggaaatcaaa   1740
acttcttgga aagccacttt tagagacttg aatctaagga taactaacca ggtagtaacc   1800
acgagtcatt gattctgtga atcttgtatg agtgggttac aggcagaaat taacttcctc   1860
tgagagcact gctgttttag aaatgcgacc tagtaattac caaaggcatt gaagccactt   1920
gactacagtc tcaggtttct gcatctgaca ttgctgggac tgtgtggggt ttatgggtgt   1980
aaaataaaac aggcgaaagg atgttgagtg aaagctttg gcttcagaat caaattccaa   2040
atcaattacc agatcaaatc aaatgccaga tcaaattaca agacttcctt atgactaaat   2100
tcttcagtga cttaggatac taatagtatc tgcctcaaaa gtgtatgtgg ttattttgt   2160 cccagtgaag ccaagattca catgctatgg gcatggattt cctgaggaca tgctagccta   2220
tggtatgagt tacttgaaag gactctgaga aatcttagtc cccagctgtg aggttttaa   2280 agatcatgct caatggaaag tggggcagta atttgagagc atggcacaaa tgaggtttta   2340
tcttttgaaa ctaagtgaat ctatgtcctt ggactagcat atttaaatc acacatcaaa   2400 tgaaatttct gttcaattcc tataaacagt ttatttcata ttttgtagtt accattttca   2460
ttaacagcat acacccttca attgtgttgc taaaactgag tcacattatt ctgtaagaac   2520
ttactccagt atcacaactt ggtgctcatc caatatttt attttcattc tattttccct   2580
gtctagccac gtatggccct attctctctt cttggattga ccctagcttc aacacaagaa   2640
agcttgcagt atttttttt tgcgcctggt tcattgtttt gtcctcaagt tctatccatg   2700
tgtccagaaa ttcgaggatt ttttaaaatt tactttctg cctaaatact ggtatgtgga   2760
tagtctgtta tttttactgt tggttgcata tctgtagcat atttctgtat ttgcaatgac   2820
tacattgaat gtcccttagt taacctcatt cttcttaact attttgtagg cgtttgctat   2880
tcaaagcaca atctcaatta aaatgttttt aatagcatct ttccacttgg atgtgtaaag   2940
aaagtatttc tagaagtctg aatttttgtt gcattgtaga tgtgtacaca atagggctgg   3000
gaaagtagct cacagtgggt aaaagccatt tgttgccaat cctaacagcc tgagttcaat   3060
cccagaatct ataaggtaga agaaaaaaac cccagctccc acaagttatc tggccctctg   3120
cacacatata aatagtgcaa taaaaattaa ccatttaaaa atataaa              3167
```

<210> SEQ ID NO 171
<211> LENGTH: 58
<212> TYPE: DNA
<213> ORGANISM: Mus musculus

<400> SEQUENCE: 171
gcagaagaaa tcgggaattt gttacaaata aaagttttaa gtacctgtga cagttaag        58

<210> SEQ ID NO 172
<211> LENGTH: 49
<212> TYPE: DNA
<213> ORGANISM: Mus musculus

<400> SEQUENCE: 172
aatttgacaa tggaaacaca gtaataaatt ttcatattct gaaaaaata                  49

<210> SEQ ID NO 173
<211> LENGTH: 264
<212> TYPE: DNA
<213> ORGANISM: Mus musculus

<400> SEQUENCE: 173
acaggttcaa tcagctgtac atttggaaaa ataaaacttt attgaatcaa atgaatgggt      60
gcatctgttt cctaaggcag ccggggagga tttggtctta ggaataatag ctggaattgg     120
tttgttggcc atgaagtcag atgcaattgc gcctgggaac cttcagcttt tccctttacg    180
tggttgcttg cttcttgttg cagcttcggt tttgaattga tgcctgaaag aaaataaaaa    240
cttagcaaga ctaatggtaa atct                                            264

<210> SEQ ID NO 174
<211> LENGTH: 71
<212> TYPE: DNA
<213> ORGANISM: Mus musculus

<400> SEQUENCE: 174
agaggccgtt ttgtaaggac ggaaggaaaa ttaccctgga aaaataaaat ggaagttgta      60
ctttacatgg c                                                          71

<210> SEQ ID NO 175
<211> LENGTH: 56
<212> TYPE: DNA
<213> ORGANISM: Mus musculus

<400> SEQUENCE: 175
aagcccctga ttgaagatga gtgggaacct tcccaataaa cacgttttgg atatat         56

<210> SEQ ID NO 176
<211> LENGTH: 38
<212> TYPE: DNA
<213> ORGANISM: Mus musculus

<400> SEQUENCE: 176
ttgtgtatgc gttaataaaa agaaggaact cgtactta                              38

<210> SEQ ID NO 177
<211> LENGTH: 92
<212> TYPE: DNA
<213> ORGANISM: Mus musculus

<400> SEQUENCE: 177

```
tcttgcagct gggttctgga tatccactac ttagcccacg gaatgatctg caactgttaa    60
ataaagcatt tatattaatt cttgtctaga aa                                  92
```

<210> SEQ ID NO 178
<211> LENGTH: 91
<212> TYPE: DNA
<213> ORGANISM: Mus musculus

<400> SEQUENCE: 178

```
gcgaccttga atggattcga ctgactacta ccaagtggaa ccgatcatgc tagtctttgt    60
acacaaagaa taaaaatgtg aagaacttta a                                   91
```

<210> SEQ ID NO 179
<211> LENGTH: 1187
<212> TYPE: DNA
<213> ORGANISM: Mus musculus

<400> SEQUENCE: 179

```
tacacgtgat atttgtaaaa ttcatatcca ataaacaatt taggacagtc atttctgctt    60
aaaggtgtta tttgttaaaa ctagtctaca gattgtcatg agtgttctgt gaaaatgtag   120
aagttaagtg caataattga aaactgcagg tgatggcata tcttgtttct gatgtacttt   180
gcattatctg cttatgagat taagtgtata tagtgtttgt gccaagtggt gttctgtgtg   240
taagaccctg taagaggtaa aaagtcctga aactgaccct ggatgtgttg gtgcatgaga   300
tagaatctac agctttacga tggcatcttt tggttcactg aagtggctgc ttgggagttt   360
gatgagtaca aactttatag agttggattt tgcttagaaa tgtgtaggaa gagagggttt   420
caaaacctgt tttgtgcata gaaaagtgag atcaactata acccacattt tgagaattga   480
atccagtgtt attttcagaa gaccaggtaa atttgttgga agaggtttca ctttctgttg   540
gatctagagt atggatttgg agatgaaggt tgaacattgg atgtagtagg gcttatttag   600
ggcagattat ttccattaga tttgtaaact tggttgtggt tgcaagttaa tatcaaccaa   660
gcaaatataa gtttgattaa gcttgcagac attaagcttt tctagcagct ggtgtgtgca   720
gaggcagatg gctctctggt tccaggacta cctacaatat agagaaattt tctctattcc   780
agtcaattca tcatgggtaa gaatagtcca ttttggtagt gttatttcat cgtttacaat   840
ctacctatgg gtagtggctg gtaactgcct ggatgttgac atttcacaaa ggccatactt   900
aaccacactt ttatttctat ttgtgcgatg ccttggagta gtttcccaaa gtgattttga   960
gtgtggaaga aatggtattg tccccgaaca gctggcttgg tctcaaaatc taattgatgc  1020
ttttattaaa ttggttttcc tttggagatt ttaaaggat gatttgattt ccagaaaata  1080
ctagactcaa atcttgata gctaaaattc ttttctattc agcaaaacaa gtcactgtat  1140
agaggttgtt caaatcaact aaagtaataa atgtcttaaa caagtgg                1187
```

<210> SEQ ID NO 180
<211> LENGTH: 43
<212> TYPE: DNA
<213> ORGANISM: Mus musculus

<400> SEQUENCE: 180

```
gggtttttat atgagaaaaa taaagaatt aagtctgctg att                       43
```

<210> SEQ ID NO 181
<211> LENGTH: 259
<212> TYPE: DNA
<213> ORGANISM: Mus musculus

<400> SEQUENCE: 181
ggctacacag aataataaag gttcttttg acggtggtaa atctcatgtg tggactctaa   60
gcttgtcgcc aagtgggaaa tagactggtg ggattgtaga taggatgggc tacttaaact  120
cattctaccc aggccttagt acttagcata cagccagagt caaactgatc ctttatacag  180
ggggtaccat gacagtacaa cagtgtcgtt aaccctaaca aataaatttc ccaccaacgg  240
gtggaattcc ttcattttg                                              259

<210> SEQ ID NO 182
<211> LENGTH: 48
<212> TYPE: DNA
<213> ORGANISM: Mus musculus

<400> SEQUENCE: 182
acaggacttc tcattatttt ctgttaataa attgctttgt gtaagcta               48

<210> SEQ ID NO 183
<211> LENGTH: 67
<212> TYPE: DNA
<213> ORGANISM: Mus musculus

<400> SEQUENCE: 183
aggcttcaat agttctccta taccctacca aatcgttcaa taataaaatc tcgcatcaag   60
ttcgctt                                                            67

<210> SEQ ID NO 184
<211> LENGTH: 33
<212> TYPE: DNA
<213> ORGANISM: Mus musculus

<400> SEQUENCE: 184
gatgctccaa taaacctcac tgctgccact cag                               33

<210> SEQ ID NO 185
<211> LENGTH: 36
<212> TYPE: DNA
<213> ORGANISM: Mus musculus

<400> SEQUENCE: 185
gatgacaacg acaataaagt gcgagactga ctggct                            36

<210> SEQ ID NO 186
<211> LENGTH: 388
<212> TYPE: DNA
<213> ORGANISM: Mus musculus

<400> SEQUENCE: 186
acccaataaa gactgtttgc ctcatgcctg cctggcctgc ccttcctccg ccgccaacta   60
gggaagtggg gaccaaaggt tccttaggca ctgctcctgt gggtagaggg gacattagag  120
agctgacagc gcaccacctg catgagtttt tattaaagtg caaaccatgg gatgaatcag  180
ttgagcttca gtgttgaaaa tgagtagcag ggctgcccca cccacctgac caagtaccct  240
attctgcagc tatgaaaatg agatctgcac atgagctggg gttcacaagt gcacacttgg  300
agcactgcct tgctccttcc cagcagacca caaagcagta ttttctggaa ggattttatg  360
tgctaataaa ttatttgact taagtgtg                                    388

<210> SEQ ID NO 187

```
<211> LENGTH: 32
<212> TYPE: DNA
<213> ORGANISM: Mus musculus

<400> SEQUENCE: 187
tgaaccctcc cccaataaaa gatggttcct ac                                    32

<210> SEQ ID NO 188
<211> LENGTH: 103
<212> TYPE: DNA
<213> ORGANISM: Mus musculus

<400> SEQUENCE: 188
gcagattttg ttatgaagac aataaaatct tgacctttca acccctttga ttgcagttgt      60
tcgtttggga gggaatacat taaaagcttt cagaaattac ctg                       103

<210> SEQ ID NO 189
<211> LENGTH: 277
<212> TYPE: DNA
<213> ORGANISM: Mus musculus

<400> SEQUENCE: 189
gccagcccgt gcacctacga cgcctgcagg agcagaagtg agggatgctg agggccggga      60
caagctatcg gactgtgtgc tgccatcggt aatgagtctc agtagacctg gaacgtcacc     120
tcgccgcgat cgcctggaga aatgaccgcc tttcttacaa ccaaaacagt ccctctgccc     180 tggaccccg gcactctgga ctagctctgt tctcttgtgg ccaagtgtag ctcgtgtaca      240
ataaaccctc ttgcagtcag ctgaagaatc aaactgc                              277

<210> SEQ ID NO 190
<211> LENGTH: 44
<212> TYPE: DNA
<213> ORGANISM: Mus musculus

<400> SEQUENCE: 190
gtctctgggc ctttgctgtt aataaatagt ttatatacct atga                      44

<210> SEQ ID NO 191
<211> LENGTH: 404
<212> TYPE: DNA
<213> ORGANISM: Mus musculus

<400> SEQUENCE: 191
aatacctagc agtgagtgga gattggatac agccaaagga gtagatctgc ggtgacttga      60
tgttttgctg tgatgtgcag atttctgaga ggacaaataa actaaaaagc tcctacacgt     120
ctgctctgct gcttattggg cattagaaga atcaggtggc tgcttgggtg ttgatgcagt     180
caagtgcact gggcttggtg aaaagcccag tgtaagaggc cggtacagat ccttcctggc     240
agagggtggt gatggagaga acataaataa ctacatgggc aaagtgtagg accaattacc     300
ctgttagcat cgtctttgct caacacctt ctgtgtccct agactctgag ttttttttcta     360 attgattttt attgaacact gagtgttttg aggttttatt tttt                      404

<210> SEQ ID NO 192
<211> LENGTH: 39
<212> TYPE: DNA
<213> ORGANISM: Mus musculus

<400> SEQUENCE: 192
agttcaggag ctaataaagt acgtcctttg gctaatccg                             39
```

<210> SEQ ID NO 193
<211> LENGTH: 48
<212> TYPE: DNA
<213> ORGANISM: Mus musculus

<400> SEQUENCE: 193
atatgcacat tttttaagta ataaaaatca agacttgatc tacgcttc                    48

<210> SEQ ID NO 194
<211> LENGTH: 36
<212> TYPE: DNA
<213> ORGANISM: Mus musculus

<400> SEQUENCE: 194
tctgttatgc catattttca ataaacctga aaacaa                                 36

<210> SEQ ID NO 195
<211> LENGTH: 875
<212> TYPE: DNA
<213> ORGANISM: Mus musculus

<400> SEQUENCE: 195
gctgctgtgc aggtgcctga gcaaagggaa aaaagatgga aggaaaataa agttgctaaa       60
agctgtctta tggtcctcac tgcagactgt acctggattg gcatttggct atacaacaga      120
ggcatggtcc tactgacatg ttttgtgttg aatacttaag catgtgaaca catgggtttt      180 ttttttttt aatgtaaaat gtagtaacac aatgtttagg tggctttggt gttagctctg       240
gagacttcat gtgtcatcta ggtgaggtgt tctttaacac agggtctctg ttctgtcatg      300
cctcatagat ccttctacct ccagattgga gagggaaaag gcttatgtca ctgaacctgg      360
ccagattggg attttgtgtc ccaggaacaa agttaatgct aaaaagttaa tgccttggtg      420
agactgatag tctgatggtg tgaattcaca gtaagtggtt gggattgcca gatggaattc      480
cctgagctgc cgtgacaggt ggcattgcag aagtgaagga ttcaggaatt tgagtgttgg      540 gtggggggcct gtgaatagca cttggctgg gaggggagac tgctgcccct gaatgtcctg      600
gaattcaagg acagtacctg gttaaatgtt tttctagctt ttctaaaaag tttgttaggc      660
ctggcattgg cggcgcacac cttta atccc agcacttggg agtcaggcag gtggatttct      720
ggcctggtct acagagagtt ccaggatagc caggataca cagaaatcct gcctcaggaa       780
aaaaccaaaa agaagtttgc taaaaataag cattttgct tgatggtatt gaagattgta       840
agacattaaa ttgtgtcatt acttctccag gtact                                 875

<210> SEQ ID NO 196
<211> LENGTH: 67
<212> TYPE: DNA
<213> ORGANISM: Mus musculus

<400> SEQUENCE: 196
agctgtggtc atacctggca tgtgaccccg ggaccaaata aagtcccctt ccatccactg       60
gagcagc                                                                67

<210> SEQ ID NO 197
<211> LENGTH: 50
<212> TYPE: DNA
<213> ORGANISM: Mus musculus

<400> SEQUENCE: 197

```
gtcctattgc caccctgcca tgctaataaa gccactgtgt ccagacttct            50
```

<210> SEQ ID NO 198
<211> LENGTH: 84
<212> TYPE: DNA
<213> ORGANISM: Mus musculus

<400> SEQUENCE: 198

```
ttggcctctg cttgtaatac aatgaaagta ttctaaagaa atataaaatt ggactttatg   60
agaaaataaa agtcatttca ctct                                          84
```

<210> SEQ ID NO 199
<211> LENGTH: 36
<212> TYPE: DNA
<213> ORGANISM: Mus musculus

<400> SEQUENCE: 199

```
tctgttatgc catattttca ataaacctga aaacaa                             36
```

<210> SEQ ID NO 200
<211> LENGTH: 446
<212> TYPE: DNA
<213> ORGANISM: Mus musculus

<400> SEQUENCE: 200

```
ggaaccacac gtacttatgc tgtaacttac tgtagcgttt acagcgttac cgctgtctgg   60
acagctgagt gtgtttctta ggaatataag ttttctttct gtgctttagt gagttcattc  120
agcagttcag taataaatat gtgaaacctt ttgtttcgaa aaaaattgct tctgtgttac  180
aacttacttt gttttatggt tcaggatcat ctgcataata gacaagtatt ctatcagtga  240
gcgatatcct ggatcttgtt tgtgtagttt ggggttgaga caagtccaga ctgccctaaa  300
actcacgatc ttccttcctc ggccttctaa atgattggag gactccaaac ctaagtgatg  360
gaagtaaaaa gaaacttata tgtcaagact cattttctct atcatttcat gtgacaattg  420
aaattagatt atttctttttt tcaatc                                      446
```

<210> SEQ ID NO 201
<211> LENGTH: 332
<212> TYPE: DNA
<213> ORGANISM: Mus musculus

<400> SEQUENCE: 201

```
ggactttgct ggcagaaaag aagtacagat gaggttatag tttgaaaaac gttaattccg   60
tttattgact ttagaatgtt actttgcata gtatagacca ttacaatgga agtacctgc  120 cttaagaaac aagaaaactg cagtttatag agaaagaatt ttcaattttg acccatgtac  180
ttaaaatttt tggtgtatac tgcagtgtag caaatgtttt gtggtgacgg tataaatggt  240
actgtttgtt atcttggatt aagagtggct agagaagttg gaagacgtgt gagaagttct  300
ttatagagaa ttaaacatga aaattacatc tc                                332
```

<210> SEQ ID NO 202
<211> LENGTH: 80
<212> TYPE: DNA
<213> ORGANISM: Mus musculus

<400> SEQUENCE: 202

```
aacttgtgtt ctctgagagg aaaatactga agcagtagag aaatgacctg ctagagaata   60
aagttactgt taatgatacc                                               80
```

<210> SEQ ID NO 203
<211> LENGTH: 93
<212> TYPE: DNA
<213> ORGANISM: Mus musculus

<400> SEQUENCE: 203
gatgtctgga atggagcaca cctgggatgt agcactcttg ctatctgtcc ggtccttttt    60
gttcaataaa gtcctgaggc aactctctct gtc                                 93

<210> SEQ ID NO 204
<211> LENGTH: 152
<212> TYPE: DNA
<213> ORGANISM: Mus musculus

<400> SEQUENCE: 204
tgagctatga agttccggaa tttgtgtttt tcacagaaag ccttaccaac ttcagttact    60
ttaccaagac aatgtaatta ttgtttgatt ttataaagtc tacaacaatg atctcctatt   120
ttggtgtcag ttttttcaata aagttttaat ta                                152

<210> SEQ ID NO 205
<211> LENGTH: 1841
<212> TYPE: DNA
<213> ORGANISM: Mus musculus

<400> SEQUENCE: 205
agcaggagca ggttttccaa aagcacccct cggaagtgtt tttgtcgtcg tttaaaatta    60
tcaagtatct tcagagaaga ttattttctg ccttcagaaa ctgaaggaag gcttgggcct   120
agagaacgac agtaaggtgc gagcaccgga gacacttaac acagctcagt ccatggaagg   180
acgagttccc tcattggctg cctgtctcga atccacgca agctgtggag gaaagaatta   240
ccctgctcat cctgccttct atcttggtgt ttaatgttgg gtgggcaaca agcacaaacc   300
tccctcccac ccctccaag actgttagag cagtgggcca gaccaagcgg cgcacttgaa   360
catggatcaa gagggtcccg gttttacttt ttattttgt cagggtaggc agtcttgtgt   420
ttgctttgtt caaagcaggg tctccctgtt ggccctggct ggccttatac tccacagcag   480
tcctgcctcc tcctcctagg tgctgggatt aaaggcgtgc gccaccacgc ccggctacag   540
cctgcatttt tatgcacatt ggtctgttaa gctagttgca ttctgtgcta ccggagggga   600
ctgaagttta atcacttgtc ttctattaaa aactagtgtt tgcctgggcc tggtgtgtat   660
acctttagtt gcagcgcttg ggaggcagag gcaggcagac ttcatgagtt cagggacagg   720
caagcctgct ctacagattt ccaggatacc cagggctaca catagagaaa atgttaaaga   780
taaacaaaaa gctggacagt gggggagcac acctttaatc ccagcactcg ggaggcagag   840
gcaggcggat ttctgagttc gaggccagcc tggtctacag agtgagttcc aggacagcca   900
ggactacaca gagaaaccct gtctcagaaa aaaacaaaa caaaaaccaa tgcagtgata   960
gattgttgtt tcctaaaacca catgtaccca ggaaatgccc actaaatttc acctggatca  1020
gtgttaactg atcattggga aatgaggtga ccaaaaatgc atcgcaacct tggacaaaca  1080
gcatggctat ttaacattct gggatcctgc agaatcctgc atcttcctaa gtagggaagc  1140
actgtagcat tggagagagg cctgggcgag cagagctaag gcttccattt ctggcttgct  1200 tggaattttaa aacaagcttt tttctatata gtaaagatt gttttaaga ttttgcgtg    1260 tgagtacatg ccaaagtagc caggaagtgt cacttgccct ggagctagaa ttactggcaa  1320

| | |
|---|---|
| atgaaggctc agaggtggat gctgggacca attctaggcc ctctgagaaa gcaggtgcac | 1380 |
| ttggcttgtg cctccagccc caaaggcgat ggcttattgt gagcctgagg ccagccaggg | 1440 |
| ttacagagac tcaagaaaca agtggggttg tccatgttgc tggagatgac ccaggtctat | 1500 |
| taggaccttg actacatgga tagacattct ggcagctagt atactgccat tggggcctat | 1560 |
| ggagaagtag ccaccgagcc tatttagaaa gaaggactgc tggcaagctt ggtgtcacta | 1620 |
| tgaaggcaga caaagatcga tgtattaacg accccgactc caaaaacact cgaggggcc | 1680 |
| caaggtgggc tcagtggtta agagccgttc gcccaggggc tggagagttg gctcagtggt | 1740 |
| accacatggt ggctcacaac catctgtaat gagatctgac gccctcttct ggtgtatctg | 1800 |
| aagacagcta cagtgtactt acataaaata aataaatctt t | 1841 |

<210> SEQ ID NO 206
<211> LENGTH: 2035
<212> TYPE: DNA
<213> ORGANISM: Artificial Sequence
<220> FEATURE:
<223> OTHER INFORMATION: sequence encoding the mRNA rpl32 - PpLuc(GC) - albumin - A64 - C30 - histoneSL

<400> SEQUENCE: 206

| | |
|---|---|
| ggggcgctgc ctacggaggt ggcagccatc tccttctcgg catcaagctt gaggatggag | 60 |
| gacgccaaga acatcaagaa gggcccggcg cccttctacc cgctggagga cgggaccgcc | 120 |
| ggcgagcagc tccacaaggc catgaagcgg tacgccctgg tgccgggcac gatcgccttc | 180 |
| accgacgccc acatcgaggt cgacatcacc tacgcggagt acttcgagat gagcgtgcgc | 240 |
| ctggccgagg ccatgaagcg gtacggcctg aacaccaacc accggatcgt ggtgtgctcg | 300 |
| gagaacagcc tgcagttctt catgccggtg ctgggcgccc tcttcatcgg cgtggccgtc | 360 |
| gccccggcga acgacatcta caacgagcgg gagctgctga acagcatggg gatcagccag | 420 |
| ccgaccgtgg tgttcgtgag caagaagggc ctgcagaaga tcctgaacgt gcagaagaag | 480 |
| ctgcccatca tccagaagat catcatcatg gacagcaaga ccgactacca gggcttccag | 540 |
| tcgatgtaca cgttcgtgac cagccacctc ccgccgggct tcaacgagta cgacttcgtc | 600 |
| ccggagagct tcgaccggga caagaccatc gccctgatca tgaacagcag cggcagcacc | 660 |
| ggcctgccga gggggtggc cctgccgcac cggaccgcct gcgtgcgctt ctcgcacgcc | 720 |
| cgggacccca tcttcggcaa ccagatcatc ccggacaccg ccatcctgag cgtggtgccg | 780 |
| ttccaccacg gcttcggcat gttcacgacc ctgggctacc tcatctgcgg cttccgggtg | 840 |
| gtcctgatgt accggttcga ggaggagctg ttcctgcgga gcctgcagga ctacaagatc | 900 |
| cagagcgcgc tgctcgtgcc gaccctgttc agcttcttcg ccaagagcac cctgatcgac | 960 |
| aagtacgacc tgtcgaacct gcacgagatc gccagcgggg cgccccgct gagcaaggag | 1020 |
| gtgggcgagg ccgtggccaa gcggttccac ctcccgggca tccgccaggg ctacggcctg | 1080 |
| accgagacca cgagcgcgat cctgatcacc cccgaggggg acgacaagcc gggcgccgtg | 1140 |
| ggcaaggtgg tcccgttctt cgaggccaag gtggtggacc tggacaccgg caagaccctg | 1200 |
| ggcgtgaacc agcggggcga gctgtgcgtg cgggggccga tgatcatgag cggctacgtg | 1260 |
| aacaacccgg aggccaccaa cgccctcatc gacaaggacg ctggctgca cagcggcgac | 1320 |
| atcgcctact gggacgagga cgagcacttc ttcatcgtcg accggctgaa gtcgctgatc | 1380 |
| aagtacaagg gctaccaggt ggcgccggcc gagctggaga gcatcctgct ccagcacccc | 1440 |
| aacatcttcg acgccggcgt ggccgggctg ccggacgacg acgccggcga gctgccggcc | 1500 |

```
gcggtggtgg tgctggagca cggcaagacc atgacggaga aggagatcgt cgactacgtg   1560
gccagccagg tgaccaccgc caagaagctg cggggcggcg tggtgttcgt ggacgaggtc   1620
ccgaagggcc tgaccgggaa gctcgacgcc cggaagatcc gcgagatcct gatcaaggcc   1680
aagaagggcg gcaagatcgc cgtgtaagac tagtgcatca catttaaaag catctcagcc   1740
taccatgaga ataagagaaa gaaatgaag atcaatagct tattcatctc tttttctttt    1800
tcgttggtgt aaagccaaca ccctgtctaa aaaacataaa tttctttaat cattttgcct   1860
cttttctctg tgcttcaatt aataaaaaat ggaaagaacc tagatctaaa aaaaaaaaaa   1920
aaaaaaaaaa aaaaaaaaaa aaaaaaaaaa aaaaaaaaaa aaaaaaaaaa atgcatcccc   1980
cccccccccc cccccccccc ccccccaaa ggctcttttc agagccacca gaatt         2035
```